United States Patent
Chellappan et al.

(10) Patent No.: US 10,851,119 B2
(45) Date of Patent: *Dec. 1, 2020

(54) BORON-CONTAINING DIACYLHYDRAZINES

(71) Applicant: Intrexon Corporation, Blacksburg, VA (US)

(72) Inventors: Sheela K. Chellappan, Clarksburg, MD (US); Robert E. Hormann, Melrose Park, PA (US); Inna Shulman, Langhorne, PA (US)

(73) Assignee: INTREXON CORPORATION, Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/580,343

(22) Filed: Sep. 24, 2019

(65) Prior Publication Data
US 2020/0157122 A1    May 21, 2020

Related U.S. Application Data

(63) Continuation of application No. 15/354,239, filed on Nov. 17, 2016, now Pat. No. 10,464,951, which is a continuation of application No. 14/805,837, filed on Jul. 22, 2015, now Pat. No. 9,512,148, which is a continuation of application No. 14/212,526, filed on Mar. 14, 2014, now Pat. No. 9,127,024.

(60) Provisional application No. 61/792,412, filed on Mar. 15, 2013.

(51) Int. Cl.
*C07F 5/02* (2006.01)
*C07F 5/04* (2006.01)
*C07F 7/08* (2006.01)

(52) U.S. Cl.
CPC .............. *C07F 5/025* (2013.01); *C07F 5/027* (2013.01); *C07F 5/04* (2013.01); *C07F 7/0803* (2013.01)

(58) Field of Classification Search
CPC ..... C07F 5/02; C07F 5/04; C07F 5/08; A61K 31/495
See application file for complete search history.

(56) References Cited

U.S. PATENT DOCUMENTS

| | | | |
|---|---|---|---|
| 4,631,211 A | 12/1986 | Houghten | |
| 4,814,349 A | 3/1989 | Addor et al. | |
| 4,859,609 A | 8/1989 | Dull et al. | |
| 4,906,280 A | 3/1990 | Sandler et al. | |
| 4,950,666 A | 8/1990 | Peake et al. | |
| 4,954,655 A | 9/1990 | Kelly | |
| 4,981,784 A | 1/1991 | Evans et al. | |
| 4,985,461 A | 1/1991 | Hsu et al. | |
| 5,010,175 A | 4/1991 | Rutter et al. | |
| 5,071,773 A | 12/1991 | Evans et al. | |
| 5,075,471 A | 12/1991 | Michelotti et al. | |
| 5,117,057 A | 5/1992 | Hsu et al. | |
| 5,171,671 A | 12/1992 | Evans et al. | |
| 5,225,443 A | 7/1993 | Murphy et al. | |
| 5,283,173 A | 2/1994 | Fields et al. | |
| 5,344,958 A | 9/1994 | Lidert et al. | |
| 5,354,762 A | 10/1994 | Hsu et al. | |
| 5,358,966 A | 10/1994 | James, Jr. et al. | |
| 5,378,726 A | 1/1995 | Yanagi et al. | |
| 5,424,333 A | 6/1995 | Wing | |
| 5,429,952 A | 7/1995 | Garner et al. | |

(Continued)

FOREIGN PATENT DOCUMENTS

| | | |
|---|---|---|
| CA | 2 103 110 C | 5/1994 |
| CN | 1245638 A | 3/2000 |

(Continued)

OTHER PUBLICATIONS

Antoniewski, C. et al., "The Ecdysone Response Enhancer of the Fbp1 Gene of *Drosophila melanogaster* Is a Direct Target for the Ecr/USP Nuclear Receptor," Mol. Cell. Biol. 14:4465-4474, American Society for Microbiology (1994).

Ashburner, M. et al., "Temporal Control of Puffing Activity in Polytene Chromosomes," *Cold Spring Harb. Symp. Quant. Biol.* 38:655-662, Cold Spring Harbor Laboratory Press (1974).

(Continued)

*Primary Examiner* — D Margaret M Seaman
(74) *Attorney, Agent, or Firm* — Sterne, Kessler, Goldstein & Fox P.L.L.C.

(57) ABSTRACT

The present disclosure provides boron-containing diacylhydrazines having Formula I:

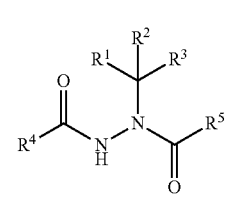

and the pharmaceutically acceptable salts and solvates thereof, wherein $R^1$, $R^2$, $R^3$, $R^4$, and $R^5$ are defined as set forth in the specification. The present disclosure also provides the use of boron-containing diacylhydrazines is ecdysone receptor-based inducible gene expression systems. Thus, the present disclosure is useful for applications such as gene therapy, treatment of disease, large scale production of proteins and antibodies, cell-based screening assays, functional genomics, proteomics, metabolomics, and regulation of traits in transgenic organisms, where control of gene expression levels is desirable.

20 Claims, 7 Drawing Sheets
Specification includes a Sequence Listing.

(56) References Cited

U.S. PATENT DOCUMENTS

| | | | |
|---|---|---|---|
| 5,459,127 A | 10/1995 | Felgner et al. |
| 5,482,962 A | 1/1996 | Hormann |
| 5,514,578 A | 5/1996 | Hogness et al. |
| 5,530,021 A | 6/1996 | Yanagi et al. |
| 5,530,028 A | 6/1996 | Lidert et al. |
| 5,599,904 A | 2/1997 | Evans et al. |
| 5,641,652 A | 6/1997 | Oro et al. |
| 5,668,175 A | 9/1997 | Evans et al. |
| 5,710,004 A | 1/1998 | Evans et al. |
| 5,723,329 A | 3/1998 | Mangelsdorf et al. |
| 5,880,333 A | 3/1999 | Goff et al. |
| 5,919,667 A | 7/1999 | Gage et al. |
| 5,945,400 A | 8/1999 | Scherman et al. |
| 5,948,406 A | 9/1999 | Stavinski et al. |
| 5,981,196 A | 11/1999 | Stavinski et al. |
| 5,989,863 A | 11/1999 | Tang et al. |
| 6,013,836 A | 1/2000 | Hsu et al. |
| 6,025,483 A | 2/2000 | Yanofsky |
| 6,096,787 A | 8/2000 | Evans et al. |
| 6,107,286 A | 8/2000 | Byk et al. |
| 6,117,639 A | 9/2000 | Germann et al. |
| 6,147,282 A | 11/2000 | Goff et al. |
| 6,245,531 B1 | 6/2001 | Hogness et al. |
| 6,258,603 B1 | 7/2001 | Carlson et al. |
| 6,265,173 B1 | 7/2001 | Evans et al. |
| 6,281,330 B1 | 8/2001 | Evans et al. |
| 6,300,488 B1 | 10/2001 | Gage et al. |
| 6,326,403 B1 | 12/2001 | Hölzemann et al. |
| 6,333,318 B1 | 12/2001 | Evans et al. |
| 6,379,945 B1 | 4/2002 | Jepson et al. |
| 6,458,926 B1 | 10/2002 | Evans et al. |
| 6,723,531 B2 | 4/2004 | Evans et al. |
| 6,756,491 B2 | 6/2004 | Evans et al. |
| 6,875,569 B2 | 4/2005 | Gage et al. |
| 6,939,711 B2 | 9/2005 | Goff et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 | 8/2006 | Palli et al. |
| 7,119,077 B1 | 10/2006 | Evans et al. |
| 7,304,161 B2 | 12/2007 | Hormann et al. |
| 7,456,315 B2 | 11/2008 | Hormann et al. |
| 7,563,928 B2 | 7/2009 | Hormann et al. |
| 7,851,220 B2 | 12/2010 | Hormann et al. |
| 8,076,517 B2 | 12/2011 | Hormann et al. |
| 8,524,948 B2 | 9/2013 | Hormann et al. |
| 9,127,024 B2 * | 9/2015 | Chellappan | C07F 5/027 |
| 9,272,986 B2 | 3/2016 | Hormann et al. |
| 9,512,148 B2 * | 12/2016 | Chellappan | C07F 5/04 |
| 10,464,951 B2 * | 11/2019 | Chellappan | C07F 5/04 |
| 2002/0110861 A1 | 8/2002 | Dhadialla et al. |
| 2002/0119521 A1 | 8/2002 | Palli et al. |
| 2002/0177564 A1 | 11/2002 | Evans et al. |
| 2003/0010253 A1 | 1/2003 | Oki et al. |
| 2003/0203360 A1 | 10/2003 | Weinstein et al. |
| 2004/0033600 A1 | 2/2004 | Palli et al. |
| 2004/0096942 A1 | 5/2004 | Kapitskaya et al. |
| 2004/0197861 A1 | 10/2004 | Palli |
| 2004/0235097 A1 | 11/2004 | Zhang et al. |
| 2005/0209283 A1 | 9/2005 | Hormann et al. |
| 2005/0266457 A1 | 12/2005 | Palli et al. |
| 2006/0100416 A1 | 5/2006 | Palli et al. |
| 2007/0161086 A1 | 7/2007 | Palli et al. |
| 2008/0064741 A1 | 3/2008 | Hormann et al. |
| 2008/0103113 A1 | 5/2008 | Hormann et al. |
| 2008/0194521 A1 | 8/2008 | Hormann et al. |
| 2008/0214627 A1 | 9/2008 | Hormann et al. |
| 2012/0116090 A1 | 5/2012 | Hormann et al. |
| 2012/0316066 A1 | 12/2012 | Hormann et al. |
| 2013/0035487 A1 | 2/2013 | Hormann et al. |
| 2014/0045903 A1 | 2/2014 | Hormann et al. |
| 2016/0083403 A1 | 3/2016 | James et al. |

FOREIGN PATENT DOCUMENTS

| | | |
|---|---|---|
| CN | 1161325 C | 8/2004 |
| DE | 198 37 620 A1 | 2/1999 |
| EP | 0 228 564 B1 | 7/1987 |
| EP | 0 232 075 A1 | 8/1987 |
| EP | 0 234 944 A1 | 9/1987 |
| EP | 0 236 618 A2 | 9/1987 |
| EP | 0 245 950 A2 | 11/1987 |
| EP | 0 253 468 A2 | 1/1988 |
| EP | 0 339 854 B1 | 11/1989 |
| EP | 0 347 216 A2 | 12/1989 |
| EP | 0 361 645 A2 | 4/1990 |
| EP | 0 395 581 A1 | 10/1990 |
| EP | 0 286 746 B1 | 2/1991 |
| EP | 0 461 809 A1 | 12/1991 |
| EP | 0 496 342 B1 | 7/1992 |
| EP | 0 639 559 A1 | 2/1995 |
| EP | 0 798 378 A2 | 10/1997 |
| EP | 0 965 644 A2 | 12/1999 |
| EP | 0 984 009 A1 | 3/2000 |
| EP | 1 266 015 B1 | 12/2002 |
| GB | 2 231 268 A | 11/1990 |
| JP | 62-209053 A | 9/1987 |
| JP | 62-263150 A | 11/1987 |
| JP | 2-207066 A | 8/1990 |
| JP | 3-141245 A | 6/1991 |
| JP | 3-145447 A | 6/1991 |
| JP | 4-089471 A | 3/1992 |
| JP | 4-178380 A | 6/1992 |
| JP | 4-235177 A | 8/1992 |
| JP | 5-39252 A | 2/1993 |
| JP | 6-172342 A | 6/1994 |
| JP | 6-184076 A | 7/1994 |
| JP | 8-231528 A | 9/1996 |
| JP | 8-231529 A | 9/1996 |
| JP | 9-100262 A | 4/1997 |
| JP | 2000-26423 A | 1/2000 |
| WO | WO 89/12690 A1 | 12/1989 |
| WO | WO 94/28028 A1 | 12/1994 |
| WO | WO 95/18863 A1 | 7/1995 |
| WO | WO 95/21931 A1 | 8/1995 |
| WO | WO 96/17823 A1 | 6/1996 |
| WO | WO 96/25508 A1 | 8/1996 |
| WO | WO 96/27673 A1 | 9/1996 |
| WO | WO 96/37609 A1 | 11/1996 |
| WO | WO 97/38117 A1 | 10/1997 |
| WO | WO 99/02683 A1 | 1/1999 |
| WO | WO 99/10510 A2 | 3/1999 |
| WO | WO 99/36520 A1 | 7/1999 |
| WO | WO 99/58155 A1 | 11/1999 |
| WO | WO 01/36447 A2 | 5/2001 |
| WO | WO 01/62780 A1 | 8/2001 |
| WO | WO 01/70816 A2 | 9/2001 |
| WO | WO 02/29075 A2 | 4/2002 |
| WO | WO 02/066612 A2 | 8/2002 |
| WO | WO 02/066613 A2 | 8/2002 |
| WO | WO 02/066614 A2 | 8/2002 |
| WO | WO 02/066615 A2 | 8/2002 |
| WO | WO 03/105849 A1 | 12/2003 |
| WO | WO 2004/005478 A2 | 1/2004 |
| WO | WO 2004/072254 A2 | 8/2004 |
| WO | WO 2004/078924 A2 | 9/2004 |
| WO | WO 2005/017126 A2 | 2/2005 |
| WO | WO 2005/108617 A2 | 11/2005 |
| WO | WO 2006/083253 A1 | 8/2006 |

OTHER PUBLICATIONS

Belshaw, P.J. et al., "Rational Design of Orthogonal Receptor-Ligand Combinations," Angew. Chem. Int. Ed. Engl. 34:2129-2132, VCH Verlagsgesellschaft mbH, Weinheim (1995).

Cao, S. et al., "N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis," Can. J. Chem. 79:272-278, NRC Canada (2001).

Cao, S. et al., "Synthesis of N-Tert-butyl-N,N'-aroyl(aryloxyacetyl)hydrazine," Huadong Ligong Daxue Xuebao 27:316-319, Huodeng Shifan Daxue Chubanshe, China (2001).

(56) References Cited

OTHER PUBLICATIONS

Carlson, G.R. et al., "The chemical and biological properties of methoxyfenozide, a new insecticidal cedysteroid agonist," *Pest Manag. Sci.* 57:115-119, Society of Chemical Industry (2001).

Cherbas, L. et al., "Identification of Ecdysone response elements by analysis of the *Drosophila* Eip28/29 gene," *Genes & Develop.* 5:120-131, Cold Spring Harbor Laboratory Press (1991).

Cho, W.-L. et al., "Mosquito Ecdysteroid Receptor: Analysis of the cDNA and Expression During Vitellogenesis," *Insect Biochem. Molec. Biol.* 25:19-27, Elsevier Science Ltd. (1995).

Christopherson, K.S. et al., "Ecdysteroid-dependent regulation of genes in mammalian cells by a *Drosophila* ecdysone receptor and chimeric transactivators," *PNAS* 89:6314-6318, National Academy of Sciences (1992).

Chung, A.C.-K. et al., "Cloning of crustacean ecdysteroid receptor and retinoid-X receptor gene homologs and elevation of retinoid-X receptor mRNA by retinoic acid," *Mol. Cell. Endocrinol.* 139:209-227, Elsevier Science Ireland Ltd. (1998).

D'Avino, P.P. et al., "The moulting hormone ecdysone is able to recognize target elements composed of direct repeats," *Mol. Cell. Endocrinol.* 113:1-9, Elsevier Science Ireland Ltd. (1995).

Dhadialla, T.S. et al., "New Insecticides With Ecdysteroidal and Juvenile Hormone Activity," *Annu. Rev. Entomol.* 43:545-569, Annual Reviews Inc. (1998).

Evans, R.M., "The Steroid and Thyroid Hormone Receptor Superfamily," *Science* 240:889-895, American Association for the Advancement of Science (1988).

Fujiwara, H. et al., "Cloning of an Ecdysone Receptor Homolog from *Manduca sexta* and the Developmental Profile of Its mRNA in Wings," *Insect Biochem. Molec. Biol.* 25:845-856, Elsevier Science Ltd. (1995).

Godowski, P.J. et al., "Signal Transduction and Transcriptional Regulation by Glucocorticoid Receptor-LexA Fusion Proteins," *Science* 241:812-816, American Association for the Advancement of Science (1988).

Guo, X. et al., "Isolation of a Functional Ecdysteroid Receptor Homologue from the Ixodid Tick *Amblyomma americanum* (L.)," *Insect Biochem. Molec. Biol.* 27:945-962, Elsevier Science Ltd. (1998).

Hannan, G.N. and Hill, R.J., "Cloning and Characterization of LcEdR: A Functional Ecdysone Receptor from the Sheep Blowfly *Lucilia cuprina,*" *Insect Biochem. Molec. Biol.* 27:479-488, Elsevier Science Ltd. (1997).

Hayward, D.C. et al., "The structure of the USP/RXR of *Xenos pecki* indicates that Strepsiptera are not closely related to Diptera," *Dev. Genes Evol.* 215:213-219, Springer-Verlag (2005).

Heberlein, U. et al., "Characterization of *Drosophila* Transcription Factors That Activate the Tandem Promoters of the Alcohol Dehydrogenase Gene," *Cell* 41:965-977, MIT (1985).

Holt, J.R. et al., "Functional Expression of Exogenous Proteins in Mammalian Sensory Hair Cells Infected With Adenoviral Vectors," *J. Neurophysiol.* 81:1881-1888, American Physiological Society (1999).

Hoppe, U.C. et al., "Adenovirus-Mediated Inducible Gene Expression in Vivo by a Hybrid Ecdysone Receptor," *Mol. Ther.* 1:159-164, The American Society of Gene Therapy (2000).

Imhof, M.O. et al., "Cloning of a *Chironomus tentans* cDNA Encoding a Protein (cEcRH) Homologous to the *Drosophila melanogaster* Ecdysteroid Receptor (dEcR)," *Insect Biochem. Molec. Biol.* 23:115-124, Pergamon Press Ltd. (1993).

International Search Report and the Witten Opinion of the International Searching Authority for International Appl. No. PCT/US2014/028768, dated Jul. 8, 2014, United States Patent and Trademark Office, Alexandria, VA.

Kakizawa, T. et al., "Ligand-dependent Heterodimerization of Thyroid Hormone Receptor and Retinoid X Receptor," *J. Biol. Chem.* 272:23799-23804, The American Society for Biochemistry and Molecular Biology, Inc. (1997).

Koelle, M.R. et al., "The *Drosophila* EcR Gene Encodes an Ecdysone Receptor, a New Member of the Steroid Receptor Superfamily," *Cell* 67:59-77, Cell Press (1991).

Kothapalli, R. et al., "Cloning and Developmental Expression of the Ecdysone Receptor Gene From the Spruce Budworm, *Choristoneura fumiferana,*" *Dev. Genet.* 17:319-330, Wiley-Liss, Inc. (1995).

Kumar, M.B. et al., "A single point mutation in ecdysone receptor leads to increased ligand specificity: Implications for gene switch applications," *PNAS* 99:14710-14715, National Academy of Sciences (2002).

Le, D.P. et al., "RH-2485: A New Selective Insecticide for Caterpillar Control," Brighton Crop Protection Conference—*Pests and Diseases* 2:481-486, British Crop Protection Council (1996).

Leid, M. et al., "Purification, Cloning, and RXR Identity of the HeLa Cell Factor with Which RAR or TR Heterodimerizes to Bind Target Sequences Efficiently," *Cell* 68:377-395, Cell Press (1992).

Leonhardt, S.A. et al.,"Agonist and Antagonists Induce Homodimerization and Mixed Ligand Heterodimerization of Human Progesterone Receptors in Vivo by a Mammalian Two-Hybrid Assay," *Mol. Endocrinol.* 12:1914-1930, The Endocrine Society (1998).

Licitra, E.J. and Liu, J.O., "A three-hybrid system for detecting small ligand-protein receptor interactions," *PNAS* 93:12817-12821, National Academy of Sciences (1996).

Martinez, A. et al., "Creation of ecdysone receptor chimeras in plants for controlled regulation of gene expression," *Mol. Gen. Genet.* 261:546-552, Springer-Verlag, Germany (1999).

Metzger, D. et al., "The human oestrogen receptor functions in yeast," *Nature* 334:31-36, Nature Publishing Group (1988).

Morrison, D.A. et al., "Isolation of Transformation-Deficient *Streptococcus pneumoniae* Mutants Defective in Control of Competence, Using Insertion-Duplication Mutagenesis with the Erythromycin Resistance Determinant of pAMβ1," *J. Bacteriol.* 159:870-876, American Society for Microbiology (1984).

Mouillet J.-F. et al., "Cloning of two putative ecdysteroid receptor isoforms from *Tenebrio molitor* and their developmental expression in the epidermis during metamorphosis," *Eur. J. Biochem.* 248:856-863, FEBS (1997).

Nakagawa, Y. et al., "Quantitative Structure-Activity Relationships and Designed Synthesis of Larvicidal N,N'-Dibenzoyl-N-tert-butylhydrazines against *Chilo suppressalis,*" *Pestic. Sci.* 44:102-105, SCI (1995).

Nakagawa, Y. et al., "Quantitative Structure—Activity Studies of Insect Growth Regulators. XI. Stimulation and Inhibition of N-Acetylglucosamine Incorporation in a Cultured Integument System by Substituted N-tert-Butyl-N,N'-dibenzoylhydrazines,"*Pestic. Sci.* 43:339-345, SCI (1995).

Nakagawa, Y. et al., "Quantitative structure-activity studies of insect growth regulators: XIX. Effects of substituents on the aromatic moiety of dibenzoylhydrazines on larvicidal activity against the beet armyworm *Spodoptera exigua,*" *Pest Manag. Sci.* 58:131-138, published online by EarlyView in Wiley InterScience (2001).

Nakagawa, Y. et al., "Quantitative structure-activity studies of insect growth regulators: XVI. Substituent effects of dibenzoylhydrazines on the insecticidal activity to Colorado potato beetle *Leptinotarsa decemlineata,*" *Pestic. Sci.* 55:909-918, Society of Chemical Industry (1999).

Nakagawa, Y. et al., "Quantitative structure-activity studies of insect growth regulators: XVIII. Effects of substituents on the aromatic moiety of dibenzoylhydrazines on larvicidal activity against the Colorado potato beetle *Leptinotarsa decemlineato,*" *Pest Manag. Sci.* 57:858-865, SCI (2001).

Neuberger, M.S. et al., "Recombinant antibodies possessing novel effector functions," *Nature* 312:604-608, Nature Publishing Group (1984).

Nie, K.-S. et al., "New Insect Growth Regulators—Central Tebufenozide," *Nongyaoxue Xuebao* 40:42-43, Gai Kan Bianjibu, Beijing (2001).

No, D. et al., "Ecdysone-inducible gene expression in mammalian cells and transgenic mice," *PNAS* 93:3346-3351, National Academy of Sciences (1996).

Oikawa, N. et al., "Quantitative Structure-Activity Analysis of Larvicidal 1-(Substituted benzoyl)-2-benzoyl-1-tert-butylhydrazines against *Chilo suppressalis,"* *Pestic. Sci.* 41:139-147, SCI (1994).

(56) References Cited

OTHER PUBLICATIONS

Peet, D.J. et al., "Engineering novel specificities for ligand-activated transcription in the nuclear hormone receptor RXR," *Chem. & Biol.* 5:13-21, Current Biology Ltd. (1998).
Perera, S.C. et al., "An Analysis of Ecdysone Receptor Domains Required for Heterodimerization With Ultraspiracle," *Arch. Insect Biochem. Physiol.* 41:61-70, Wiley-Liss, Inc. (1999).
Perera, S.C. et al., "Studies on two ecdysone receptor isoforms of the spruce budworm, *Choristoneura fumiferana,*" *Mol. Cell. Endocrinol.* 152:73-84, Elsevier Science Ireland Ltd. (1999).
Pierce, A.C. and Jorgensen, W.L., "Computational Binding Studies of Orthogonal Cyclosporin-Cyclophilin Pairs," *Angew. Chem. Int. Ed. Engl.* 36:1466-1469, VCH Verlagsgesellschaft mbH, Weinheim (1997).
Riddiford, L.M. et al., "Ecdysone Receptors and Their Biological Actions," *Vitamins and Hormones* 60:1-73, Academic Press (2001).
Saleh, D.S. et al., "Cloning and characterization of an ecdysone receptor cDNA from *Locusta migratoria,*" *Mol. Cell. Endocrinol.* 143:91-99, Elsevier Science Ireland Ltd. (1998).
Sawada. Y. et al., "Synthesis and Insecticidal Activity of 3,5-Dimethylbenzoyl Moiety Modified Analogues of N-tert-Butyl-N'-(4-ethylbenzoyl)-3,5-dimethylbenzohydrazide," *J. Pesticide Sci.* 27:365-373, Pesticide Science Society of Japan, Tokyo (2002).
Sawada, Y. et al., "Synthesis and insecticidal activity of benzoheterocyclic analogues of N'-benzoyl-N-(tert-butyl)benzohydrazide: Part 2. Introdution of substituents on the benzene rings of the benzoheteroycle moiety," *Pest Manag. Sci.* 59:36-48, published online by EarlyView in Wiley InterScience (2002).
Sawada, Y. et al., "Synthesis and insecticidal activity of benzoheterocyclic analogues of N'-benzoyl-N-(tert-butyl)benzohydrazide: Part 3. Modification of N-tert-butylhydrazine moiety," *Pest Manag. Sci.* 59:49-57, published online by EarlyView in Wiley InterScience (2002).
Sawada. Y. et al., "Synthesis and insecticidal activity of benzoheterocyclic analogues of N'-benzoyl-N-tert-butyl)benzohydrazide: Part 1. Design of benzoheterocyclic analogues," *Pest Manag. Sci.* 59:25-35, published online by EarlyView in Wiley InterScience (2003).
Suhr, S.T. et al., "High level transactivation by a modified *Bombyx* ecdysone receptor in mammalian cells without exogenous retinoid X receptor," *PNAS* 95:7999-8004, National Academy of Sciences (1998).
Swevers, L. et al., "The Silkmoth Homolog of the *Drosophila*Ecdysone Receptor (B1 Isoform): Cloning and Analysis of Expression During Follicular Cell Differentiation," *Insect Biochem. Molec. Biol.* 25:857-866, Elsevier Science Ltd. (1995).
Tice, C.M. et al., "Optimization of α-Acylaminoketone Ecdysone Agonists for Control of Gene Expression," *Biorg. Med. Chem. Letts.* 13:1883-1886, Elsevier Science Ltd. (2003).
Verras, M. et al., "Cloning and characterization of CcEcR, An ecdysone receptor homolog from the Mediterranean fruit fly *Ceratitis capitata,*" *Eur. J. Biochem.* 265:798-808, FEBS (1999).
Wheelock, C.E. et al., "High-throughput screening of ecdysone agonists using a reporter gene assay followed by 3-D QSAR analysis of the molting hormonal activity," *Bioorg. Med. Chem.* 14:1143-1159, Elsevier Ltd. (2006).
Wilson, J.M. et al., "Hepatocyte-directed Gene Transfer in Vivo Leads to Transient Improvement of Hypercholesterolemia in Low Density Lipoprotein Receptor-deficient Rabbits," *J. Biol. Chem.* 267:963-967, The American Society for Biochemistry and Molecular Biology, Inc. (1992).
Wing, K.D., "RH 5849, a Nonsteroidal Ecdysone Agonist: Effects on a *Drosophila* Cell Line," *Science* 241:467-469, The American Association for the Advancement of Science ( 1988).
Yao, T.-P. et al., "*Drosophila* ultraspiracle Modulates Ecdysone Receptor Function via Heterodimer Formation," *Cell* 71:63-72, Cell Press (1992).
Yao, T.-P. et al., "Functional ecdysone receptor is the product of EcR and *Ultraspiracle* genes," *Nature* 366:476-479, Nature Publishing Group (1993).
Zhang, X.-N. et al., "Innovation Hydrazines insect growth regulator JS118 the synthesis and biological activity. Synthesis and Study of Ait of New Diacylhydrazines IGRs JS118," *Pesticides* 42:18-20 (2003).
Zou X.-J. et al., "Synthesis and Crystal Structure of N-tert-butyl-N'-(2,4-dichlorobenzoyl)-N-[1-(4-chlorophenyl)-1,4-dihydro-6-methylpyridazine-4-oxo-3-carbonyl] hydrazine," *Jiegou Huaxue* 20:344-348, Zhingguo ke xue Yuan, Fujian wu zhi jie gou yan jiusuo, China (2001).
Zou, X.-J. And Jin G.-Y., "Synthesis of N-tert-butyl-N'(N)-(1-aryl-1,4-dihydro-6-methylpyridazine-4-oxo-3-carbonyl)-N (N')-(substituted) benzoylhydrazine," *Indian J. Chem.* 42B:2608-2611, Council of Scientific & Industrial Research, New Delhi (2003).
Chan, T. et al., Gene Therapy of Cancer: Translational Approaches from Preclinical Studies to Clinical Implementation 363-376 (Edmund C. Lattime & Stanton L. Gerson eds., 3$^{rd}$ ed. 2014) Elsevier Inc.
Del Vecchio, M. et al., "Interleukin-12: Biological Properties and Clinical Application," *Clin. Cancer Res.* 13:4677-4685, American Association for Cancer Research (2007).
Baker, S.J. e al., "Boron-containing inhibitors of synthetases," *Chem. Soc. Rev.* 40:4279-4285, The Royal Society of Chemistry, United Kingdom (Feb. 7, 2011).
Akdis, M. et al., "Interleukins, from 1 to 37, and interferon-γ: Receptors, functions, and roles in diseases," *J Allergy Clin Immunol* 127:701-721.e70, American Academy of Allergy, Asthma & Immunology (2010).
Sereti, I. et al., "IL-2-induced CD4+ T-cell expansion in HIV-infected patients is associated with long-term decreases in T-cell proliferation," *Blood* 104:775-780, The American Society of Hematology (2004).
Romani, L. et al., "Interleukin-12 in Infectious Diseases," *Clinical Microbiology Reviews* 10:611-636, American Society for Microbiology (1997).
Fehniger, T. et al., "Interleukin 15: biology and relevance to human disease," *Blood* 97:14-32, The American Society of Hematology (2001).
Koreth, J. et al., "Low-dose Interleukin-2 in the Treatment of Autoimmune Disease," *Oncology & Hematology Review* 10:157-163, Touch Medical Media (2014).

\* cited by examiner

Fig. 2A

```
GCTGAGCTATGCCTAATCAAGTCACGGTAACTATGACTCTCTTAAGGTAGCCAAATGGCG
CCACGAAAGGAGGTCGTGAAATGGATAAAAAAATACAGCGTTTTTCATGTACAACTATAC
TAGTTGTAGTGCCTAAATAATGCTTTTAAAACTTAAAAATATCAGATAACAGCTTGGTGG
CACCCATTGTGTTCACAGGAGATACAGCTTTATCTGTACTGATATTAATGACATGCTGCA
CTCGGTGTGAAAGGGCATCTAGTAGGCTATGGCAGGGCCTGCCGCCCCGACGTTGGCTGC
GAGCCCTGGGCCTTCACCCGAACTTGGGGGGTGGGGTGGGGAAAAGGAAGAAACGCGGGC
GTATTGGCCCCAATGGGGTCTCGGTGGGGTATCGACAGAGTGCCAGCCCTGGGACCGAAC
CCCGCGTTTATGAACAAACGACCCAACACCGTGCGTTTTATTCTGTCTTTTTATTGCCGT
CATAGCGCGGGTTCCTTCCGGTATTGTCTCCTTCCGTGTTTCATCAGAAAAACTCGTCCA
GCAGGCGGTAGAAAGCGATGCGCTGAGAATCTGGTGCAGCGATGCCGTACAGAACCAGGA
AGCGGTCAGCCCATTCGCCGCCCAGTTCTTCAGCGATGTCGCGGGTAGCCAGAGCGATGT
CCTGGTAGCGGTCAGCAACGCCCAGACGACCACAGTCGATGAAGCCAGAGAAGCGGCCGT
TTTCAACCATGATGTTCGGCAGGCAAGCGTCGCCGTGGGTAACAACCAGGTCTTCGCCGT
CTGGCATACGAGCTTTCAGGCGAGCGAACAGTTCAGCCGGAGCCAGGCCCTGGTGTTCTT
CGTCCAGGTCGTCCTGGTCAACCAGGCCAGCTTCCATGCGGGTGCGAGCGCGTTCGATGC
GGTGTTTAGCCTGGTGGTCGAACGGACAAGTAGCCGGGTCCAGGGTGTGCAGGCGGCGCA
TAGCGTCAGCCATGATAGAAACTTTTTTCAGCCGGAGCCAGGTGAGAAGACAGCAGATCCT
GGCCCGGAACTTCGCCCAGCAGCAGCCAGTCGCGGCCAGCTTCGGTAACAACGTCCAGAA
CAGCAGCGCACGGAACGCCGGTGGTAGCCAGCCAAGACAGGCGAGCAGCTTCGTCTTGCA
GTTCGTTCAGAGCGCCAGACAGGTCGGTTTTAACGAACAGAACCGGGCGGCCCTGAGCAG
ACAGGCGGAAAACAGCAGCGTCAGAGCAGCCGATGGTTTGTTGTGCCCAGTCGTAACCAA
ACAGACGTTCAACCCAAGCAGCCGGAGAGCCAGCGTGCAGGCCGTCCTGTTCGATCATGG
TGGCCCCCCCCCCCCCGGAATAGCTCTGAGGCCGAGGCAGCTTCGGCCTCTGCATAAAT
AAAAAAAATTAGTCAGCCATGGGGCGGAGAATGGGCGGAACTGGGCGGAGTTAGGGGCGG
GATGGGCGGAGTTAGGGGCGGGACTATGGTTGCTGACTAATTGAGATGCTTGCTTTGCAT
ACTTCTGCCTGCTGGGGAGCCTGGGGACTTTCCACACCTGGTTGCTGACTAATTGAGATG
CTTGCTTTGCATACTTCTGCCTGCTGGGGAGCCTGGGGACTTTCCACACCCTAACCATGC
ATTCAACTATCCCAACGAGGGATTCGAAGGACGATACCTACGTTAGACTTAACTATAACG
GTCCTAAGGTAGCGACCACTTAGACGTGTTGAAACCCTAGGGCCGCACAGGCCCGCCGAC
GATCCGAGCGTGGCCATCGTGGCCCACCTAAGTGGTCCAGGAACGGCGTGGGCTCGTTTA
AACCGTACCATTAGGGAAAGTACCCACTTATGTGGGCGATCGCTTAATTAAGGCCGGCCG
CCGCAATAAAATATCTTTATTTTCATTACATCTGTGTGTTGGTTTTTTGTGTGAATCCAT
AGTACTAACATACGCTCTCCATCAAAACAAAACGAAACAAAACAAACTAGCAAAATAGGC
TGTCCCCAGTGCAAGTCCAGGTGCCAGAACATTTCTCTATCCATAATGCAGGGGTACCGG
GTGATGACGGTGAAAACCTCCAATTG[CGGAGTACTGTCCTCCGAGCGGAGTACTGTCCT
CCGAGCGGAGTACTGTCCTCCGAGCGGAGTACTGTCCTCCGAGCGGAGTACTGTCCTCCG
AGCGGAGTACTGTCCTCCGAGCGGAGAGTC]¹CCCGGGGACCTAGAGGGTATATAATGGG
TGCCTTAGCTGGTGTGTGACCTCATCTTCCTGTACGCCCTGCAGGGGCGCGCCACGCGT
CCGCGGGCTAGCGCCACC[ATGGAAGATGCCAAAAACATTAAGAAGGGCCCAGCGCCATT
CTACCCACTCGAAGACGGGACCGCTGGCGAGCAGCTGCACAAAGCCATGAAGCGCTACGC
CCTGGTGCCCGGCACCATCGCCTTTACCGACGCACATATCGAGGTGGACATTACCTACGC
CGAGTACTTCGAGATGAGCGTTCGGCTGGCAGAAGCTATGAAGCGCTATGGGCTGAATAC
```

---
[6x GalRE]¹

Fig. 2B

```
AAACCATCGGATCGTGGTGTGCAGCGAGAATAGCTTGCAGTTCTTCATGCCCGTGTTGGG
TGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCA
AAAGATCCTCAACGTGCAAAAGAAGCTACCGATCATACAAAAGATCATCATCATGGATAG
CAAGACCGACTACCAGGGCTTCCAAAGCATGTACACCTTCGTGACTTCCCATTTGCCACC
CGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCAC
CGCTTGTGTCCGATTCAGTCATGCCCGCGACCCCATCTTCGGCAACCAGATCATCCCCGA
CACCGCTATTCTCAGCGTGGTGCCATTTCACCACGGCTTCGGCATGTTCACCACGCTGGG
CTACTTGATCTGCGGCTTTCGGGTCGTGCTCATGTACCGCTTCGAGGAGGAGCTATTCTT
GCGCAGCTTGCAAGACTATAAGATTCAATCTGCCCTGCTGGTGCCCACACTATTTAGCTT
CTTCGCTAAGAGCACTCTCATCGACAAGTACGACCTAAGCAACTTGCACGAGATCGCCAG
CGGCGGAGCGCCTCTCAGCAAGGAGGTAGGTGAGGCCGTGGCCAAACGCTTCCACCTACC
AGGCATCCGCCAGGGCTACGGCCTGACAGAAACAACCAGCGCCATTCTGATCACCCCCGA
AGGGACGACAAGCCTGGCGCAGTAGGCAAGGTGGTGCCCTTCTTCGAGGCTAAGGTGGT
GGACTTGGACACAGGTAAGACCCTGGGTGTGAACCAGCGCGGCGAGCTGTGCGTCCGTGG
CCCCATGATCATGAGCGGCTACGTGAACAACCCCGAGGCTACAAACGCTCTCATCGACAA
GGACGGCTGGCTGCACAGCGGCGACATCGCCTACTGGGACGAGGACGAGCACTTCTTCAT
CGTGGACCGGCTCAAGAGCCTGATCAAATACAAGGGCTACCAGGTAGCCCCAGCCGAACT
GGAGAGCATCCTGCTGCAACACCCCAACATCTTCGACGCCGGGGTCGCTGGCCTGCCCGA
CGACGATGCTGGCGAGCTGCCCGCCGCAGTCGTCGTGCTGGAACACGGTAAAACCATGAC
CGAGAAGGAGATCGTGGACTATGTGGCCAGCCAGGTTACAACCGCCAAGAAGCTGCGCGG
TGGTGTTGTGTTCGTGGACGAGGTGCCTAAAGGACTGACCGGCAAGTTGGACGCCCGCAA
GATCCGCGAGATTCTCATTAAGGCCAAGAAGGGCGGCAAGATCGCCGTGTAA]²ATCGAT
TGCGCAAAGCTTTCGCGATAGGCGAGACCAATGGGTGTGTACGTAGCGGCCGCGTCGACT
GATGGGTGGCATCCCTGTGACCCCTCCCCAGTGCCTCTCCTGGCCCTGGAAGTTGCCACT
CCAGTGCCCACCAGCCTTGTCCTAATAAAATTAAGTTGCATCATTTTGTCTGACTAGGTG
TCCTTCTATAATATTATGGGGTGGAGGGGGTGGTATGCAGCAAGGGGCAAGTTGCGAAG
ACAACCTGTAGGGCCTGCGGGGTCTATTGGGAACCAAGCTGGAGTGCAGTGGCACAATCT
TGGCTCACTGCAATCTCCGCCTCCTGGGTTCAAGCGATTCTCCTGCCTCAGCCTCCCGAG
TTGTTGGGATTCCAGGCATGCATGACCAGGCTCAGCTAATTTTTGTTTTTTGGTAGAGA
CGGGGTTTCACCATATTGGCCAGGCTGGTCTCCAACTCCTAATCTCAGGTGATCTACCCA
CCTTGGCCTCCCAAATTGCTGGGATTACAGGCGTGAACCACTGCTCCCTTCCCTGTCCTT
CTGATTTTAAAATAACTATACCAGCAGGAGGACGTCCACACACAGCATAGGCTACCTGGC
CATGCCCAACCGGTGGGACATTTGAGTTGCTTGCTTGGCACTGTCCTCTCATGCGTTGGG
TCCACTCAGTAGATGCCTGTTGAATTATTTAAATCGGTCCGCGTACGGCTCTTCTCCCCC
TCGAGGGCCTCCGCGCCGGGTTTTGGCGCCTCCCGCGGGCGCCCCCTCCTCACGGCGAG
CGCTGCCACGTCAGACGAAGGGCGCAGCGAGCGTCCTGATCCTTCCGCCCGGACGCTCAG
GACAGCGGCCCGCTGCTCATAAGACTCGGCCTTAGAACCCAGTATCAGCAGAAGGACAT
TTTAGGACGGGACTTGGGTGACTCTAGGGCACTGGTTTCTTTCCAGAGAGCGGAACAGG
CGAGGAAAAGTAGTCCCTTCTCGGCCATTCTGCGGAGGCATCTCCGTGGGGCGGTCAACG
CCGATGATTATATAAGGACGCGCCGCGTGTGGCACAGCTAGTTCCGTCGCAGCCGGGATT
```

[fLuc]²

Fig. 2C

```
TGGGTCGCGGTTCTTGTTTGTGGATCGCTGTGATCGTCACTTGGTGAGTAGCGGGCTGCT
GGGCTGGGTACGTGCGCTCGGGGTTGGCGAGTGTGTTTTGTGAAGTTTTTTAGGCACCTT
TTGAAATGTAATCATTTGGGTCAATATGTAATTTTCAGTGTTAGACTAGTAAATTGTCCG
CTAAATTCTGGCCGTTTTTGGCTTTTTTGTTAGACGCCGCGGGGGGGGGGGGGGCTAG
CGCCACC[ATGGGCCCCAAGAAGAAAAGGAAGGTGGCCCCCCCCACCGACGTGAGCCTGG
GCGACGAGCTGCACCTGGACGGCGAGGACGTGGCCATGGCCCACGCCGACGCCCTGGACG
ACTTCGACCTGGACATGCTGGGCGACGGCGACAGCCCCGGCCCCGGCTTCACCCCCACG
ACAGCGCCCCTACGGCGCCCTGGACATGGCCGACTTCGAGTTCGAGCAGATGTTCACCG
ACGCCCTGGGCATCGACGAGTACGGCGGC]³GAATTC[GAGATGCCCGTGGACAGGATTC
TGGAGGCCGAACTCGCCGTGGAGCAGAAAAGCGACCAGGGCGTGGAGGGCCCCGGCGGAA
CCGGCGGCAGCGGCAGCAGCCCCAACGACCCCGTGACCAACATCTGCCAGGCCGCCGACA
AGCAGCTGTTCACCCTGGTGGAGTGGGCCAAGAGGATTCCCCACTTCAGCAGCCTGCCCC
TGGACGACCAGGTGATCCTGCTGAGGGCCGGATGGAACGAGCTGCTGATCGCCAGCTTCA
GCCACAGGAGCATCGACGTGAGGGACGGCATCCTGCTGGCCACCGGCCTGCACGTCCATA
GGAACAGCGCCCACAGCGCCGGAGTGGGCGCCATCTTCGACAGGGTGCTGACCGAGCTGG
TGAGCAAGATGAGGGACATGAGGATGGACAAGACCGAGCTGGGCTGCCTGAGGGCCATCA
TCCTGTTCAACCCCGAGGTGAGGGGCCTGAAAAGCGCCCAGGAGGTGGAGCTGCTGAGGG
AGAAGGTGTACGCCGCCCTGGAGGAGTACACCAGGACCACCCACCCCGACGAGCCCGGCA
GATTCGCCAAGCTGCTGCTGAGGCTGCCCAGCCTGAGGAGCATCGGCCTGAAGTGCCTGG
AGCACCTGTTCTTCTTCAGGCTGATCGGCGACGTGCCCATCGACACCTTCCTGATGGAGA
TGCTGGAGAGCCCCAGCGACAGCTGA]⁴ GCATGCCCCCTCTCCCTCCCCCCCCCTAAC
GTTACTGGCCGAAGCCGCTTGGAATAAGGCCGGTGTGCGTTTGTCTATATGTTATTTTCC
ACCATATTGCCGTCTTTTGGCAATGTGAGGGCCCGGAAACCTGGCCCTGTCTTCTTGACG
AGCATTCCTAGGGGTCTTTCCCCTCTCGCCAAAGGAATGCAAGGTCTGTTGAATGTCGTG
AAGGAAGCAGTTCCTCTGGAAGCTTCTTGAAGACAAACAACGTCTGTAGCGACCCTTTGC
AGGCAGCGGAACCCCCCACCTGGCGACAGGTGCCTCTGCGGCCAAAAGCCACGTGTATAA
GATACACCTGCAAAGGCGGCACAACCCCAGTGCCACGTTGTGAGTTGGATAGTTGTGGAA
AGAGTCAAATGGCTCTCCTCAAGCGTATTCAACAAGGGGCTGAAGGATGCCCAGAAGGTA
CCCCATTGTATGGGATCTGATCTGGGGCCTCGGTGCACATGCTTTACATGTGTTTAGTCG
AGGTTAAAAAACGTCTAGGCCCCCCGAACCACGGGGACGTGGTTTTCCTTTGAAAAACAC
GATCCATATGGCCACC[ATGAAGCTGCTGAGCAGCATCGAGCAGGCTTGCGACATCTGCA
GGCTGAAGAAGCTGAAGTGCAGCAAGGAGAAGCCCAAGTGCGCCAAGTGCCTGAAGAACA
ACTGGGAGTGCAGATACAGCCCCAAGACCAAGAGGAGCCCCCTGACCAGGGCCCACCTGA
CCGAGGTGGAGAGCAGGCTGGAGAGGCTGGAGCAGCTGTTCCTGCTGATCTTCCCCAGGG
AGGACCTGGACATGATCCTGAAGATGGACAGCCTGCAAGACATCAAGGCCCTGCTGACCG
GCCTGTTCGTGCAGGACAACGTGAACAAGGACGCCGTGACCGACAGGCTGGCCAGCGTGG
AGACCGACATGCCCCTGACCCTGAGGCAGCACAGGATCAGCGCCACCAGCAGCAGCGAGG
AGAGCAGCAACAAGGGCCAGAGGCAGCTGACCGTGAGCCCCGAGTTT]⁵ CCCGGG[ATCA
GGCCCGAGTGCGTGGTGCCCGAGACCCAGTGCGCCATGAAAAGGAAGGAGAAGAAGGCCC
AGAAGGAGAAGGACAAGCTGCCCGTGAGCACCACCACCGTCGATGACCACATGCCCCCA
```

[VP16]³

[RXR]⁴

[Gal4DBD]⁵

Fig. 2D

```
TCATGCAGTGCGAGCCCCCCCCCCCGAGGCCGCCAGGATTCACGAGGTCGTGCCCAGGT
TCCTGAGCGACAAGCTGCTGGTGACCAACAGGCAGAAGAACATCCCCCAGCTGACCGCCA
ACCAGCAGTTCCTGATCGCCAGGCTGATCTGGTATCAGGACGGCTACGAGCAGCCCAGCG
ACGAGGACCTGAAAAGGATCACCCAGACCTGGCAGCAGGCCGACGACGAGAACGAGGAGA
GCGACACCCCCTTCAGGCAGATCACCGAGATGACCATCCTGACCGTGCAGCTGATCGTGG
AGTTCGCCAAGGGCCTGCCCGGATTCGCCAAGATCAGCCAGCCCGACCAGATCACCCTGC
TGAAGGCTTGCAGCAGCGAGGTGATGATGCTGAGGGTGGCCAGGAGGTACGACGCCGCCA
GCGACAGCATCCTGTTCGCCAACAACCAGGCTTACACCAGGGACAACTACAGGAAGGCTG
GCATGGCCGAGGTGATCGAGGACCTCCTGCACTTCTGCAGATGTATGTACAGCATGGCCC
TGGACAACATCCACTACGCCCTGCTGACCGCCGTGGTGATCTTCAGCGACAGGCCCGGCC
TGGAGCAGCCCCAGCTGGTGGAGGAGATCCAGAGGTACTACCTGAACACCCTGAGGATCT
ACATCCTGAACCAGCTGAGCGGCAGCGCCAGGAGCAGCGTGATCTACGGCAAGATCCTGA
GCATCCTGAGCGAGCTGAGGACCCTGGGAATGCAGAACAGCAATATGTGTATCAGCCTGA
AGCTGAAGAACAGGAAGCTGCCCCCCTTCCTGGAGGAGATTTGGGACGTGGCCGACATGA
GCCACACCCAGCCCCCCCCCATCCTGGAGAGCCCCACCAACCTGTGA]⁶ ATCGATTAGAC
ATGATAAGATACATTGATGAGTTTGGACAAACCACAACTAGAATGCAGTGAAAAAAATGC
TTAATTTGTGAAATTTGTGATGCTATTGCTTAATTTGTAACCATTATAAGCTGCAATAAA
CAAGTTAATAAAACATTTGCATTCATTTTATGTTTCAGGTTCAGGGGGAGATGTGGGAGG
TTTTTTAAAGCAAGTAAAACCTCTACAAATGTGGTATCTAGAGCTCTTCCAAAATTAATA
CGCATTCGCGTGCGAAATCATTACCCTGTTATCCCTACGCCTAGCCTTAGGGTTCACATC
TATGTCGGGTGCGGAGAAAGAGGTAATGAAATGGCAATAACAGGCTAGAACCAGCTAACG
TTAGGAGCATAGATTGGGGCATTCCGGAACTATAAATTGCGTTGCGCTCACTGCCCGCTT
TCCAGTCGGGAAACCTGTCGTGCCAGCTGCATAAATGAATCGGCCAACGCGCGGGGAGAG
GCGGTTTGCGTATTGGGCGCGCTTCCGCTTCCTCGCTCACTGACTCGCTGCGCTCGGTCG
TTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCTGACGAGCATCACAAAA
ATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGT
CCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAAA
ACTCACGTTAAGGGATTTTGGTCATGAGATTATCAAAAGGATCTTCACCTAGATCCTTT
TAAATTAAAAATGAAGTTTTAAATCAATCTAAAGTATATATGAGTAAACTTGGTCTGACA
TGCGCAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAG
```

[EcR VY]⁶

Fig. 2E

CAATAAACCAGCCAGCCGGAAGCGCCGAGCGCAGAAGTGGTCCTGCAACTTTATCCGCCT
CCATCCAGTCTATTAACTGTTGCCGGGAAGCTAGAGTAAGTAGTTCGCCAGTTAATAGTT
TGCGGAGCGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCA
AAAAAGCGGTTAGCTCCTTCGGTCCTCCGATGGTTGTCAGAAGTAAGTTGGCCGCAGTGT
TATCACTCATGGTTATGGCAGCACTGCATAATTCTCTTACTGTCATGCCATCCGTAAGAT
GCTTTTCTGTGACTGGTGAGTATTCAACCAAGTCATTCTGAGAATAGTGTATGCGGCGAC
CGAGTTGCTCTTGCCCGGCGTCAATACGGGATAATACCGCGCCACATAGCAGAACTTTAA
AAGTGCTCATCATTGGGAAGCGTTCTTCGGGGCGAAAACTCTCAAGGATCTTACCGCTGT
TGAGATCCAGTTCGATGTAACCCACACGAGCACCCAACTGATCTTCAGCATCTTTTACTT
TCACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCATTT
ATCAGGGTTATTGTCTCATGAGCGGATACATATTTGAATGTATTTAGAAAAAATAAACAAA
TAGGGGTTCCGCGCACATTTCCCCGAAAAGTGCCACCTGAGGTCTAAGAAACCATTATTA
TCATGACATTAACCTATAAAAATAGGCGTATCACGAGGCCCTTTCTTCTCGCGCGTTTCG
GTGATGACGGTGAAAACCTCTGACACATGCAGCTCCCGGATACGGTCACAGCTTGTCTGT
AAGCGGATGCCGGGAGCAGACAAGCCCGTCAGGGCGCGTCAGCGGGTGTTGGCGGGTGTC
GGGGCTGGCTTAA   (SEQ ID NO: 1)

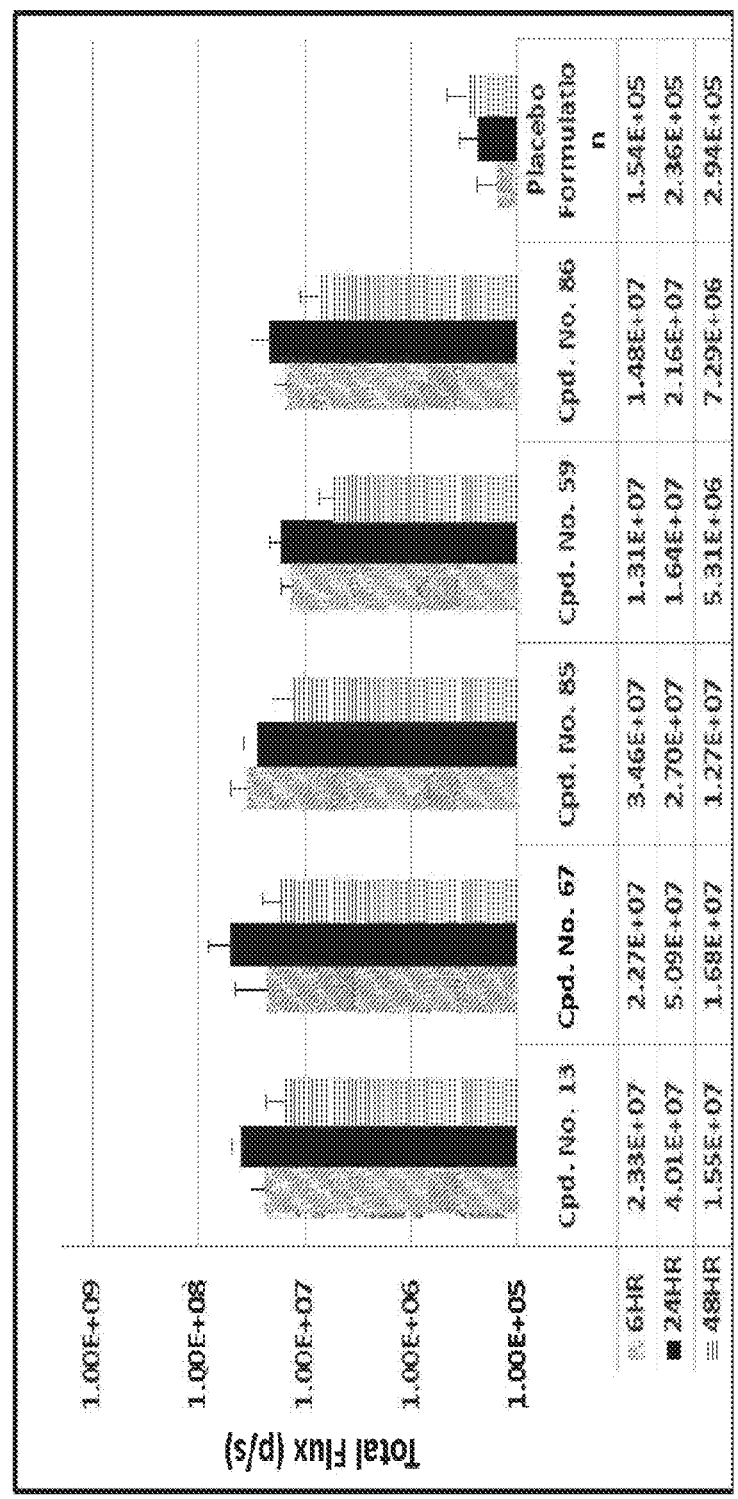

BORON-CONTAINING DIACYLHYDRAZINES

BACKGROUND OF THE INVENTION

Field of the Invention

This invention is in the fields of biotechnology, genetic engineering, gene expression, and medicinal chemistry. The invention provides novel boron-containing diacylhydrazines and the use of these compounds in nuclear receptor-based inducible gene expression systems.

Background

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., *Proc. Natl. Acad. Sci. USA* 83:5414-5418 (1986); Ambheiter et al., *Cell* 62:51-61 (1990); Filmus et al., *Nucleic Acids Research* 20:27550-27560 (1992)). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FKS06-cyclosporine (FKCsA) can then be used to induce dimerization of these molecules (Spencer et al., *Science* 262.1019-24 (1993); Belshaw et al., *Proc Natl Acad Sci USA* 93:4604-7 (1996)). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla et al., *Annu. Rev. Entomnol.* 43: 545-569 (1998)). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al., *Cell*, 67:59-77 (1991)). EcR receptors are responsive to a number of steroidal compounds such as ponasterone A and muristerone A Non-steroidal compounds with ecdysteroid agonist activity have been described, including the commercially available insecticides tebufenozide and methoxyfenozide that are marketed by Rohm and Haas Company (see WO 96/27673 and U.S. Pat. No. 5,530,028). Both analogs have exceptional safety profiles in other organisms.

The insect ecdysone receptor (EcR) heterodimerizes with Ultraspiracle (USP), the insect homologue of the mammalian retinoid X receptor (RXR), and binds ecdysteroids and ecdysone receptor response elements to activate transcription of ecdysone responsive genes. The EcR/USP/ligand complexes play important roles during insect development and reproduction. The EcR has five modular domains, A/B (transactivation), C (DNA binding, heterodimerization), D (Hinge, heterodimerization), E (ligand binding, heterodimerization and transactivation) and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of an EcR-based gene switch used *Drosophila melanogaster* EcR (DmEcR) and *Mus musculus* RXR (MmRXR) and showed that these receptors in the presence of steroid, ponasterone A, transactivate reporter genes in mammalian cell lines and transgenic mice (Christopherson et al., *Proc. Natl. Acad Sci. U.S.A.* 89:6314-6318 (1992), No et al., *Proc. Natl. Acad. Sci. U.S.A.* 93:3346-3351 (1996)). Later. Suhr et al., *Proc. Natl. Acad Sci.* 95-7999-8004 (1998) showed that non-steroidal ecdysone agonist, tebufenozide, induced high level of transactivation of reporter genes in mammalian cells through *Bombyx mori* EcR (BmEcR) in the absence of exogenous heterodimer partner.

WO 97/38117 and WO99/58155 disclose methods for modulating the expression of an exogenous gene in which a DNA construct comprising the exogenous gene and an ecdysone response element is activated by a second DNA construct comprising an ecdysone receptor that, in the presence of a ligand therefore, and optionally in the presence of a receptor capable of acting as a silent partner, binds to the ecdysone response element to induce gene expression. The ecdysone receptor of choice was isolated from *Drosophila melanogaster* Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. WO 99/02683 discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila* melanogasier ultraspiracle receptor (USP) or fragments thereof comprising at least the dimerization domain of USP for use in a gene expression system. U.S. Pat. No. 5,880,333 discloses a *Drosophila melwogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in WO 99/02683 or as modified EcR as in WO 97/38117) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880,333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and, at the same time, is insensitive to the natural steroids. Thus, improved systems that are simple, compact, and dependent on ligands that are relatively inexpensive, readily available, and of low toxicity to the host would prove useful for regulating biological systems.

It has been shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (see WO 01/70816 A1). This two-hybrid system is a significantly improved inducible gene expression modulation system compared to the two systems disclosed in applications WO 97/38117 and WO 99/02683. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. Furthermore, the two-hybrid system avoids some side effects due to overexpression of RXR that often occur when unmodified RXR is used as a heterodimer receptor partner. In one two-hybrid system, native DNA binding and transactivation domains of EcR or RXR are eliminated and as a result, these hybrid molecules have less chance of interacting with other steroid hormone receptors present in the cell resulting in reduced side effects. Additional gene switch systems include those described in the following patents and patent applications: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. Nos. 7,304,162; and 7,304,161.

With the improvement in ecdysone receptor-based gene regulation systems, there has been an increase in their use for various applications. Diacylhydrazine ("DAH") compounds, and their application as ligands in ecdysone receptor-based gene regulation systems are disclosed U.S. Pat. Nos. 8,076,517; 7,456,315; 7,304,161; and 6,258,603, and patents cited therein. However, a need exists for DAHs with improved physiochemical and/or pharmacological properties.

BRIEF SUMMARY OF THE FIGURES

FIGS. 2A-2E set forth the nucleic acid sequence (SEQ ID NO: 1) for the vector map of FIG. 1. The nucleic acid sequence set forth in brackets represent the following vector sequence components: [6×GalRE][1], [fLuc][2], [VP16][3], [RXR][4], [Gal4DBD][5] and [EcR VY][6].

FIG. 3 is a bar graph showing the expression of luciferase in mouse grastroc muscle by injection of Ad-RTS-tLUC via IM on the right and left gastroc muscle and oral administration of Cpd. Nos 13, 59, 67, 85, and 86 at 100 mg/kg body weight.

BRIEF SUMMARY OF THE INVENTION

Figure 1:
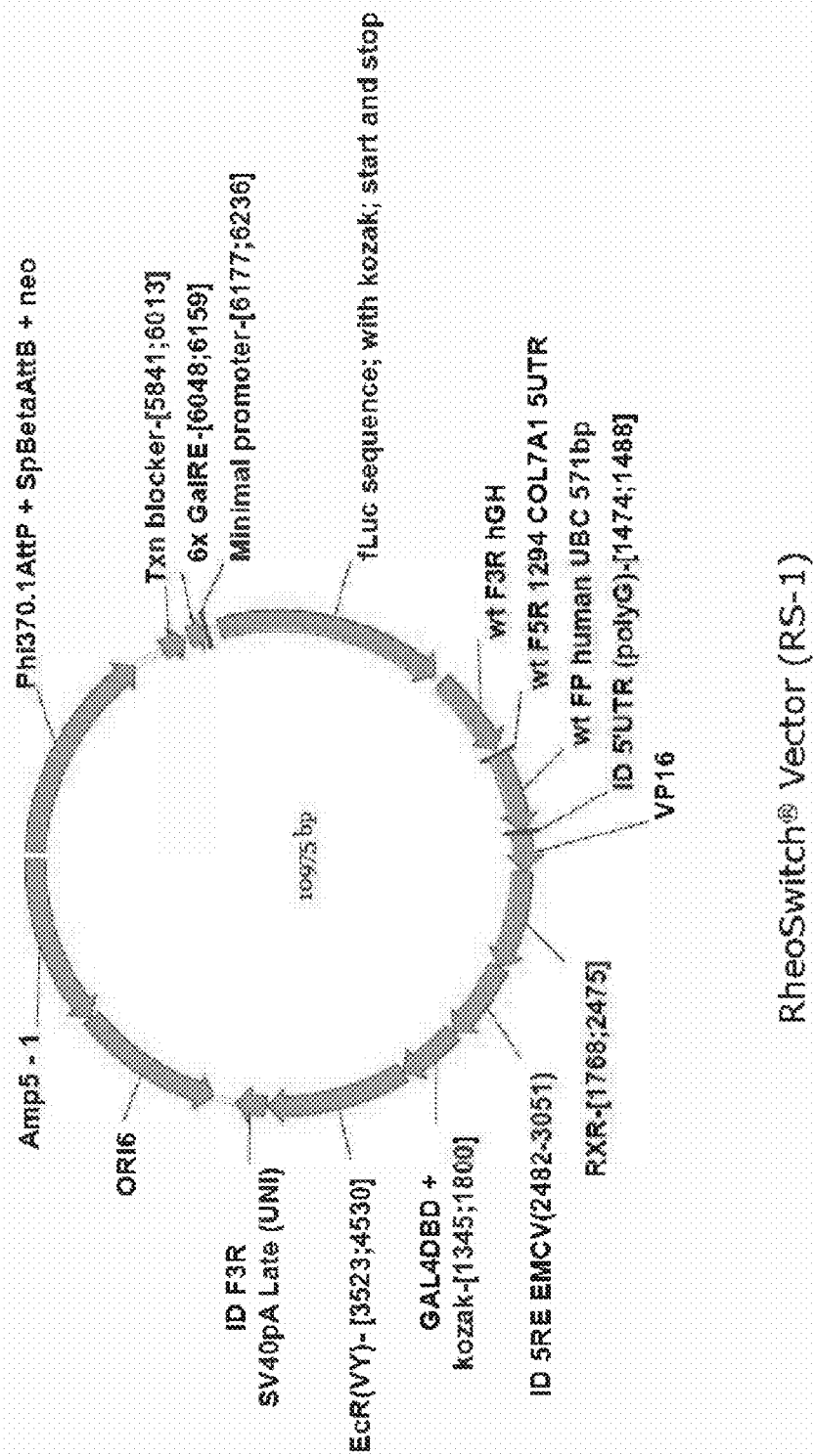
FIG. 1 is a vector map for the RheoSwitch® Vector (RS-1).

In one aspect, the present disclosure provides boron-containing diacylhydrazine compounds represented by Formulae I-XI, I-A, II-A, X-A, or XI-A, below, and the pharmaceutically acceptable salts and solvates thereof, collectively referred to herein as "Compounds of the Disclosure." Compounds of the Disclosure contain at least one boron atom in their structure.

In another aspect, the present disclosure provides compositions comprising a Compound of the Disclosure and one or more excipients. In a further aspect, the composition is a pharmaceutically acceptable composition.

In another aspect, the present disclosure provides Compounds of the Disclosure for use as ligands in ecdysone receptor-based inducible gene expression systems. An advantage of the present disclosure is that it provides a means to regulate gene expression and to tailor expression levels to suit the user's requirements.

In another aspect, the present disclosure provides methods of regulating gene expression of a gene of interest in an isolated host cell, comprising contacting the host cell with a Compound of the Disclosure, or composition thereof.

In another aspect, the present disclosure provides methods of regulating gene expression of a gene of interest in a non-human organism, comprising contacting the non-human organism with a Compound of the Disclosure, or composition thereof.

In another aspect, the present disclosure provides methods of treating a disease, disorder, injury, or condition in a subject, comprising administering to the subject a Compound of the Disclosure, or composition thereof.

In another aspect, the present disclosure provides a Compound of the Disclosure, or composition thereof, for use in treating a disease, disorder, injury, or condition.

In another aspect, the present disclosure provides a Compound of the Disclosure, or composition thereof, for use in the manufacture of a medicament for treating a disease, disorder, injury, or condition.

In another aspect, the present disclosure provides a method of controlling insects, comprising contacting said insects or their habitat with an insecticidally effective amount of a Compound of the Disclosure, or composition thereof.

DETAILED DESCRIPTION OF THE INVENTION

In one embodiment, Compounds of the Disclosure are compounds having Formula I:

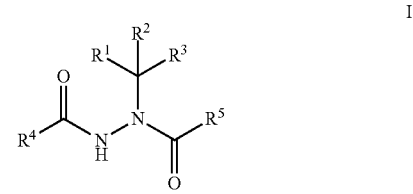

wherein:

$R^1$ and $R^2$ are each independently selected from the group consisting of hydrogen, optionally substituted alkyl, and haloalkyl; or $R^1$ and $R^2$ taken together with the carbon atom to which they are attached form a 4- to 8-membered cycloalkyl;

$R^3$ is selected from the group consisting of hydrogen, optionally substituted alkyl, haloalkyl, optionally substituted cycloalkyl, optionally substituted alkenyl, optionally substituted aryl, and optionally substituted heteroaryl;

$R^4$ is selected from the group consisting of:

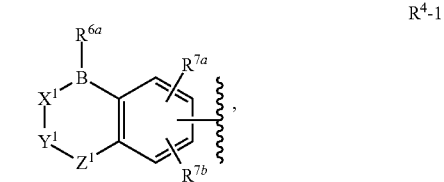

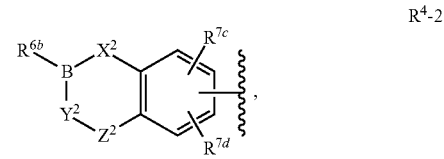

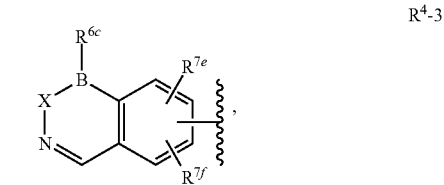

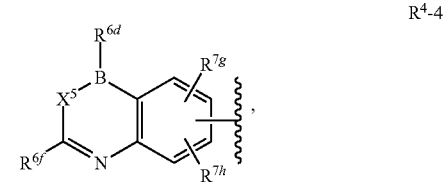

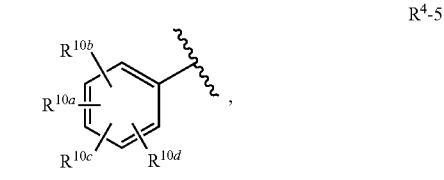

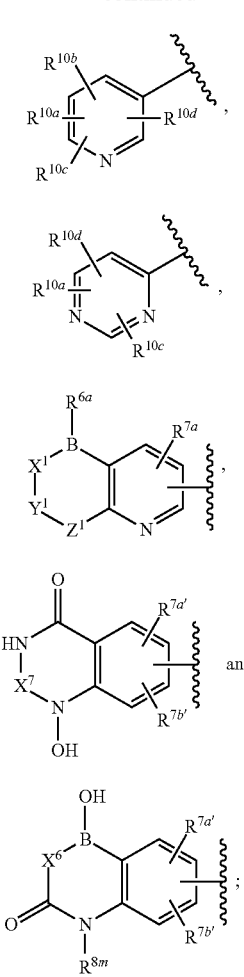

$X^1$ is selected from the group consisting of —O— and —N($R^{8a}$)—;

$Y^1$ is —($CR^{9a}R^{9b}$)$_m$—;

$Z^1$ is selected from the group consisting of —O— and —N($R^{8b}$)—, or Z is absent;

$R^{6a}$ is selected from the group consisting of hydroxy, alkyl, and alkoxy; or $R^{6a}$ forms a hydroxy acid adduct or an amino acid adduct;

$R^{7a}$ and $R^{7b}$ are each independently selected from the group consisting of hydrogen, halo, nitro, cyano, hydroxy, amino, optionally substituted alkyl, haloalkyl, hydroxyalkyl, alkoxy, and alkylthio:

$R^{7a'}$ and $R^{7b'}$ are each independently selected from the group consisting of hydrogen, halo, nitro, cyano, hydroxy, amino, optionally substituted alkyl, haloalkyl, hydroxyalkyl, alkoxy, and alkylthio:

$R^{8a}$ and $R^{8b}$ are each independently selected from the group consisting of hydrogen and alkyl;

$R^{9a}$ and $R^{9b}$ are each independently selected from the group consisting of hydrogen and alkyl;

m is 1, 2, 3, or 4;

$X^2$ is selected from the group consisting of —O— and —N($R^{8c}$)—;

$Y^2$ is —($CR^{9c}R^{9d}$)$_n$—;

$Z^2$ is selected from the group consisting of —O— and —N($R^{8d}$)—, or Z is absent;

$R^{6b}$ is selected from the group consisting of hydroxy, alkyl, and alkoxy; or $R^{6b}$ forms a hydroxy acid adduct or an amino acid adduct;

$R^{7c}$ and $R^{7d}$ are each independently selected from the group consisting of hydrogen, halo, nitro, cyano, hydroxy, amino, optionally substituted alkyl, haloalkyl, hydroxyalkyl, alkoxy, and alkylthio;

$R^{8c}$ and $R^{8d}$ are each independently selected from the group consisting of hydrogen and alkyl;

$R^{9}$ and $R^{9d}$ are each independently selected from the group consisting of hydrogen and alkyl;

n is 1, 2, 3, or 4;

X is selected from the group consisting of —O— and —N($R^{8e}$)—;

$R^{6c}$ is selected from the group consisting of hydroxy, alkyl, and alkoxy; or $R^{6c}$ forms a hydroxy acid adduct or an amino acid adduct;

$R^{7e}$ and $R^{7f}$ are each independently selected from the group consisting of hydrogen, halo, nitro, cyano, hydroxy, amino, optionally substituted alkyl, haloalkyl, hydroxyalkyl, alkoxy, and alkylthio;

$R^{8e}$ is selected from the group consisting of hydrogen and alkyl;

$R^{6d}$ is selected from the group consisting of hydroxy, alkyl, and alkoxy; or $R^{6d}$ forms a hydroxy acid adduct or an amino acid adduct;

$R^{6f}$ is selected from the group consisting of hydrogen, alkyl, amino, and hydroxy;

$X^5$ is selected from the group consisting of —O— and —N($R^{8k}$)—;

$R^{7g}$ and $R^{7h}$ are each independently selected from the group consisting of hydrogen, halo, nitro, cyano, hydroxy, amino, optionally substituted alkyl, haloalkyl, hydroxyalkyl, alkoxy, and alkylthio;

$R^{8k}$ is selected from the group consisting of hydrogen and alkyl;

$X^6$ is selected from the group consisting of —O— and —N($R^{8l}$)—;

$X^7$ is selected from the group consisting of —O— and —N($R^{8n}$)—;

$R^{8l}$ is selected from the group consisting of hydrogen and alkyl;

$R^{8m}$ is selected from the group consisting of hydrogen and alkyl;

$R^{8n}$ is selected from the group consisting of hydrogen and alkyl;

$R^{10a}$ is selected from the group consisting of hydrogen and —($CR^{11a}R^{11b}$)$_o$—B($R^{12a}$)($R^{12b}$); and $R^{10b}$, $R^{10c}$, and $R^{10d}$ are each independently selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —$COR^{16}$, —$SO_2R^{17}$, —N($R^{18}$)$COR^{19}$, —N($R^{18}$)$SO_2R^{20}$ or N($R^{18}$)C=N($R^{21}$)-amino; or $R^{10b}$ is selected from the group consisting of hydrogen, halo, nitro, cyano, hydroxy, —N(H)CHO, —N(H)CN, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{16}$, —SO$_2$R$^{17}$, —N(R$^{18}$)COR$^{19}$, —N(R$^{18}$)SO$_2$R$^{20}$ or N(R$^{18}$)C=N(R$^{21}$)-amino, and/or R$^{10c}$ and R$^{10d}$ taken together with two adjacent carbon atoms form a fused optionally substituted cycloalkyl, optionally substituted heterocyclo, or optionally substituted heteroaryl group, e.g., R$^4$-5 is:

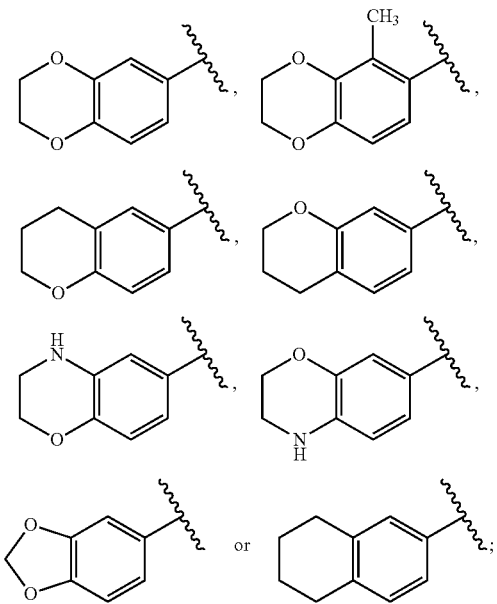

e.g., R$^4$-6 is:

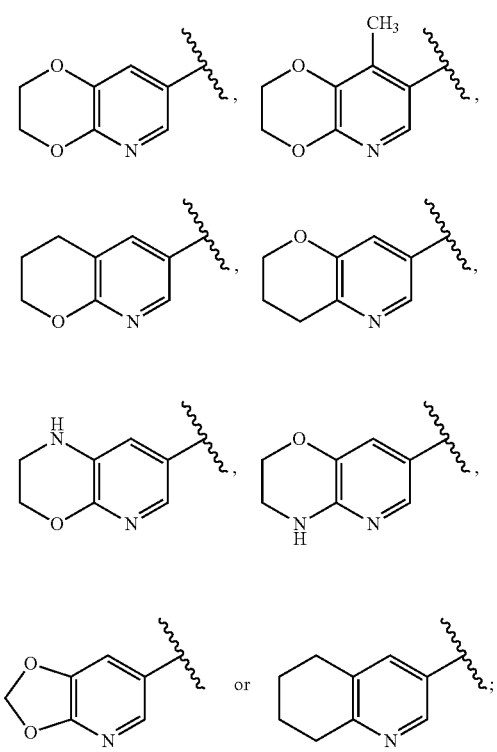

e.g., R$^4$-7 is:

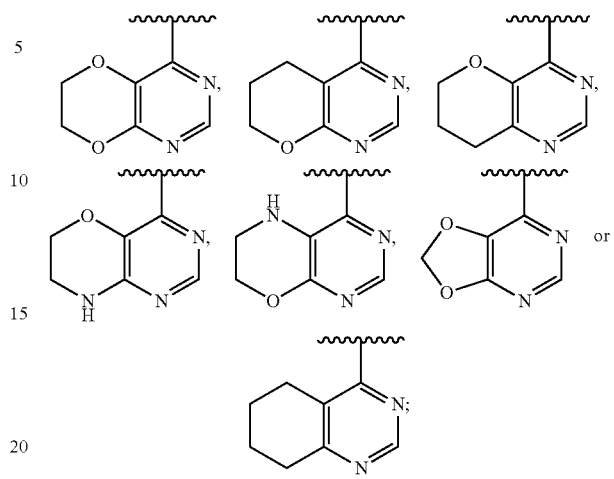

R$^{11a}$ and R$^{11b}$ are each independently selected from the group consisting of hydrogen and alkyl;

R$^{12a}$ and R$^{12b}$ are selected from the group consisting of hydroxy and alkoxy; or R$^{12a}$ and R$^{12b}$ taken together form a linkage —O(CR$^{13a}$R$^{13b}$)$_p$O—; or —B(R$^{12a}$)(R$^{12b}$) forms a fluoride adduct;

R$^{13a}$ and R$^{13b}$ are each independently selected from the group consisting of hydrogen and C$_{1-4}$ alkyl:

o is 0, 1, 2, 3, 4, or 5;

p is 2, 3, or 4:

R$^5$ is R$^4$-3, R$^4$-4, R$^4$-8, R$^4$-9, or R$^4$-10; or R$^5$ is selected from the group consisting of

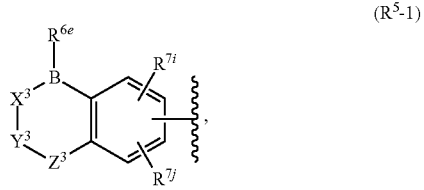 (R$^5$-1)

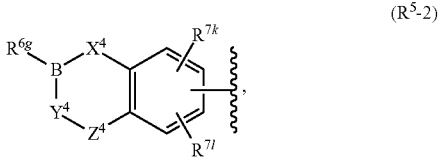 (R$^5$-2)

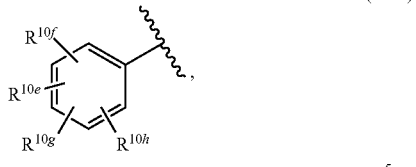 (R$^5$-3)

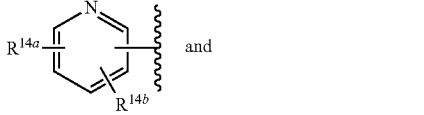 (R$^5$-4)

and

-continued

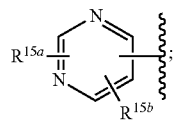

X³ is selected from the group consisting of —O— and —N(R⁸ᶠ)—;
Y is —(CR⁹ᵉR⁹ᶠ)_q—;
Z³ is selected from the group consisting of —O— and —N(R⁸ᵍ)—, or Z³ is absent;
R⁶ᵉ is selected from the group consisting of hydroxy and alkyl; or
R⁶ᵉ forms a hydroxy acid adduct or an amino acid adduct;
R⁷ⁱ and R⁷ʲ are each independently selected from the group consisting of hydrogen, halo, nitro, cyano, hydroxy, amino, optionally substituted alkyl, haloalkyl, hydroxyalkyl, alkoxy, and alkylthio;
R⁸ᶠ and R⁸ᵍ are each independently selected from the group consisting of hydrogen and alkyl;
R⁹ᶜ and R⁹ᶠ are each independently selected from the group consisting of hydrogen and alkyl;
q is 1, 2, 3, or 4;
X⁴ is selected from the group consisting of —O— and —N(R⁸ʰ)—;
Y⁴ is —(CR⁹ᵍR⁹ʰ)_r—;
Z⁴ is selected from the group consisting of —O— and —N(R⁸ⁱ)—, or Z⁴ is absent;
R⁶ᵍ is selected from the group consisting of hydroxy and alkyl; or
R⁶ᵍ forms a hydroxy acid adduct or an amino acid adduct
R⁷ᵏ and R⁷ˡ are each independently selected from the group consisting of hydrogen, halo, nitro, cyano, hydroxy, amino, optionally substituted alkyl, haloalkyl, hydroxyalkyl, alkoxy, and alkylthio;
R⁸ʰ and R⁸ⁱ are each independently selected from the group consisting of hydrogen and alkyl:
R⁹ᵍ and R⁹ʰ are each independently selected from the group consisting of hydrogen and alkyl;
r is 1, 2, 3, or 4;
R¹⁰ᵉ is selected from the group consisting of hydrogen and —(CR¹¹ᶜR¹¹ᵈ)_s—B(R¹²ᶜ)(R¹²ᵈ); and
R¹⁰ᶠ, R¹⁰ᵍ, and R¹⁰ʰ are independently selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR¹⁶, —SO₂R¹⁷, —N(R¹⁸)COR¹⁹, —N(R¹⁸)SO₂R²⁰ or N(R¹⁸)C=N(R²¹)-amino; or
R¹⁰ᶠ is selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR¹⁶, —SO₂R¹⁷, —N(R¹⁸)COR¹⁹, —N(R¹⁸)SO₂R²⁰ or N(R¹⁸)C=N(R²¹)-amino; and
R¹⁰ᵍ and R¹⁰ʰ taken together with two adjacent carbon atoms form a fused optionally substituted cycloalkyl, optionally substituted heterocyclo, or optionally substituted heteroaryl group; e.g., R³-3 is:

R¹¹ᶜ and R¹¹ᵈ are each independently selected from the group consisting of hydrogen and alkyl;
R¹²ᶜ and R¹²ᵈ are selected from the group consisting of hydroxy and alkoxy; or
R¹²ᶜ and R¹²ᵈ taken together form a linkage —O(CR¹³ᶜR¹³ᵈ)_t—O—; or
—B(R¹²ᶜ)(R¹²ᵈ) forms a fluoride adduct;
R¹³ᶜ and R¹³ᵈ are each independently selected from the group consisting of hydrogen and C₁₋₄ alkyl;
s is 0, 1, 2, 3, 4, or 5;
t is 2, 3, or 4;
R¹⁴ᵃ and R¹⁴ᵇ are each independently selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR¹⁶, —SO₂R¹⁷, —N(R¹⁸)COR¹⁹, —N(R¹⁸)SO₂R²⁰ or N(R¹⁸)C=N(R²¹)-amino;
R¹⁵ᵃ and R¹⁵ᵇ are each independently selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR¹⁶, —SO₂R¹⁷, N(R¹⁸)COR¹⁹—N(R¹⁸)SO₂R²⁰ or N(R¹⁸)C=N(R²¹)-amino;
R¹⁶ is selected from the group consisting of hydrogen, hydroxy, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, and arylalkyloxy;
R¹⁷ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

$R^{18}$ is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

$R^{19}$ is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, arylalkyloxy, and amino;

$R^{20}$ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, and amino;

$R^{21}$ is selected from the group consisting of hydrogen, alkyl, aryl, cyano, and nitro;

with the provisos:

a) when $R^4$ is $R^4$-5, $R^4$-6, or $R^4$-7 and $R^5$ is $R^5$-3, then one of $R^{10a}$ or $R^{10c}$ is not hydrogen; or b) when $R^4$ is $R^4$-5, $R^4$-6, or $R^4$-7 and $R^5$ is $R^5$-4 or $R^5$-5, then $R^{10a}$ is not hydrogen, and the pharmaceutically acceptable salts and solvates thereof.

In another embodiment, Compounds of the Disclosure are compounds having Formula I-A:

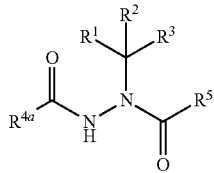

I-A and the pharmaceutically acceptable salts and solvates thereof, wherein:

$R^1$, $R^2$, $R^3$, and $R^5$ are as defined in connection with Formula I, and $R^{4a}$ is selected from the group consisting of $R^4$-1, $R^4$-2, $R^4$-3, $R^4$-4, $R^4$-8, $R^4$-9, $R^4$-10,

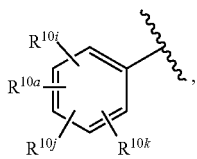

$R^4$-11

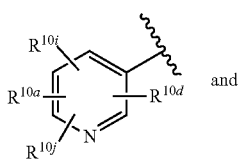

$R^4$-12
and

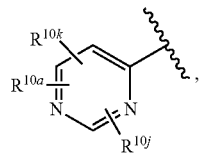

$R^4$-13 wherein:

$R^4$-1, $R^4$-2, $R^4$-3, $R^4$-4, $R^4$-8, $R^4$-9, $R^4$-10, and $R^{10a}$ are as defined in connection with Formula I; and $R^{10i}$, $R^{10j}$, and $R^{10k}$ are each independently selected from the group consisting of hydrogen, halo, nitro, cyano, hydroxy, amino, —N(H)CHO, —N(H)CN, optionally substituted alkyl, haloalkyl, alkoxyalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{16}$, —SO$_2$R$^{17}$, —N(R$^{18}$)COR$^{19}$, —N(R$^{18}$)SO$_2$R$^{20}$ or N(R$^{18}$)C=N(R$^{21}$)-amino; or $R^{10i}$ is selected from the group consisting of hydrogen, halo, nitro, cyano, hydroxy, —N(H)CHO, —N(H)CN, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{16}$, —SO$_2$R$^{17}$, —N(R$^{18}$)COR$^{19}$, —N(R$^{18}$)SO$_2$R$^{20}$ or N(R$^{18}$)C=N(R$^{21}$)-amino; and/or $R^{10j}$ and $R^{10k}$ taken together with two adjacent carbon atoms form a fused optionally substituted cycloalkyl, optionally substituted heterocyclo, or optionally substituted heteroaryl group.

In another embodiment, Compounds of the Disclosure are compounds having Formula I, and the pharmaceutically acceptable salts and solvates thereof, wherein $R^5$ is selected from the group consisting of $R^5$-1, $R^5$-2, $R^5$-3, $R^5$-4, and $R^5$-5; and $R^1$, $R^2$, $R^3$, and $R^4$ are as defined in connection with Formula I.

In another embodiment, Compounds of the Disclosure are compounds having Formula I-A, and the pharmaceutically acceptable salts and solvates thereof, wherein $R^{4a}$ is selected from the group consisting of $R^4$-11, $R^4$-12, and $R^4$-13, and $R^1$, $R^2$, $R^3$, and $R^5$ are as defined in connection with Formula I.

In another embodiment, Compounds of the Disclosure are compounds having Formula I-A, and the pharmaceutically acceptable salts and solvates thereof, wherein $R^{4a}$ is selected from the group consisting of $R^4$-11, $R^4$-12, and $R^4$-13, $R^5$ is selected from the group consisting of $R^5$-3, $R^5$-4, and $R^5$-5; $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-1; $R^5$ is selected from the group consisting of $R^3$-3, $R^5$-4, and $R^5$-5; $R^{10e}$ is hydrogen; and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-2; $R^5$ is selected from the group consisting of $R^5$-3, $R^5$-4, and $R^5$-5; $R^{10e}$ is hydrogen; and $R^1$, $R^2$, and $R^3$ are as defined in connection with Formula I.

In another embodiment, Compounds of the Disclosure are compounds having Formula I. and the pharmaceutically acceptable salts and solvates thereof, wherein $R^4$ is $R^4$-3; $R^5$ is selected from the group consisting of $R^5$-3, $R^5$-4, and $R^5$-5; $R^{10e}$ is hydrogen; and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-4; $R^5$ is selected from the group consisting of $R^5$-3, $R^5$-4, and $R^5$-5; $R^{10e}$ is hydrogen; and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-5; $R^5$ is selected from the group consisting of $R^5$-3, $R^5$-4, and $R^5$-5; $R^{10e}$ is $-(CR^{11a}R^{11b})_o-B(R^{12a})(R^{12b})$; and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-5; $R^5$ is $R^5$-3; $R^{10e}$ is $-(CR^{11c}R^{11d})_s-B(R^{12c})(R^{12d})$; and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-6; $R^5$ is selected from the group consisting of $R^5$-3, $R^5$-4, and $R^5$-5; $R^{10a}$ is $-(CR^{11a}R^{11b})_o-B(R^{12a})(R^{12b})$; and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-7. $R^5$ is selected from the group consisting of $R^5$-3, $R^5$-4, and $R^5$-5; $R^{10a}$ is $-(CR^{11a}R^{11b})_o-B(R^{12a})(R^{12b})$, and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-8; $R^5$ is selected from the group consisting of $R^5$-3, $R^5$-4, and $R^5$-5; and $R^{10a}$ is $-(CR^{11a}R^{11b})_o-B(R^{12a})(R^{12b})$; and $R^1$, $R^2$, and $R^3$ are as defined in connection with Formula I.

In another embodiment, Compounds of the Disclosure are compounds having Formula I, and the pharmaceutically acceptable salts and solvates thereof, wherein $R^4$ is $R^4$-9 $R^5$ is selected from the group consisting of $R^5$-3, $R^5$-4, and $R^5$-5; and $R^{10e}$ is hydrogen; and $R^1$, $R^2$, and $R^3$ are as defined in connection with Formula I.

In another embodiment, Compounds of the Disclosure are compounds having Formula I-A, and the pharmaceutically acceptable salts and solvates thereof, wherein $R^{4a}$ is $R^4$-11; $R^5$ is selected from the group consisting of $R^5$-3, $R^5$-4, and $R^5$-5, $R^{10e}$ is hydrogen; and $R^1$, $R^2$, and $R^3$ are as defined in connection with Formula I.

In another embodiment, Compounds of the Disclosure are compounds having Formula I-A, and the pharmaceutically acceptable salts and solvates thereof, wherein $R^{4a}$ is $R^4$-12; $R^5$ is selected from the group consisting of $R^5$-3, $R^5$-4, and $R^5$-5; $R^{10c}$ is hydrogen; and $R^1$, $R^2$, and $R^3$ are as defined in connection with Formula I.

In another embodiment, Compounds of the Disclosure are compounds having Formula I-A, and the pharmaceutically acceptable salts and solvates thereof, wherein $R^{4a}$ is $R^4$-13; $R^5$ is selected from the group consisting of $R^5$-3, $R^5$-4, and $R^5$-5; $R^{10a}$ is hydrogen; and $R^1$, $R^2$, and $R^3$ are as defined in connection with Formula I.

In another embodiment, Compounds of the Disclosure are compounds having Formula II:

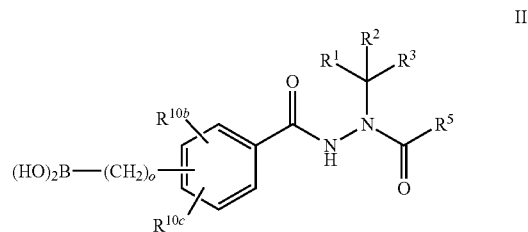

wherein $R^5$ is selected from the group consisting of $R^5$-3, $R^5$-4, and $R^5$-5; and $R^1$, $R^2$, $R^3$, $R^5$-3. $R^5$-4, $R^5$-5, $R^{10b}$, $R^{10c}$, and o are as defined in connection with Formula I, and the pharmaceutically acceptable salts and solvates thereof. In a further embodiment, o is 0. In further embodiment, $R^{10b}$ and $R^{10c}$ are each independently selected from the group consisting of hydrogen, halogen, hydroxy. $C_{1-4}$ alkyl, $C_{1-4}$ haloalkyl, $C_{1-4}$ alkoxy, and $C_{1-4}$ haloalkoxy. In a further embodiment, $R^5$ is 3,5-dimethylphenyl.

In another embodiment, Compounds of the Disclosure are compounds having Formula II-A:

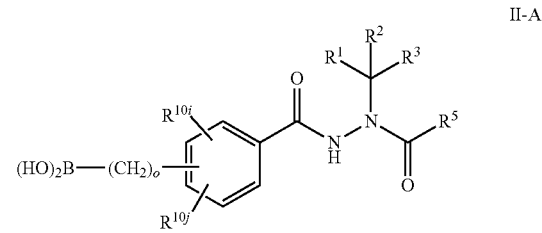

wherein $R^5$ is selected from the group consisting of $R^5$-3, $R^5$-4, and $R^5$-5; $R^1$, $R^2$, $R^3$. $R^5$-3, $R^5$-4, $R^5$-5, and o are as defined in connection with Formula I, and $R^{10i}$ and $R^{10j}$ are as defined in connection with Formula I-A, and the pharmaceutically acceptable salts and solvates thereof. In a further embodiment, o is 0. In further embodiment, $R^{10i}$ and $R^{10j}$ are each independently selected from the group consisting of hydrogen, alkyl, halo, and alkoxyalkyl. In a further embodiment, at least one of $R^{10i}$ or $R^{10j}$ is alkoxyalkyl. In a further embodiment, $R^5$ is 3,5-dimethylphenyl.

In another embodiment, Compounds of the Disclosure are compounds having Formula III:

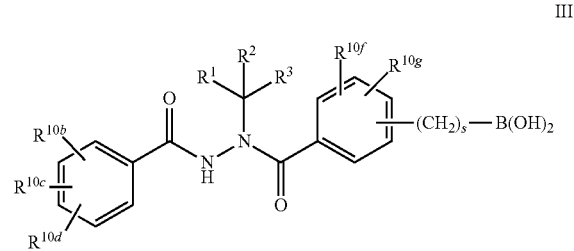

Wherein $R^1$, $R^2$, $R^3$, $R^{10b}$, $R^{10c}$, $R^{10d}$, $R^{10f}$, $R^{10g}$ and s are as defined in connection with Formula I, and the pharmaceutically acceptable salts and solvates thereof. In a further embodiment, s is 0. In a further embodiment, $R^{10b}$, $R^{10c}$, and $R^{10d}$ are independently selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy; or $R^{10b}$ is selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy; and $R^{10c}$ and $R^{10d}$ taken together with two adjacent carbon atoms form a fused optionally substituted cycloalkyl, optionally substituted heterocyclo, or optionally substituted heteroaryl group.

In another embodiment, Compounds of the Disclosure are compounds having Formula IV:

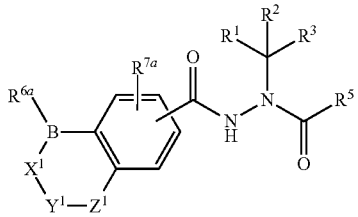

IV wherein $R^5$ is selected from the group consisting of $R^5$-3, $R^5$-4 and $R^5$-5; $R^{10c}$ is hydrogen, $R^{6a}$ is hydroxy, and $R^1$, $R^2$, $R^3$, $R^{7a}$, $X^1$, $Y^1$, and $Z^1$ are as defined in connection with Formula I, and the pharmaceutically acceptable salts and solvates thereof. In a further embodiment, $R^{7a}$ is selected from the group consisting of hydrogen, halogen, and alkyl. In a further embodiment, $Z^1$ is absent. In a further embodiment, $Z^1$ is —O—. In a further embodiment, $Z^1$ is —N(H)—. In a further embodiment, $X^1$ is —O—. In a further embodiment, $X^1$ is —N(H)—. In a further embodiment, $R^{9a}$ and $R^{9b}$ are selected from the group consisting of hydrogen and methyl. In a further embodiment, $Z^1$ is absent and m is 1, 2, or 3. In a further embodiment, $Z^1$ is absent and m is 1. In a further embodiment, $R^5$ is 3,5-dimethylphenyl.

In another embodiment, Compounds of the Disclosure are compounds having Formula V:

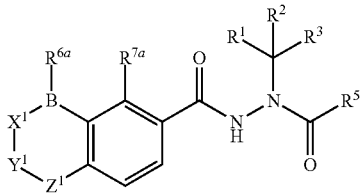

V wherein $R^5$ is selected from the group consisting of $R^5$-3, $R^5$-4 and $R^5$-5; $R^{10e}$ is hydrogen, $R^{6a}$ is hydroxy; and $R^1$, $R^2$, $R^3$, $R^{7a}$, $X^1$, $Y^1$, and $Z^1$ are as defined in connection with Formula I, and the pharmaceutically acceptable salts and solvates thereof. In a further embodiment, $R^{7a}$ is selected from the group consisting of hydrogen, halogen, and alkyl. In a further embodiment, $Z^1$ is absent. In a further embodiment, $Z^1$ is —O—. In a further embodiment, $Z^1$ is —N(H)—. In a further embodiment, $X^1$ is —O—. In a further embodiment, $X^1$ is —N(H)—. In a further embodiment, $R^{9a}$ and $R^{9b}$ are selected from the group consisting of hydrogen and methyl. In a further embodiment, $Z^1$ is absent and m is 1, 2, or 3. In a further embodiment, $Z^1$ is absent and m is 1. In a further embodiment, $R^5$ is 3,5-dimethylphenyl.

In another embodiment, Compounds of the Disclosure are compounds having Formula VI:

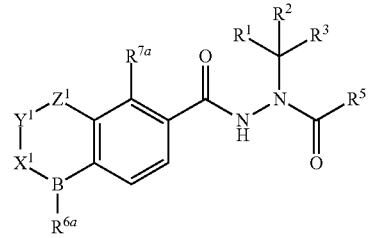

VI wherein $R^5$ is selected from the group consisting of $R^5$-3, $R^5$-4 and $R^5$-5; $R^{10c}$ is hydrogen; $R^{6a}$ is hydroxy; and $R^1$, $R^2$, $R^3$, $R^{7a}$, $X^1$, $Y^1$, and $Z^1$ are as defined in connection with Formula I, and the pharmaceutically acceptable salts and solvates thereof. In a further embodiment, $R^{7a}$ is selected from the group consisting of hydrogen, halogen, and alkyl. In a further embodiment, $Z^1$ is absent. In a further embodiment, $Z^1$ is —O—. In a further embodiment, $Z^1$ is —N(H)—. In a further embodiment, $X^1$ is —O—. In a further embodiment, $X^1$ is —N(H)—. In a further embodiment, $R^{9a}$ and $R^{9b}$ are selected from the group consisting of hydrogen and methyl. In a further embodiment, $Z^1$ is absent and m is 1, 2, or 3. In a further embodiment, $Z^1$ is absent and m is 1. In a further embodiment. $R^5$ is 3,5-dimethylphenyl.

In another embodiment, Compounds of the Disclosure are compounds having Formula VII.

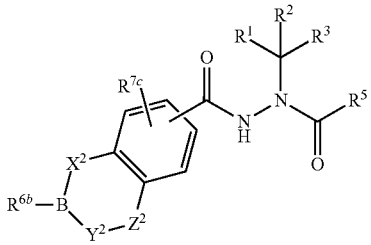

VII wherein $R^5$ is selected from the group consisting of $R^5$-3, $R^5$-4 and $R^5$-5; $R^{6b}$ is hydroxy; $R^{10c}$ is hydrogen, and $R^1$, $R^2$, $R^3$, $R^{7c}$, $X^2$, $Y^2$, and $Z^2$ are as defined in connection with Formula I, and the pharmaceutically acceptable salts and solvates thereof. In a further embodiment, $R^{7c}$ is selected from the group consisting of hydrogen, halogen, and alkyl. In a further embodiment, $Z^2$ is absent. In a further embodiment, $Z^2$ is —O—. In a further embodiment, $Z^2$ is —N(H)—. In a further embodiment, $X^2$ is —O—. In a further embodiment, $X^2$ is —N(H)— In a further embodiment, $R^{9c}$ and $R^{9d}$ are selected from the group consisting of hydrogen and methyl. In a further embodiment, $Z^2$ is absent and n is 1, 2, or 3. In a further embodiment, $Z^2$ is absent and n is 1. In a further embodiment, $R^5$ is 3,5-dimethylphenyl.

In another embodiment, Compounds of the Disclosure are compounds having Formula VIII:

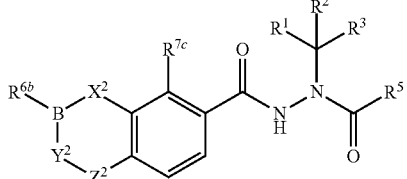

VIII wherein $R^5$ is selected from the group consisting of $R^5$-3, $R^5$-4 and $R^5$-5; $R^{6b}$ is hydroxy; $R^{10e}$ is hydrogen, and $R^1$, $R^2$, $R^3$, $R^{7c}$, $X^2$, $Y^2$, and $Z^2$ are as defined in connection with Formula I, and the pharmaceutically acceptable salts and solvates thereof. In a further embodiment, $R^{7c}$ is selected from the group consisting of hydrogen, halogen, and alkyl. In a further embodiment, $Z^2$ is absent. In a further embodiment, $Z^2$ is —O—. In a further embodiment, $Z^2$ is —N(H)—. In a further embodiment, $X^2$ is —O—. In a further embodiment, $X^2$ is —N(H)—. In a further embodiment, $R^{9c}$ and $R^{9d}$ are selected from the group consisting of hydrogen and methyl. In a further embodiment, $Z^2$ is absent and n is 1, 2, or 3. In a further embodiment, $Z^2$ is absent and n is 1. In a further embodiment, $R^5$ is 3,5-dimethylphenyl.

In another embodiment, Compounds of the Disclosure are compounds having Formula IX:

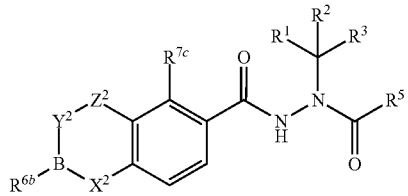

IX wherein $R^5$ is selected from the group consisting of $R^5$-3, $R^5$-4 and $R^5$-5; $R^{6b}$ is hydroxy; $R^{10e}$ is hydrogen, and $R^1$, $R^2$, $R^3$, $R^{7c}$, $X^2$, $Y^2$, and $Z^2$ are as defined in connection with Formula I, and the pharmaceutically acceptable salts and solvates thereof. In a further embodiment, $R^{7c}$ is selected from the group consisting of hydrogen, halogen, and alkyl. In a further embodiment, $Z^2$ is absent. In a further embodiment, $Z^2$ is —O—. In a further embodiment, $Z^2$ is —N(H)—. In a further embodiment, $X^2$ is —O—. In a further embodiment, $X^2$ is —N(H)—. In a further embodiment, $R^{9c}$ and $R^{9d}$ are selected from the group consisting of hydrogen and methyl. In a further embodiment, $Z^2$ is absent and n is 1, 2, or 3. In a further embodiment, $Z^2$ is absent and n is 1 In a further embodiment, $R^5$ is 3,5-dimethylphenyl.

In another embodiment, Compounds of the Disclosure are compounds having Formula I, wherein $R^4$ is selected from the group consisting of:

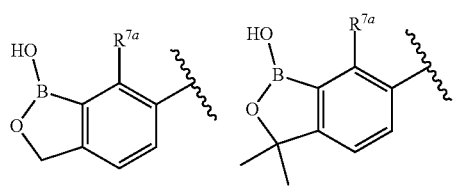

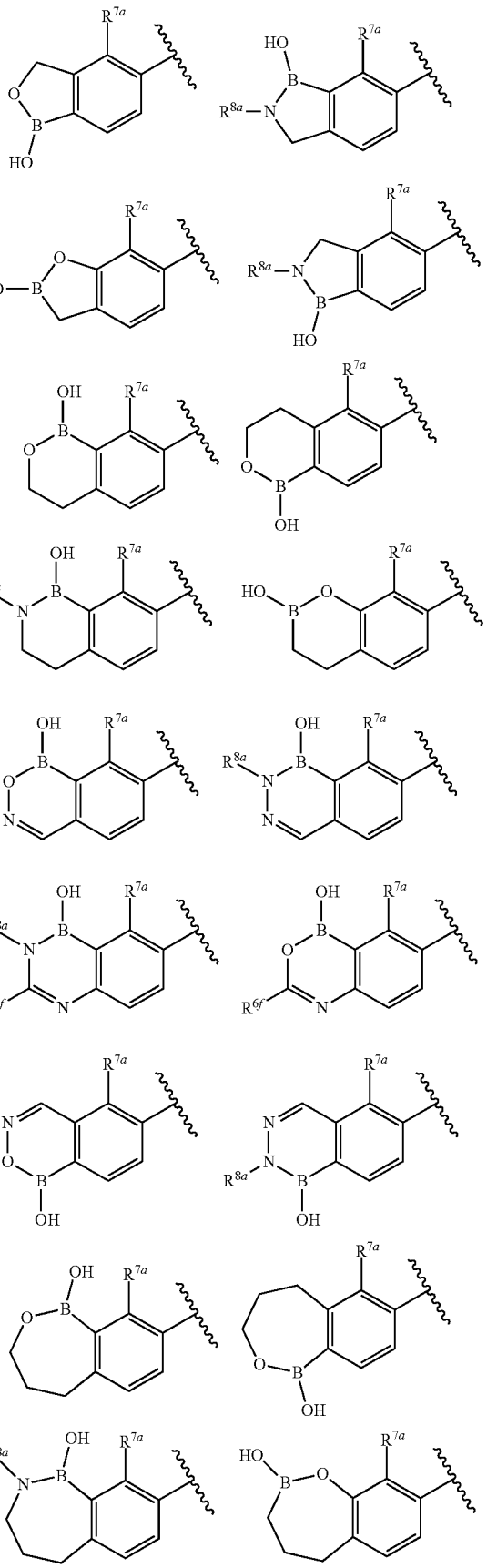

-continued

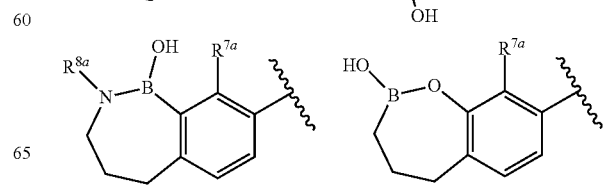

-continued

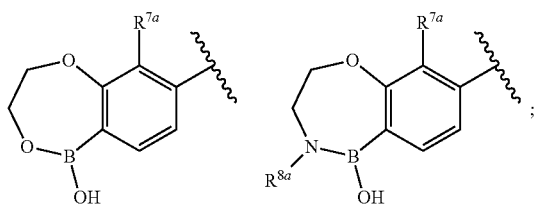

$R^5$ is selected from the group consisting of $R^5$-3, $R^5$-4, and $R^5$-5; $R^{10c}$ is hydrogen; and $R^1$, $R^2$, and $R^3$ are as defined in connection with Formula I, and the pharmaceutically acceptable salts and solvates thereof. In a further embodiment, $R^{7a}$ is selected from the group consisting of hydrogen, halogen, hydroxy. $C_{1-4}$ alkyl, $C_{1-4}$ haloalkyl, $C_{1-4}$ alkoxy, and $C_{1-4}$ haloalkoxy; $R^{8a}$ is selected from the group consisting of hydrogen and $C_{1-4}$ alkyl; and $R^{6f}$ is selected from the group consisting of hydrogen, $C_{1-4}$ alkyl, hydroxy, and —NH$_2$.

In another embodiment, Compounds of the Disclosure are compounds having Formula I, wherein:

$R^4$ is $R^4$-5;

$R^{10a}$ is hydrogen;

$R^{10b}$, $R^{10c}$, and $R^{10d}$ are independently selected from the group consisting of hydrogen, halogen, amino, cyano, —N(H)CHO, —N(H)CN, hydroxy, $C_{1-4}$ alkyl, $C_{1-4}$ haloalkyl, $C_{1-4}$ alkoxy, and $C_{1-4}$ haloalkoxy; or $R^{10b}$ is selected from the group consisting of hydrogen, halogen, hydroxy, amino, cyano, —N(H)CHO, —N(H)CN. $C_{1-4}$ alkyl, $C_{1-4}$ haloalkyl, $C_{1-4}$ alkoxy, and $C_{1-4}$ haloalkoxy; and $R^{10c}$ and $R^{10d}$ taken together with two adjacent carbon atoms form a fused optionally substituted cycloalkyl, optionally substituted heterocyclo, or optionally substituted heteroaryl group;

$R^5$ is selected from the group consisting of:

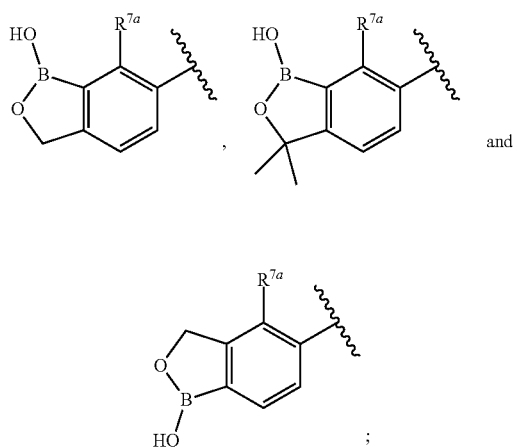

$R^{7a}$ is selected from the group consisting of hydrogen, halogen, hydroxy, $C_{1-4}$ alkyl. $C_{1-4}$ haloalkyl, $C_{1-4}$ alkoxy, and $C_{1-4}$ haloalkoxy; and $R^1$, $R^2$, and $R^3$ are as defined in connection with Formula I, and the pharmaceutically acceptable salts and solvates thereof.

In another embodiment, Compounds of the Disclosure are compounds having Formula I, wherein:

$R^4$ is selected from the group consisting of.

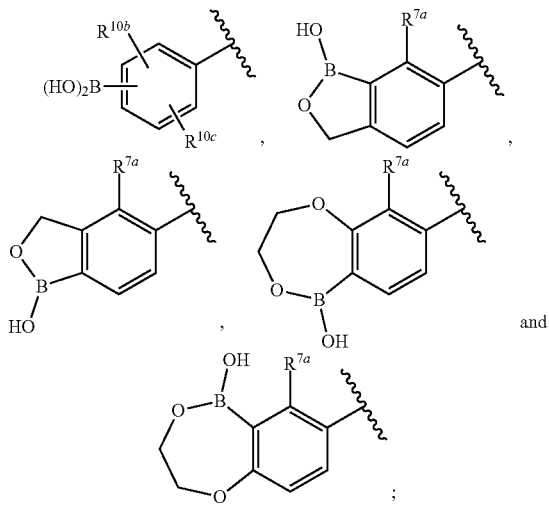

$R^5$ is selected from the group consisting of $R^5$-3, $R^5$-4, and $R^5$-5;

$R^{10e}$ is hydrogen; and $R^1$, $R^2$, and $R^3$ are as defined in connection with Formula I. and the pharmaceutically acceptable salts and solvates thereof.

In another embodiment, Compounds of the Disclosure are compounds having Formula I-A, wherein:

$R^{4a}$ is $R^4$-11, $R^5$ is selected from the group consisting of $R^5$-3, $R^5$-4, and $R^5$-5;

$R^{10e}$ is hydrogen; and $R^1$, $R^2$, $R^3$, $R^5$-3, $R^5$-4, and $R^5$-5 are as defined in connection with Formula I. and the pharmaceutically acceptable salts and solvates thereof.

In another embodiment, Compounds of the Disclosure are compounds having Formula I-A, wherein:

$R^{4a}$ is:

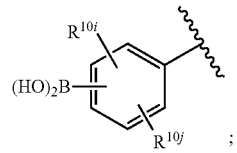

$R^5$ is $R^5$-3;

$R^{10e}$ is hydrogen; and $R^1$, $R^2$, $R^3$, and $R^5$-3 are as defined in connection with Formula I, and the pharmaceutically acceptable salts and solvates thereof. In another embodiment, $R^{10f}$ and $R^{10g}$ are each alkyl and $R^{10h}$ is hydrogen. In another embodiment, $R^{10i}$ and $R^{10j}$ are each independently selected from the group consisting of hydrogen, halogen, hydroxy, $C_{1-4}$ alkyl, alkoxyalkyl, $C_{1-4}$ haloalkyl, $C_{1-4}$ alkoxy, and $C_{1-4}$ haloalkoxy. In another embodiment, $R^{10i}$ and $R^{10j}$ are each independently selected from the group consisting of hydrogen, halogen, and alkoxyalkyl. In another embodiment, at least one of $R^{10i}$ or $R^{10j}$ is alkoxyalkyl.

In another embodiment, Compounds of the Disclosure are compounds having Formula I, wherein:
$R^4$ is:

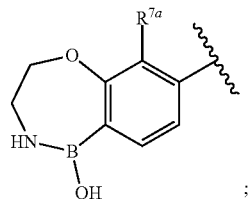

$R^{7a}$ is selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy;
$R^5$ is selected from the group consisting of $R^5$-3, $R^5$-4, and $R^5$-5, and
$R^{10e}$ is hydrogen.

In another embodiment, Compounds of the Disclosure are compounds having any one of Formulae I-IX, wherein R is optionally substituted $C_{1-6}$ alkyl; $R^2$ is selected from the group consisting of hydrogen and optionally substituted $C_{1-6}$ alkyl; $R^3$ is optionally substituted $C_{1-6}$ alkyl; and $R^4$ and $R^5$ are as defined in connection with Formula I, and the pharmaceutically acceptable salts and solvates thereof.

In another embodiment, Compounds of the Disclosure are compounds having Formula I-A or II-A, wherein $R^1$ is optionally substituted $C_{1-6}$ alkyl; $R^2$ is selected from the group consisting of hydrogen and optionally substituted $C_{1-6}$ alkyl; and $R^3$ is optionally substituted $C_{1-6}$ alkyl, and the pharmaceutically acceptable salts and solvates thereof.

In another embodiment, Compounds of the Disclosure are compounds having any one of Formulae I-LX, wherein $R^1$ is selected from the group consisting of methyl, ethyl, n-propyl, and n-butyl; $R^2$ is selected from the group consisting of hydrogen and methyl; and $R^4$ and $R^5$ are as defined in connection with Formula I, and the pharmaceutically acceptable salts and solvates thereof. In a further embodiment, $R^3$ is selected from the group consisting of methyl and tert-butyl. In a further embodiment, $R^2$ is hydrogen and $R^3$ is tert-butyl.

In another embodiment, Compounds of the Disclosure are compounds having Formula I-A or H-A, wherein $R^1$ is selected from the group consisting of methyl, ethyl, n-propyl, and n-butyl; and $R^2$ is selected from the group consisting of hydrogen and methyl, and the pharmaceutically acceptable salts and solvates thereof. In a further embodiment, $R^3$ is selected from the group consisting of methyl and tert-butyl. In a further embodiment, $R^2$ is hydrogen and $R^3$ is tert-butyl.

In another embodiment, Compounds of the Disclosure are compounds having any one of Formulae L-IX, wherein $R^1$ is optionally substituted $C_{1-6}$ alkyl; $R^2$ is hydrogen; $R^3$ is selected from the group consisting of optionally substituted phenyl, optionally substituted pyridyl, and optionally substituted pyrimidinyl; and $R^4$ and $R^5$ are as defined in connection with Formula I, and the pharmaceutically acceptable salts and solvates thereof. In a further embodiment, $R^3$ is selected from the group consisting of optionally substituted pyridyl and optionally substituted pyrimidinyl.

In another embodiment, Compounds of the Disclosure are compounds having Formula I-A or II-A, wherein $R^1$ is optionally substituted $C_{1-6}$ alkyl; $R^2$ is hydrogen; and $R^3$ is selected from the group consisting of optionally substituted phenyl, optionally substituted pyridyl, and optionally substituted pyrimidinyl, and the pharmaceutically acceptable salts and solvates thereof. In a further embodiment, $R^3$ is selected from the group consisting of optionally substituted pyridyl and optionally substituted pyrimidinyl.

In another embodiment, Compounds of the Disclosure are compounds having any one of Formulae I-IX, wherein $R^1$, $R^2$, and $R^3$ are each methyl; and $R^4$ and $R^5$ are as defined in connection with Formula I, and the pharmaceutically acceptable salts and solvates thereof.

In another embodiment, Compounds of the Disclosure are compounds having Formula I-A or II-A, wherein $R^1$, $R^2$, and $R^3$ are each methyl, and the pharmaceutically acceptable salts and solvates thereof.

In another embodiment, Compounds of the Disclosure are compounds having any one of Formulae I-IX, wherein the compound does not exhibit optical activity. i.e., the compound is achiral or racemic, or a pharmaceutically acceptable salt or solvate thereof.

In another embodiment, Compounds of the Disclosure are compounds having Formula I-A or II-A, wherein the compound does not exhibit optical activity, i.e., the compound is achiral or racemic, or a pharmaceutically acceptable salt or solvate thereof.

In another embodiment, Compounds of the Disclosure are compounds having any one of Formulae I-IX, wherein the carbon atom bearing $R^1$, $R^2$, and $R^3$ is an asymmetric carbon atom and the absolute configuration of said asymmetric carbon atom is R, i.e., the compound is enantiomerically enriched in the R isomer, and the pharmaceutically acceptable salts and solvates thereof. In a further embodiment, Compounds of the Disclosure are compounds having any one of Formulae I-IX, wherein the enantiomeric excess of the R isomer is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of the R isomer is at least about 90%/o. In a further embodiment, the enantiomeric excess of the R isomer is at least about 95%. In a further embodiment, the enantiomeric excess of the R isomer is at least about 98%. In a further embodiment, the enantiomeric excess of the R isomer is at least about 98%.

In another embodiment, Compounds of the Disclosure are compounds having Formula I-A or II-A, wherein the carbon atom bearing $R^1$, $R^2$, and $R^1$ is an asymmetric carbon atom and the absolute configuration of said asymmetric carbon atom is R, i.e., the compound is enantiomerically enriched in the R isomer, and the pharmaceutically acceptable salts and solvates thereof. In a further embodiment, Compounds of the Disclosure are compounds having Formula I-A or II-A, wherein the enantiomeric excess of the R isomer is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of the R isomer is at least about 90%. In a further embodiment, the enantiomeric excess of the R isomer is at least about 95%. In a further embodiment, the enantiomeric excess of the R isomer is at least about 98%. In a further embodiment, the enantiomeric excess of the R isomer is at least about 98%.

In another embodiment, Compounds of the Disclosure are compounds having any one of Formulae I-LX, wherein the carbon atom bearing $R^1$, $R^2$, and $R^3$ is an asymmetric carbon atom and the absolute configuration of said asymmetric carbon atom is S, i.e., the compound is enantiomerically enriched in the S isomer, and the pharmaceutically acceptable salts and solvates thereof. In a further embodiment, Compounds of the Disclosure are compounds having any one of Formulae I-IX, wherein the enantiomeric excess of the S isomer is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of the S isomer is at least about 90% In a further embodiment, the enantiomeric excess of the S isomer is at least about 95%. In a further embodiment, the enantiomeric excess of the S isomer is at least about 98%. In a further embodiment, the enantiomeric excess of the S isomer is at least about 99%.

In another embodiment, Compounds of the Disclosure are compounds having Formula I-A or II-A, wherein the carbon atom bearing $R^1$, $R^2$, and $R^3$ is an asymmetric carbon atom and the absolute configuration of said asymmetric carbon atom is S, i.e., the compound is enantiomerically enriched in the S isomer, and the pharmaceutically acceptable salts and solvates thereof. In a further embodiment, Compounds of the Disclosure are compounds having Formula I-A or II-A, wherein the enantiomeric excess of the S isomer is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of the S isomer is at least about 90%. In a further embodiment, the enantiomeric excess of the S isomer is at least about 95%. In a further embodiment, the enantiomeric excess of the S isomer is at least about 98%. In a further embodiment, the enantiomeric excess of the S isomer is at least about 99%.

In another embodiment, Compounds of the Disclosure are compounds having Formula X:

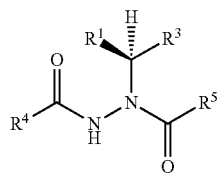

X wherein $R^1$ does not equal $R^3$, and $R^1$, $R^3$, $R^4$, and $R^5$ are as defined in connection with Formula I, and the pharmaceutically acceptable salts and solvates thereof. In a further embodiment, the enantiomeric excess of a compound having Formula X, in a mixture of compounds having Formulae X and XI, is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of a compound having Formula X is at least about 90% In a further embodiment, the enantiomeric excess of a compound having Formula X is at least about 95%. In a further embodiment, the enantiomeric excess of a compound having Formula X is at least about 98% In a further embodiment, the enantiomeric excess of a compound having Formula X is at least about 99%.

In another embodiment, Compounds of the Disclosure are compounds having Formula X-A:

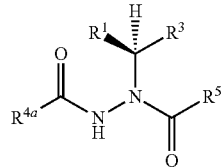

X-A wherein $R^1$ does not equal $R^3$, and $R^1$, $R^3$, and $R^5$ are as defined in connection with Formula I. and $R^{4a}$ is as defined in connection with Formula I-A, and the pharmaceutically acceptable salts and solvates thereof. In a further embodiment, the enantiomeric excess of a compound having Formula X-A, in a mixture of compounds having Formulae X-A and XI-A, is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of a compound having Formula X-A is at least about 90%. In a further embodiment, the enantiomeric excess of a compound having Formula X-A is at least about 95%. In a further embodiment, the enantiomeric excess of a compound having Formula X-A is at least about 98%. In a further embodiment, the enantiomeric excess of a compound having Formula X-A is at least about 99%.

In another embodiment, Compounds of the Disclosure are compounds having Formula XI:

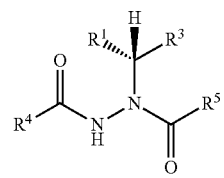

XI wherein $R^1$ does not equal $R^3$, and $R^1$, $R^3$, $R^4$, and $R^5$ are as defined in connection with Formula I, and the pharmaceutically acceptable salts and solvates thereof. In a further embodiment, the enantiomeric excess of a compound having Formula XI, in a mixture of compounds having Formulae X and XI, is at least about 60%, e.g. at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of a compound having Formula XI is at least about 90%. In a further embodiment, the enantiomeric excess of a compound having Formula XI is at least about 95%. In a further embodiment, the enantiomeric excess of a compound having Formula XI is at least about 98% In a further embodiment, the enantiomeric excess of a compound having Formula XI is at least about 99%.

In another embodiment, Compounds of the Disclosure are compounds having Formula XI-A:

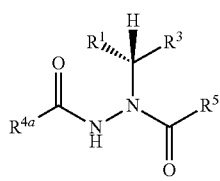

XI-A wherein $R^1$ does not equal $R^3$, and $R^1$, $R^3$, and $R^5$ are as defined in connection with Formula I, and $R^{4a}$ is as defined in connection with Formula I-A, and the pharmaceutically acceptable salts and solvates thereof. In a further embodiment, the enantiomeric excess of a compound having Formula XI-A, in a mixture of compounds having Formulae X-A and XI-A, is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of a compound having Formula XI-A is at least about 90%. In a further embodiment, the enantiomeric excess of a compound having Formula XI-A is at least about 95%. In a further embodiment, the enantiomeric excess of a compound having Formula XI-A is at least about 98% In a further embodiment, the enantiomeric excess of a compound having Formula XI-A is at least about 99%.

In another embodiment, Compounds of the Disclosure are compounds having Formula X or XI, wherein:
$R^4$ is selected from the group consisting of

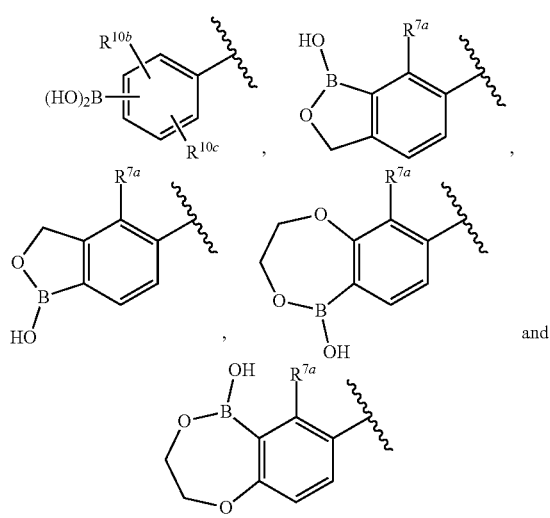

$R^5$ is selected from the group consisting of $R^5$-3, $R^5$-4, and $R^5$-5;
$R^{10c}$ is hydrogen, and
$R^1$, $R^2$, and $R^3$ are as defined in connection with Formula I, and the pharmaceutically acceptable salts and solvates thereof. In a further embodiment, $R^{7a}$ is selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy. In a further embodiment. $R^{10b}$ and $R^{10c}$ are each independently selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy. In a further embodiment, $R^5$ is $R^5$-3. In a further embodiment, $R^{10f}$, $R^{10g}$, and $R^{10h}$ are each independently selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy. In a further embodiment, $R^1$ is selected from the group consisting of ethyl and n-propyl and $R^3$ is tert-butyl. In a further embodiment, $R^1$ is tert-butyl and $R^3$ is optionally substituted phenyl. In a further embodiment, $R^5$ is 3,5-dimethylphenyl.

In another embodiment, Compounds of the Disclosure are compounds having Formula X or XI, wherein:
$R^4$ is:

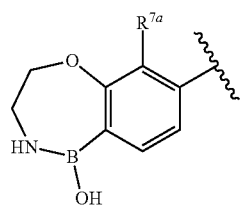

$R^5$ is selected from the group consisting of $R^5$-3, $R^5$-4, and $R^5$-5;
$R^{7a}$ is selected from the group consisting of hydrogen, halogen, and $C_{1-4}$ alkyl, $C_{1-4}$ haloalkyl, $C_{1-4}$ alkoxy, and $C_{1-4}$ haloalkoxy, and
$R^{10e}$ is hydrogen; and
$R^1$, $R^2$, and $R^3$ are as defined in connection with Formula I, and the pharmaceutically acceptable salts and solvates thereof. In a further embodiment, $R^{7a}$ is selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy. In a further embodiment, $R^{10b}$ and $R^{10c}$ are each independently selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy. In a further embodiment, $R^5$ is $R^5$-3. In a further embodiment, $R^{10f}$, $R^{10g}$, and $R^{10h}$ are each independently selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy. In a further embodiment, $R^1$ is selected from the group consisting of ethyl and n-propyl and $R^3$ is tert-butyl. In a further embodiment. $R^1$ is tert-butyl and $R^3$ is optionally substituted phenyl. In a further embodiment, $R^5$ is 3,5-dimethylphenyl.

In another embodiment, Compounds of the Disclosure are compounds having Formula X-A or XI-A, wherein:
$R^{4a}$ is selected from the group consisting of:

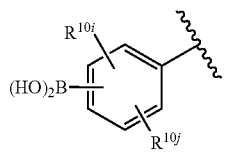

$R^5$ is selected from the group consisting of $R^5$-3, $R^5$-4, and $R^5$-5;

$R^{10c}$ is hydrogen; and $R^1$, $R^2$, $R^3$, $R^5$-3, $R^5$-4, and $R^5$-5 are as defined in connection with Formula I, and the pharmaceutically acceptable salts and solvates thereof. In a further embodiment, $R^{10i}$ and $R^{10j}$ are each independently selected from the group consisting of hydrogen, halogen, hydroxy, $C_{1-4}$ alkyl, alkoxyalkyl, $C_{1-4}$ haloalkyl, $C_{1-4}$ alkoxy, and $C_{1-4}$ haloalkoxy. In a further embodiment, $R^5$ is $R^5$-3 In a further embodiment, $R^{10f}$, $R^{10g}$, and $R^{10h}$ are each independently selected from the group consisting of hydrogen, halogen, hydroxy, $C_{1-4}$ alkyl, $C_{1-4}$ haloalkyl, $C_{1-4}$ alkoxy, and $C_{1-4}$ haloalkoxy. In a further embodiment, $R^1$ is selected from the group consisting of ethyl and n-propyl and $R^3$ is tert-butyl. In a further embodiment, $R^1$ is tert-butyl and $R^3$ is optionally substituted phenyl. In a further embodiment, at least one of $R^{10i}$ or $R^{10j}$ is alkoxyalkyl. In a further embodiment, R is 3,5-dimethylphenyl.

In another embodiment, Compounds of the Disclosure are compounds having any one of Formulae I-XI, and the pharmaceutically acceptable salts and solvates thereof, wherein $R^4$ is $R^4$-1 or $R^4$-8; $R^{6a}$ forms a hydroxy acid adduct, and $R^1$, $R^2$, $R^3$, and $R^5$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^4$ is $R^4$-2; $R^{6c}$ forms a hydroxy acid adduct; and $R^1$, $R^2$, $R^1$, and $R^5$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^4$ is $R^4$-3, $R^{6b}$ forms a hydroxy acid adduct, and $R^1$, $R^2$, $R^3$, and $R^5$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^4$ is $R^4$-4; $R^{6d}$ forms a hydroxy acid adduct, and $R^1$, $R^2$, $R^3$ and $R^5$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^5$ is $R^5$-1; $R^{6e}$ forms a hydroxy acid adduct, and $R^1$, $R^2$, $R^3$, and $R^4$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^5$ is $R^5$-2; $R^{6g}$ forms a hydroxy acid adduct, and $R^1$, $R^2$, $R^3$, and $R^4$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^4$ is $R^4$-1 or $R^4$-8; $R^{6a}$ forms an amino acid adduct, and $R^1$, $R^2$, $R^3$, and $R^5$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^4$ is $R^4$-2; $R^{61}$ forms an amino acid adduct; and $R^1$, $R^2$, $R^3$, and $R^5$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^4$ is $R^4$-3; $R^{6e}$ forms an amino acid adduct, and $R^1$, $R^2$, $R^3$, and $R^5$ are as defined in connection with Formula I. and the pharmaceutically acceptable salts and solvates thereof.

In another embodiment. Compounds of the Disclosure are compounds having any one of Formulae I-XI, and the pharmaceutically acceptable salts and solvates thereof, wherein $R^4$ is $R^4$-4; $R^{6d}$ forms an amino acid adduct, and $R^1$, $R^2$, $R^3$ and $R^5$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^5$ is $R^5$-1. $R^{6e}$ forms an amino acid adduct, and $R^1$, $R^2$, $R^3$, and $R^4$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^5$ is $R^5$-2; $R^{6g}$ forms an amino acid adduct, and $R^1$, $R^2$, $R^3$, and $R^4$ are as defined in connection with Formula I, and the pharmaceutically acceptable salts and solvates thereof.

In another embodiment, Compounds of the Disclosure are compounds having any one of Formulae I-XI, and the pharmaceutically acceptable salts and solvates thereof, wherein $R^4$ is $R^4$-5, $R^4$-6, or $R^4$-7; $R^{10a}$ is —$(CR^{11a}R^{11b})_o$—$B(R^{12a})(R^{12b})$; —$B(R^{12c})(R^{12d})$ forms a fluoride adduct; and $R^1$, $R^2$, $R^3$, and $R^5$ are as defined in connection with Formula I, and the pharmaceutically acceptable salts and solvates thereof.

In another embodiment, Compounds of the Disclosure are compounds having any one of Formulae I-XI and the pharmaceutically acceptable salts and solvates thereof, wherein $R^4$ is $R^4$-5, $R^4$-6, or $R^4$-7; $R^{10e}$ is —$(CR^{11c}R^{11d})$—$B(R^{12c})(R^{12b})$; —$B(R^{12c})(R^{12d})$ forms a fluoride adduct; and $R^1$, $R^2$, $R^3$, and $R^5$ are as defined in connection with Formula I, and the pharmaceutically acceptable salts and solvates thereof.

In another embodiment, Compounds of the Disclosure are compounds having any one of Formulae IA, II-A, X-A, or XI-A, and the pharmaceutically acceptable salts and solvates thereof, wherein $R^{4a}$ is $R^4$-11, $R^4$-12, or $R^4$-12; $R^{10e}$ is —$(CR^{11c}R^{11d})_g$—$B(R^{12c})(R^{12d})$; —$B(R^{12a})(R^{12b})$ forms a fluoride adduct; and $R^1$, $R^2$, $R^3$, and $R^5$ are as defined in connection with Formula I. and the pharmaceutically acceptable salts and solvates thereof.

In another embodiment. Compounds of the Disclosure are compounds having the formula:
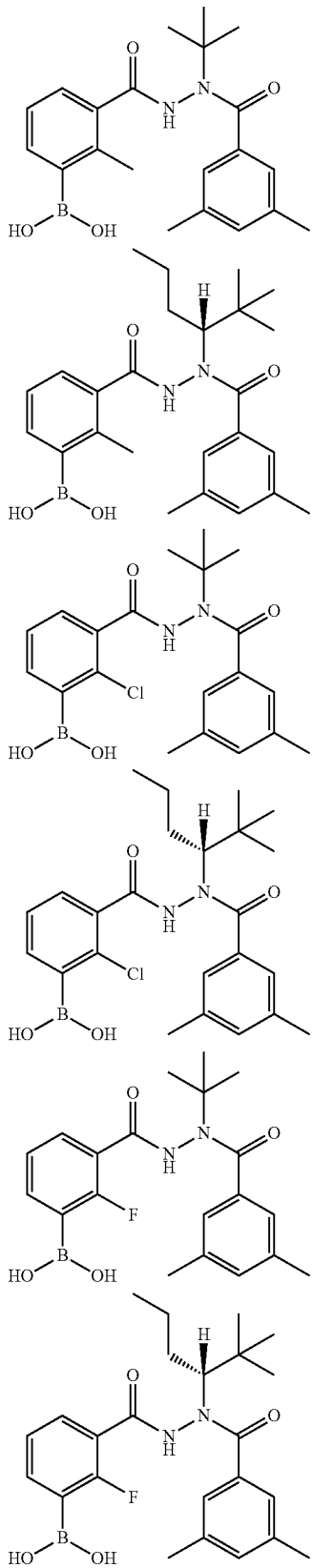
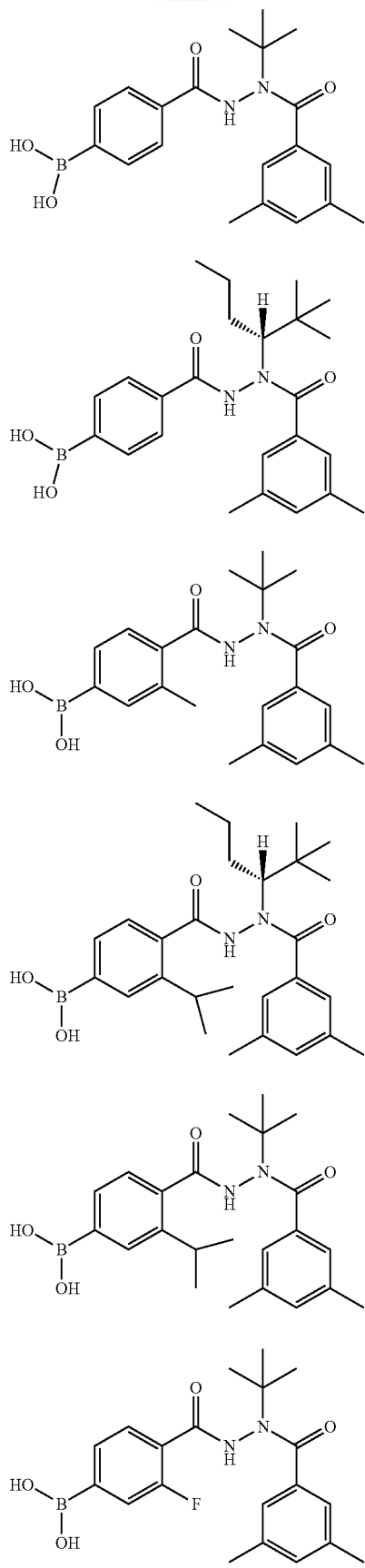 [SMILES: Cc1cc(C)cc(C(=O)N(NC(=O)c2ccc(B(O)O)cc2)C(C)(C)C)c1 ; CCC[C@@H](N(NC(=O)c1ccc(B(O)O)cc1)C(=O)c1cc(C)cc(C)c1)C(C)(C)C ; Cc1cc(C)cc(C(=O)N(NC(=O)c2ccc(B(O)O)cc2C)C(C)(C)C)c1 ; CCC[C@@H](N(NC(=O)c1ccc(B(O)O)cc1C(C)C)C(=O)c1cc(C)cc(C)c1)C(C)(C)C ; Cc1cc(C)cc(C(=O)N(NC(=O)c2ccc(B(O)O)cc2C(C)C)C(C)(C)C)c1 ; Cc1cc(C)cc(C(=O)N(NC(=O)c2ccc(B(O)O)cc2F)C(C)(C)C)c1]

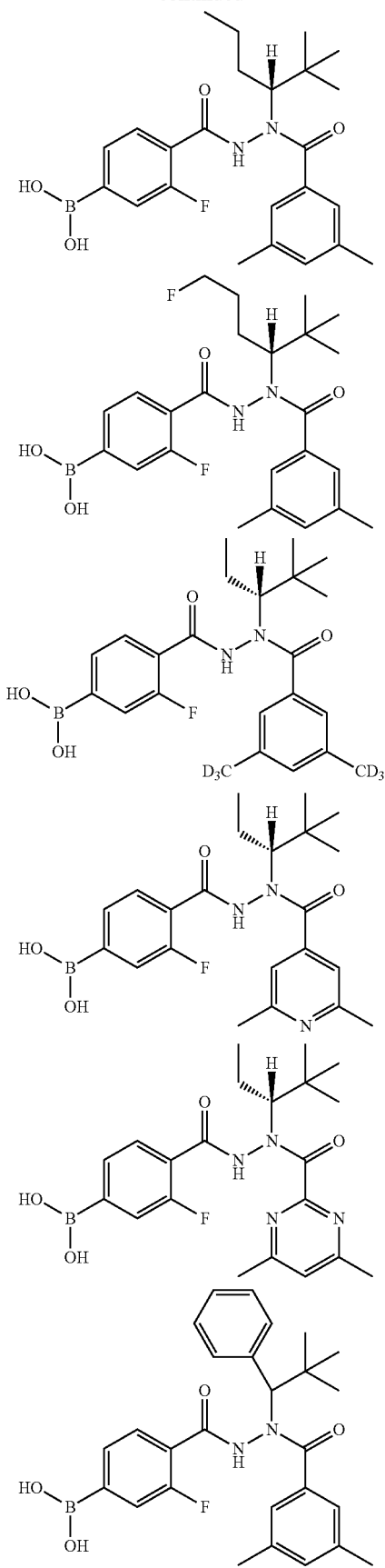
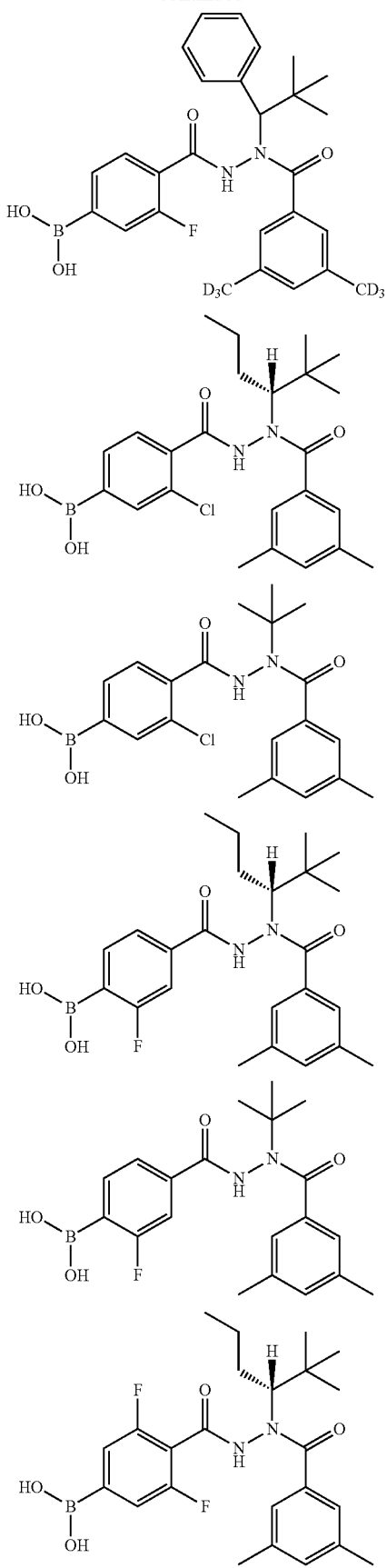

35
-continued
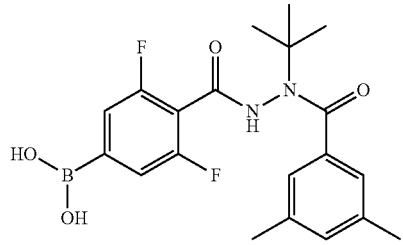
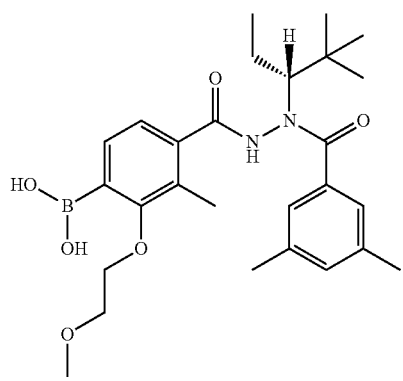
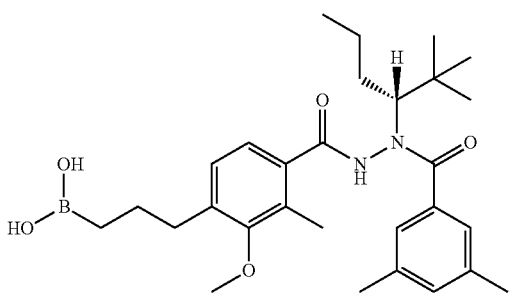
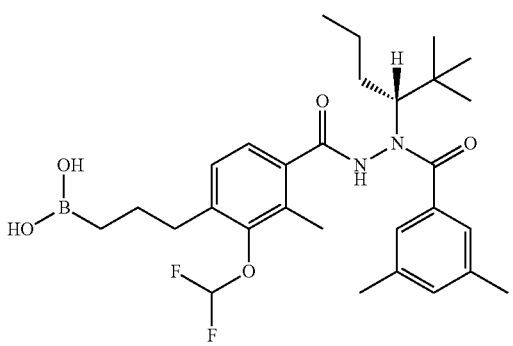
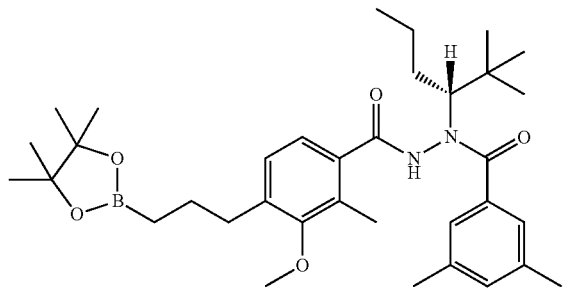
36
-continued
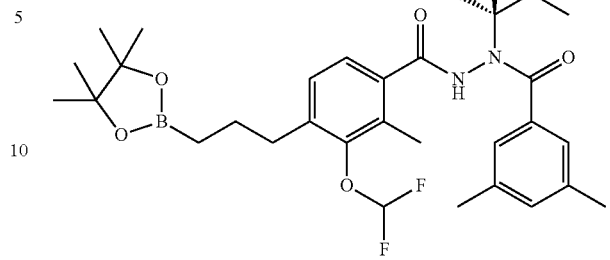
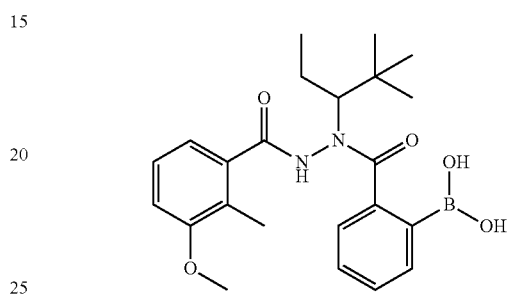
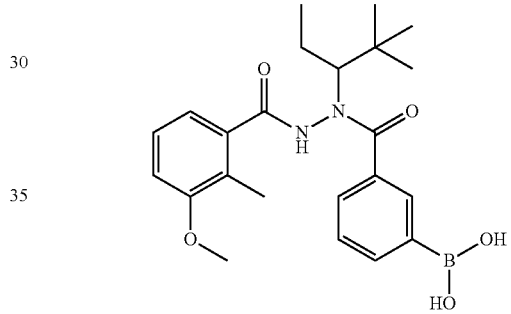
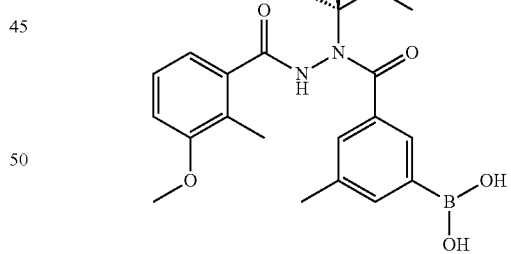
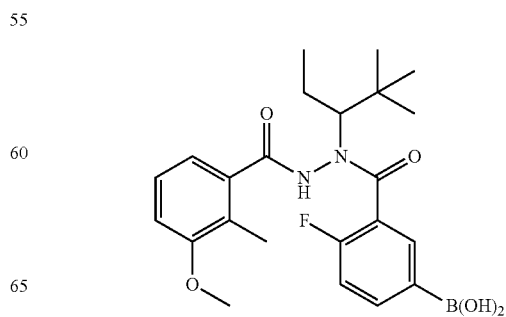

-continued
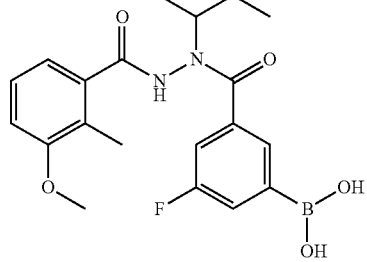
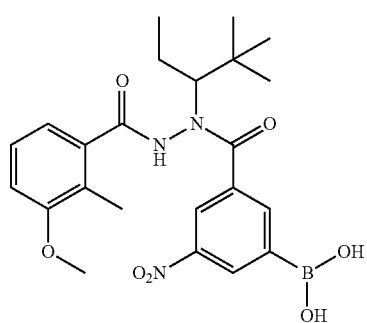
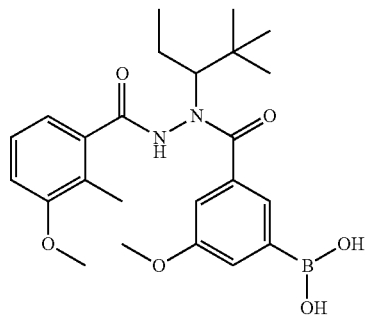
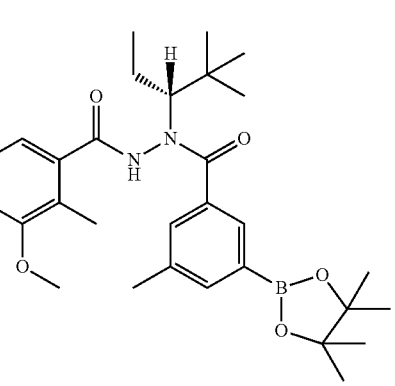
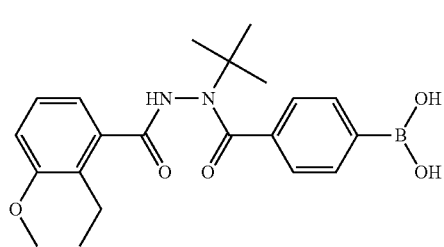
-continued
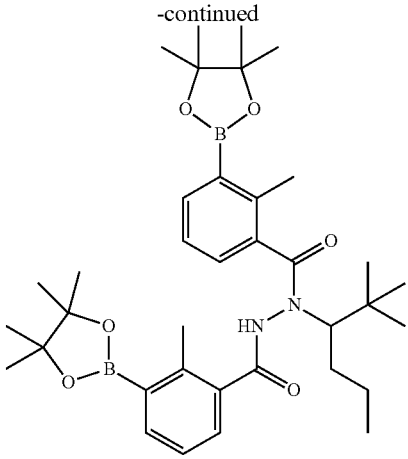
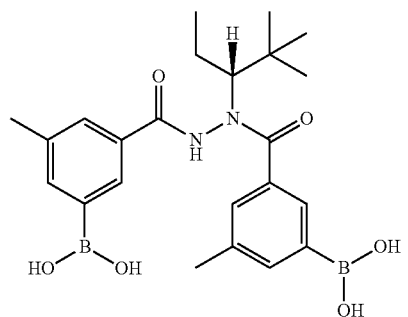
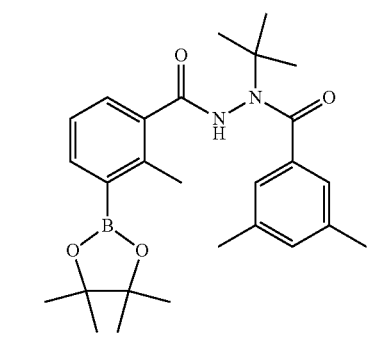
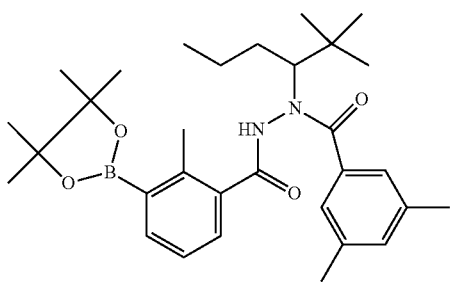

-continued
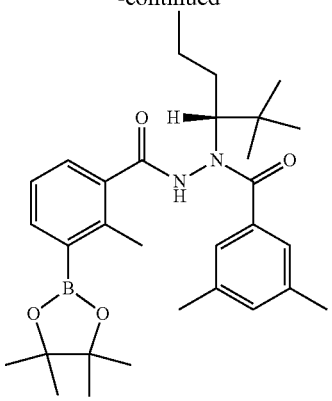
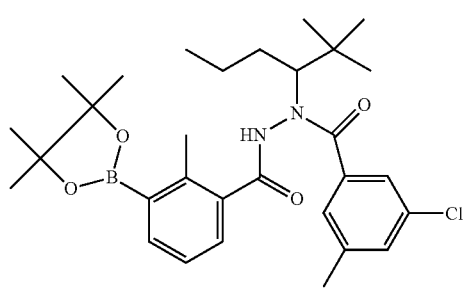
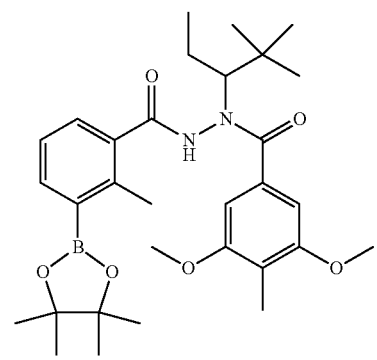
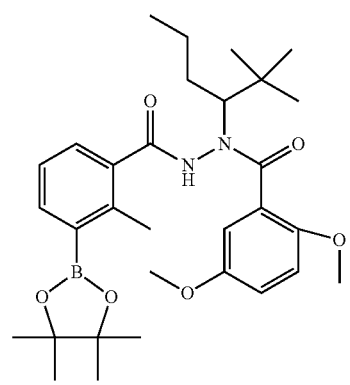
-continued
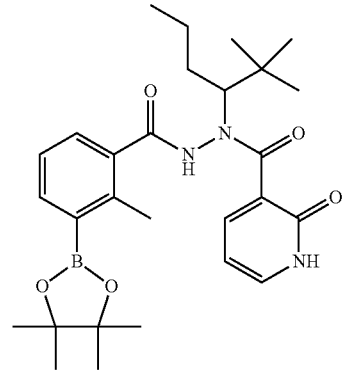
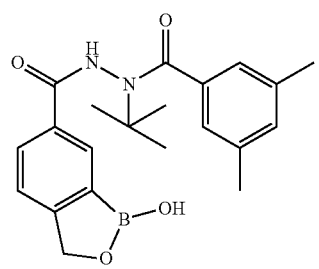
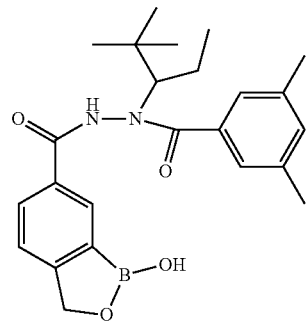
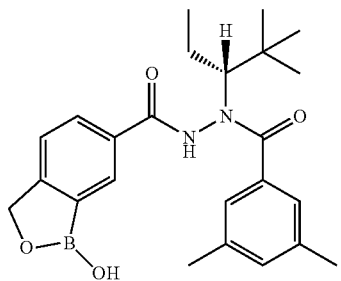
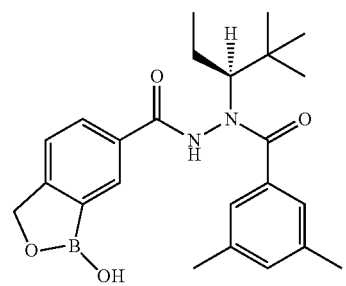

-continued
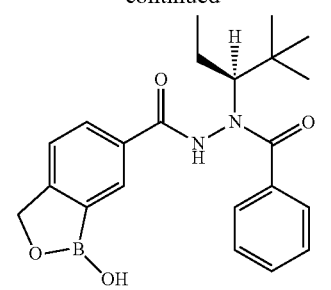
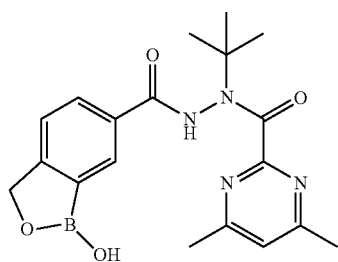
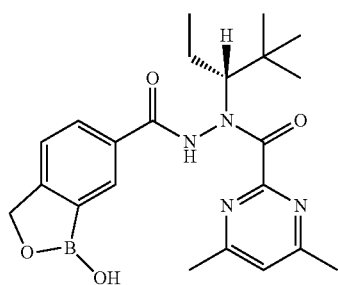
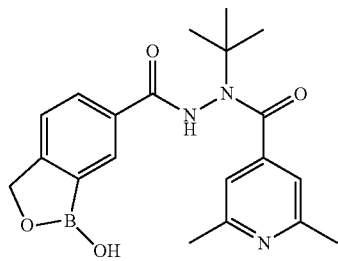
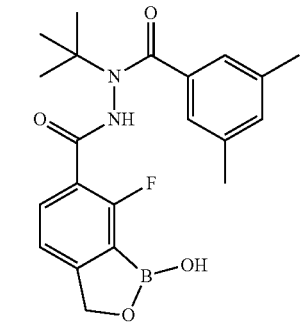
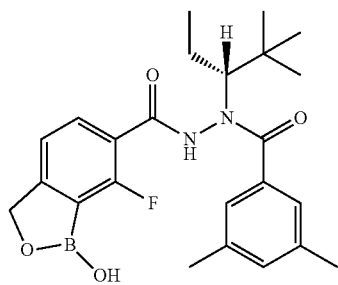
-continued
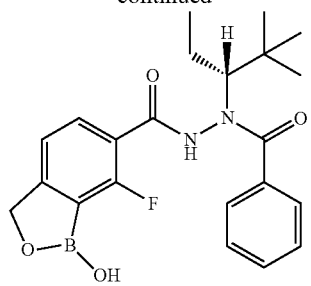
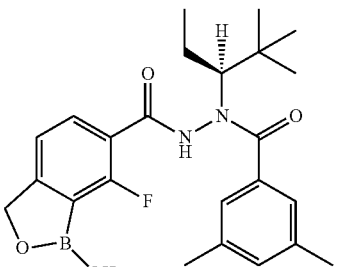
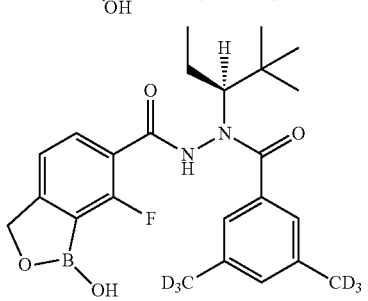
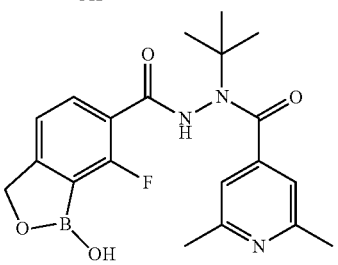
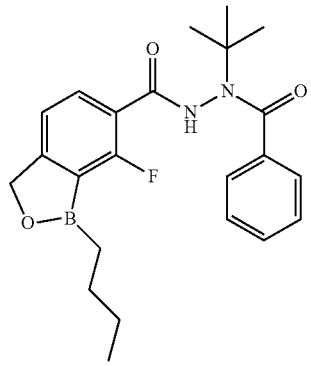
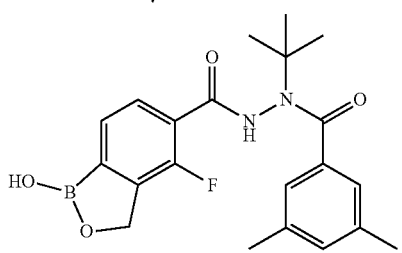

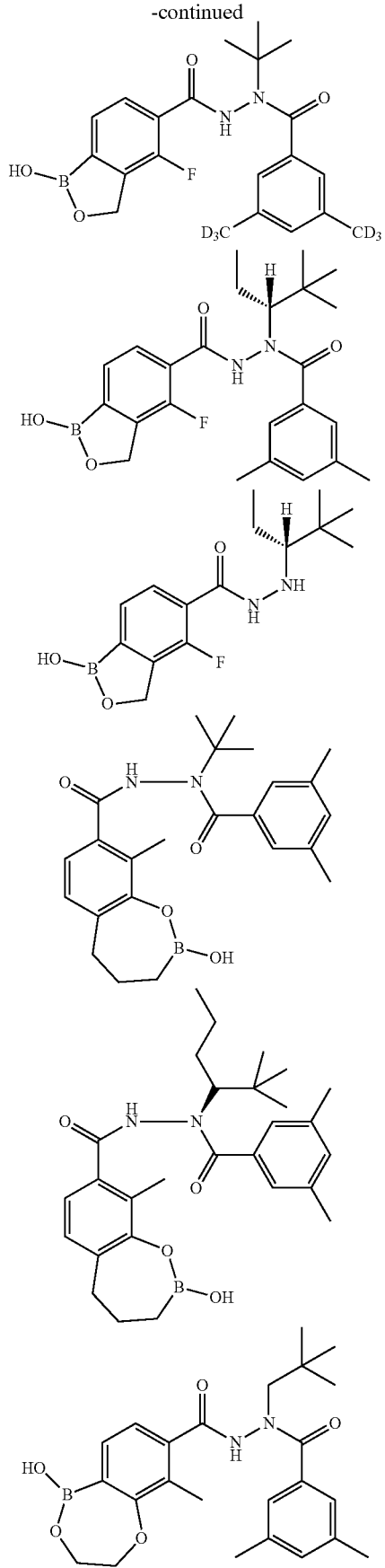
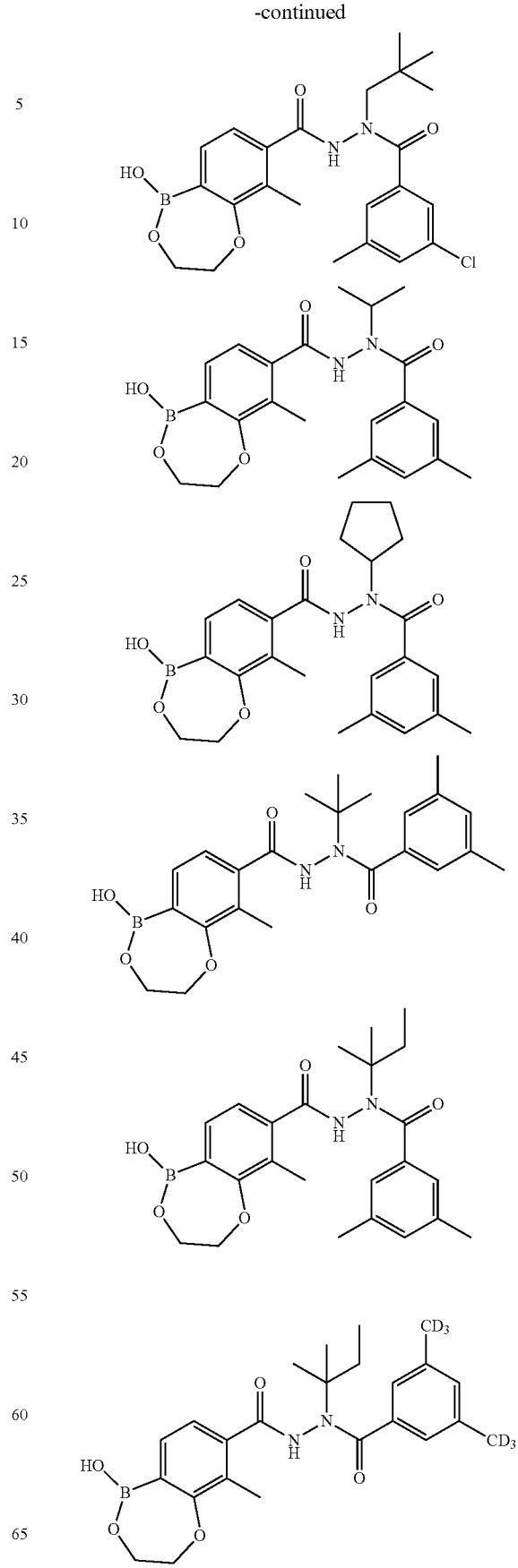

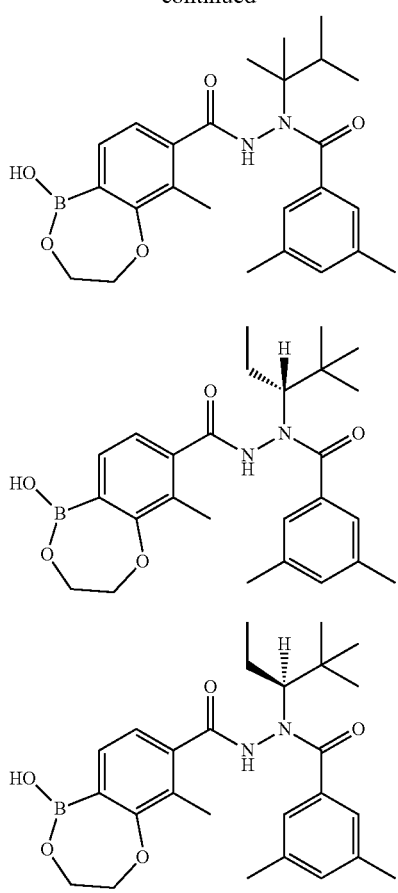
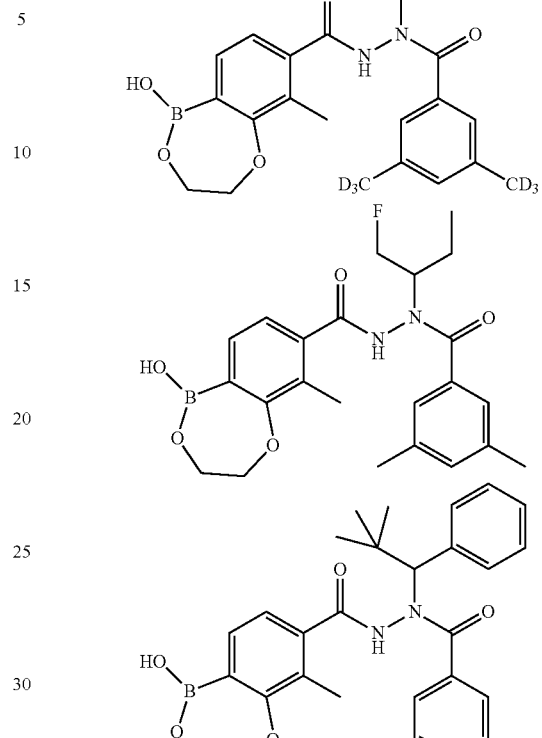
In another embodiment, Compounds of the Disclosure are compounds of Table A.
TABLE A
| Cpd No. | Structure | Name |
| --- | --- | --- |
| 85 | 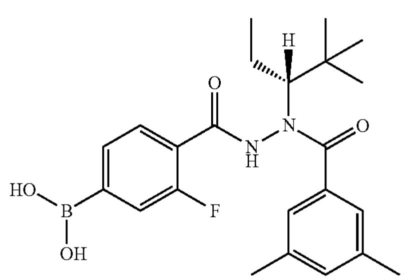 [SMILES: CC[C@@H](N(NC(=O)c1ccc(B(O)O)cc1F)C(=O)c1cc(C)cc(C)c1)C(C)(C)C] | (R)-(4-(2-(3,5-dimethylbenzoyl)-2-(2,2-dimethylpentan-3-yl)hydrazine-1-carbonyl)-3-fluorophenyl)boronic acid |
| 86 | 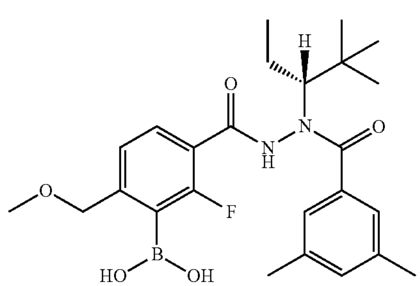 | (R)-(3-(2-(3,5-dimethylbenzoyl)-2-(2,2-dimethylpentan-3-yl)hydrazine-1-carbonyl)-2-fluoro-6-(methoxymethyl)phenyl)boronic acid |

TABLE A-continued

| Cpd No. | Structure | Name |
|---|---|---|
| 87 | 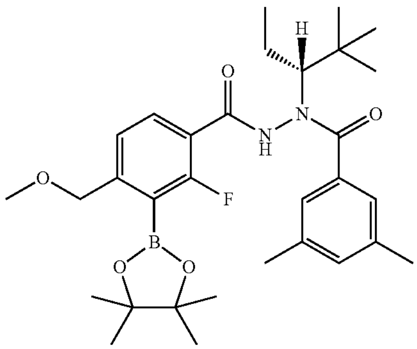 | (R)-N'-(3,5-dimethylbenzoyl)-N'-(2,2-dimethylpentan-3-yl)-2-fluoro-4-(methoxymethyl)-3-(4,4,5,5-tetramethyl-1,3,2-dioxaborolan-2-yl)benzohydrazide |
| 88 | 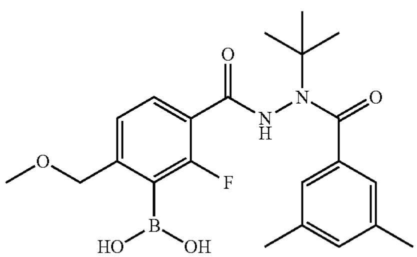 | (3-(2-(tert-butyl)-2-(3,5-dimethylbenzoyl)hydrazine-1-carbonyl)-2-fluoro-6-(methoxymethyl)phenyl)boronic acid |
| 89 | 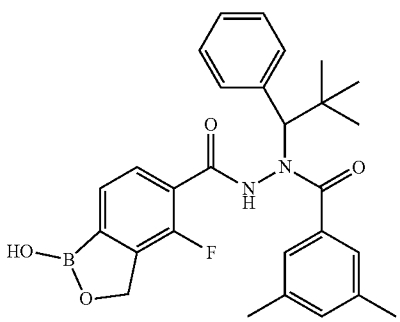 [SMILES: Cc1cc(C)cc(C(=O)N(NC(=O)c2ccc3c(c2F)COB3O)C(c2ccccc2)C(C)(C)C)c1] | N'-(2,2-dimethyl-1-phenylpropyl)-N'-(3,5-dimethylbenzoyl)-4-fluoro-1-hydroxy-1,3-dihydrobenzo[c][1,2]oxaborole-5-carbohydrazide |
| 90 | 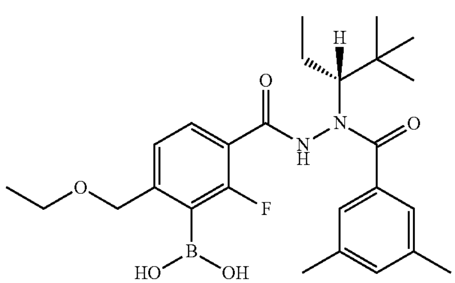 [SMILES: CCOCc1ccc(C(=O)NN(C(=O)c2cc(C)cc(C)c2)[C@H](CC)C(C)(C)C)c(F)c1B(O)O] | (R)-(3-(2-(3,5-dimethylbenzoyl)-2-(2,2-dimethylpentan-3-yl)hydrazine-1-carbonyl)-6-(ethoxymethyl)-2-fluorophenyl)boronic acid |
| 91 | 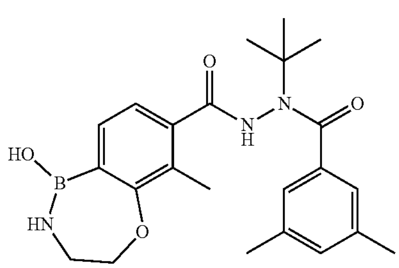 [SMILES: Cc1cc(C)cc(C(=O)N(NC(=O)c2ccc3c(c2C)OCCNB3O)C(C)(C)C)c1] | N'-(tert-butyl)-N'-(3,5-dimethylbenzoyl)-1-hydroxy-6-methyl-1,2,3,4-tetrahydrobenzo[f][1,4,5]oxazaborepine-7-carbohydrazide |

TABLE A-continued

| Cpd No. | Structure | Name |
|---|---|---|
| 92 | 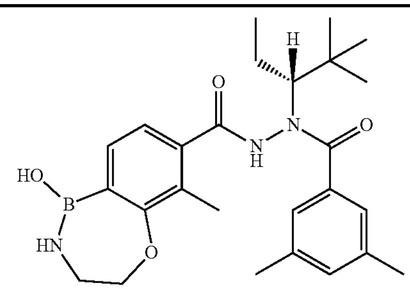 | (R)-N'-(3,5-dimethylbenzoyl)-N'-(2,2-dimethylpentan-3-yl)-1-hydroxy-6-methyl-1,2,3,4-tetrahydrobenzo[f][1,4,5]oxazaborepine-7-carbohydrazide |
| 93 | 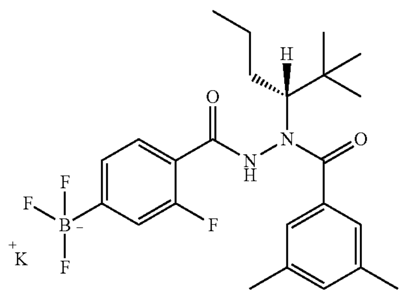 | potassium (R)-(4-(2-(3,5-dimethylbenzoyl)-2-(2,2-dimethylhexan-3-yl)hydrazine-1-carbonyl)-3-fluorophenyl)trifluoroborate |
| 94 | 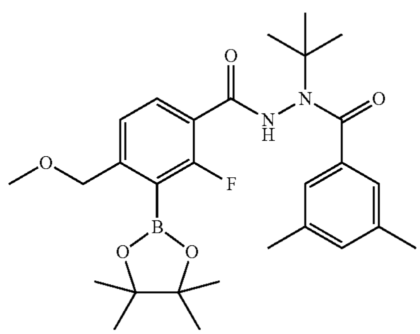 | N'-(tert-butyl)-N'-(3,5-dimethylbenzoyl)-2-fluoro-4-(methoxymethyl)-3-(4,4,5,5-tetramethyl-1,3,2-dioxaborolan-2-yl)benzohydrazide |
| 95 | 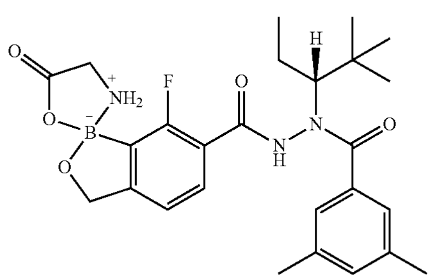 | N'-(3,5-dimethylbenzoyl)-N'-((R)-2,2-dimethylpentan-3-yl)-7-fluoro-5'-oxo-3H-1λ4-spiro[benzo[c][1,2]oxaborole-1,2'-[1,3,2]oxazaborolidine]-6-carbohydrazide |

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-10}$ alkyl groups include methyl (including —CD₃), ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, aylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$CH$_2$CO$_2$H, —CH$_2$CH$_2$SO$_2$CH$_3$, —CH$_2$CH$_2$COPh, —CH$_2$C$_6$H$_{11}$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent.

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl, cyclohexenyl and the like.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl. (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy; alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as pan of another group refers to a sulfur atom substituted by an optionally substituted alkyl group. In one embodiment, the alkylthio group is chosen from a $C_1$-4 alkylthio group. Non-limiting exemplary alkylthio groups include —$SCH_3$, and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized, and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —$CH_2OCH_2CH_2OCH_3$, —$OCH_2CH_2OCH_2CH_2OCH_3$, —$CH_2NHCH_2CH_2OCH_2$, —$OCH_2CH_2NH$, —$NHCH_2CH_2N(H)CH_3$, and —$OCH_2CH_2OCH_3$.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl. In one embodiment, the aryl group is phenyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-difluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include:

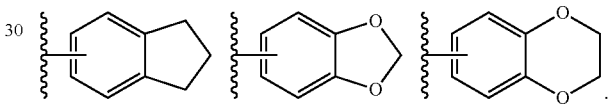

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "heteroaryloxy" as used by itself or as part of another group refers to an optionally substituted heteroaryl attached to a terminal oxygen atom.

For the purpose of the present disclosure, the term "aralkyloxy" or "arylalkyloxy" as used by itself or as part of another group refers to an aralkyl group attached to a terminal oxygen atom A non-limiting exemplary aralkyloxy group is $PhCH_2O$—.

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl; (carboxamido)alkyl, mercaptoalkyl, (heterocyclo)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-oxopyrrolidin-3-yl, 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino. (alkylamino)alkyl, (dialkylamino)alkyl, (cyano)alkyl, (carboxamido)alkyl, mercaptoalkyl, (heterocyclo)alkyl, (heteroaryl)alkyl, and the like. Substitution may occur on any available carbon or nitrogen atom, and may form a spirocycle.

For the purpose of the present disclosure, the term "amino" as used by itself or as part of another group refers to $-NH_2$.

For the purpose of the present disclosure, the term "alkylamino" as used by itself or as part of another group refers to $-NHR^{22}$, wherein $R^{22}$ is alkyl.

For the purpose of the present disclosure, the term "dialkylamino" as used by itself or as part of another group refers to $-NR^{23a}R^{23b}$, wherein $R^{23a}$ and $R^{23b}$ are each independently alkyl or $R^{23a}$ and $R^{23b}$ are taken together to form a 3- to 9-membered optionally substituted heterocyclo.

For the purpose of the present disclosure, the term "hydroxyalkylamino" as used by itself or as part of another group refers to $-NHR^{24}$, wherein $R^{24}$ is hydroxyalkyl.

For the purpose of the present disclosure, the term "cycloalkylamino" as used by itself or as part of another group refers to $-NR^{25a}R^{25b}$, wherein $R^{25a}$ is optionally substituted cycloalkyl and $R^{25b}$ is hydrogen or alkyl.

For the purpose of the present disclosure, the term "(amino)alkyl" as used by itself or as part of another group refers to an alkyl group substituted with an amino group. Non-limiting exemplary amino alkyl groups include $-CH_2CH_2NH_2$, $-CH_2CH_2CH_2NH_2$, $-CH_2CH_2CH_2CH_2NH_2$ and the like.

For the purpose of the present disclosure, the term "(alkylamino)alkyl" as used by itself or as part of another group refers to an alkyl group substituted with an alkylamino group. A non-limiting exemplary (alkylamino)alkyl group is $-CH_2CH_2N(H)CH_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is $-CH_2CH_2N(CH_3)_2$.

For the purpose of the present disclosure, the term "(cycloalkylamino)alkyl" as used by itself or as part of another group refers to an alkyl group substituted by a cycloalkylamino group. Non-limiting exemplary (cycloalkylamino) alkyl groups include $-CH_2N(H)cyclopropyl$, $-CH_2N(H)cyclobutyl$, and $-CH_2N(H)cyclohexyl$.

For the purpose of the present disclosure, the term "(cyano)alkyl" as used by itself or as part of another group refers to an alkyl group substituted with one or more cyano, e.g., $-CN$, groups. Non-limiting exemplary (cyano)alkyl groups include $-CH_2CH_2CN$, $-CH_2CH_2CH_2CN$, and $-CH_2CH_2CH_2CH_2CN$.

For the purpose of the present disclosure, the term "carboxamido" as used by itself or as part of another group refers to a radical of formula $-C(=O)NR^{26a}R^{26b}$, wherein $R^{26a}$ and $R^{26b}$ are each independently hydrogen, optionally substituted alkyl, optionally substituted aryl, or optionally substituted heteroaryl, or $R^{26a}$ and $R^{26b}$ taken together with the nitrogen to which they are attached from a 3- to 8-membered heterocyclo group. In one embodiment, $R^{26a}$ and $R^{26b}$ are each independently hydrogen or optionally substituted alkyl. Non-limiting exemplary carboxamido groups include $-CONH_2$, $-CON(H)CH_3$, $CON(CH_3)_2$, and $CON(H)Ph$.

For the purpose of the present disclosure, the term "(carboxamido)alkyl" as used by itself or as part of another group refers to an alkyl group substituted with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "sulfonamido" as used by itself or as part of another group refers to a radical of the formula —SO$_2$NR$^{27a}$R$^{27b}$, wherein R$^{27a}$ and R$^{27b}$ are each independently hydrogen, optionally substituted alkyl, or optionally substituted aryl, or R$^{27a}$ and R$^{27b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups are —CO$_2$Me and —CO$_2$Et.

For the purpose of the present disclosure, the term "aralkyl" as used by itself or as part of another group refers to an alkyl group substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, phenethyl, —CHPh$_2$, and —CH(4-F-Ph)$_2$.

For the purpose of the present disclosure, the term "ureido" as used by itself or as part of another group refers to a radical of the formula —NR$^{30a}$—C(=O)—NR$^{30b}$R$^{30c}$, wherein R$^{22a}$ is hydrogen, alkyl, or optionally substituted aryl, and R$^{30b}$ and R$^{30c}$ are each independently hydrogen, alkyl, or optionally substituted aryl, or R$^{30b}$ and R$^{30c}$ taken together with the nitrogen to which they are attached form a 4- to 8-membered heterocyclo group. Non-limiting exemplary ureido groups include —NH—C(C=O)—NH$_2$ and —NH—C(C=O)—NHCH$_3$.

For the purpose of the present disclosure, the term "guanidino" as used by itself or as part of another group refers to a radical of the formula —NR$^{28a}$—C(=NR$^{29}$)—NR$^{28b}$R$^{28c}$, wherein R$^{28a}$, R$^{28b}$, and R$^{28c}$ are each independently hydrogen, alkyl, or optionally substituted aryl, and R$^{29}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, —NH—C(C=NH)—NHCH$_3$ and the like.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a C$_{1-4}$ alkyl substituted with one optionally substituted heterocyclo group.

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a C$_{1-4}$ alkyl substituted with one optionally substituted heteroaryl group.

For the purpose of the present disclosure, the term "alkylcarbonylamino" as used by itself or as part of another group refers to an alkylcarbonyl group attached to an amino. A non-limiting exemplary alkylcarbonylamino group is —NHCOCH$_3$.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^1$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, AND $^{36}$Cl, respectively, e.g., $^3$H, $^{11}$C, and $^{14}$C. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number." Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well. For example, the following tautomers of R⁴-5 of Formula I are encompassed by the present disclosure:

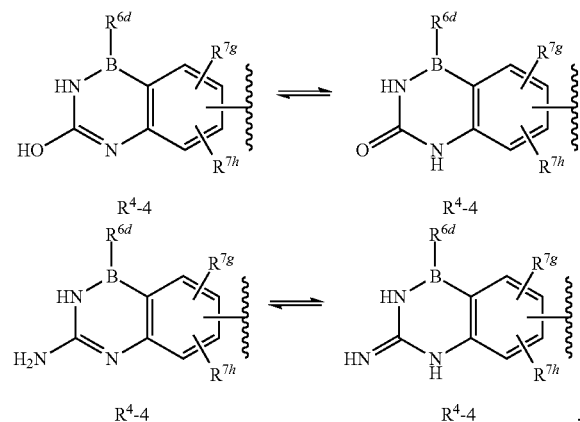

The following tautomers of R⁴-6 and R⁵-4 of Formula I are encompassed by the present disclosure:

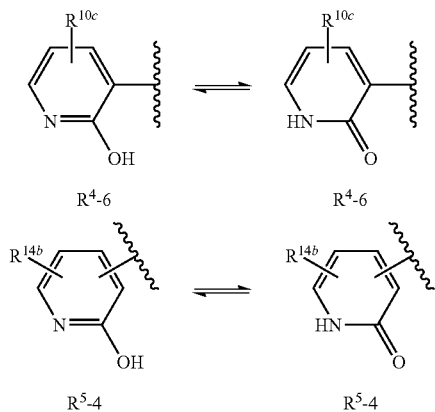

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68.2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The term "pharmaceutically acceptable salt" is meant to include boronic acid salts having the general formula:

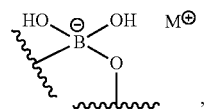

wherein M' is H' or a monovalent cation. By way of example, Compound 53 (see below) is converted to a pharmaceutically acceptable salt by reaction with NaOH according to the following scheme:

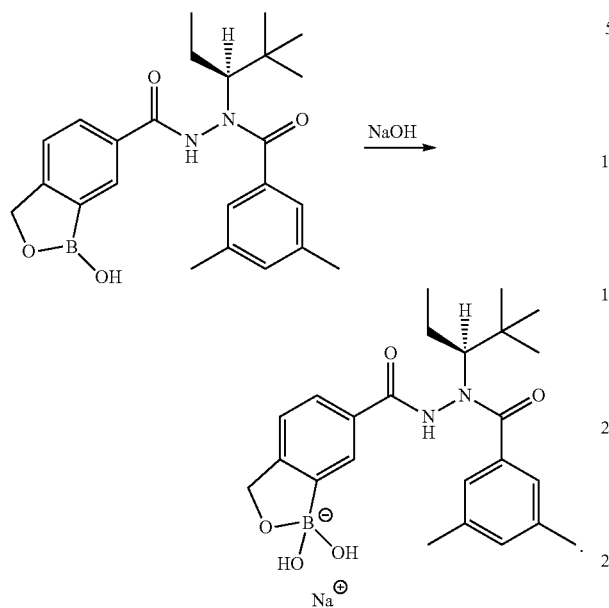

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93 (3); 601-611 (2004), which describes the preparation of solvates of fluconazole with ethyl acetate and with water. Similar preparation of solvates, hemisolvates, hydrates, and the like are described by E C, van Tonder et al., *AAPS Pharm. Sci. Tech*, 5 (1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25'C, then cooling the solution at a rate sufficient to form crystals, and isolating the crystals by known methods, e.g., filtration. Analytical techniques such as infrared spectroscopy can be used to confirm the presence of the solvent in a crystal of the solvate.

The term "fluoride adduct" as used herein refers to the condensation product of a boronic acid having the general formula $RB(OH)_2$ and $KHF_2$. The general structure of a fluoride adduct is:

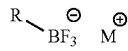

wherein $M^+$ is a monovalent cation. For example, the fluoride adduct of group $R^4$-5 of Formula I, wherein $R^{10a}$ is $-B(OH)_2$ is:

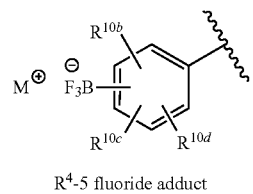

$R^4$-5 fluoride adduct

The term "hydroxy acid adduct" as used herein refers to the condensation product of a boronic acid having the general formula $(R)(RO)B-OH$ and a hydroxy acid having formula $HOOC-C(R')(R'')-OH$. $R'$ and $R''$ are each independently selected from hydrogen, carboxy, optionally substituted alkyl, aralkyl, aminoalkyl, haloalkyl, cyano, (cyano) alkyl. (carboxamido)alkyl, (carboxy)alkyl or hydroxyalkyl, and the like. $R'$ and $R''$ taken together with the carbon atom to which they are attached form a cycloalkyl or heterocyclo group. Non-limiting exemplary $R'/R''$ groups include hydrogen, $-CH_3$, $-OH$, $-CH(CH_3)_2$, $-CH(CH_3)(Et)$, $-CH_2Ph$, $-CH_2CH_2SCH_3$, $-CH_2CO_2H$, $-CH_2CH_2CO_2H$, $-(CH_2)_4NH_2$, $-CH_2OH$, $-CH(CH_3)OH$, $-CH_2Ph-OH$, $-CH_2$-imidazole, $-CH_2SH$, $-CH_2C(O)NH_2$, $-CH_2CH_2C(O)NH_2$, $-CH_2CH_2-$, $-CH_2CH_2CH_2-$, $-CH_2CH_2CH_2CH_2-$, $-CH_2CH_2CH_2CH_2CH_2-$, and $-CH_2CH_2OCH_2CH_2-$. In one embodiment, $R'$ is selected from the group consisting of $-CH_2Ph$, $-CO_2H$, $-CH_2CO_2H$, and $-CH_2CONH_2$. The general structure of a hydroxy acid adduct is:

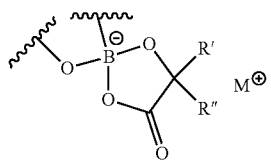

wherein $M^+$ is a monovalent cation. For example, the hydroxy acid adduct of group $R^4$-1 of Formula I is.

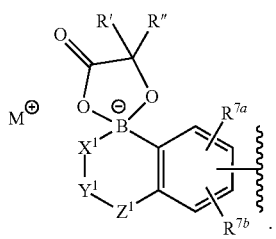

$R^4$-1 hydroxy acid adduct

The term "amino acid adduct" as used herein refers to the condensation product of a boronic acid having the general formula (R)RO)B—OH and a natural or unnatural, D- or L-, amino acid, including β-amino acids, e.g., an amino acid having formula HOOC—C(R'''XR'''')—NH$_2$. Suitable unnatural amino acids include, without limitation, the enantiomeric and racemic forms of 2-methylvaline, 2-methylalanine, (2-i-propyl)-β-alanine, phenylglycine, 4-methyl phenyl glycine, 4-i sopropylphenylglycine, 3-bromophenylglycine, 4-bromophenylglycine, 4-chlorophenylglycine, 4-methoxyphenylglycine, 4-ethoxyphenylglycine, 4-hydroxyphenylglycine, 3-hydroxyphenylglycine, 3,4-dihydroxyphenylglycine, 3,5-dihydroxyphenylglycine, 2,5-dihydrophenylglycine, 2-fluorophenylglycine, 3-fluorophenylglycine, 4fluorophenylglycine, 2,3-difluorophenylglycine, 2,4-difluorophenylglycine, 2,5-difluorophenylglycine, 2,6-difluorophenylglycine, 3,4-di fluorophenylglycine, 3,5-difluorophenylglycine, 2-(trifluoromethyl)phenylglycine, 3-(trifluoromethyl)phenylglycine, 4-(trifluoromethyl)phenylglycine, 2-(2-thienyl)glycine, 2-(3-thienyl)glycine, 2-(2-furyl)glycine, 3-pyridylglycine, 4-fluorophenylalanine, 4-chlorophenylalanine, 2-bromophenylalanine, 3-bromophenylalanine, 4-bromophenylalanine, 2-naphthylalanine, 3-(2-quinolyl)alanine, 3-(9-anthracenyl)alanine, 2-amino-3-phenylbutanoic acid, 3-chlorophenylalanine, 3-(2-thienyl)alanine, 3-(3-thienyl)alanine, 3-phenylserine, 3-(2-pyridyl)serine, 3-(3-pyridyl)serine, 3-(4-pyridyl)serine, 3-(2-thienyl)serine, 3-(2-furyl)serine, 3-(2-thiazolyl)alanine, 3-(4-thiazolyl)alanine, 3-(1,2,4-triazol-1-yl)-alanine, 3-(1,2,4-triazol-3-yl)-alanine, hexafluorovaline, 4,4,4-trifluorovaline, 3-fluorovaline, 5,5,5-trifluoroleucine, 2-amino-4,4,4-trifluorobutyric acid, 3-chloroalanine, 3-fluoroalanine, 2-amino-3-flurobutyric acid, 3-fluoronorleucine, 4,4,4-trifluorothreonine, L-allylglycine, tert-Leucine, propargylglycine, vinylglycine, S-methyicysteine, cyclopentylglycine, cyclohexylglycine, 3-hydroxynorvaline, 4-azalcucine, 3-hydroxyleucine, 2-amino-3-hydroxy-3-methylbutanoic acid, 4-thiaisoleucine, acivicin, ibotenic acid, quisqalic acid, 2-indanylglycine, 2-aminoisobutyric acid, 2-cyclobutyl-2-phenylglycine, 2-isopropyl-2-phenylglycine, 2-methylvaline, 2,2-diphenylglycine, 1-amino-1-cyclopropanecarboxylic acid, 1-amino-1-cyclopentanecarboxylic acid, 1-amino-1-cyclohexanecarboxylic acid, 3-amino-4,4,4-trifluorobutyric acid, 3-phenylisoserine, 3-amino-3-hydroxy-5-methylhexanoic acid, 3-amino-2-hydroxy-4-phenylbutyric acid, 3-amino-3-(4-bromophenyl)propionic acid, 3-amino-3-(4-chlorophenyl)propionic acid, 3-amino-3-(4-methoxyphenyl)propionic acid, 3-amino-3-(4-fluorophenyl)propionic acid, 3-amino-3-(2-fluorophenyl)propionic acid, 3-amino-3-(4-nitrophenyl)propionic acid, and 3-amino-3-(1-naphthyl)propionic acid. These non-natural amino acids are commercial available from the following commercial suppliers including Aldrich, Sigma, Fluka, Lancaster. ICN, TCI, Advanced ChemTech, Oakwood Products, Indofine Chemical Company, NSC Technology, PCR Research Chemicals, Bachem, Acros Organics, Celgene, Bionet Research, Tyger Scientific, Tocris, Research Plus, Ash Stevens, Kanto, Chiroscience, and Peninsula Lab. The following amino acids can be synthesized according to literature procedures; 3,3,3-trifluoroalanine (Sakai, T.; et al., Tetrahedron 1996, 52, 233) and 3,3-difluoroalanine (D'Orchymont, H. Synthesis 1993, 10, 961). Other N-protecting groups that can be used in the place of Z include Acetyl (Ac), tert-butoxycarbonyl (Boc), methoxycarbonyl, or ethoxycarbonyl. Non-limiting exemplary R'''/R'''' groups include hydrogen. CH$_3$, OH, —CH(CH$_3$)$_2$, —CH(CH)(Et), —CH$_2$Ph. —CH$_2$CH$_2$SCH$_3$, —CH$_2$CH, —CH$_2$CH$_2$CO$_2$H, —(CH$_2$)$_4$NH$_2$, —CH$_2$OH, —CH(CH$_3$)OH, —CH$_2$Ph-OH, —CH$_2$-imidazole, —CH$_2$SH, —CH$_2$C(O)NH$_2$, and —CH$_2$CH$_2$C(O)NH$_2$. The general structure of a hydroxy acid adduct is:

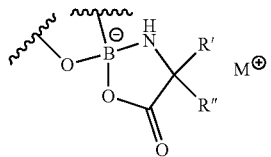

wherein M$^-$ is H$^+$ or a monovalent cation. By way of example, the amino acid adduct of group R$^4$-1 of Formula I is:

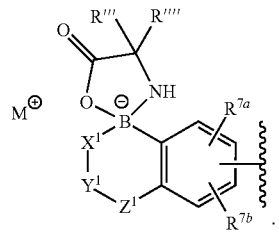

R$^4$-1 amino acid adduct

The term "monovalent cation" as used herein refers to inorganic cations such as, but not limited to, alkaline metal ions, e.g., Na' and K', as well as organic cations such as, but not limited to, ammonium and substituted ammonium ions, e.g., NH$_4^+$, NHMe$_3^+$, NH$_2$Me$_2^+$, NHMe$_3^+$ and NMe$_4^+$.

As used herein, the term "micronization" refers to a process or method by which the size of a population of particles is reduced, typically to the micron scale.

As used herein, the term "micron" or "μm" refer to "micrometer," which is 1×10$^{-6}$ meter.

In another aspect, the present disclosure provides compositions comprising a Compound of the Disclosure and one or more excipients. In one embodiment, the excipient comprises dimethyl sulfoxide or acetone. In one embodiment, the composition comprises a pharmaceutically acceptable excipient, to provide a "pharmaceutically acceptable composition." In another embodiment, the composition comprises micronized Compounds of the Disclosure. In another embodiment, the pharmaceutically acceptable excipient comprises Miglyol 812, phospholipon 90G, or tocopheryl polyethylene glycol 1000 succinate, or a mixture thereof. In another embodiment, the pharmaceutically acceptable excipient consists essentially of Miglyol 812, phospholipon 90G, and tocopheryl polyethylene glycol 1000 succinate. In another embodiment, the pharmaceutically acceptable excipient comprises Labrasol®. In another embodiment, the pharmaceutically acceptable excipient comprises sorbitan monolaurate, hydtoxypropylmethylcellulose acetate succinate, sodium taurocholate, Ethocel™ or palmitoyl-oleoyl-phosphatidylcholine, or a mixture thereof. In another embodiment, the pharmaceutically acceptable excipient comprises hydrogenated soy lecithin. Compound of the Disclosure can be admixed with one or more excipients using method well known to those of ordinary skill in the art.

In another embodiment, the excipient comprises ethanol, isopropand, propylene glycol, benzyl alcohol, glycerin, sorbitol, sucrose, carbopol, maltodextrin, lycasin (maltitol), sodium benzoate, sodium saccharide, lutrol E, F, methyl paraben, propyl paraben, citric acid, capryol 90, Tween 80 (polysorbate 80), Kollidon® CL-M, polyoxyl stearate, hydroxypropyl methyl cellulose, Cremophor® RH 40, Cremophor® EL, sodium carboxymetyhl cellulose (CMC), guar gum, xanthan gum, polyethylene glycol, or polyvinyl pyrrolidone, or a mixture thereof.

In another embodiment, the excipient comprises Labrafil®, Labrasol®, Gelucire®, Labrafac®, Lauroglycol™ 90, Peceol™, Transcutol®, Compritol®, Geloil®, Geleol™, or Precirol®, or a mixture thereof.

In another embodiment, the excipient comprises capmul, Captex®, or Acconon®, or a mixture thereof.

In another embodiment, the excipient comprises DYNACERIN®, DYNACET®, DYNASAN, GALENOL®, IMWITOR (Glyceryl Monooleate, Stearate, Caprylate), ISOFOL® (long chain alcohols), LIPOXOL® (Macrogol), MASSA ESTARINUM (Hydrogenated Coco-Glycerides), MIGLYOL (Caprylic/Capric Triglyceride), NACOL®, Nafol (alcohols), SOFTIGEN®, SOFTISAN®, WITEPSOL (Hydrogenated Coco-Glycerides), or WITOCAN® (Hydrogenated Coco-Gly), or a mixture thereof.

In another embodiment, the excipient comprises hypromellose acetate succinate.

In another embodiment, the excipient comprises Soluplus® (polyvinylcaprolactam-polyvinyl acetate-polyethylene glycol graft copolymer.

Compositions may contain from 0.01% to 99% by weight of a Compound of the Disclosure, e.g., about 1%, about 2%, about 3%, about 4%, about 5%, about 6%, about 7%, about 8%, about 9%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. The amount in any particular composition will depend upon the effective dose, that is, the dose required to elicit the desired level of gene expression.

In another aspect, the present disclosure provides micronized Compounds of the Disclosure, and compositions thereof. In one embodiment, the average particle size distribution of the micronized form of a Compound of the Disclosure is about 20 μm or less, e.g., about 19 μm, about 18 μm, about 17 μm, about 16 μm, about 15 μm, about 14 μm, about 13 μm, about 12 μm, or about 11 μm, or less. In another embodiment, the average particle size distribution is about 10 μm or less, e.g., about 9 μm, about 8 μm, about 7 μm, about 6 μm, or about 5 μm, or less. In another embodiment, the average particle size distribution is about 5 μm or less, e.g. about 4 μm, about 3 μm, about 2 μm, or about 1 μm, or less. In another embodiment, the average particle size distribution is about 1 μm or less, e.g., about 0.9 μm, about 0.8 μm, about 0.7 μm, about 0.6 μm, about 0.5 μm, about 0.4 μm, about 0.3 μm, about 0.2 μm, about 0.1 μm, about 0.09 μm, about 0.08 μm, about 0.07 μm, about 0.06 μm, about 0.05 μm, about 0.04 μm, about 0.03 μm, about 0.02 μm, or about 0.01 μm or less.

In another aspect, the present disclosure provides methods of making a composition, comprising admixing a Compound of the Disclosure, or a micronized Compound of the Disclosure, with one or more excipients. In one embodiment, the excipient is a pharmaceutically acceptable excipient.

In another aspect, the present disclosure provides methods of regulating gene expression of a gene of interest in a host cell, comprising contacting the host cell with a Compound of the Disclosure, or a composition thereof. In one embodiment, the host cell comprises a polynucleotide encoding a gene switch comprising a ligand binding domain that binds a Compound of the Disclosure, wherein the level of expression of the gene of interest is increased, relative to the level of expression of the gene of interest in the absence of a Compound of the Disclosure. In another embodiment, the host cell is an isolated host cell. In certain other embodiments, an isolated host cell is genetically modified ex-vivo (e.g., transformed, transfected or infected) with a polynucleotide construct encoding a gene switch comprising a ligand binding domain that binds a Compound of the Disclosure. In another embodiment, the ex-vivo genetically modified host cell is administered to a subject. In certain embodiments, the expression of a gene of interest is under the control of the gene switch comprising a ligand binding domain that binds a Compound of the Disclosure. In another embodiment, the host cell is in a subject. e.g., an animal, e.g., a human. For example, one or more cells (host cells) in a subject may be genetically modified in-vivo by administering a viral vector to the subject (or a select population of host cells thereof), wherein the viral vector comprises a polynucleotide encoding a gene switch comprising a ligand binding domain that binds a Compound of the Disclosure. In yet other embodiments, the host cell is an autologous host cell obtained from a mammalian subject, wherein the autologous host cell is genetically modified with a polynucleotide construct encoding a gene switch comprising a ligand binding domain that binds a Compound of the Disclosure. In another embodiment, the host cell is an allogeneic stem cell or immune cell, wherein the allogenic host cell is genetically modified with a polynucleotide construct encoding a gene switch comprising a ligand binding domain that binds a Compound of the Disclosure. In another embodiment, a Compound of the Disclosure is administered to a subject as a pharmaceutically acceptable composition. In another embodiment, the gene switch comprises an ecdysone receptor (EcR) ligand binding domain that binds a Compound of the Disclosure. In another embodiment, the gene switch further comprises a second ligand binding domain that dimerizes with a first ligand binding domain (for example, an EcR ligand binding domain) that binds a Compound of the Disclosure. In one embodiment, an EcR ligand binding domain comprises one or more amino acid substitutions compared to the corresponding wild-type EcR polypeptide sequence. In another embodiment, the second ligand binding domain is a retinoic X receptor ligand binding domain. In another embodiment, the second ligand binding domain is a wild-type insect USP (Ultraspiracle protein). In another embodiment, the retinoic X receptor (RxR) ligand binding domain is a chimeric retinoic X receptor ligand binding domain. In another embodiment, the chimeric ligand binding domain is an mammalian RxR/invertebrate USP chimera. In another embodiment, the host cell further comprises a polynucleotide encoding a peptide, protein or polypeptide whose expression is regulated by the gene switch.

In another aspect, the present disclosure provides methods of treating a disease, disorder, injury, or condition in a subject, comprising administering to the subject a Compound of the Disclosure, or a composition thereof. In one embodiment, a vector (or two or more vectors) comprises a polynucleotide (or polynucleotides) encoding a gene switch that comprises a ligand binding domain that binds a Compound of the Disclosure. In one embodiment, the vector (or vectors) may be a DNA or RNA vector. In one embodiment, the vector (or vectors) may be a plasmid or viral vector (for example, an adenovirus vector or an adeno-associated viral vector). In one embodiment, a vector (or vectors) comprising a polynucleotide (or polynucleotides) encoding a gene switch that comprises a ligand binding domain that binds a Compound of the Disclosure is administered to a subject to treat a disease, disorder, injury, or condition in the subject. In one embodiment, following administration of a Compound of the Disclosure, a gene-of-interest (GOI) is expressed in vivo in a subject from a vector (or vectors) comprising a polynucleotide (or polynucleotides) encoding a GOI and comprising a gene switch that comprises a ligand binding domain that binds a Compound of the Disclosure. In one embodiment, a host cell within the subject comprises a polynucleotide encoding a gene switch that comprises a ligand binding domain that binds a Compound of the Disclosure. In one embodiment, a host cell within a non-human organism comprises a polynucleotide encoding a gene switch that comprises a ligand binding domain that binds a Compound of the Disclosure. In another embodiment, the subject is human. In another embodiment, the disease, disorder, injury, or condition is selected from the group consisting of cancer, metabolic-related disorder, kidney disease, anemia, autoimmune disorder, ocular disorder, blood disorder, neurological disorder, lung disorder, rheumatologic disorder, and infectious disease. In another embodiment, the disease, disorder, injury, or condition is selected from the group consisting of cancer, metabolic-related disorder, kidney disease, anemia, autoimmune disorder, ocular disorder, blood disorder, neurological disorder, pulmonary (lung) disorder, rheumatologic disorder, cardiac disorder, hepatic (liver) disorder and infectious disease. In another embodiment, the disease, disorder, injury, or condition is selected from the group consisting of cardiac disorder and hepatic (liver) disorder. In another embodiment, the disease, disorder, injury, or condition is cancer. In another embodiment, the cancer is melanoma. In another embodiment, the gene switch comprises an ecdysone receptor (EcR) ligand binding domain. In another embodiment, the gene switch further comprises a second ligand binding domain that dimerizes with a first ligand binding domain (for example, an EcR ligand binding domain) that binds a Compound of the Disclosure. In one embodiment, an EcR ligand binding domain comprises one or more amino acid substitutions compared to the corresponding wild-type EcR polypeptide sequence. In another embodiment, the second ligand binding domain is a wild-type insect USP (Ultraspiracle protein). In another embodiment, the second ligand binding domain is a retinoic X receptor ligand binding domain. In another embodiment, the retinoic X receptor (RxR) ligand binding domain is a chimeric retinoic X receptor ligand binding domain. In another embodiment, the chimeric ligand binding domain is a mammalian RxR/invertebrate USP chimera. In another embodiment, the host cell further comprises a polynucleotide encoding a peptide, protein, or polypeptide whose expression is regulated by the gene switch. In another embodiment, the gene switch regulates the expression of a polynucleotide encoding IL-12 or a subunit thereof. (See, for example, US 2011/0268766).

In another embodiment, the present disclosure provides a Compound of the Disclosure, or a composition thereof, for use in treating a disease, disorder, injury, or condition in a subject.

In another embodiment, the present disclosure provides a Compound of the Disclosure, or a composition thereof, for use in the manufacture of a medicament for treating a disease, disorder, injury, or condition in a subject.

In another aspect, the present disclosure provides kits comprising a Compound of the Disclosure, or kits comprising a composition of a Compound of the Disclosure and one or more excipients. In one embodiment, the kit further comprises instructions for administering a Compound of the Disclosure to an isolated host cell or a subject. In another embodiment, the kit further comprises the RHEOSWITCH THERAPEUTIC SYSTEM® (see, for example, the Instruction Manual for "RHEOSWITCH ® Mammalian Inducible Expression System," New England BioLabs' Inc., Version 1.3, November 2007; Karzenowski, D. et al., *BioTechiques* 39:191-196 (2005); Dai, X el aL, *Protein Expr. Purif.* 42:236-245 (2005); Palli, S. R. et al., *Eur. J. Biochem.* 270:1308-1515 (2003); Dhadialla, T. S. et al., *Annual Rev. Entomol.* 43.545-569 (1998); Kumar, M. B. et al., *J. Biol. Chem.* 279:27211-27218 (2004); Verhaegent, M. and Christopoulos, T. K., *Annal. Chem.* 74:4378-4385 (2002); Katalam, A. K., et al., *Molecular Therapy* 13; S103 (2006); and Karzenowski, D. et al., *Molecular Therapy* 13; S194 (2006)).

Compounds of the Disclosure may be administered to a subject in conjunction with other pharmaceutically active compounds. It will be understood by those skilled in the art that pharmaceutically active compounds to be used in combination the Compound of the Disclosure will be selected in order to avoid adverse effects on the recipient or undesirable interactions between the compounds. Examples of other pharmaceutically active compounds which may be used in combination a Compound of the Disclosure, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflammatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases a Compound of the Disclosure may be useful as an adjunct to drug therapy, for example, to "turn off" a gene that produces an enzyme that metabolizes a particular drug.

For agricultural applications, Compounds of the Disclosure, or compositions thereof, may be used to control the expression of pesticidal proteins such as *Bacillus thuringiensis* (Bt) toxin. Such expression may be tissue or plant specific. In addition, particularly when control of plant pests is also needed, one or more pesticides may be combined with Compound of the Disclosure, or compositions thereof, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone Examples of pesticides which can be combined in compositions with Compounds of the Disclosure include fungicides, herbicides, insecticides, miticides, and microbicides.

In other agricultural embodiments, Compounds of the Disclosure may be used to control the expression of one or more genes of interest (GOIs). Exemplary GOIs include any desired trait, whether the trait is an agronomic trait, input trait, such as herbicide- or insecticide-resistance, nutritionally-desirable GOIs for the end consumer (animal or human), as well as desired GOIs for efficient processing of the plant product. Thus, in certain embodiments, a plant cell, a plant tissue, a whole plant and the like, is genetically modified with a polynucleotide encoding a gene switch, wherein the expression of one or more GOIs are under the control of the gene switch. Likewise, in certain embodiments, a fungal cell, a bacterial cell or a yeast cell is genetically modified with a polynucleotide encoding a gene switch, wherein the expression of one or more GOIs are under the control of the gene switch.

Ecdysone receptors in insects are naturally responsive to the ecdysone steroid hormone (molting hormone) and other steroidal compounds such as ponasterone A and muristerone A. (Graham et al., *Insect Biochemistry and Molecular Biology* 37:611-626 (2007); Dinan and Hormann, "Ecdysteroid Agonists and Antagonists," *Comprehensive Molecular Insect Science*, 1st ed.: 197-242, (2005)). Diacylhydrazines having ecdysone receptor agonist activity have been described as insecticides. (See U.S. Pat. No. 5,530,028).

In another aspect, the present disclosure provides a method of controlling, e.g., reducing or preventing the spread of, or killing, insects comprising contacting the insects or their habitat with an insecticidally effective amount of a Compound of the Disclosure, or a composition thereof. In another embodiment, Compounds of the Disclosure, or a composition thereof, are insecticidally active against:

(1) insects from the order of the lepidopterans (Lepidoptera), for example, *Agrotis ipsilon, Agrotis segetum, Alabama argillacea, Anficarsia gemmatalis, Argyresthia conjugella, Autographa gamma. Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitdalls, Dlatraea grandiosella, Earias insulana, Elasmopalpus lignosellus, Eupoecilia ambiguella, Evetria houliana, Feltia subterranea, Galleria mellonella, Grapholitha funebrana, Grapholitha molesta, Heliothis armigera, Hellothis virescens, Heliothis zea. Hellula undalis, Hibernia defoliaria, Hyphantria cunea, Hyponomeuta malinellus, Keiferia lycopersicella, Lambina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetra clerkella, Malacosoma neustria, Mamestra brassicae, Orgyia pseudotsugata, Ostrinia mibilalls, Panolls flammea, Pectinophora gossvpiella, Peridroma saucia, Phalera bucephala, Phthorimaea operculella, Phyllocnistis citrella, Pieris brassicae, Plathypena scabra, Plutella rylostella, Pseudophisia includens, Rhyacionia frustrana, Scrobipalpula absoluta, Sitotroga cerealella, Sparganothis pilleriana, Spodoptera fruglperda, Sodoptera littoralls, Spodoptera litura, Thaumatopoea pityucumpa, Tortrix vtridana, Trichoplusia ni* and *Zeiraphera Canadensis;*

(2) beetles (Coleoptera), for example, *Agrilus simiatus, Agriotes lineatus, Agriotes obscurus, Amphimalus solstitialis, Anisadrus dispar, Anthonomus grandis, Anthonomus pomorum, Aphthona euphoridae, Athous haemorrhoidals, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa. Diabrotica virgifera, Epilachna varivestis, Epitrix hiirtpennis, Eutinobothrus brasiilensis, Hylobius abietis, Hypera brurmeipennis, Hypera postica, lps typographus, Lema bilineata, Lema melanopus, Leptinotarsa decemlineata, Limonius californtius, Lissorhopirus oryzophilus, Melanotus communis, Meligethes aeneus, Melolontha hippocastani, Melolontha melolontha, Oulema oryzae, Otiorrhynchus sulcatus, Otiorrhynchns ovatus, Phaedon cochlearia, Phyllobius pyri, Phyllotrela chrymocephala, Phyllophaga* sp., *Phyllopertha horticola, Phyllotreta nemorum, Phyilotreca striolaia, Popillia japonica, Sitona lineatus* and *Sitophilus granaria;*

(3) flies, mosquitoes (Diptera), for example, *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrycsomya hominivorax, Chrysomya macellaria, Chrysops discails, Chrysops silacea, Chrysops allanticus, Cochliomyla hominivorax, Contarinia sorghicola, Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicaie, Delia antique, Delia coarctata, Della platura, Della radicum, Dermnatobia hominis, Fannia canicularis, Geomyza Tripunctata, Gasterophilus intesvinalis, Glossina morsifians, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativa, Liriomyza trifolii, Lucilia caprina, Lucilia cuprina, Lucilla sericata, Lycoria pectoralis, Mansonia titillanus, Mayetiola destructor, Musca domestic, Muscina stabulans, Oestus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimullum mixtum, Rhagoletis cerasi, Rhagoletis pomonella, Sarcophaga haemorrhoidalis, Sarcophaga* sp., *Simulium vittatum, Stomoxys calitrans, Tabanus bovinus, Tabamus atratus, Tabanus lineola,* and *Tabanus similis, Tipula oleracea,* and *Tipulapaludosa:*

(4) thrips (Thysanoptera), for example, *Dichromothrips corbetti, Dichromothrips ssp, Frankliniella fusca, Frankllniella occidentalls, Frankllniella tritici, Scirtothrlps citri, Thrips olyzae, Thrips palmi* and *Thrips tabaci.*

(5) termites (Isoptera), for example, *Calotermes flavicollis, Leucotermes flavipes, Heterotermes aureus, Reticultermes flavipes, Retfculltermes virginicus, Reticulltermes lucifugus, Termes natalensis,* and *Coptotermec formocanuc,*

(6) cockroaches (Blattaria-Blattodea), for example, *Blattella germanica, Blanilla asahinae, Periplaneta americana, Periplaneta japonica, Periplaneta brunnea, Periplaneta fuligginosa, Periplaneta ausiralasiae,* and *Blatta orientalis;*

(7) true bugs (Hemiptera), for example, *Acrosternum hilare, Blissus leucopterus, Cyrtopeltis notatus, Dysdercus cingulatus, Dygsdercus intermedius, Eurygaster intergriceps, Euschistus impictivenfris, Leptoglossus phyllopus, Lygus llneolaris, Lygus pratensis, Nezara viriduia, Piesma quadrata, Solubea insularis, Thyanta perditor, Acyrthosiphon onobrychis, Adelges laricis, Aphidula nasturti; Aphis fabae, Aphis forbesi, Aphis pomi, Aphis gossypii, Aphis grossulariae, Aphis schneideri, Aphis spiraecola, Aphis sambuci, Acyrihosiphon pisum, Aulacofthum solani, Bemisia argetifolii, Brachycaudus cardui, Brachycaudus helichrysi, Brachycaudus persicae, Brachycaudtrc pruinicola, Brevicoryne brassicae, Capiftophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dycaphis pyri, Empaosca fabae, Hyalopterus pruni, Hyperomyzus, lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mall, Psylla piri, Rhopalomyzus ascalonicus, Rhopalosiphum maidis, Rhopalosiphum padi, Rhopalosiphum inserfum, Sappaphic mala, Sappaphis mali, Schizaphis gramimum, Schizoneura lanuginosa, Sitobion avenae, Trialeurodes vaporariorum, Toxoptera aurantiiand, Viteus vitifolli, Cimex lectularius, Cimex hemipterus, Reduvius senilis, Triatoma spp.,* and *Arilus criatus;*

(8) ants, bees, wasps, sawflies (Hymenoptera), for example, *Athalia rosae, Atta cephalotes, Atta capiguara, Atta cephalotes, Afta laevigata, Atta robusta, Atta sexdens, Alta texana, Crematogaster* spp., *Hoplocampa minuta, Hoplocampa testudinea, Monomorium pharaonls, Solenopsis geminata, Solenopsis invicta, Solenopsis richteri, Soenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vesspa crabro, Polistes rubiginosa, Camponotus floridamus,* and *Linepithema humile;*

(9) crickets, grasshoppeis, locusts (Orthopteta), for example, *Acheta domestica, Gryllotalpa gryliotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americans, Schistocerca gregaria, Dociostaurus maroccanus, Tachycines asynamorus, Oedaleus senegalensis, Zonozerus variegatus, Hieroglyphus daganensis, Krasusaria angulifera, Calliptamus itallcus, Chortoicetes terminifera,* and *Locustana pardalina;*

(10) Arachnoidea, such as arachnids (Acarina), for example, of the families Argasidae, Ixodidae and Sarcoptidae, such as *Amblyomma americanum, Amblyomma variegatum, Ambryomma maculatum, Argas persicus, Boophilus antmulatus, Boophilus decoloratus, Boophilus microplus, Dermacentor silvarum, Dermacentor andersoni, Dermacentor variabllis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni, Tarsonemidae* spp. such as *Phytonemts pallidus* and *Polyphagotarsonemus latus; Temripalpidae* spp. such as *Brevipalpus phoenicis; Tetrarychidae* spp. such as *Tetranychus cinnabarinus, Tetranychus kanzawai, Tetrawychus pacificus, Tetranychus telarius* and *Tetranychus urticae, Panonychus ulmi, Panonychus citri,* and *Oligonychus pratensis; Araneida,* e.g., *Lafrodectus mactans,* and *Loxosceles reclusa,*

(11) fleas (Siphonaptera), for example, *Ctenocephalides felis, Ctenocephalides canis, Xenopsylla cheopis, Pulex irrifians, Tunga penefrans,* and *Nosopsyllus fasciatus,*

(12) silverfish, firebrat (Thysanura), for example, *Lepisma saccharins* and *Thermobia* domestics:

(13) centipedes (Chilopoda), for example, *Scutigera coleoptrata,*

(14) millipedes (Diplopoda), for example, *Narceus* spp.,

(15) Earwigs (Dermaptera), for example, *forifcula auricularia;* and/or

(16) lice (Phthiraptera), for example, *Pediculus humamus capitis, Pediculus humanus corporis, Pthirus pubis, Haematopinus eurystermus, Haematopinus suis, Linognathus vituli, Bovicola bovis, Menopan gallinae, Menacanthus stramimeus* and *Solenopotes capillatus.*

In another embodiment, Compounds of the Disclosure, or compositions thereof, are insecticidally active against insects of the order Diptera, Hemiptera, and/or Lepidoptera. In another embodiment, Compounds of the Disclosure, or a composition thereof, are insecticidally active against insects of the order Lepidoptera. In another embodiment, Compound of the Disclosures, or a composition thereof, are insecticidally active against insects of the order Hemiptera.

Compounds of the Disclosure, or compositions thereof, can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, and the ligand application rate. It may be desirable to include additional adjuvants in the spray tank. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials,* and McCutcheon's Functional Materials, all published annually by McCutcheon Division of MC Publishing Company (New Jersey). Compounds of the Disclosure, or compositions thereof, can also be mixed with fertilizers or fertilizing materials before their application. Compounds of the Disclosure, or compositions thereof, and solid fertilizing material can also be admixed in mixing or blending equipment, or they can be incorporated with fertilizers in granular formulations. Any relative proportion of fertilizer can be used which is suitable for the crops and weeds to be treated. Compounds of the Disclosure, or compositions thereof, will commonly comprise from 5% to 50% of the fertilizing composition. These compositions provide fertilizing materials which promote the rapid growth of desired plants, and at the same time control gene expression.

As used herein, the term "therapeutically effective amount," refers to the amount of a Compound of the Disclosure sufficient to treat one or more symptoms of a disease, condition, injury, or disorder, or prevent advancement of disease, condition, injury, or disorder, or cause regression of the disease, condition, injury, or disorder. For example, with respect to the treatment of cancer, in one embodiment, a therapeutically effective amount will refer to the amount of a Compound of the Disclosure that decreases the rate of tumor growth, decreases tumor mass, decreases the number of metastases, increases time to tumor progression, or increases survival time by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

As used herein, the term "insecticidally effective amount" refers to the amount of a Compound of the Disclosure sufficient to control, e.g., reduce or prevent the spread of, or kill, insects. For example, an insecticidally effect amount will refer to the amount of a Compound of the Disclosure that induces premature molting and death in an insect.

The terms "a" and "an" refer to one or more than one.

The term "about," as used herein, includes the recited number f 10%. Thus, "about 10" means 9 to 11.

As used herein, the term "excipient" refers to any ingredient in a composition other than the Compound of the Disclosure. An excipient is typically an inert substance added to a composition to facilitate processing, handling, administration, etc., of Compound of the Disclosure. Useful excipients include, but are not limited to, adjuvants, antiadherents, binders, carriers, disintegrants, fillers, flavors, colors, diluents, lubricants, glidants, preservatives, sorbents, solvents, surfactants, and sweeteners.

Conventional pharmaceutical excipients are well known to those of skill in the art. In particular, one of skill in the art will recognize that a wide variety of pharmaceutically acceptable excipients can be used in admixture with Compounds of the Disclosure, including those listed in the *Handbook of Pharmaceutical Excipients*, Pharmaceutical Press 4th Ed. (2003), and *Remington: The Science and Practice of Pharmacy*, Lippincott Williams & Wilkins, 21st ed. (2005). In one embodiment, the composition comprises one or more of the following excipients; water, Labrasol. Lauroglycol 90, Phosal 53 MCT, Miglyol, Cremophor® EL, polysorbate 80, Crillet 1 HP, Isopropyl myristate, Oleic acid, and/or PEG 400 NF. In another embodiment, the composition comprises a lipid.

Pharmaceutically acceptable carriers include fillers such as saccharides, for example, trehalose, lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the is dissolved or suspended in suitable liquids, such as fatty oils, or liquid paraffin, optionally with stabilizers.

Fatty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil, coconut oil; corn oil; cottonseed oil; evening primrose oil; grapeseed oil; groundnut oil, mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate, glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX® 355. Other triglycerides are caprylic-capric acid triglycerides such as known and commercially available under the trade name MYRITOL, including the product MYRITOL 813. Further triglycerides of this class are CAPMUL MCT, CAPTEX® 200, CAPTEX® 300, CAPTEX® 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

In another embodiment, the pharmaceutically acceptable carrier comprises LABRASOL (Gattefosse SA), which is PEG-8 caprylic/capric glycerides. In another embodiment, the pharmaceutically acceptable carrier comprises PL90G, vitamin E TPGS, and Miglyol 812N.

As used herein, the term "treat," "treating," or "treatment" is meant to encompass administering to a subject a Compound of the Disclosure, or a composition thereof, for the purposes of amelioration or cure of a disease, disorder, injury, or condition, including preemptive treatment.

As used herein, the term "subject" refers to an insect, plant, algae, or animal, e.g., human or veterinary animal, e.g., cow, sheep, pig, horse, dog, or cat. In one embodiment, a host cell of the subject comprises a polynucleotide encoding a gene switch that comprises a ligand binding domain that binds a Compound of the Disclosure.

As used herein, the term "gene of interest" is any gene that one wishes to express that encodes a peptide, protein, or polypeptide.

As used herein, the term "gene expression" refers to the transcription of DNA to messenger RNA (mRNA), and/or the translation of mRNA to amino acid sequence.

As used herein, the term "regulating gene expression" refers to increasing the level of gene expression in response to contact of a Compound of the Disclosure with the ligand binding domain that binds a Compound of the Disclosure, relative to the level of gene expression in the absence of contacting the ligand binding domain that binds a Compound of the Disclosure.

As used herein, the term "gene switch" refers to peptide, protein, or polypeptide complex that functions to (a) bind a Compound of the Disclosure, i.e., the ligand, and (b) regulate the transcription of a gene of interest in a ligand-dependent fashion. Gene switches are useful for various applications such as gene therapy, production of proteins in cells, cell based high throughput screening assays, functional genomics, and regulation of traits in transgenic plants and animals.

In one embodiment, the polynucleotide encoding a gene switch is a recombinant polynucleotide, i.e., a polynucleotide, that has been engineered, by molecular biological manipulation, to encode the gene switch. In another embodiment, the recombinant polynucleotide is a synthetic polynucleotide. See, e.g., US Pat. Appl. Pub. Nos. 2012/0322148, 2012/0185954, and 2011/0059530.

As used herein, the term "gene" refers to a polynucleotide comprising nucleotides that encode a functional molecule, including functional molecules produced by transcription only (e.g., a bioactive RNA species) or by transcription and translation (eg, a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" or "exogenous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

In one embodiment, Compounds of the Disclosure are administered to an isolated host cell or a subject as a composition. In another embodiment, Compounds of the Disclosure are administered to an isolated host cell or a subject as a pharmaceutically acceptable composition.

As used herein, the term "dimerizes with the ligand binding domain that binds a Compound of the Disclosure" refers to a selective protein-protein interaction.

In one embodiment, the gene switch efficacy or "$EC_{50}$" of a Compound of the Disclosure is about 20 µM or less, about 10 µM or less, about 5 µM or less, about 3 µM or less, about 2 µM or less, about 1 µm or less, about 500 nM or less, about 300 nM or less, about 200 nM or less, or about 100 nM or less, e.g., about 75 nM about 50 nM, about 25 nM, about 15 nM, about 10 nM, about 9 nM, about 8 nM, about 7 nM, about 6 nM, about 5 nM, about 4 nM, about 3 nM, about 2 nM, about 1 nM, about 0.5 nM, or less in a cellular gene switch assay. Examples of m vitro assays for measuring gene switch-regulated gene expression are well known to those of ordinary skill in the art. See, for example, Karzenowski et al, *BioTechniques* 39: 191-200 (2005).

As used herein, the "$EC_{50}$" is the "half maximal effective concentration," which refers to the concentration of a Compound of the Disclosure that induces a gene switch-regulated change in expression of a polynucleotide encoding an gene of interest that is halfway between the baseline level of expression and the maximum level of expression after a specified exposure time.

As used herein, the term "ligand binding domain that binds a Compound of the Disclosure" refers to an amino acid sequence that selectively binds a Compound of the Disclosure. In the methods disclosed herein, a Compound of the Disclosure binds to a ligand binding domain, e.g., an ecdysone receptor ligand binding domain, that is part of a ligand-dependent transcriptional activation complex that regulates the expression of a polynucleotide sequence that encodes a gene of interest. Hence, the expression of the gene of interest is regulated in a ligand (Compound of the Disclosure) dependent fashion.

In one embodiment, the ligand binding domain that binds a Compound of the Disclosure, e.g., an ecdysone receptor ligand binding domain, dimerizes with another ligand binding domain, e.g., a retinoid X receptor ligand binding domain, to form a protein-protein complex.

In one embodiment, the expression of the gene of interest is regulated by a Compound of the Disclosure in an on/off fashion that is independent of the concentration or dosage of the Compound of the Disclosure. In another embodiment, the expression of the gene of interest is regulated by a Compound of the Disclosure in a concentration (or dosage)-dependent fashion, i.e., there is a dose-response relationship between the concentration (or dosage) of a Compound of the Disclosure and the level of gene expression of the gene of interest. See, e.g., US 2009/0123441.

The term "operably linked" refers to the association of polynucleotide sequences on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

In one embodiment, the host cell is an isolated host cell. In one embodiment, an "isolated" host cell refers to a cell that is not present in a subject. In one embodiment, an "isolated" host cell refers to one or more host cells in a cell culture apparatus or in a cell culture preparation.

In one embodiment, the host cell is within a subject, and the host cell is contacted by a Compound of the Disclosure by administering the Compound of the Disclosure, or a composition thereof, to the subject. In another embodiment, the host cell is contacted with a Compound of the Disclosure, or a composition thereof, in vitro. In another embodiment, the host cell is contacted with a Compound of the Disclosure, or a composition thereof, ex vivo. In another embodiment, the host cell is in a human subject. In another embodiment, the host cell is in an animal subject. In another embodiment, the host cell is in a plant subject. In another embodiment, the host cell is in an algae subject.

In one embodiment, Compounds of the Disclosure, or compositions thereof, are administered to a subject. In one embodiment, Compounds of the Disclosure, or compositions thereof, are administered to a subject orally. In another embodiment, Compounds of the Disclosure, or compositions thereof, are administered to a subject parenterally. In another embodiment, Compounds of the Disclosure, or compositions thereof, are administered subcutaneously, intramuscularly, intravenously, intraperitoneally or intratumorally.

In addition to or together with the above modes of administration, Compounds of the Disclosure, or compositions thereof, can be added to food consumed by a subject. In one embodiment, Compounds of the Disclosure, or compositions thereof, are combined, blended, or admixed with food material to provide a "food product." The term "food material" is used in its broadest possible sense, and includes any form, e.g., solid, emulsion, liquid, of ingestible materials consumed by an animal, e.g., a human. Food products may be formulated so the subject takes in an appropriate quantity of a Compound of the Disclosure, or composition thereof, with its diet. In another embodiment, a Compound of the Disclosure, or composition thereof, is formulated as a premix for addition to food material. In one embodiment, the food product or premix comprises a Compound of the Disclosure, or composition thereof and one or more lipids.

In one embodiment, the ligand binding domain in the gene switch that binds a Compound of the Disclosure is a Group H nuclear receptor ligand binding domain, or a mutant thereof, that binds a Compound of the Disclosure. In another embodiment, the Group H nuclear receptor ligand binding domain is selected from the group consisting of an ecdysone receptor ligand binding domain, a ubiquitous receptor ligand binding domain, an orphan receptor-1 ligand binding domain, an NER-1 ligand binding domain, a receptor-interacting protein-15 ligand binding domain, a liver X receptor-3 ligand binding domain, a steroid hormone receptor-like protein ligand binding domain, a liver X receptor ligand binding domain, a liver X receptor ligand binding domain, a farnesoid X receptor ligand binding domain, a receptor-interacting protein-14 ligand binding domain, and a farnesol receptor ligand binding domain ligand binding domain, or a mutant thereof, that binds a Compound of the Disclosure.

In another embodiment, the Group H nuclear receptor ligand binding domain is an ecdysone receptor ligand binding domain, or a mutant thereof, that binds a Compound of the Disclosure. In another embodiment, the ecdysone receptor ligand binding domain is selected from the group consisting of an *Arthropod* ecdysone receptor ligand binding domain a *Lepidopteran* ecdysone receptor ligand binding domain, a Dipteran ecdysone receptor ligand binding domain, an *Orthopteran* ecdysone receptor ligand binding domain, a *Homopteran* ecdysone receptor ligand binding domain and a *Hemipteran* ecdysone receptor ligand binding domain, a spruce budworm *Choristoneura fumiferana* ecdysone receptor ligand binding domain, a beetle *Tenebrio molitor* ecdysone receptor ligand binding domain, a *Manduca sexta* ecdysone receptor ligand binding domain, a *Heliothies virescens* ecdysone receptor ligand binding domain, a midge *Chirononmus tentans* ecdysone receptor ligand binding domain, a silk moth *Bombyx mori* ecdysone receptor ligand binding domain, a squinting bush brown *Bicyclus anynana* ecdysone receptor ligand binding domain, a buckeye *Junonia coema* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a blowfly *Calliphora vicinia* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myrus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly *Bamecia argentifoli* ecdysone receptor ligand binding domain, a leafhopper *Nephotetix cincticeps* ecdysone receptor ligand binding domain, or a mutant thereof, that binds a Compound of the Disclosure. In another embodiment, the ecdysone receptor ligand binding domain is a spruce budworm *Choristoneura fumiferana* ecdysone receptor ligand binding domain, for which the amino acid sequence is set forth in U.S. Patent Publication No. 2006/0100416 A1.

In another embodiment, the ecdysone receptor ligand binding domain is a mutant of the spruce budworm *Choristoneura fumiferana* ecdysone receptor ligand binding domain that binds a Compound of the Disclosure.

Suitable ecdysone receptor ligand binding domains include those disclosed, for example, in U.S. Pat. Nos. 7,935,510; 7,919,269; 7,563,879; and in U.S. Patent Publication No. 2006/0100416 A1.

In one embodiment, the gene switch comprises a ligand binding domain that dimerizes with the ligand binding domain that binds a Compound of the Disclosure. In one embodiment, the ligand binding domain that dimerizes with the ligand binding domain that hinds a Compound of the Disclosure is a Group B nuclear receptor ligand binding domain. In another embodiment, the Group B nuclear receptor ligand binding domain is selected from the group consisting of a retinoid X receptor ligand binding domain, an H-2 region II binding protein ligand binding domain, a nuclear receptor co-regulator-1 ligand binding domain, an ultraspiracle protein ligand binding domain, a 2C1 nuclear receptor ligand binding domain, and a chorion factor 1 ligand binding domain. In another embodiment, a ligand binding domain that dimerizes with the ligand binding domain that binds a Compound of the Disclosure is not an ecdysone receptor ligand binding domain.

In one embodiment, the ligand binding domain that dimerizes with the ligand binding domain that binds a Compound of the Disclosure is a retinoic X receptor ligand binding domain. In another embodiment, the retinoic X receptor ligand binding domain is a vertebrate retinoic X receptor ligand binding domain. In another embodiment, the retinoic X receptor ligand binding domain is a *Homo sapiens* retinoic X receptor ligand binding domain. In another embodiment, the retinoic X receptor ligand binding domain is a retinoic X receptor α isoform. In another embodiment, the retinoic X receptor ligand binding domain is a retinoic X receptor β isoform. In another embodiment, the retinoic X receptor ligand binding domain is a retinoic X receptor γ isoform.

In another embodiment, the retinoic X receptor ligand binding domain is an invertebrate retinoic X receptor ligand binding domain. In another embodiment, the invertebrate retinoic X receptor ligand binding domain is a *Locusta migratoria* retinoic X receptor ligand binding domain.

In another embodiment, the invertebrate retinoic X receptor ligand binding domain is a non-*Lepidopteran*, non-*Dipteran* retinoic X receptor ligand binding domain.

In one embodiment, the retinoid receptor ligand binding domain is a vertebrate retinoid X receptor ligand binding domain, an invertebrate retinoid X receptor ligand binding domain, an ultraspiracle protein ligand binding domain, or a chimeric retinoid X receptor ligand binding domain.

In one embodiment, the chimeric retinoid X receptor ligand binding domain comprises two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, a different invertebrate retinoid X receptor ligand binding domain, or a different ultraspiracle protein ligand binding domain.

In another embodiment, the chimeric retinoid X receptor ligand binding domain is one that is disclosed in U.S. Pat. No. 7,531,326.

In another embodiment, the first polypeptide fragment of the chimeric retinoid X receptor ligand binding domain comprises helices 1-6, helices 1-7, helices 1-8, helices 1-9, helices 1-10, helices 1-11, or helices 1-12 of a first species of retinoid X receptor, and the second polypeptide fragment of the chimeric retinoid X receptor ligand binding domain comprises helices 7-12, helices 8-12, helices 9-12, helices 10-12, helices 11-12, helix 12, or F domain of a second species of retinoid X receptor, respectively.

In another embodiment, the first polypeptide fragment of the chimeric retinoid X receptor ligand binding domain comprises helices 1-6 of a first species RXR according to the disclosure, and the second polypeptide fragment of the chimeric retinoid X receptor ligand binding domain comprises helices 7-12 of a second species of retinoid X receptor.

In another embodiment, the first polypeptide fragment of the chimeric retinoid X receptor ligand binding domain comprises helices 1-7 of a first species retinoid X receptor according to the disclosure, and the second polypeptide fragment of the chimeric retinoid X receptor ligand binding domain comprises helices 8-12 of a second species retinoid X receptor.

In another embodiment, the first polypeptide fragment of the chimeric retinoid X receptor ligand binding domain comprises helices 1-8 of a first species of retinoid X receptor, and the second polypeptide fragment of the chimeric retinoid X receptor ligand binding domain comprises helices 9-12 of a second species of retinoid X receptor.

In another embodiment, the first polypeptide fragment of the chimeric retinoid X receptor ligand binding domain comprises helices 1-9 of a first species of retinoid X receptor, and the second polypeptide fragment of the chimeric retinoid X receptor ligand binding domain comprises helices 10-12 of a second species of retinoid X receptor.

In another embodiment, the first polypeptide fragment of the chimeric retinoid X receptor ligand binding domain comprises helices 1-10 of a first species of retinoid X receptor, and the second polypeptide fragment of the chimeric retinoid X receptor ligand binding domain comprises helices 11-12 of a second species of retinoid X receptor.

In another embodiment, the first polypeptide fragment of the chimeric retinoid X receptor ligand binding domain comprises helices 1-11 of a first species of retinoid X receptor, and the second polypeptide fragment of the chimeric retinoid X receptor ligand binding domain comprises helix 12 of a second species of retinoid X receptor.

In another preferred embodiment, the first polypeptide fragment of the chimeric retinoid X receptor ligand binding domain comprises helices 1-12 of a first species of retinoid X receptor, and the second polypeptide fragment of the chimeric retinoid X receptor ligand binding domain comprises an F domain of a second species of retinoid X receptor.

In one embodiment, the first polypeptide fragment in the chimeric retinoid X receptor ligand binding domain is human retinoid X receptor sequence, and the second polypeptide fragment in the chimeric retinoid X receptor ligand binding domain is invertebrate retinoid X receptor sequence. In another embodiment, the invertebrate retinoid X receptor sequence is *Locusta migratoria* retinoid X receptor sequence.

In another embodiment, the first polypeptide fragment of the chimeric retinoid X receptor ligand binding domain comprises helices 1-8 of a human retinoid X receptor, and the second polypeptide fragment of the chimeric retinoid X receptor ligand binding domain comprises helices 9-12 of *Locusta migratoria* retinoid X receptor.

In one embodiment, the gene switch further comprises a DNA binding domain ("DBD"). In another embodiment, the DBD is selected from the group consisting of a GAL4 DBD, a LexA DBD, a transcription factor DBD, a steroid/thyroid hormone nuclear receptor superfamily member DBD, a bacterial LacZ DBD, and a yeast DBD.

In one embodiment, the gene switch further comprises a transactivation domain ("TD"). In another embodiment, the transactivation domain is selected from the group consisting of a VP16 TD, a GAL4 TD, an NF-κB TD, a BP64 TD, and a B42 acidic TD.

In one embodiment, a DNA binding domain, the ligand binding domain that binds a Compound of the Disclosure, a ligand binding domain that dimerizes with the ligand binding domain that binds a Compound of the Disclosure, and a transactivation domain are encoded by polynucleotide sequences that are contained in the same polynucleotide.

In another embodiment, a DNA binding domain, a ligand binding domain that binds a Compound of the Disclosure, a ligand binding domain that dimerizes with the ligand binding domain that binds a Compound of the Disclosure, and a transactivation domain are encoded by polynucleotide sequences that are contained in one or more separate polynucleotide sequences.

In another embodiment, a DNA binding domain, a ligand binding domain that binds a Compound of the Disclosure, a ligand binding domain that dimerizes with the ligand binding domain that binds a Compound of the Disclosure, and a transactivation domain are encoded by polynucleotide sequences that are contained in two separate polynucleotide sequences.

In another embodiment, a DNA binding domain and a ligand binding domain that binds a Compound of the Disclosure are encoded by polynucleotide sequences that are contained in a first polynucleotide sequence, and a ligand binding domain that dimerizes with the ligand binding domain that binds a Compound of the Disclosure and a transactivation domain are encoded by polynucleotide sequences that are contained in a second polynucleotide sequence.

In another embodiment, a DNA binding domain and a ligand binding domain that dimerizes with the ligand binding domain that binds a Compound of the Disclosure are encoded by polynucleotide sequences that are contained in a first polynucleotide sequence, and a ligand binding domain that binds a Compound of the Disclosure and a transactivation domain are encoded by polynucleotide sequences that are contained in a second polynucleotide sequence.

In embodiments in which one or more of the DNA binding domain, a ligand binding domain that binds a Compound of the Disclosure, a ligand binding domain that dimerizes with the ligand binding domain that binds a Compound of the Disclosure. and a transactivation domain are encoded by polynucleotide sequences that are contained in one or more separate polynucleotide sequences, then the one or more separate polynucleotide sequences is operably linked to one or more separate promoters. In another embodiment, the one or more separate polynucleotide sequences arc operably linked to one or more separate enhancer elements. In another embodiment, the promoter(s) and/or the enhancer(s) are constitutively active. In another embodiment, the promoter(s) and/or the enhancer(s) are tissue specific promoters and/or enhancers.

In one embodiment, the gene switch comprises a DNA binding domain, an ecdysone receptor ligand binding domain, a ligand binding domain that dimerizes with the cedysone receptor ligand binding domain, and a transactivation domain.

In another embodiment, the gene switch comprises a DNA binding domain, an ecdysone receptor ligand binding domain, a retinoid X receptor ligand binding domain, and a transactivation domain.

In another embodiment, the gene switch comprises a DNA binding domain, an ecdysone receptor ligand binding domain, a chimeric vertebrate/invertebrate retinoid X receptor ligand binding domain, and a transactivation domain.

In another embodiment, the gene switch comprises a first polypeptide comprising a DNA binding domain (DBD) and a first ligand binding domain (LBD) and comprises a second polypeptide comprising a transactivation domain (TAD) and a second LBD. In one embodiment, the first LBD is an EcR ligand binding domain. In one embodiment the first LBD is an RxR, a USP, a chimeric LBD, or a chimeric RxR/USP LBD. In one embodiment, the second LBD is an EcR ligand binding domain. In one embodiment the second LBD is an RxR, a USP, a chimeric LBD, or a chimeric RxR/USP LBD. In one embodiment, the DBD is a Gal4 DNA binding domain. In one embodiment, the TAD is a VP16 transactivation domain. In one embodiment, the gene switch comprises a first polypeptide comprising a Gal4 DNA binding domain and an EcR ligand binding domain (LBD) and comprises a second polypeptide comprising a VP16 transactivation domain and chimeric RxR/USP ligand binding domain. In one embodiment, the EcR ligand binding domain comprises one or more amino acid substitutions compared to the corresponding wild-type EcR polypeptide sequence.

In another embodiment, the gene switch comprises a GAL4 DNA binding domain, a *Choristoneura fumiferana* ecdysone receptor ligand binding domain that is engineered to contain the mutations V107I and Y127E of the *Choristoneura fumiferana* ecdysone receptor sequence set forth in U.S. Patent Publication No. 2006/0100416 A1, a chimeric *Homo sapiens/Locusta migratoria* retinoid X receptor ligand binding, and a VP16 transactivation domain.

The term "V107I" means that the valine amino acid residue at position 107 in the *Choristoneura fumiferana* ecdysone receptor sequence set forth in U.S. Patent Publication No. 2006/0100416 A1 is changed to isoleucine. The term "Y127E" means that the tyrosine amino acid residue at position 127 in the *Choristoneura fumiferana* ecdysone receptor sequence set forth in U.S. Patent Publication No. 2006/0100416 A1 is changed to glutamate.

In another embodiment, the host cell further comprises a polynucleotide encoding a peptide, protein or polypeptide whose expression is regulated by the gene switch. A promoter that binds the gene switch complex is operably linked to the polynucleotide encoding a peptide, protein or polypeptide whose expression is regulated by the gene switch.

In another embodiment, the polynucleotide encoding a peptide, protein or polypeptide whose expression is regulated by the gene switch is contained in the same polynucleotide as a polynucleotide that encodes one or more of a DNA binding domain, the ligand binding domain that binds a Compound of the Disclosure, a ligand binding domain that dimerizes with the ligand binding domain that binds a Compound of the Disclosure, and a transactivation domain. Such constructs are disclosed, for example, in U S. Patent Publication No. 2009/0123441.

In another embodiment, the polynucleotide encoding a peptide, protein or polypeptide whose expression is regulated by the gene switch is contained in a different polynucleotide than a polynucleotide that encodes one or more of a DNA binding domain, the ligand binding domain that binds a Compound of the Disclosure, a ligand binding domain that dimerizes with the ligand binding domain that binds a Compound of the Disclosure, and a transactivation domain.

In one embodiment, the gene switch is more sensitive to a Compound of the Disclosure than to a steroid hormone. In another embodiment, the gene switch is more sensitive to a Compound of the Disclosure 1 than to another diacylhydrazine compound.

The sensitivity of a gene switch to a Compound of the Disclosure, relative to another ligand, can readily be determined in an in vitro assay, for example, an in vitro assay that employs a reporter gene, such as firefly luciferase. Examples of such in vitro assays are well known to those of ordinary skill in the art. See, for example, Karzenowski et al, *BioTechniques* 39: 191-200 (2005).

In one embodiment, the polynucleotide encoding the gene switch is contained in a vector. In one embodiment, the vector selected from the group consisting of a plasmid, an expression vector, a replicon, a phage vector, a cosmid, a viral vector, a liposome, an electrically charged lipid (e.g., a cytofectin), a DNA-protein complex, and a biopolymer.

In another embodiment, the vector is a retroviral vector. In another embodiment, the vector is selected from the group consisting of an adeno-associated viral vector, a pox viral vector, a baculoviral vector, a vaccinia viral vector, a herpes simplex viral vector, an Epstein-Barr viral vector, an adenoviral vector, a gemini viral vector, and a caulimo viral vector.

In one embodiment, the host cell is a prokaryotic host cell. In another embodiment, the host cell is a eukaryotic host cell. In other embodiments, the host cell is an immune cell (e.g., a T-cell, a B-cell, a Natural Killer cell and the like) or a stem cell (e.g., a mesenchymal stem cell (MSC), an endometrial derived stem cell, an endometrial regenerative cell and the like).

In another embodiment, the host cell is a vertebrate host cell. In another embodiment, the host cell is an invertebrate host cell.

In another embodiment, the host cell is selected from the group consisting of a bacterial cell, a fungal cell, a yeast cell, a nematode cell, an insect cell, a fish cell, a plant cell, an avian cell, an algae cell, an animal cell, and a mammalian cell.

In another embodiment, the host cell is selected from the group consisting of a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, and a human cell.

In another embodiment, the host cell is selected from the group consisting of an *Aspergillus* cell, a *Trichoderma* cell, a *Saccharomyces* cell, a *Pichia* cell, a *Candida* cell, a *Hansenula* cell.

In another embodiment, the host cell is selected from the group consisting of a *Synechocystis* cell, a *Synechococcus* cell, a *Salmonella* cell, a *Bacillus* cell, a *Acinetobacter* cell, a *Rhodococcus* cell, a *Streptomyces* cell, an *Escherichia* cell, a *Pseudomonas* cell, a *Methylomonas* cell, a *Methylobacter* cell, a *Alcaligenes* cell, a *Synechocystis* cell, a *Anabaena* cell, a *Thiobacillus* cell, a *Methanobacterium* cell and a *Klebsiella* cell.

In another embodiment, the host cell is selected from the group consisting of an apple cell, an *Arabidopsis* cell, a bajra cell, a banana cell, a barley cell, a bean cell, a beet cell, a blackgram cell, a chickpea cell, a chili cell, a cucumber cell, an eggplant cell, a favabean cell, a maize cell, a melon cell, a millet cell, a mungbean cell, an oat cell, an okra cell, a *Panicum* cell, a *papaya* cell, a peanut cell, a pea cell, a pepper cell, a pigeonpea cell, a pineapple cell, a *Phaseolus* cell, a potato cell, a pumpkin cell, a rice cell, a sorghum cell, a soybean cell, a squash cell, a sugarcane cell, a sugarbeet cell, a sunflower cell, a sweet potato cell, a tea cell, a tomato cell, a tobacco cell, a watermelon cell, a mushroom cell, and a wheat cell.

In another embodiment, the host cell is selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid (or vector) transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art. Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification (e.g., glycosylation, cleavage (e.g., of signal sequence)) of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

In one embodiment, the host cell comprises two or more orthogonal gene switches. Two or more individually operable gene regulation systems are said to be "orthogonal" when (a) modulation of each of the given gene switches by its respective ligand results in a measurable change in the magnitude of expression of the gene that is regulated by that gene switch, and (b) the change is statistically significantly different than the change in expression of all other gene switches that are in the host cell. In one embodiment, regulation of each individually operable gene switch system effects a change in gene expression at least 2-fold, 3-fold, 4-fold, 5-fold, 10-fold, 20-fold, 50-fold, 70-fold, 100-fold, 200-fold, 300 fold, 400-fold or 500-fold greater than all of the other operable gene switches in the host cell. Non-limiting examples of orthogonal gene switch systems are set forth in U.S. Patent Publication No. US 2002/0110861 A1.

In another embodiment, a Compound of the Disclosure, or composition thereof, is administered to a subject to treat cancer in the subject, for example, a cancer selected from the group consisting of myelodysplasia, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macroglobulinemia, and retinoblastoma, and the like.

In another embodiment, a Compound of the Disclosure, or composition thereof, is administered to a subject to treat a metabolic-related disorder in the subject, for example, a metabolic disorder selected from the group consisting of dyslipidemia, atherosclerosis, insulin resistance, diabetes (e.g., diabetes type L diabetes type II, MODY, and gestational diabetes), obesity, impaired glucose tolerance, atheromatous disease, hypertension, heart disease (which includes, but is not limited to, coronary heart disease, stroke, cardiac insufficiency, coronary insufficiency, and high blood pressure), hyperlipidemia, glucose intolerance, insulin resistance, hyperglycemia, hyperinsulinemia, metabolic syndrome X (or syndrome X, or insulin resistance syndrome, or Reaven's syndrome, or the metabolic cardiovascular risk syndrome), hypertension, chronic fatigue, accelerated aging, degenerative disease, endocrine deficiencies of aging, $G_m1$ gangliosidosis, Morquio-B disease, Krabbe's disease, Fabry's disease, Gaucher's disease, Tay-Sachs disease, Sandhoff disease, fucosidosis, disorders of carbohydrate metabolism (e.g., glycogen storage disease), disorders of amino acid metabolism (e.g., phenylketonuria, maple syrup urine disease, glutaric acidemia type 1), disorders of organic acid metabolism (e.g., alcaptonuria), disorders of fatty acid oxidation and mitochondrial metabolism (e.g., medium chain acyl dehydrogenase deficiency), disorders of porphyrin metabolism (e.g., acute intermittent porphyria), disorders of purine or pyrimidine metabolism (e.g., Lesch-Nyhan syndrome), disorders of steroid metabolism (e.g., congenital adrenal hyperplasia), disorders of mitochondrial function (e.g., Kearns-Sayre syndrome), and disorders of peroxisomal function (e.g., Zellweger syndrome).

In another embodiment, a Compound of the Disclosure, or composition thereof, is administered to a subject to treat kidney disease in the subject. In one embodiment, the kidney disease is renal failure. In another embodiment, the kidney disease is chronic renal failure.

In another embodiment, a Compound of the Disclosure, or composition thereof, is administered to a subject to treat anemia in the subject. In one embodiment, the anemia is anemia associated with kidney disease, for example, renal failure or chronic renal failure. In another embodiment, the anemia is associated with cancer therapy with, for example, one or more chemotherapeutic agents. In another embodiment, the anemia is associated with advanced age. In another embodiment, the anemia is associated with impaired lung function. In another embodiment, the anemia is associated with myelodisplasia. In another embodiment, the anemia is associated with radiation therapy. In another embodiment, the anemia is associated with a critical illness. In another embodiment, the anemia is associated with cardiac disease. In another embodiment, the anemia is not a cardiac disease. Nonlimiting types of "cardiac disease" are congestive heart failure, hypoxia, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, cardiogenic shock, thrombosis, embolism, atherosclerosis, and arterial stenosis.

In another embodiment, a Compound of the Disclosure, or composition thereof, are administered to a subject to treat an autoimmune disorder in the subject, for example, an autoimmune disorder selected from the group consisting of Achlorhydra Autoimmune Active Chronic Hepatitis, Acute Disseminated Encephalomyelitis. Acute hemorrhagic leukoencephalitis, Addison's Disease, gammaglobulinemia, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome. Arthritis, Atopic allergy, Atopic Dermatitis, Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy. Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chronic Fatigue Immune Dysfunction Syndrome, chronic inflammatory demyelinating polyneuropathy, Chronic recurrent multifocal ostomyelitis, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease, Cushing's Syndrome. Cutaneous leukocytoclastic angiitis, Dego's disease, Dermatitis herpetiformis, Dermatomyositis. Diabetes mellitus type 1. Diffuse cutaneous systemic sclerosis, Dressler's syndrome, Discoid lupus erythematosus, eczema, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyositis, Fibrosing aveolitis, Gastritis, Gastrointestinal pemphigoid, Giant cell arteritis, Goodpasture's syndrome, Graves' disease, Guillain-Barré syndrome (GBS), Hashimoto's encephalitis, Hashimoto's thyroiditis, Hemolytic anaemia, Henoch-Schonlein purpura, Herpes gestationis. Hughes syndrome (or Antiphospholipid syndrome), Hypogammaglobulinemia, Idiopathic Inflammatory Demyelinating Diseases, Idiopathic pulmonary fibrosis. Idiopathic thrombocytopenic purpura, IgA nephropathy (or Berger's disease), Inclusion body myositis, ory demyelinating polyneuopathy, Juvenile idiopathic arthritis, Juvenile rheumatoid arthritis, Lambert-Eaton myasthenic syndrome, Leukocytoclastic vasculitis, Lichen planus, Lichen sclerosus, Linear IgA disease (LAD), Lou Gehrig's Disease, Lupoid hepatitis, Lupus erythematosus, Majeed syndrome, Mdnire's disease, Microscopic polyangiitis, Miller-Fisher syndrome, Mixed Connective Tissue Disease, Mucha-Habermann disease, Muckle-Wells syndrome, Multiple Myeloma, Myasthenia gravis, Myositis. Narcolepsy, Neuromyelitis optica (also Devic's Disease), Occular cicatricial pemphigoid, Ord thyroiditis, Palindromic rheumatism, PANDAS (Pediatric Autoimmune Neuropsychiatric Disorders Associated with *Streptococcus*), Paraneoplastic cerebellar degeneration, Paraneoplastic cerebellar degeneration, Parry Romberg syndrome, Parsonnage-Turner syndrome, Pars planitis, Pemphigus, Pemphigus vulgaris, Pernicious anaemia, Perivenous encephalomyelitis. POEMS syndrome. Polyarteritis nodosa, Polymyalgia rheumatica, Polymyositis, Primary biliary cirrhosis, psoriasis, psoriatic arthritis, Pyoderma gangrenosum, pure red cell aplasia, Rasmussen's encephalitis, Raynaud phenomenon, Relapsing polychondritis, Reiter's syndrome, Retroperitoneal fibrosis, Rheumatoid arthritis, Rheumatoid fever, Schmidt syndrome, Schnitzler syndrome, Scleritis, Sjögren's syndrome, Spondyloarthropathy, sticky blood syndrome, Still's Disease, Subacute bacterial endocarditis (SBE), Susac's syndrome, Sweet syndrome, Sydenham Chorea, Sympathetic ophthalmia, Takayasu's arteritis, Temporal arteritis, Tolosa-Hunt syndrome, Transverse Myelitis, Ulcerative Colitis, Undifferentiated connective tissue disease, Undifferentiated spondyloarthropathy, vasculitis, Wegener's granulomatosis, Wilson's syndrome, and Wiskott-Aldrich syndrome.

In another embodiment, a Compound of the Disclosure, or composition thereof, is administered to a subject to treat an ocular disorder in the subject, for example, an ocular disorder selected from the group consisting of glaucoma including Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-induced Glaucoma, Neovascular Glaucoma (e.g., using vectors composed of Vascular Endothelial Growth Factor (VEGF) decoy, Pigment Derived Growth Factor (PDGF), Endostatin, Angiostatin, or Angiopoetin-1), Post-Traumatic Glaucoma, Steroid-Induced Glaucoma, Sturge-Weber Syndrome Glaucoma, and Uveitis-Induced Glaucoma, diabetic retinopathy (e.g., using vectors composed of VEGF decoy, PDGF, Endostatin, Angiostatin, or Angiopoetin-1), macular degeneration (e.g., vectors composed of VEGF decoy, PDGF, Endostatin, Angiostatin, Angiopoetin-1, ATP Binding Casette Subfamily A Member 4), macular degeneration (e.g., using vectors composed of VEGF decoy, PDGF, Endostatin, Angiostatin, Angiopoetin-1, ATP Binding Casette Subfamily A Member 4), choroidal neovascularization, (e.g., using vectors composed of VEGF decoy. PDGF, Endostatin. Angiostatin, or Angiopoetin-1), vascular leak, and/or retinal edema, bacterial conjunctivitis, fungal conjunctivitis, viral conjunctivitis, uveitis, keratic precipitates, macular edema (e.g., using vectors composed of VEGF decoy, PDGF, Endostatin, Angiostatin, or Angiopoetin-1), inflammation response after intra-ocular lens implantation, uveitis syndromes (for example, chronic iridocyclitis or chronic endophthalmitis), retinal vasculitis (for example, as seen in rheumatoid arthritis, juvenile rheumatoid arthritis, systemic lupus erythymatosus, progressive systemic sclerosis, polyarteritis nodosa, Wegener's granulomatosis, termporal arteritis, Adamantiades Bechcet disease, Sjorgen's, relapsing polychondritis and HLA-B27 associated spondylitis), sarcoidosis, Eales disease, acute retinal necrosis, Vogt Koyanaki Harada syndrome, occular toxoplasmosis, radiation retinopathy, proliferative vitreoretinopathy, endophthalmitis, ocular glaucomas (for example, inflammatory glaucomas), optic neuritis, ischemic optic neuropathy (e.g., vectors composed of Allotopic NADH dehydrogenase Unit 4), thyroid associated orbitopathy, orbital pseudotumor, pigment dispersion syndrome (pigmentary glaucoma), scleritis, episcleritis choroidopathies (for example, "White-dot" syndromes including, but not limited to, acute multifocal posterior placoid), retinopathies (for example, cystoid macular edema, central serous choroidopathy and presumed ocular histoplasmosis syndrome (e.g., vectors composed of Glial Cell Derived Neurotropic Factor, Peripherin-2)), retinal vascular disease (for example, diabetic retinopathy, Coat's disease and retinal arterial macroaneurysm), retinal artery occlusions, retinal vein occlusions, retinopathy of prematurity, retinitis pigmentosa (e.g., vectors composed of Retinal Pigment Specific 65 kDa protein), familial exudative vitreoretinopathy (FEVR), idiopathic polypoidal choroidal vasculopathy, epiretinal macular membranes and cataracts.

In another embodiment, a Compound of the Disclosure, or composition thereof, is administered to a subject to treat an ocular disorder in the subject, wherein the ocular disorder is selected from the group consisting of glaucoma, wet and dry age-related macular degeneration, diabetic retinopathy, and macular oedema.

In another embodiment, a Compound of the Disclosure, or composition thereof, is administered to a subject to treat a blood disorder in the subject, for example, a blood disorder selected from the group consisting of a blood disorder selected from the group consisting of anemia, bleeding and clotting disorders (e.g., disseminated intravascular coagulation (DIC), hemophilia, Henoch-Schonlien Purpura, hereditary hemorrhagic telangiectasia, thrombocytopenia (ITP, TTP), thrombophilia, Von Willebrand's disease), leukemias (e.g., acute lymphocytic leukemia, acute myelocytic leukemia, chronic lymphocytic leukemia, chronic myelocytic leukemia), lymphomas (e.g., Hodgkin lymphoma, non-Hodgkin lymphoma), myeloproliferative disorders (e.g., myelofibrosis, Polycythemia Vera, thrombocythemia), plasma cell disorders (e.g., macroglobulinemia, monoclonal gammopathies of undetermined significance, multiple lyeloma), spleen disorders, white blood cell disorders (e g, basophilic disorder, eosinophilic disorder, lymphocytopenia, monocyte disorders, neutropenia, neutrophillic leukocytosis), thrombosis, deep vein thrombosis (DVT), hemochromatosis, menorrhagia, sickle cell disease, and thalassemia.

In another embodiment, a Compound of the Disclosure, or composition thereof, is administered to a subject to treat a neurological disorder in the subject, for example, a neurological disorder selected from the group consisting of Gaucher disease, Parkinson's disease, Alzheimer's disease, amyotrophic lateral sclerosis (ALS), multiple sclerosis (MS), Huntington's disease, Fredrich's ataxia, Mild Cognitive Impairment, Cerebral Amyloid Angiopathy, Parkinsonism Disease, Lewy Body Disease, Frontotemporal Dementia (FTD) Multiple System Atrophy (MSA), Progressive Supranuclear Palsy, and movement disorders (including ataxia, cerebral palsy, choreoathetosis, dystonia, Tourette's syndrome, kernicterus) and tremor disorders, and leukodystrophies (including adrenoleukodystrophy, metachromatic leukodystrophy, Canavan disease, Alexander disease, Pelizaeus-Merzbacher disease), neuronal ceroid lipofucsinoses, ataxia telangectasia, Rett Syndrome, alpha.-synucleinopathy (e.g., Lewy Body Disease, Multiple System Atrophy, Hallervorden-Spatz disease, or Frontotemporal Dementia), Niemann-Pick Type C disease (NPCD), spinocerebellar ataxia Type 1, Type 2, and Type 3, and dentatorubral pallidoluysian atrophy (DRLPA).

In another embodiment, a Compound of the Disclosure, or composition thereof, is administered to a subject to treat a lung disorder in the subject, for example, a lung disorder selected from the group consisting of asthma, atelectasis, bronchitis, COPD (chronic obstructive pulmonary disease), emphysema, Lung cancer, mesothelioma, pneumonia, asbestosis, Aspergilloma, Aspergillosis, Aspergillosis—acute invasive, bronchiectasis, bronchiolitis obliterans organizing pneumonia (BOOP), eosinophilic pneumonia, necrotizing pneumonia, ral effusion, pneumoconiosis, pneumothorax, pulmonary *actinomycosis*, monary alveolar proteinosis, pulmonary anthrax, pulmonary arteriovenous malformation, pulmonary fibrosis, pulmonary embolus, pulmonary histiocytosis X (eosinophilic granuloma), pulmonary hypertension, pulmonary edema, pulmonary hemorrhage, pulmonary nocardiosis, pulmonary tuberculosis, pulmonary veno-occlusive disease, rheumatoid lung disease, sarcoidosis, radiation fibrosis, hypersensitivity pneumonitis, acute respiratory distress syndrome (ARDS), infant respiratory distress syndrome, idiopathic pulmonary fibrosis, idiopathic interstitial pneumonia, lymphangioleiomyomatosis, pulmonary langerhans' cell histiocytosis, pulmonary alveolar proteinosis, sinusitis, tonsillitis, otitis media, pharyngitis, laryngitis, Pulmonary hamartoma, pulmonary sequestration, congenital cystic adenomatoid malformation (CCAM), and cystic fibrosis.

In another embodiment, a Compound of the Disclosure, or composition thereof, is administered to a subject to treat a rheumatologic disorder in the subject, for example, a rheumatologic disorder selected from the group consisting of systemic lupus erythematosus, dermatomyositis, scleroderma, systemic necrotizing arteritis, cutaneous necrotizing venulitis, rheumatoid arthritis, Sjogren's Syndrome, Raynaud's phenomenon, Reiter's syndrome, arthritis, psoriatic arthritis, seronegative spondyloarthropathies, Sjogren's syndrome, systemic sclerosis, dermatomyositis/polymyositis, mixed connective tissue disease, and ankylosing spondylitis.

In another embodiment, a Compound of the Disclosure, or composition thereof, is administered a subject to treat an infectious disease in the subject, for example, an infectious disease selected from the group consisting of fungal diseases such as dermatophytosis (e.g., trichophytosis, ringworm or tinea infections), athletes foot, paronychia, *Pityriasis versicolor*, erythrasma, intertrigo, fungal diaper rash, *Candida vulvitis, Candida balanitis*, otitis extema, candidiasis (cutaneous and mucocutaneous), chronic mucocandidiasis (e.g., thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia, *Acinetobacter* infections. *Actinomycosis*, African sleeping sickness. AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, atrovirus infection, Babesiosis. *Bacillus cereus* infection, Bacterial pneumonia, Bacterial vaginosis (BV), *Bacteroides* infection, *Balantidiasis, Baylisascaris* infection, BK virus infection, Black piedra, *Blastocystis hominis* infection, *Borrelia* infection, Botulism (and Infant botulism), Brazilian hemorrhagic fever, *Brucellosis, Burkholderia* infection, Buruli ulcer. Calcivirus infection (Norovirus and Sapovirus), Candidiasis, Cat-scratch disease, Cellulitis, Chagas Disease (American trypanosomiasis), Chancroid. Chickenpox, *Chlamydia*, Cholera, Chromoblastomycosis, Clonorchiasis, *Clostridium difficile*, Coccidioidomycosis, Colorado tick fever (CTF), Common cold (Acute viral rhinopharyngitis; Acute coryza), Creutzfeldt-Jakob disease (CJD), Cryptococcosis, Cryptosporidiosis, ous larva migrans (CLM), Dengue fever, Dientamoebiasis, Diphtheria, Diphyllobothriasis, Diphyllobothriasis, Dracunculiasis, Ebola hemorrhagic fever, Echinococcosis. Ehrlichiosis, Enterobiasis (Pinworm infection), *Enterococcus* infection, Enterovirus infection, Epidemic typhus, Erythema infectiosum, Exanthem subitum, Fasciolopsiasis, Fasciolosis, Fatal familial insomnia (FFI), Filariasis, *Fusobacterium* infection, Gas gangrene (Clostridial myonecrosis), Geotrichosis, Gerstmann-Sträussler-Scheinker syndrome (GSS), Giardiasis Glanders, Gnathostomiasis, Gonorrhea, Granuloma inguinale (Donovanosis), Group A streptococcal infection, Group B streptococcal infection, *Haemophilus influenzae*, Hand, foot and mouth disease (HFMD), Hantavirus Pulmonary Syndrome (HPS) *Helicobacter pylori* infection, ic-uremic syndrome (HUS), Hemorrhagic fever with renal syndrome (HFRS), Hepatitis A, B, C, D, E, Herpes simplex, Histoplasmosis, Hookworm infection, n bocavirus infection, Human ewingii ehrlichiosis, Human granulocytic anaplasmosis (HGA), Human granulocytic anaplasmosis (HGA), Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis). Lymphatic filariasis (Elephantiasis), Lymphocytic choriomeningitis, Malaria, Marburg hemorrhagic fever (MHF). Measles. Melioidosis (Whitmore's disease), Meningitis. Meningococcal disease, Metagonimiasis, Microsporidiosis, Molluscum contagiosum (MC), Mumps, Murine typhus (Endemic typhus). *Mycoplasma* pneumonia, Mycetoma, Myiasis, Neonatal conjunctivitis (Ophthalmia neonatorum). (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, Poliomyelitis, *Prevotella* infection, mary amoebic meningoencephalitis (PAM), Progressive multifocal leukoencephalopathy, Psittacosis, Q fever, Rabies, Rat-bite fever, Respiratory syncytial virus infection, Rhinosporidiosis, inovirus infection, Rickettsial infection, Rickettsialpox, Rift Valley fever (RVF), Rocky mountain spotted fever (RMSF), Rotavirus infection, Rubella, *Salmonellosis*, SARS (Severe Acute Respiratory Syndrome), Scabies. Schistosomiasis, Sepsis, Shigellosis (Bacillary dysentery), Shingles (Herpes zoster). Smallpox (Variola), Sporotrichosis, Staphylococcal food poisoning, Staphylococcal infection, Strongyloidiasis. Syphilis, Taeniasis, tanus (Lockjaw), Tinea barbae (Barber's itch), Tinea capitis (Ringworm of the Scalp), Tinea corporis (Ringworm of the Body), Tinea cruris (Jock itch). Tinea manuum (Ringworm of the Hand). Tinea nigra, Tinea unguium (Onychomycosis), Tinea *versicolor* (*Pityriasis versicolor*), Toxocariasis (Visceral Larva Migrans (VLM)), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, viral pneumonia, West Nile Fever, White *piedra* (Tinea blanca), *Yersinia pseudontuberculosis* infection, Yersiniosis, Yellow fever, and Zygomycosis.

In another embodiment, a Compound of the Disclosure, or composition thereof, is administered to a subject to treat angioedema in the subject. In another embodiment, the angioedema is hereditary angioedema.

In another embodiment, a Compound of the Disclosure, or composition thereof, is administered to a subject treat a disease, condition or disorder selected from the group consisting of sepsis, hypercoagulability, pulmonary dysfunction, hypoxemia, hemorrhagic pancreaitis, myocardial infarction, lung transplantation, trauma, thermal injury and vascular leak in the subject.

In another embodiment, a Compound of the Disclosure, or composition thereof, is administered to a subject to treat a disease, condition or disorder in which inhibition of kallikrein provides a therapeutically beneficial effect. Examples of such diseases, conditions or disorders include, but are not limited to, disease, conditions or disorders of the contact system. See e.g., Shariat-Madar et al., *Innate Immunity*, vol. 10, no. 1, 3-13 (2004) and Frick, el al., *EMBO. J.*, (2006) 25, 5569-5578 (2006). In another embodiment, a Compound of the Disclosure, or composition thereof, is administered a subject to treat a disease, condition or disorder selected from the group consisting of atherothrombosis, coronary artery disease, Alzheimer's Disease, inflammatory bowel disease (for example, Crohn's Disease), vascular leak, acute respiratory distress syndrome and bradykinin-mediated inflammation in the subject.

In another embodiment, a Compound of the Disclosure, or composition thereof, is administered to a subject to treat a disease, condition or disorder in which inhibition of bradykinin B2 receptor provides a therapeutically beneficial effect. In another embodiment, a Compound of the Disclosure, or composition thereof, is administered to a subject treat a disease, condition or disorder selected from the group consisting of glomerulosclerosis, Alzheimer's Disease, cerebral edema, vascular leak, acute respiratory distress syndrome, pain, inflammation, trauma, burns, shock, allergy, and cardiovascular disease in the subject.

In another embodiment, a Compound of the Disclosure, or composition thereof, is administered to a subject to treat an infectious disease in the subject, for example, an infectious disease selected from the group consisting of Bovine respiratory disease, Porcine respiratory disease, Avian influenza, Avian infectious bronchitis, Bovine spongiform encephalopathy, Canine leishmaniasis, Chronic wasting disease, human immune deficiency virus (HIV), hepatitis, hepatitis A, hepatitis B, hepatitis C, Classical swine fever, *Echinococcus*, Enzootic pneumonia, HIP, foot-and-mouth disease, Jaagsiekte, Maedi-Visna, Mastitis in animals, *Microsporum canis*, Orf (animal disease), Peste des petits ruminants, Pox diseases, Psittacine beak and feather disease, Rabies, Mediterranean fever (Brucellosis) or Bang's disease or undulant fever, Malta fever, contagious abortion, epizootic abortion, *Salmonella* food poisoning, enteric paratyphosis, Bacillary dysentery, *Pseudotuberculosis*, plague, pestilential fever. Tuberculosis, Vibrios, Circling disease, Weil's disease (Leptospirosis) or *canicola* fever, Hemorrhagic jaundice (Leptospira icterohaemorthagiae), dairy worker fever (L, hardjo), Relapsing fever, tick-borne relapsing fever, spirochetal fever, vagabond fever, famine fever, Lyme arthritis, Bannworth's syndrome (lime disease), tick-borne meningopolyneuritis, erythema chronicum migrans, Vibriosis, Colibacteriosis, colitoxemia, white scours, gut edema of swine, enteric paratyphosis. Staphylococcal alimentary toxicosis, staphylococcal gastroenteritis, Canine Corona Virus (CCV) or canine parvovirus enteritis, feline infectious peritonitis virus, transmissible gastroenteritis (TGE) virus. Hagerman Redmouth Disease (ERMD), Infectious Hematopoietic necrosis (IHN), porcine *Actinobacillus* (*Haemophilus*) pleuropneumonia, Hansen's disease, Streptotrichosis, Mycotic Dermatitis of Sheep, Pseudoglanders, Whitmore's disease, Francis' disease, deer-fly fever, rabbit fever, O'Hara disease. Streptobacillary fever, Haverhill fever, epidemic arthritic erythema, sodoku, Shipping or transport fever, hemorrhagic septicemia, Omithosis, Parrot Fever, Chlamydiosis, North American blastomycosis, Chicago disease, Gilchrist's disease, Cat Scratch Fever, Benign Lymphoreticulosis, Benign nonbacterial Lymphadenitis, Bacillary Angiomatosis, Bacillary Peliosis Hepatis, Query fever, Balkan influenza, Balkan grippe, abattoir fever, Tick-borne fever, pneumorickettsiosis, American Tick Typhus, Tick-borne Typhus Fever, Vesicular Rickettsiosis, Kew Gardens Spotted Fever, Fleaborne Typhus Fever. Endemic Typhus Fever, Urban Typhus, Ringworm, Dermatophytosis, Tinea, Trichophytosis, Microsporosis, Jock Itch, Athlete's Foot, *Sporothrix schenckii*, dimorphic fungus, Cryptococcosis and histoplasmosis, Benign Epidermal Monkeypox, BEMP, *Herpesvirus simiae*, Simian B Disease, Venezuelan equine encephalitis, Type C lethargic encephalitis, Yellow fever, Black Vomit, hantavirus pulmonary syndrome, Korean Hemorrhagic Fever, Nephropathia Epidemica, Epidemic Hemorrhagic Fever. Hemorrhagic Nephrosonephritis, lymphocytic choriomeningitis, California encephalitis/La crosse encephalitis, African Hemorrhagic Fever. Green or Vervet Monkey Disease, Hydrophobia, Lyssa, Infectious hepatitis, Epidemic hepatitis, Epidemic jaundice, Rubeola, Morbilli, Swine and Equine Influenza, Fowl Plague, Newcastle disease, Piroplasmosis, toxoplasmosis, African Sleeping Sickness, Gambian Trypanosomiasis, Rhodesian Trypanosomiasis, Chagas's Disease, Chagas-Mazza Disease, South American Trypanosomiasis, *Entamoeba histolytica*, Balantidial dysentery, cryptosporidiosis, giardiasis, Cutaneous leishmaniasis: Chiclero ulcer, espundia, pianbols, uta, and buba (in the Americas); oriental sore, Aleppo boil (in the Old World); Bagdad boil, Delhi boil, Bauru ulcer, Visceral leishmaniasis: kala-azar. Microsporidiosis, Anisakiasis, Trichinosis, Angiostrongylosis, eosinophilic meningitis or meningoencephalitis (*A. cantonensis*), abdominal angiostrongylosis (*A. costaricensis*), Uncinariasis, Necatoriasis, Hookworm Disease, Capillariasis, Brugiasis, Toxocariasis, Oesophagostomiasis, Strongyloidiasis, Trichostrongylosis, Ascaridiasis. Diphyllobothriasis, Sparganosis, Hydatidosis, Hydatid Disease, *Echinococcus* granulosis, Cystic hydatid disease, Tapeworm Infection, and *Schistosoma*.

In another embodiment, a Compound of the Disclosure, or composition thereof, is administered to a subject to treat chronic renal disease, osteoarthritis, oncology, viral upper respiratory infection, feline plasma cell stomatitis, feline eosinophillic granulomas, feline leukemia virus infection, canine distemper infection, systemic fungal infections, cardiomyopathy, and mucopolysaccharidosis VII in the subject.

In the methods of the present disclosure, the gene switch regulates the expression of a polynucleotide encoding a peptide, protein, or polypeptide. In one embodiment, gene switch regulates the expression of a polynucleotide encoding a peptide, protein, or polypeptide of therapeutic interest for the treatment of a disease, condition, or disorder in a subject, e.g., a human. In another embodiment, the peptide, protein, or polypeptide of interest is selected from the group consisting of Her-2/neu (ERBB2/c-erbB-2), Osteocalcin, stromelysin-1, prostate specific antigen, human sodium-iodide symporter, H19, IF-1, IGF-2, thymosin $\beta$15, T cell factor, cartilage-derived retinoic acid-sensitive protein, Prostasin, telomerase catalytic subunit, cyclin-A, midkine; c-erbB-2, prostate-specific membrane antigen, p51, telomerase RNA, prostatic acid phosphatase, PCA3dd3, DF3/MUC1, hex 11, cyclooxygenase-2, super PSA, skp2. PRL-3, CA125/M17S2. IAI.3B, CRG-L2, TRPM4, RTVP, TARP, telomere reverse transcriptase. A4 amyloid protein, amyloid $\beta$-protein precursor, precursor of the Alzheimer's Disease A4 amyloid protein, neuropeptide FF, endoplasmic reticulum stress elements, urocortin II, tyrosine hydroxylase, complement factor 3; serum amyloid A3, tissue inhibitor of metalloproteinase-3 (TIMP-3), p75 tumor necrosis factor receptor, tumor necrosis factor-$\alpha$, TRPM4, RTVP, TARP, telomere reverse transcriptase, A4 amyloid protein, amyloid $\beta$-protein precursor, precursor of the Alzheimer's Disease A4 amyloid protein, neuropeptide FF, endoplasmic reticulum stress elements, urocortin II, tyrosine hydroxylase, complement factor 3; serum amyloid A3, tissue inhibitor of metalloproteinase-3 (TIMP-3), p75 tumor necrosis factor receptor, tumor necrosis factor-$\alpha$, peroxisome proliferator activated receptor/IIA-1 nonpancreatic secreted phospholipase A2, SOCS-3, SR—BI, Ob, site-1 protease, TIGR, VL30, excitatory amino acid transporter-2, MDTS9, LIM, pyrroline 5-carboxylate reductase, SIM2, Bax, Fas, bbc3, PINK-1, troponin T, myoD, Actin, smooth muscle 22α, Utrophin, Myostatin, smooth muscle myosin heavy chain, cardiac ankyrin repeat protein, MLP, Smoothelin, MYBPC3, Tα1 α-tubulin, intercellular adhesion molecule-4 (ICAM-4), γ-aminobutyric acid type A receptor β1 subunit, neuronal nicotinic acetylcholine receptor β2-subunit, presenilin-1, calcium-calmodulin-dependent kinase IIα. CRF2α receptor, nerve growth factor, GLP-2 receptor, type I transglutaminase, K14, stearoyl-CoA desaturase, Megsin, Prolactin, GDF-9, PSP94, NRL, NGAL, long whey acidic protein, mammary associated amyloid A, endothelin-1, Serglycin, platelet-endothelial cell adhesion molecule-1 (PECAM-1), Tie receptor tyrosine kinase, KDR/flk-1, Endoglin, CCR5. CD11d, platelet glycoprotein IIb, preproendothelin-1, interleukin-18 binding protein, CD34, Tec tyrosine kinase, MLH1, MSH2, MSH6, PMS1, APC, LEF-1, F2 receptor. TGF-β type II receptor, EYA4, PCA3, K2, PROST 03, PCAM-1, PCADM-1, PCA3dd3, PCAV, PAcP, $ATB_0$, CSA-1, SYG972. Urb-ctf, BCU399, TBX2, Cyr61, DIAPH3, BEHAB, IL-8, BLSA, BP1, DAP-kinase, HOXA9, ARP, Nbk, CD43, β7-hcG, β6-hCG, β6e-hCG, β5-hCG, β8-hcG, β3-hCG, MTA1s, Old-35, Old-64, LAGE-1, CIF150/hTAFII150, P65 oncofetal protein, Telomerase, CYPIBI, 14-3-3σ, NESI, CAR-1, HMGI. MAG. ELL2, Ephrin B2, WAFI. CIF130. C35, BMP2. BUB3, Polymerase kappa. EAG1, EAG2, HMG 1, HLTF, Barx2, Pp 32r1, BMP4, TS10q23.3, Nuclear spindle-associating protein, PFTAIRE, SEMA3B. MOGp, Fortilin, IGFBP-3, Polyhomeotic 2, PNQALRE, SCN5A, miR15, miR16, Headpin, PAOh1/SMO, Hippo, Mst2, PSMA-like, JAB1. NF-AT, P28ING5. MTG16, ErbB-2, HDAC9, GPBP. MG20, KLF6. ARTSI, Dock 3, Annexin 8, MH15, DELTA-N p73, RapR6, StarD10, Ciz1, HLJ1, RapR7, A34, Sef, Killin, SGA-1M, TGFβ Type II receptor, GCA-associated genes, PRV-1. Vezf1, MLP, VEGI, PRO256, AOP2, Remodelin, Phosphodiesterase 4D, Prostaglandin receptor subtype EP3, CARP, HOP, PLTP, UCP-2, FLJ110I, Codanin-1, Resistin, Archipelin, Neuronatin, NcbSor, 7B2, PTHrP, PEX, KChIP1, SLIT-3, CX3CR1, SMAP-2, IC-RFX, E21G4, UCP2, Ob receptor, Ob, Dpl, NRG-1, Synapsin III, NRGIAGI, AL-2, Proline dehydrogenase, MNR2, ATM. Ho-1, CON202, Ataxin-1, NR3B, NIPA-1, DEPP, adrenomedullin, csdA, Inf-20, EOPA, SERT, FRP-1, Senim amyloid A, BMP2, BMPR1A, ACLP, Resistin-like molecule β, Dig5, TRANCE. Matrilin-3, Synoviolin, HIV LTR, SHIVA, EBI 1, EBI 2. EBI 3, NM23. Eps8, Beta-10, Hair follicle growth factor, Comeodesmosin, GCR9, Bg, FGF23, BBSR, MIC-1, MIA-2, IL-17B, Formylglycine generating enzyme, LPLA2, CXCL1O, HFE2A, IL-1, IL-2, IL-3, IL-4, IL-5, IL-7, IL-8, IL-9, IL-10R DN or a subunit thereof, IL-5, IL-18, IL-21, IL-23, IL-24. IL-27, GM-CSF. IFN-alpha, IFN-gamma, IFN-alpha 1, IFN alpha 2, IL-15-R-alpha, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, TFN-beta, TNF-alpha, dnFADD, BCG, TGF-alpha, PD-L1 RNAi, a PD-L antisense oligoiucleotide, TGFbRII DN, ICOS-L, S100, CD40L, p53, survivin, p53-survivin fusion, MAGE3, myelin basic protein, PSA and PSMA.

In another embodiment, the peptide, protein, or polypeptide of interest is ciliary neurotrophic factor, vasohibin, IL-10, Erythro-poietin, VEGF trap, or PDGF.

In another embodiment, the peptide, protein, or polypeptide of interest is a JUN-kinase inhibitor, vasoinhibin, EPO, or CTNF In another embodiment, the gene switch regulates the expression of a polynucleotide encoding an IL-12 or a subunit thereof. In another embodiment, the IL-12 or subunit thereof is human IL-12 or subunit thereof.

In another embodiment, the gene switch regulates the expression of a polynucleotide encoding a C1 esterase inhibitor (for example, a human C1 esterase inhibitor), a kallikrein inhibitor, or a bradykinin B2 receptor antagonist.

Examples of kallikrein inhibitors include, but are not limited to, ecallantide and those kallikrein inhibitors set forth U.S. Patent Publication Nos. 2010/0034805, 2009/0264350, 2009/0234009, 2008/0221031, 2007/0213275, 2006/0264603 and 2005/0089515.

Examples of bradykinin B2 receptor inhibitors include, but are not limited to, helokinestatin and anti-bradykinin B2 receptor antibodies. The amino acid sequence of helokinestatin is set forth in Kwok, H. F. et al., *Peptides* 291.65-72 (2008). Nonlimiting examples of anti-bradykinin B2 receptor antibodies are set forth in Alla, S. A. et al., *J. Biol. Chem.* 271.1748-1755 (1996).

In another embodiment, the gene switch regulates the expression of a polynucleotide encoding an IL-12 or a subunit thereof for the treatment of cancer, e.g., melanoma, in a subject, e.g., a human.

In another embodiment, a polynucleotide encodes (a) a gene switch that comprises a GAL4 DNA binding domain, the *Choristoneura fumiferana* ecdysone receptor ligand binding domain having the mutations V107I and Y127E (relative to the *Choristoneura fumifrana* ecdysone receptor sequence set forth in U S. Patent Publication No. 2006/0100416 A1), a chimeric RXR ligand binding domain consisting of helices 1-8 of *Homo sapiens* RXR and helices 9-12 of *Locusta migratoria* RXR, the VP16 transactivation domain, and (b) human IL-12, and the gene switch encoded by the polynucleotide regulates the expression of human IL-12 when the ecdysone receptor ligand binding domain in the gene switch binds a Compound of the Disclosure. In a further embodiment, the polynucleotide is administered to a subject having a cancer such as melanoma. The polynucleotide may be administered intratumorally either in a pharmaceutically acceptable carrier, or contained by an immune cell such as a dendritic cell. In one embodiment, the polynucleotide is administered to a subject followed by administration of a Compound of the Disclosure, or composition thereof. In another embodiment, a Compound of the Disclosure. or composition thereof, is administered to a subject followed by administration of the polynucleotide. For example, a Compound of the Disclosure, or composition thereof, may be administered to the subject on day −1, 0, +1, +2, +3, +4, +5, +6, +7, or more, relative to the day the polynucleotide is administered to the subject.

In another embodiment, the gene switch regulates the expression of a polynucleotide encoding a transcription factor, e.g., GATA-1, friend of GATA (FOG-1), EKLF (a Kruppel-like transcription factor), p45/nuclear factor-erythroid 2 (NF-E2), stem cell leukemia (SCL) or T-cell acute lymphocytic leukemia-1, OCT4, or Sry-related high-mobility group box transcription factor (Sox6), or growth factor, e.g., IGF11, bFGF, Flt3, stem cell factor (SCF), thrombopoietin (TPO), bone morphogenetic protein 4 (BMP4), recombinant human vascular endothelial growth factor (VEGF-A165), interleukin-3 (IL-3) interleukin-6 (IL-6), or interleukin-11 (IL-11), or erythropoietin, for use in regenerative medicine, e.g., differentiation, trans-differentiation, reprogramming, self-renewal, or expansion of hematopoietic stem cells, haematopoietic progenitor cells, or induced pluripotent stem cells in the process of blood pharming, i.e., production of red blood cells or other blood products, in a subject.

General Synthetic Methods

Compounds of the Disclosure are prepared using methods known to those skilled in the art in view of this disclosure (see, e.g., U.S. Pat. Nos. 8,076,517, 7,456,315, 7,304,161, and 6,258,603), and/or by the illustrative methods shown in the General Schemes below.

General Scheme 1

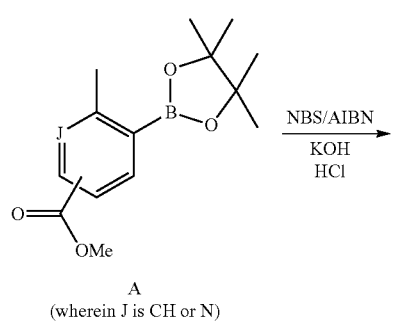

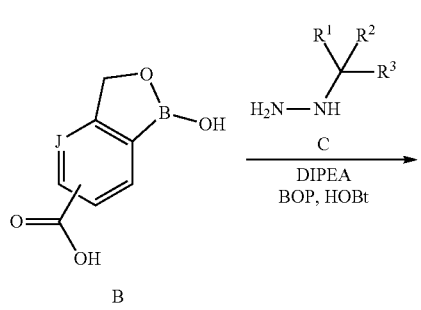

General Scheme 2

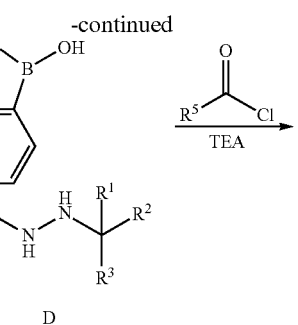

D

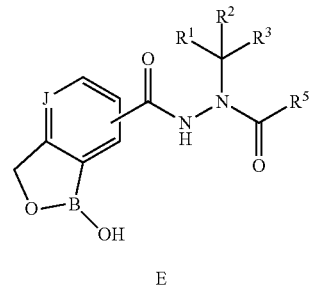

E

General Scheme 3

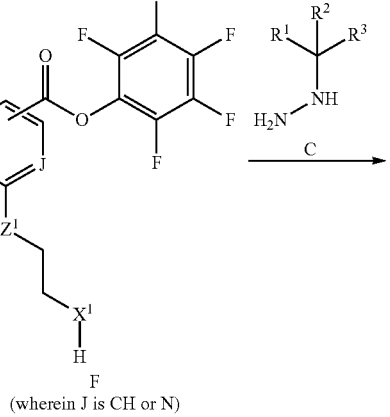

F
(wherein J is CH or N)

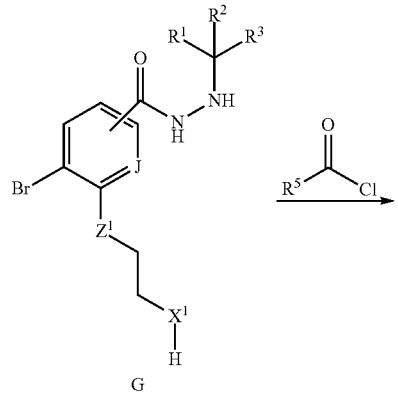

G

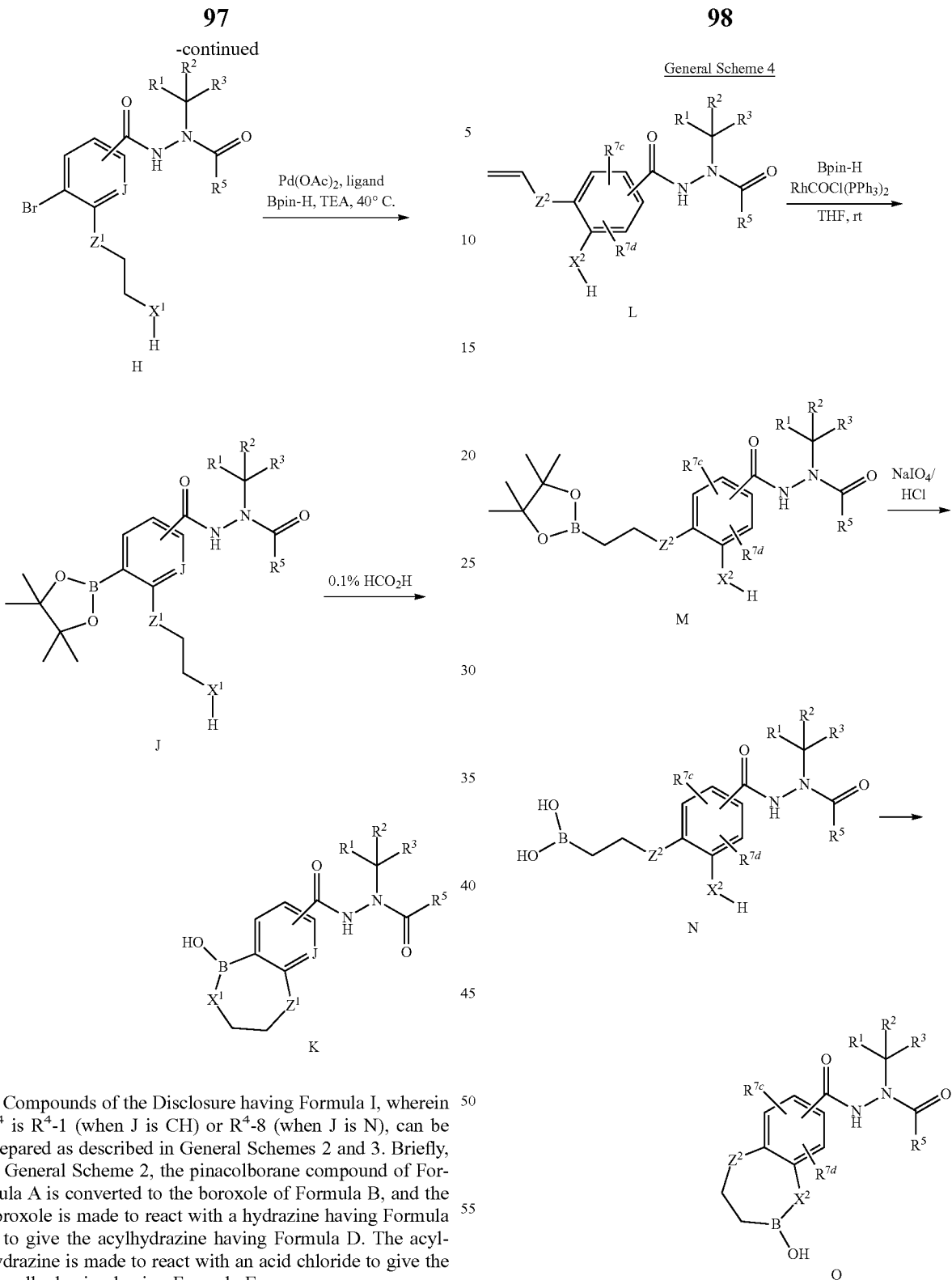

Compounds of the Disclosure having Formula I, wherein $R^4$ is $R^4$-1 (when J is CH) or $R^4$-8 (when J is N), can be prepared as described in General Schemes 2 and 3. Briefly, in General Scheme 2, the pinacolborane compound of Formula A is converted to the boroxole of Formula B, and the boroxole is made to react with a hydrazine having Formula C to give the acylhydrazine having Formula D. The acylhydrazine is made to react with an acid chloride to give the diacylhydrazine having Formula E.

In General Scheme 3, a compound having Formula P is made to react with hydrazine having Formula C to give the acylhydrazine having Formula G. The acylhydrazine is made to react with an acid chloride to give the diacylhydrazine having Formula H. The bromo group of the compound having Formula H is converted to pinacolborane having Formula J then converted to a boronic acid which cyclizes to give diacylhydrazines having Formula K Compounds of the Disclosure having Formula I, wherein $R^4$ is $R^4$-2, can be prepared as described in General Scheme 4. Briefly, the olefin of a diacylhydrazine having Formula L is converted to the pinacolborane having Formula M. The pinacolborane is converted the boronic acid having Formula N, and the compound having Formula N is cyclized to give compound O.

General Scheme 5
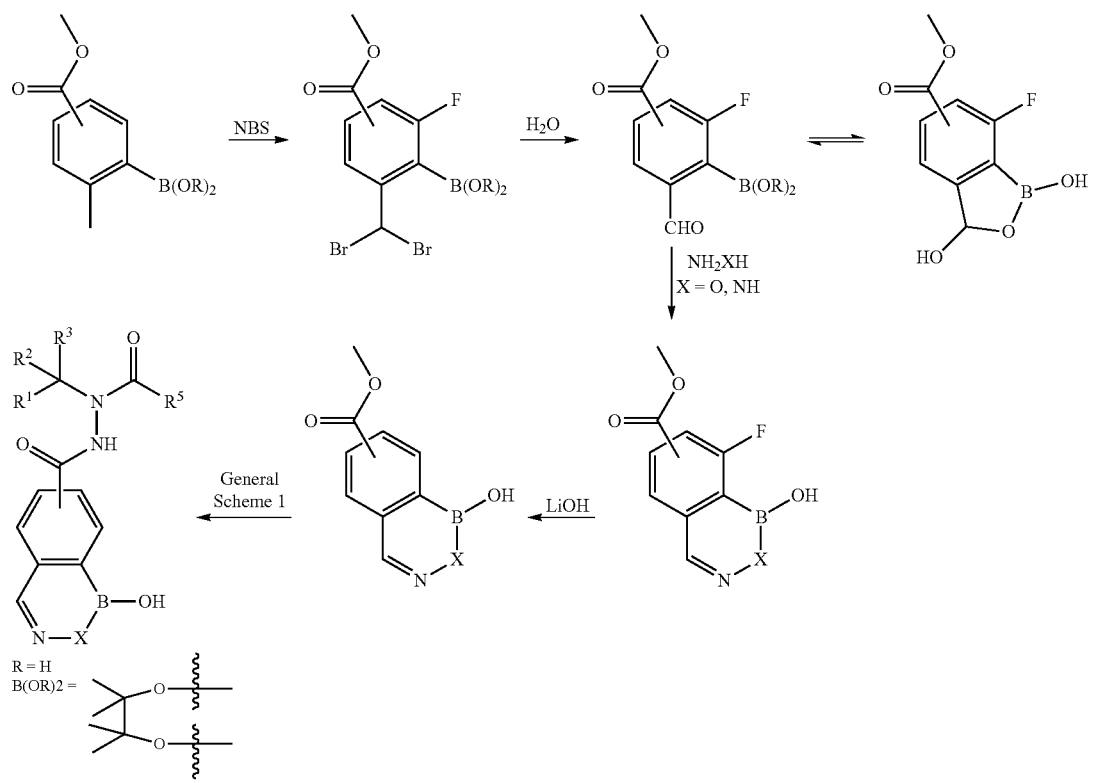
Compounds of the Disclosure having Formula I, wherein $R^4$ is $R^4$-3, $R^{6c}$ is OH, and $R^{7c}$ and $R^{7f}$ are hydrogen, can be prepared as described in General Scheme 5.
General Scheme 6
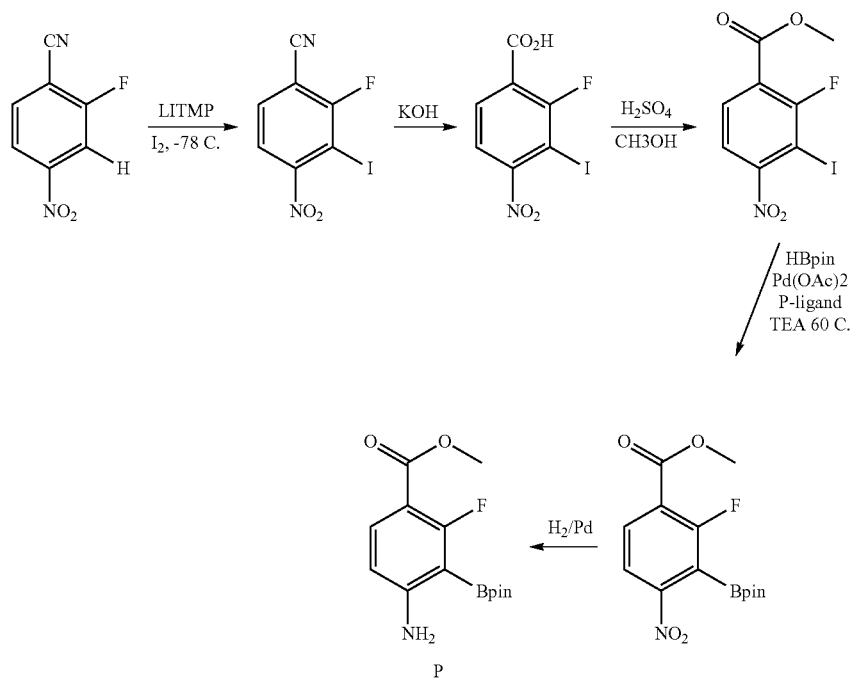

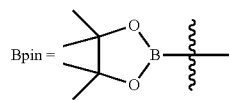
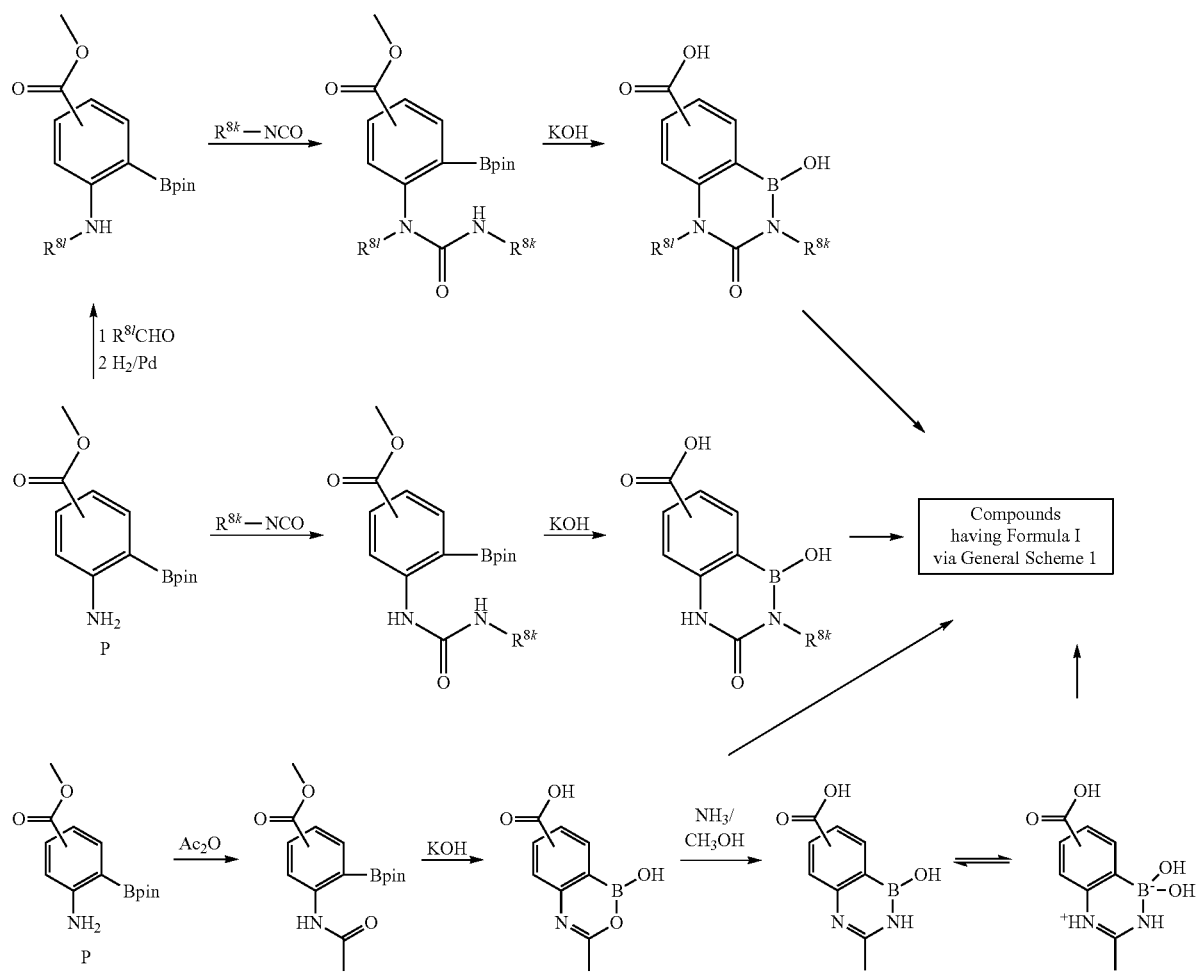
General Scheme 7
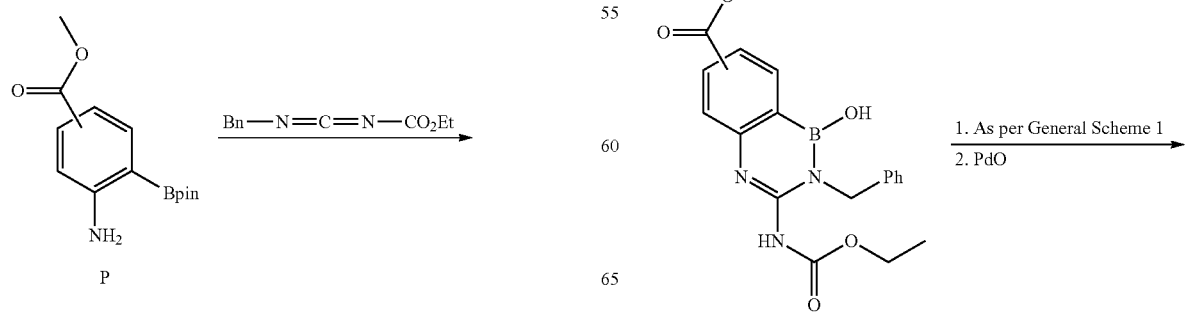
General Scheme 8

103

-continued

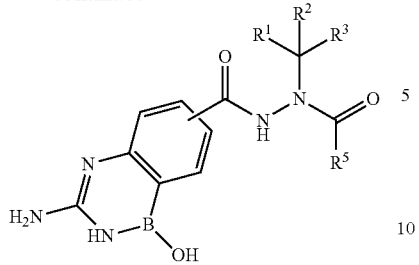

Compounds of the Disclosure having Formula I, wherein $R^4$ is $R^4$-4, $R^{6d}$ is OH, and $R^{7g}$ and $R^{7h}$ are hydrogen, can be prepared as described in General Schemes 6, 7, and 8.

General Scheme 9

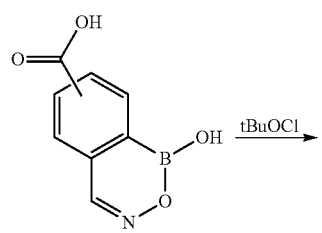

104

-continued

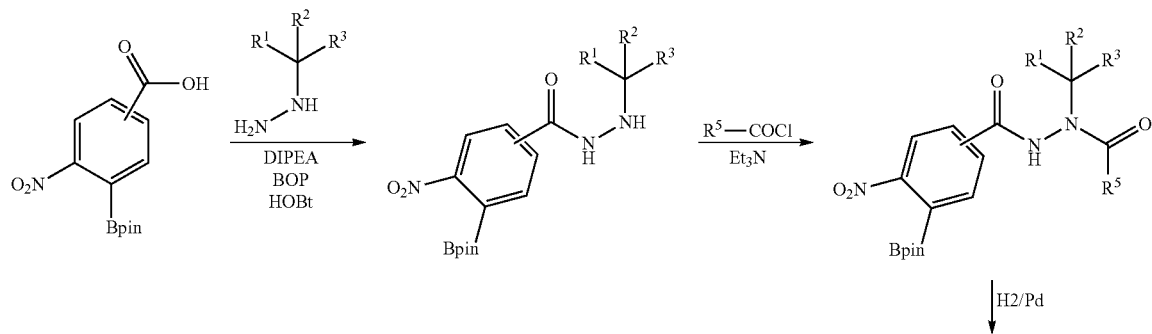

Compounds of the Disclosure having Formula I, wherein $R^1$ is $R^4$-9, and $R^{7a'}$ and $R^{7b'}$ are each hydrogen, can be prepared as described in General Scheme 9.

General Scheme 10

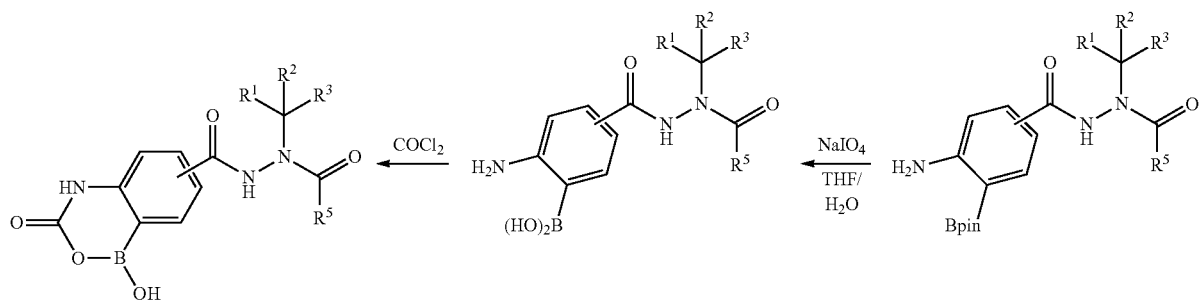

Compounds of the Disclosure having Formula I, wherein $R^4$ is $R^4$-10, $X^6$ is —O—, and $R^{7a'}$ and $R^{7b'}$ are each hydrogen, can be prepared as described in General Scheme 10. Compounds of the Disclosure having Formula I, wherein $R^4$ is $R^4$-10, $X^6$ is —N($R^{8l}$)—, and $R^{7a'}$ and $R^{7b'}$ are each hydrogen, can also be prepared as described in General Scheme 7.

EXAMPLES

Example 1

Synthesis of N'-(teri-butyl)-N'-(3,5-dimethylbenzoyl)-1-hydroxy-1,3-dihydrobenzo[c][1,2]oxaborole-6-carbohydrazide (Cpd No. 50)

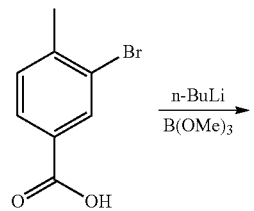

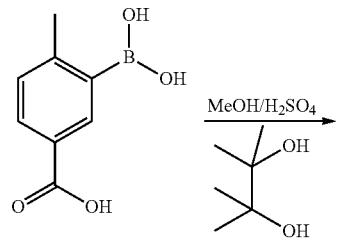

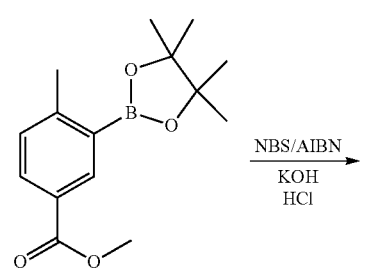

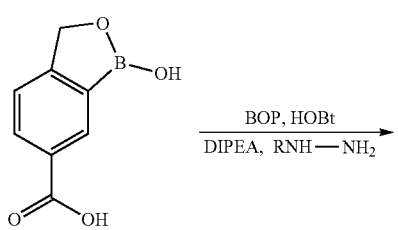

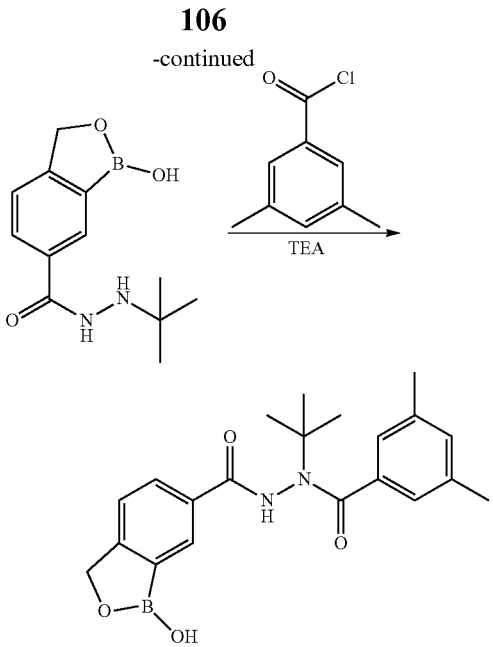

Cpd. No. 50

Step 1: Synthesis of 3-borono-4-methylbenzoic acid

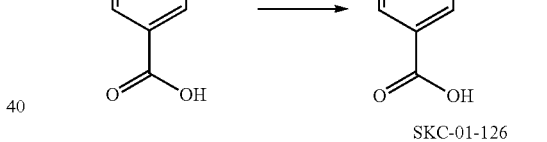

SKC-01-126

3-Bromo-4-methylbenzoic acid (11.00 g, 51.2 mmol) was dissolved in anhydrous THF (150 ml) under argon in a 500 ml 3-necked round bottom flask fitted with two dropping funnels and argon inlet. The stirred solution was cooled to −78° C. and n-BuLi (1.6M in hexane, 60.7 ml, 97.0 mmol) was added drop wise from a dropping funnel (during 1 h). After completion of the addition, the solution was stirred at −78° C. for another 1 h. To this, B(OMe)$_3$ (17.7 ml, 159.0 mmol) was added slowly from a second dropping funnel. The mixture was stirred 1 h at −78° C. and then warmed up to room temperature overnight. The solvent was evaporated under reduced pressure. The crude product was dissolved in ether and poured into aqueous HCl (1N). The mixture was extracted with ether (3×150 ml), and the combined organic layers were washed with brine, dried over anhydrous MgSO$_4$, filtered, and evaporated to dryness. The crude product was purified using an ISCO system (220 g silica column, hexane/EtOAc gradient and later DCM/MeOH gradient). The impurities washed off in hexane/EtOAc and the pure product eluted in MeOH/DCM (5:95) solvent mixture to give 3.3 g (33% yield) of pure SKC-01-126. $^1$H NMR (400 MHz, Acetone-d$_6$) δ 12.10 (br s, 1H), 8.16 (s, 1H), 7.90-7.63 (m, 1H), 7.11 (d, J=7.9 Hz, 1H), 2.42 (s, 3H).

Step 2 Synthesis of methyl 4-methyl-3-(4,4,5,5-tetramethyl-1,3,2-dioxaborolan-2-yl)benzoate

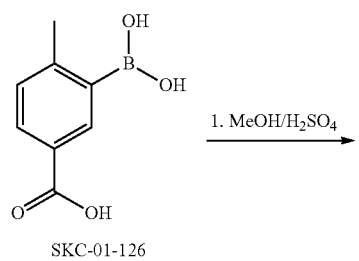

Step 3: Synthesis of 1-hydroxy-1,3-dihydrobenzo[c][1,2]oxaborole-6-carboxylic acid

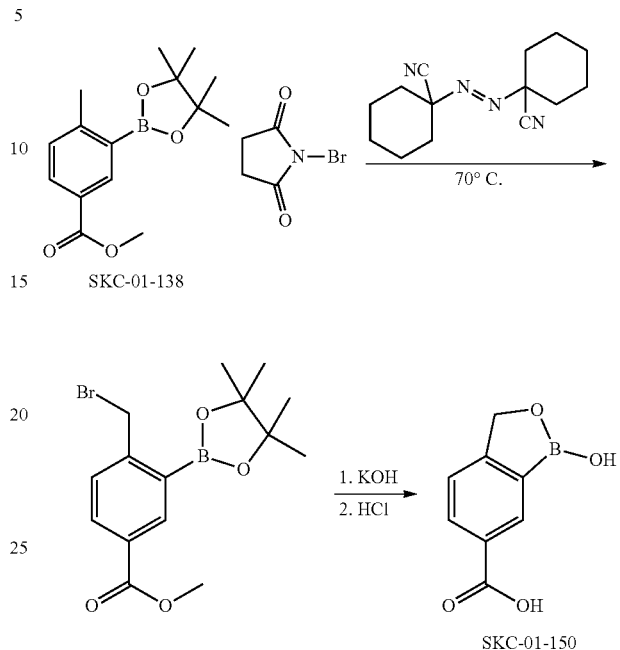

To a stirred solution of SKC-01-126 (3.3 g, 18.3 mmol) in MeOH (100 ml) in a 250 ml round bottom flask fitted with a reflux condenser and drying guard tube was added 3 ml concentrated $H_2SO_4$. The mixture was refluxed overnight. After cooling to room temperature, the solvent was evaporated in vacuum. Water was added and the product was extracted with ethyl acetate. The combined organic layers were washed with brine, dried over anhydrous $MgSO_4$, filtered, and evaporated to dryness to give the methyl ester SKC-01-127 as a white solid. Without further purification, the methyl ester (4.00 g, 20.6 mmol) was dissolved in dry toluene (100 ml) in a 250 ml round bottom flask fitted with a Dean-stark trap. To the stirred reaction mixture, 2,3-dimethylbutane-2,3-diol (3.66 g, 30.9 mmol) was added followed by catalytic amount of p-TSOH.$H_2O$ (0.196 g, 1.03 mmol). The reaction mixture was heated to reflux overnight for 2 days. Water was collected (~2 ml) and removed. After cooling, the reaction mixture became solid. The crude product was purified using an ISCO system (80 g silica column, hexane/EtOAc gradient) to give SKC-01-138. LCMS (M+H) 277. $^1$H NMR (400 MHz, $CDCl_3$) δ 8.32 (d, J=1.9 Hz, 1H), 7.87 (dd, J=8.0, 2.0 Hz, 1H), 7.12 (d, J=8.0 Hz, 1H), 3.79 (s, 3H), 2.48 (s, 3H), 1.25 (s, 12H).

To a solution of SKC-01-138 (1.50 g, 5.43 mmol) in anhydrous $CCl_4$ (30 ml) was added N-bromosuccinimide (1.01 g, 5.70 mmol). To this stirred mixture, dicyclohexanecarbonitrile was added as a catalyst (0.07 g, 0.27 mmol) in four portions during 1 h. The mixture was stirred at 70° C. overnight. LCMS showed a major peak at 5.75 min with the expected mass of the benzyl bromide. After cooling, the solvent was evaporated in vacuo. The crude product was dissolved in ether and filtered to remove any succinimide. The filtrate was extracted with KOH (15% w/v in $H_2O$, 3×70 ml). The aqueous phase was stirred 1-2 h at room temperature ("rt"). The solution was cooled at 0° C. and HCl (6N in $H_2O$, ~120 ml) was added slowly to reach pH<2. The white precipitate was collected by filtration through a fritted glass funnel and air dried to afford the 5-carboxybenzoboroxole SKC-01-150 (0.800 g, 83% yield) as a white solid powder. $^1$H NMR (400 MHz, DMSO-$d_6$) δ 12.91 (s, 1H), 9.35 (s, 1H), 8.38 (s, 1H), 8.04 (dd, J=8.0, 1.5 Hz, 1H), 7.52 (d, J=8.0 Hz, 1H), 5.05 (s, 2H).

Step 4: Synthesis of N'-(tert-butyl)-1-hydroxy-1,3-dihydrobenzo[c][1,2]oxaborole-b-carbohyrazide

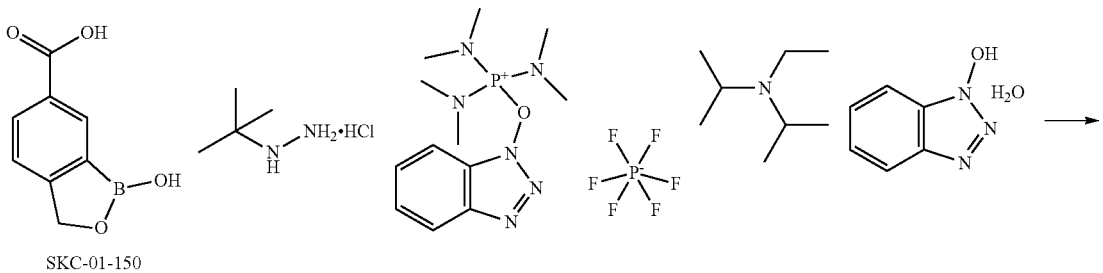

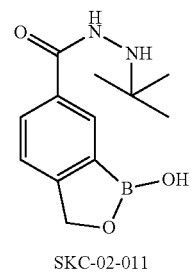

SKC-02-011

To a stirred solution of SKC-01-150 (150 mg, 0.84 mmol) in anhydrous DMF (1.5 ml) were added BOP (373 mg, 0.84 mmol), HOBt (129 mg, 0.84 mmol) and DIPEA (0.294 ml, 1.68 mmol) under argon at room temperature. The reaction mixture was stirred for 5 min. To this was added tert-butyl hydrazine hydrochloride (105 mg, 0.84 mmol) and the reaction mixture was stirred at 40° C. for 1 h. LCMS showed complete conversion of the boroxozole carboxylic acid. The reaction mixture was transferred to a scintillation vial, and the DMF was removed using a Genevac. The sticky crude mixture was dissolved in 15% aqueous KOH and ether. The reaction mixture was extracted with ether and washed three times with aqueous KOH. The aqueous fractions containing the product were cooled on an ice bath and 6N HCl was added slowly to make it to pH 1-2 The mixture was extracted using ethyl acetate. The product stayed in aqueous fractions and was evaporated to dryness under vacuum. The solid KCl was removed from the product by washing it with 5% MeOH in DCM and collecting the filtrate to get 95% pure product. This was further purified using an ISCO system after adsorbing the product on neutral alumina (24 g neutral alumina column, MeOH:DCM solvent mixture). The product eluted using ~5% MeOH in DCM. The fractions were collected and dried to give (0.187 g, 89% yield) the pure boroxazole carbohydrazide SKC-02-011. The viscous product was dissolved in water and small amount of THF, frozen and lyophilized to get light yellow powder. $^1$H NMR (400 MHz, MeOD) δ 8.11 (s, 1H), 7.93 (dd, J=8.0, 1.7 Hz, 1H), 7.52 (dd, =8.0, 0.7 Hz, 1H), 5.16 (s, 2H), 1.19 (s, 10H).

Using the procedure described above, the following reaction was conducted to give SCK-02-021:

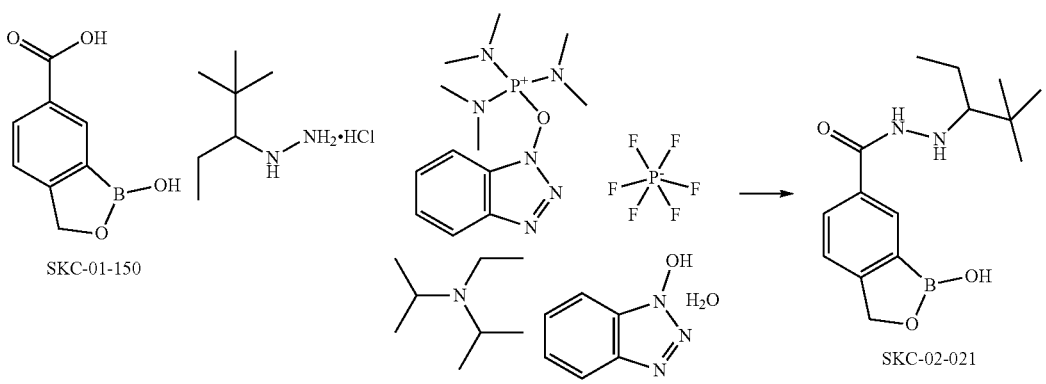

For the above reaction, SKC-01-150 (170 mg, 0.96 mmol) in anhydrous DMF (1.7 ml), BOP (423 mg, 0.96 mmol), HOBt (146 mg, 0.96 mmol), DIPEA (0.834 ml, 4.78 mmol) and hydrazine hydrochloride (105 mg, 0.84 mmol) were combined. The crude mixture was purified using an ISCO system (24 g neutral alumina, MeOH/DCM gradient). ¹H NMR (400 MHz, MeOD) δ 8.05 (s, 1H), 7.87 (d, J=7.8 Hz, 1H), 7.50 (d, J=7.8 Hz, 1H), 5.12 (s, 1H), 2.51-2.44 (m, 1H), 1.76-1.59 (m, 1H), 1.51-1.27 (m, 1H), 1.11 (t, J=7.4 Hz, 3H), 1.02 (s, 9H).

With a slight modification to the procedure described above, the following reaction was conducted to give (R)—N'-(2,2-dimethylpentan-3-yl)-7-fluoro-1-hydroxy-1,3-dihydrobenzo[c][1,2]oxaborole-6-carbohydrazide:

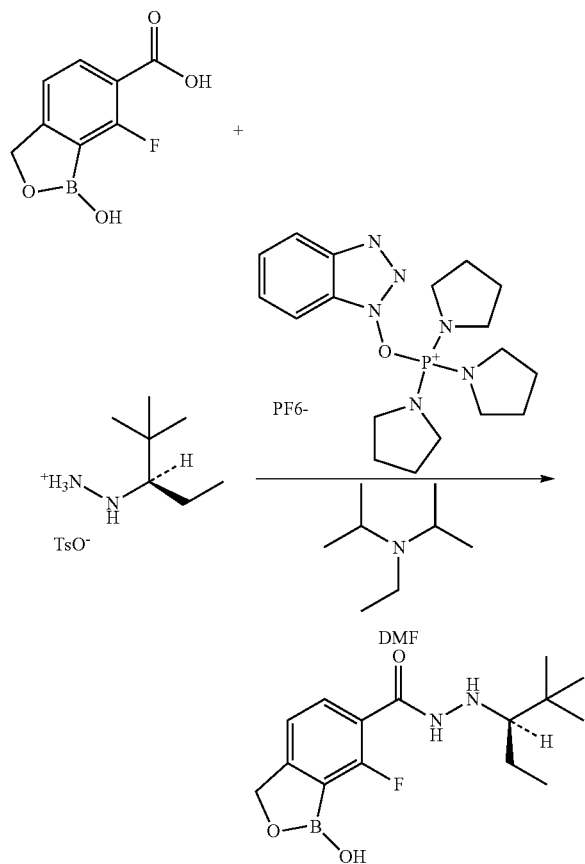

Step 4. Synthesis of N'-(tert-butyl)-N'-(3,5-dimethylbenzoyl)-1-hydroxy-1,3-dihydrobenzo[c][1,2]oxaborole-6-carbohydrazide (Cpd. No. 50)

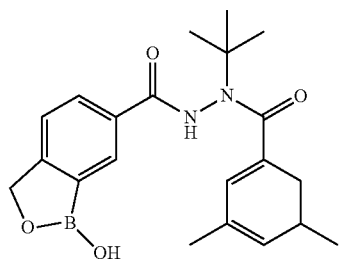

Cpd. No. 50

To a solution of the acid chloride (0.061 g, 0.363 mmol) in anhydrous DCM (2 ml) in a 100 ml round bottom flask under argon was added the boroxazole carbohydrazide SKC-02-011 (0.090 g, 0.363 mmol) followed by triethyl amine (0.051 ml, 00363 mmol). The reaction mixture was stirred overnight at room temperature. LCMS showed several peaks together with the expected product. Purification by prep HPLC gave 20 mg (14%) of Cpd. No. 50. ¹H NMR (400 MHz, DMSO-$d_6$) δ 10.63 (s, 1H), 7.89 (s, 1H), 7.54 (dd, 0.1=8 0, 1.5 Hz, 1H), 7.42 (d, 0.1=8 0 Hz, 1H), 7.09 (s, 2H), 6.91 (s, 1H), 4.99 (s, 2H), 2.20 (s, 6H), 1.49 (s, 9H).

Cpd. No. 50 was also prepared using a one pot procedure with SKC-01-150 (100 mg, 0.56 mmol), BOP (249 mg, 0.56 mmol), HOBt (86 mg, 0.56 mmol), DIPEA (0.098 ml, 0.56 mmol). All the reagents except the hydrazide were mixed in a 100 ml round bottom flask and dissolved in anhydrous DMF (2 ml) and stirred under argon for 5 min at room temperature. To this, N-(tert-butyl)-3,5-dimethylhydrazide (124 mg, 0.56 mmol) was added, and the reaction mixture was heated at 75° C. overnight. LCMS showed two close peaks, one of the peaks showed the mass of the expected product (mwt, 380.24) in ES+ and ES-mode. The reaction mixture diluted with ether and extracted with 10% w/v aqueous KOH. LCMS of the aqueous fractions showed a single peak with the expected product mass. The aqueous layer was cooled to 0° C., treated with 6N HCL drop wise to make it acidic (pH 1-2), and extracted with ethyl acetate. The organic fractions were collected, dried over anhydrous MgSO₄, filtered and concentrated. The residue was purified using prep HPLC to get 20 mg (9%) of Cpd No 50.

Using the procedure described above, the following reaction was conducted to give Cpd. No. 51.

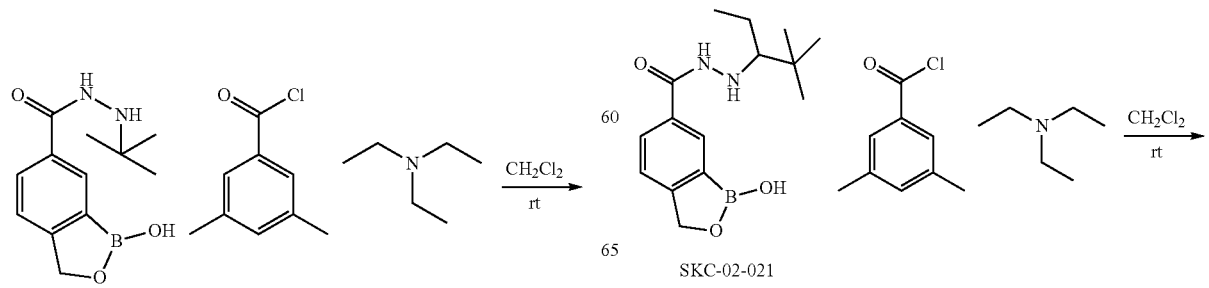

SKC-02-021

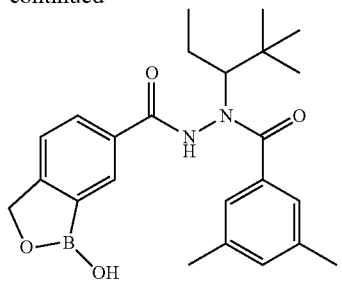

Cpd. No. 51

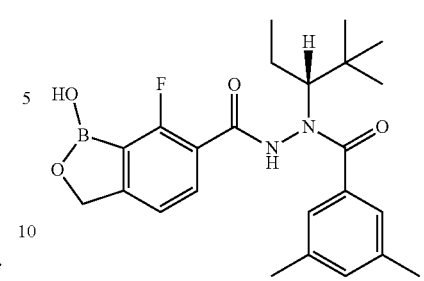

Cpd. No. 59

The reaction was conducted using SKC-02-021 (70 mg, 024 mmol), 3,5-dimethyl benzoyl chloride (40.7 mg, 0.24 mmol) and triethylamine (0.101 ml, 0.72 mmol) in 2 ml dichloromethane. The crude reaction mixture was purified using preparative HPLC to give Cpd. No. 51.

Using the procedure described above, the following reaction was conducted to give (R)—N'-(3,5-dimethylbenzoyl)-N'-(2,2-dimethylpentan-3-yl)-7-fluoro-1-hydroxy-1,3-dihydrobenzo[c][1,2]oxaborole-6-carbohydrazide (Cpd No. 59):

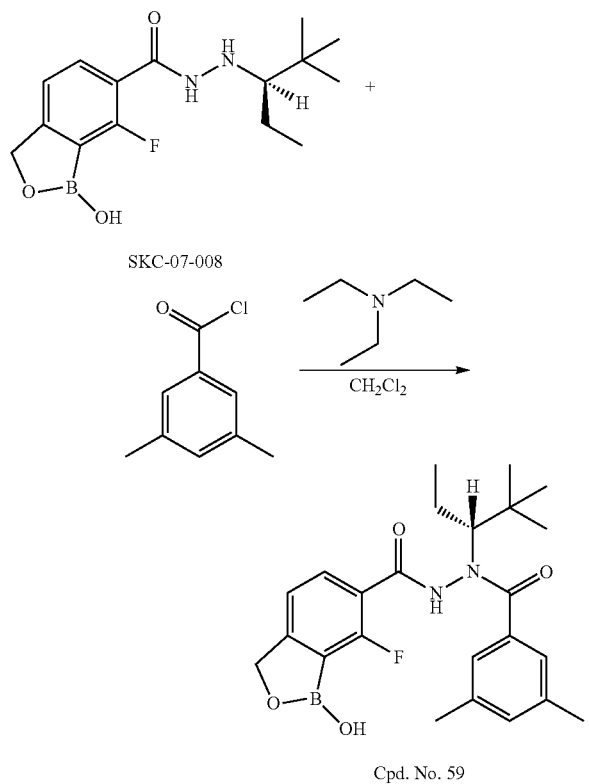

Cpd. No. 59

Cpd No. 59: LCMS [MH+]=441. $^1$H NMR (400 MHz, DMSO) δ 10.37 (d, J=54.9 Hz, 1H), 9.39 (t, J=7.9 Hz, 1H), 7.34-6.93 (m, 4H), 6.75 (td, J=13.6, 7.5 Hz, 1H), 5.16-4.87 (m, 2H), 4.54-4.17 (m, 1H), 3.17 (d, J=5.2 Hz, 1H), 1.79-1.41 (m, 2H), 1.10-0.93 (m, 12H).

N'-(3,5-dimethylbenzoyl)-N'—((R)-2,2-dimethylpentan-3-yl)-7-fluoro-5'-oxo-3H-114-spiro[benzo[c][1,2]oxaborole-1,2'-[1,3,2]oxazaborolidine]-6-carbohydrazide (Cpd. No. 95) was prepared from Cpd. No. 59 as follows:

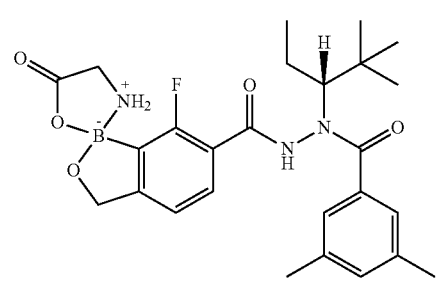

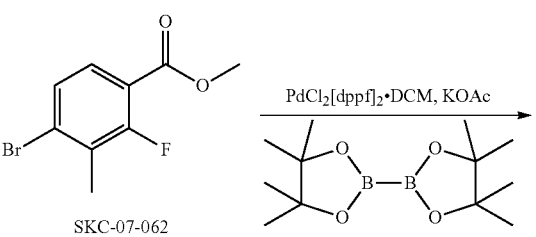

Cpd. No. 95

A solution of glycine (11.93 mg, 0.159 mmol) in 5.3 ml of dry toluene and 1 ml of dimethylsulfoxide was placed into a 25 ml flask equipped with a stirrer. (R)—N'-(3,5-dimethylbenzoyl)-N'-(2,2-dimethylpentan-3-yl)-7-fluoro-1-hydroxy-1,3-dihydrobenzo[c][1.2]oxaborole-6-carbohydrazide (70 mg, 0.159 mmol) was added and the mixture was kept under reflux for 28 h. After removal of the toluene in vacuo, the solution of the product in DMSO was transferred unto a 15.5 g Teledyne ISCO C18 reverse phase column and eluted with 0-100% $CH_3CN$—$H_2O$(30 min). The desired fractions were pooled and lyophilized to give 19 mg (11.4% yield) of the spiro adduct as a white solid. $^1$H NMR (400 MHz, DMSO) δ 10.43-10.18 (m, 1H—mixture of NH rotamers), 7.19-6.72 (m, 5H), 6.41-6.37 (t, 0.46 H, partial rotamer) 4.98-4.76 (m, 2H), 4.43-4.21 (two d, 1H. CH), 3.56-3.52 (overlapping s, 2H), 3.32 (s, DMSO-d6 water peak), 2.50 (DMSO-d6), 2.32 and 2.24 (s, 6H), 1.54-1.46 (m, 2H), 1.07-0.88 (m, 12H); MS (ESI) calcd for $C_{26}H_{32}BFN_3O_5^-$ ([M+2H]$^+$) 498, found 498.

Using the procedure described above, the following reactions were conducted to give (R)—N'-(3,5-dimethylbenzoyl)-N'-(2,2-dimethylpentan-3-yl)-4-fluoro-1-hydroxy-1,3-dihydrobenzo[c][1,2]oxaborole-5-carbohydrazide (Cpd. No. 67):

115

-continued

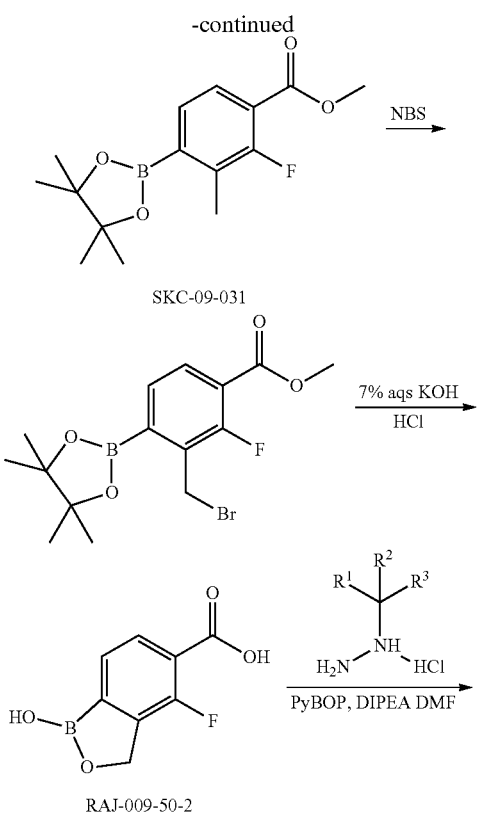

116

-continued

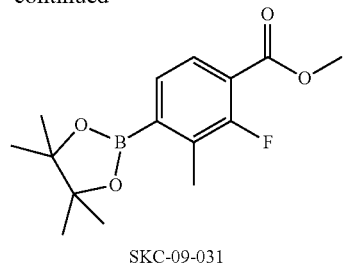

SKC-09-031

Mixed together methyl 4-bromo-2-fluoro-3-methylbenzoate (2.6 g, 10.52 mmol), potassium acetate (3.61 g, 36.8 mmol), and the dimer 4,4,4',4',5,5,5',5'-octamethyl-2-2'bis (1,3,2-dioxaborolane (4.01 g, 15.79 mmol) in anhydrous Dioxane (90 mL) in a RB flask. The mixture was evacuated and backfilled with argon three times and stirred at room temperature. To this mixture, Pd(dppf)$_2$Cl$_2$.DCM was added and evacuated and backfilled the mixture with argon three times and heated the mixture at 80° C. overnight. The dark colored reaction mixture was cooled, filtered through a short pad of celite and removed the solvent. Water and EtOAc were added and extracted the mixture. The organic fractions collected, dried over anhy MgSO$_4$, filtered and removed the solvent. The crude mixture was adsorbed on silica and purified by column chromatography to get the title compound SKC-09-031 (2.8 g, 90/o yield). $^1$H NMR (400 MHz, CDCl$_3$) δ 7.81-7.60 (m, 1H), 7.54 (d, J=7.8 Hz, 1H), 3.92 (s, 3H), 2.62-2.31 (m, 3H), 1.36 (s, 12H).

4-fluoro-1-hydroxy-1,3-dihydrobenzo[c][1,2]oxa-borole-5-carboxylic acid

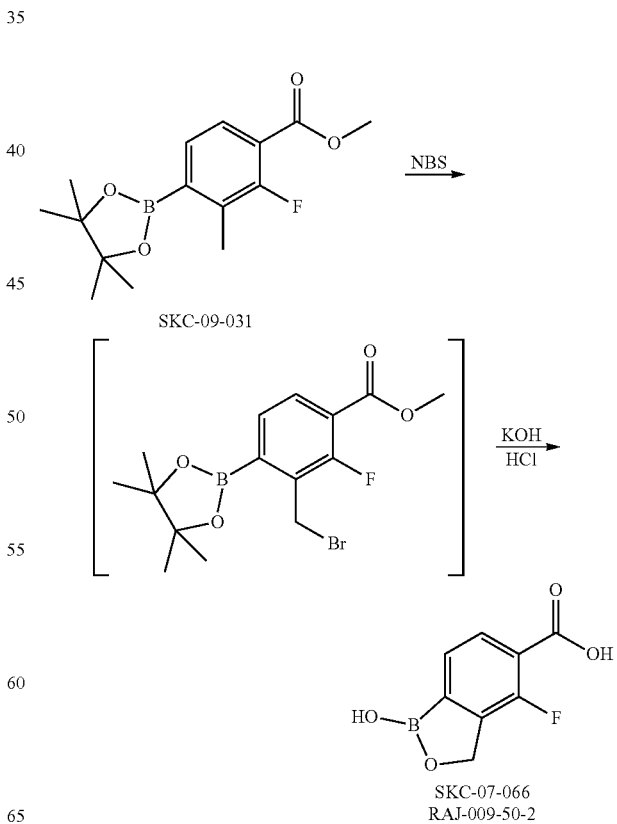

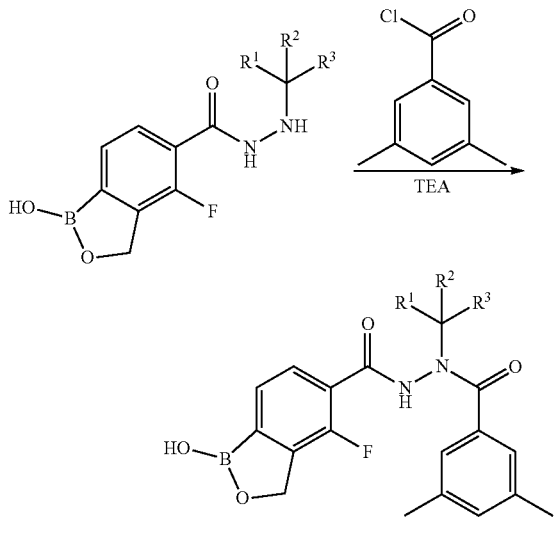

Methyl 2-fluoro-3-methyl-4-(4,4,5,5-tetramethyl-1,3,2-dioxaborolan-2-yl)benzoate

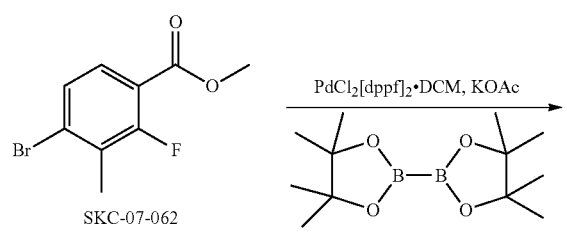

To a solution of the above ester (2.00 g, 6.80 mmol) in anhydrous CCl$_4$ (80 mL) in 200 mL RB flask fitted with a reflux condenser was added NBS (1.20 g, 6.80 mmol) and (E)-1,1'-(diazene-1,2-diyl)dicyclohexanecarbonitrile (0.166 g, 0.68 mmol) and stirred the reaction mixture at 80° C. overnight under argon. The total amount of NBS (1.2 g) and the catalyst (0.166 g) was added in four portions during 1 h. LCMS showed one major peak at 4.59. Cooled the reaction mixture, removed the solvent on a rotavapor under vacuum. Suspended the solid in ether and filtered to remove the solid. The filtrate was concentrated to remove the solvent, diluted with water and extracted with EtOAc. The organic fractions collected, dried over anhy MgSO$_4$, filtered and removed the solvent on a rotavapor. LCMS (M+2) 374.60.

7% aqueous KOH (~80 mL) was added to the crude intermediate and stirred at room temperature for 2 h. Extracted with ether, the product went in the aqueous fraction (based on LCMS), discarded the ether layer containing some impurities. Cooled the aqueous fractions and acidified slowly to pH 3 with 6N HCl. A white precipitate formed, collected the precipitate by filtration and dried under vacuum. LCMS showed a single peak at 2.55. LCMS (M+1) 197.17. $^1$H NMR (400 MHz, DMSO) δ 13.34 (s, 1H), 9.58 (s, 1H), 8.00-7.69 (m, 1H), 7.61 (d. J=7.5 Hz, 1H), 5.11 (s, 2H).

General procedure for the two step coupling: In a scintillation vial mixed together 4-fluoro-1-hydroxy-1,3-dihydrobenzo[c][1,2]oxaborole-5-carboxylic acid (1.0 equiv), PyBOP (1.0 equiv), DIEA (2.0 equiv) in DMF and stirred at 40° C. for 3 minutes under argon. To this mixture, the hydrazine salt (1 equiv) was added and stirred the mixture at 40° C. for 1-2 h. Reaction monitored by LCMS. Removed the solvent using Genevac. Added 7% aqs KOH, stirred for 15 min and extracted with ether. The aqueous fractions collected, cooled and acidified to pH 3 with 6N HCl. Immediately extracted with EtOAc, and collected the organic fractions, dried over anhy MgSO$_4$ and removed the solvent. The crude mixture was finally purified using neutral alumina column (MeOH/DCM solvent gradient) or using RediSep C18 column on ISCO (0.1% formic acid in water/acetonitrile solvent gradient).

In the 2$^{nd}$ step, to a stirred solution of the above intermediate (1.0 equiv) in DCM was added TEA (1.2 equiv) and the acid chloride (1.0 equiv) at room temperature under argon and stirred the mixture for 35 minutes. Reaction monitored by LCMS. Removed the solvent and purified the crude mixture using RediSep C18 column on ISCO (0.1% formic acid in water/acetonitrile solvent gradient).

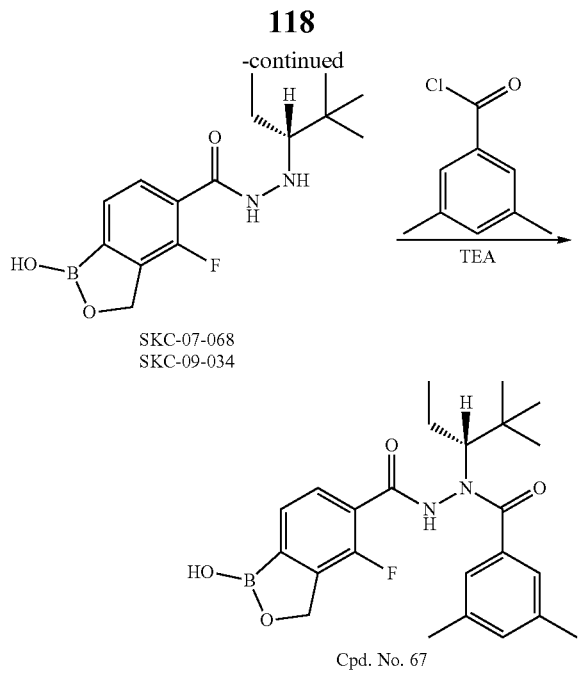

SKC-07-068
SKC-09-034

Cpd. No. 67

4-Fluoro-1-hydroxy-1,3-dihydrobenzo[c][1,2]oxaborole-5-carboxylic acid (1.0 g, 5.10 mmol), PyBOP (2.66 g, 5.10 mmol), DIEA (1.78 mL, 10.21 mmol) were mixed together in DMF (15 mL) and (R)-(2,2-dimethyl-pentan-3-yl)hydrazine 4-methylbenzenesulfonate (1.54 g, 5.10 mmol) was added. The reaction mixture was stirred at 40° C. for 1.5 h. LCMS showed single peak with the expected product mass. After the general work up procedure, the crude mixture was finally purified using a RediSep C08 column (100 g column, 0.1% formic acid in water/acetonitrile solvent gradient) on ISCO to isolate SKC-09-034 (0.820 g, 52% yield) as a colorless solid. LCMS (M+1) 308.81. $^1$H NMR (400 MHz, DMSO) δ 9.77 (s, 1H), 9.52 (s, 1H), 7.66-7.43 (m, 2H), 5.10 (s, 2H), 4.20-3.58 (m, 1H), 1.56-1.53 (m, 1H), 1.31-1.22 (m, 1-), 1.05-0.86 (m, 12H).

Cpd. No. 67 was synthesized using the intermediate SKC-09-034 (0.600 g, 1.95 mmol), TEA (0.326 mL) in DCM (10 mL) and 3,5-dimethylbenzoyl chloride (0.328 g, 1.95 mmol) at room temperature. The reaction was stopped after 35 minutes with 3 peaks (based on LCMS), one major peak with the expected product mass (441.91, M+1). After purification using Redisep C18 column (C18 100 g, 0.1% formic acid in water/acetonitrile solvent gradient), the final DAH was isolated as Cpd. No. 67 (0.575 g, 67% yield). $^1$H NMR (400 MHz, DMSO) δ 10.48 (d, J=48.2 Hz, 1H), 9.53 (s, 1H), 7.47 (d, J=7.3 Hz, 1H), 7.21-6.94 (m, 3H), 6.61 (t, J=6.3 Hz, 1H), 5.06 (s, 2H), 4.34 (dd, 0.1=72.7, 10.2 Hz, 1H), 2.25 (s, 6H), 1.74-1.39 (m, 2H), 1.10-0.91 (m, 12H).

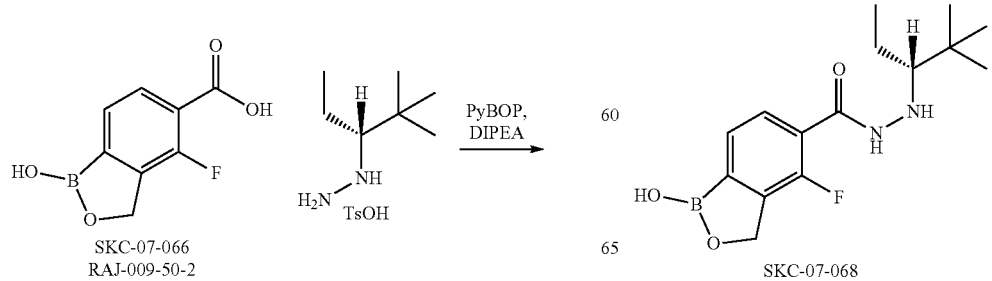

SKC-07-066
RAJ-009-50-2

SKC-07-068

119

-continued

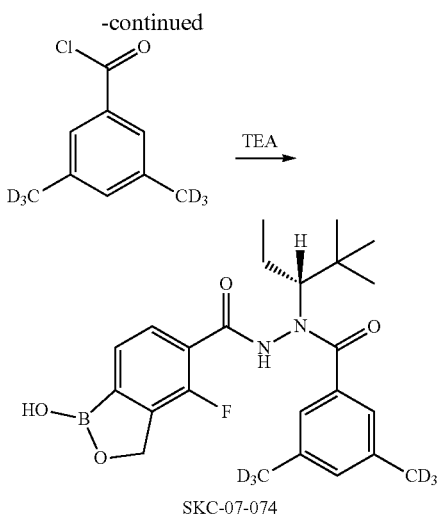

SKC-07-074

The above reaction was carried out using SKC-07-068 (0.200 g, 0.65 mmol), TEA (0.109 mL, 0.779 mmol) and 3,5-bis(methyl-d₃)benzoyl chloride (0.136 g, 0.779 mmol) in DCM (2 mL) at room temperature under argon, overnight. LCMS showed a peak with the expected product mass of 447.14 (M+1), together with two additional peaks. The product was isolated.

N'-(tert-butyl)-4-fluoro-1-hydroxy-1,3-dihydrobenzo[c][1,2]oxaborole-5-carbohydrazide

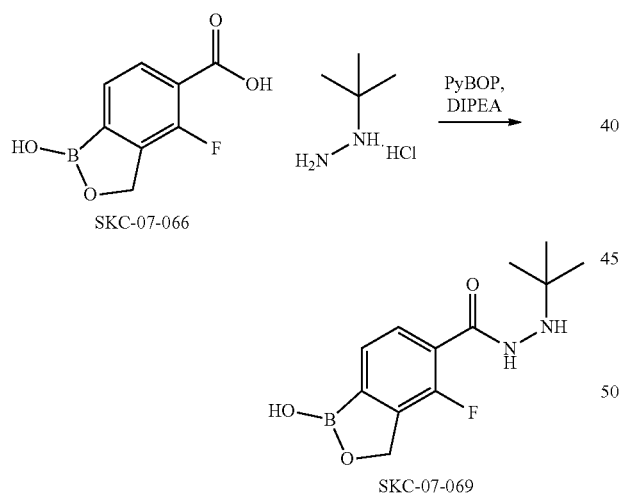

SKC-07-066

SKC-07-069

Following the general procedure, mixed together 4-fluoro-1-hydroxy-1,3-dihydrobenzo[c][1,2]oxaborole-5-carboxylic acid (0.500 g, 2.55 mmol), PyBOP (1.34 g, 2.55 mmol), DIEA (0.89 mL, 5.10 mmol) in DMF (6 mL) followed by the addition of tert-butyl hydrazine hydrochloride (0.318 g, 2.55 mmol) and stirred the mixture at 40° C. for 1 h LCMS showed a main peak at 2.43 with the expected product mass of 267.01 (Mt 1). After the general work up procedure, the crude dry sample (SKC-07-069, 0.800 g, contains some DMF) was used for the next step without further purification.

120

N'-(tert-butyl)-N'-(3,5-dimethylbenzoyl)-4-fluoro-1-hydroxy-1,3-dihydrobenzo[c][1,2]oxaborole-5-carbohydrazide

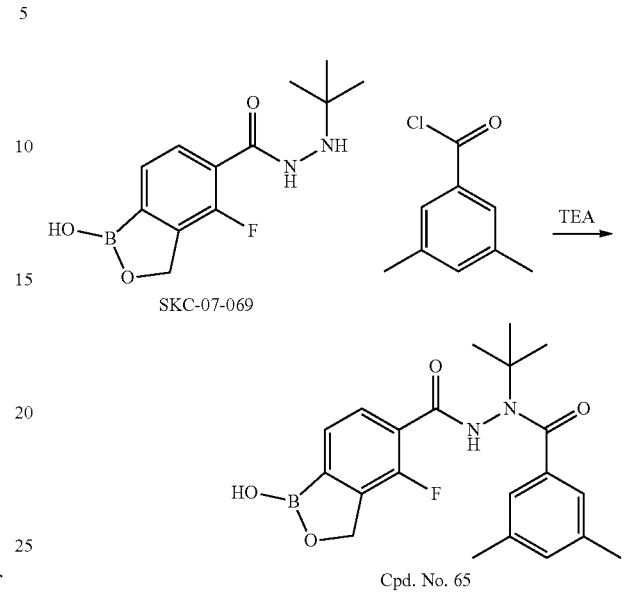

Cpd. No. 65

To a stirred solution of the above synthesized monoB (SKC-7-069, 0.400 g, 1.50 mmol) in DCM (3 mL) was added TEA (0.210 mL, 1.50 mmol) and 3,5-dimethylbenzoyl chloride (0.253 g, 1.50 mmol) at room temperature under argon overnight. LCMS showed several peaks, together with a sharp peak at 3.45 with the expected product mass of 399.09 (M+1). Removed the solvent on a rotavapor and the crude mixture was purified using prep HPLC (0.1% formic acid in water/acetonitrile solvent gradient) to get 0.080 g of the product Cpd. No. 65. LCMS: 399.09 (M+1) ¹H NMR (400 MHz, DMSO) δ 10.70 (s, 1H), 9.51 (s, 1H), 7.46 (d, J=7.3 Hz, 1H), 7.04 (d, J=7.2 Hz, 3H), 6.80-6.66 (m, 1H), 5.05 (s, 2H), 2.25 (s, 6H), 1.49 (s, 9H).

N'-(3,5-bis(methyl-d)benzoyl)-N'-(tert-butyl)-4-fluoro-1-hydroxy-1,3-dihydrobenzo[c][1,2]oxaborole-5-carbohydrazide

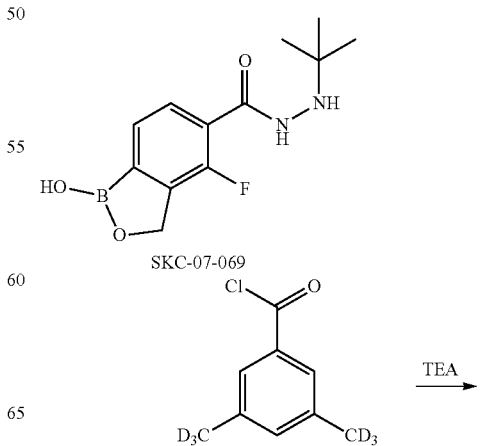

SKC-07-069

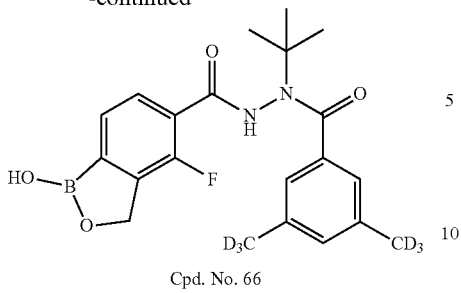

Cpd. No. 66

The title compound was synthesized using the monoB (SKC-07-069 crude, 0.400 g, 1.50 mmol), TEA (0.210 mL, 1.50 mmol) and 3,5-bis(methyl-$d_3$)benzoyl chloride (0.263 g, 1.50 mmol) in DCM (3 mL) at room temperature under argon, overnight. After purification by prep HPLC (0.1% formic acid in water/acetonitrile solvent gradient), 0.148 g of the pure product Cpd. No. 66 was isolated. LCMS: 405.07 (M+1). $^1$H NMR (400 MHz, DMSO) δ 10.70 (s, 1H), 9.51 (s, 1H), 7.46 (d, J=7.3 Hz, 1H), 7.04 (dd, J=8.4, 1.6 Hz, 3H), 6.83-6.41 (m, 1H), 5.05 (s, 2H), 2.54 (s, 1H), 1.48 (d, J=5.4 Hz, 9H).

N'-(2,2-dimethyl-1-phenylpropyl)-4-fluoro-1-hydroxy-1,3-dihydrobenzo[c][1,2]oxaborole-5-carbohydrazide

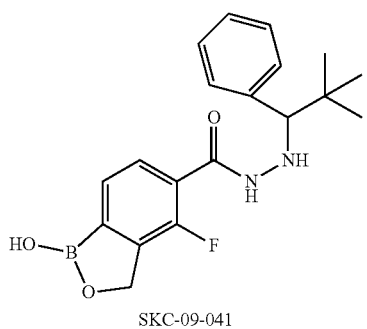

Following the general procedure, mixed together 4-fluoro-1-hydroxy-1,3-dihydrobenzo[c][1,2]oxaborole-5-carboxylic acid (0.500 g, 2.55 mmol), PyBOP (1.34 g, 2.55 mmol), DIEA (0.89 mL, 5.10 mmol) in DMF (10 mL) followed by the addition of (2,2-dimethyl-1-phenylpropyl) hydrazide hydrochloride (0.548 g) and stirred the mixture at 40° C. for 1.5 h. LCMS showed single peak with the expected product mass. After the general work up procedure, the crude mixture was finally purified using RediSep C18 column on ISCO (0.1% formic acid in water/acetonitrile solvent gradient) and isolated the title compound SKC-09-041 (0.400 g, 44% yield) as a colorless solid. LCMS (M+1) 357.25.

N'-(2,2-dimethyl-1-phenylpropyl)-N'(3,5-dimethylbenzoyl)-4-fluoro-1-hydroxy-1,3-dihydrobenzo[c][1,2]oxaborole-5-carbohydrazide

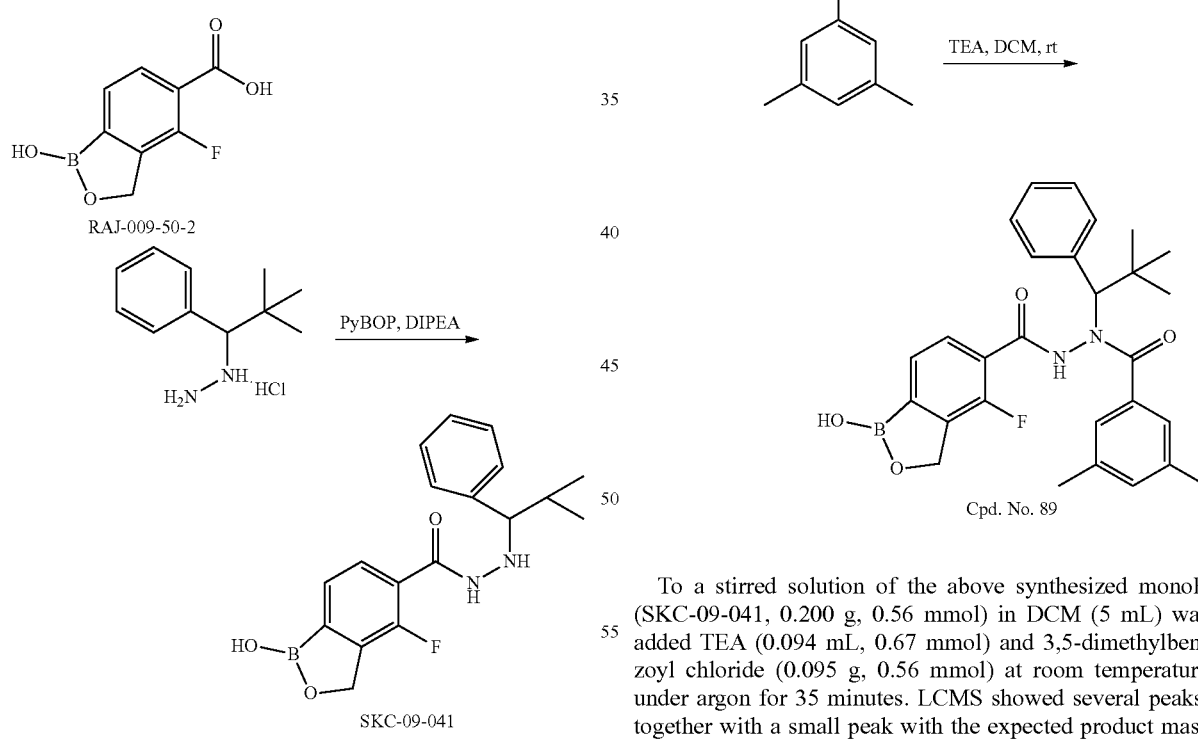

Cpd. No. 89

To a stirred solution of the above synthesized monoB (SKC-09-041, 0.200 g, 0.56 mmol) in DCM (5 mL) was added TEA (0.094 mL, 0.67 mmol) and 3,5-dimethylbenzoyl chloride (0.095 g, 0.56 mmol) at room temperature under argon for 35 minutes. LCMS showed several peaks, together with a small peak with the expected product mass and the unreacted starting material. Removed the solvent on a rotavapor and the crude mixture was purified using a RediSep Column (C18, 13 g, 0.1% formic acid in water/acetonitrile gradient) and isolated Cpd. No. 89 (0.070 g, 25% yield). LCMS (M+1) 489.28. $^1$H NMR (400 MHz, DMSO) δ 10.84 (s, 1H), 9.50 (s, 1H), 7.58-7.00 (m, 9H), 6.58-6.45 (m, 1H), 5.69 (d, J=33.9 Hz, 1H), 5.06 (s, 2H), 2.23 (s, 6H), 1.08 (s, 9H).

Example 2
Synthesis of (R)—N'-(3,5-dimethylbenzoyl)-N'-(2,2-dimethylhexan-3-yl)-2-hydroxy-9-methyl-2,3,4,5-tetrahydrobenzo[f][1,2]oxaborepine-8-carbohydrazide (Cpd. No. 70)
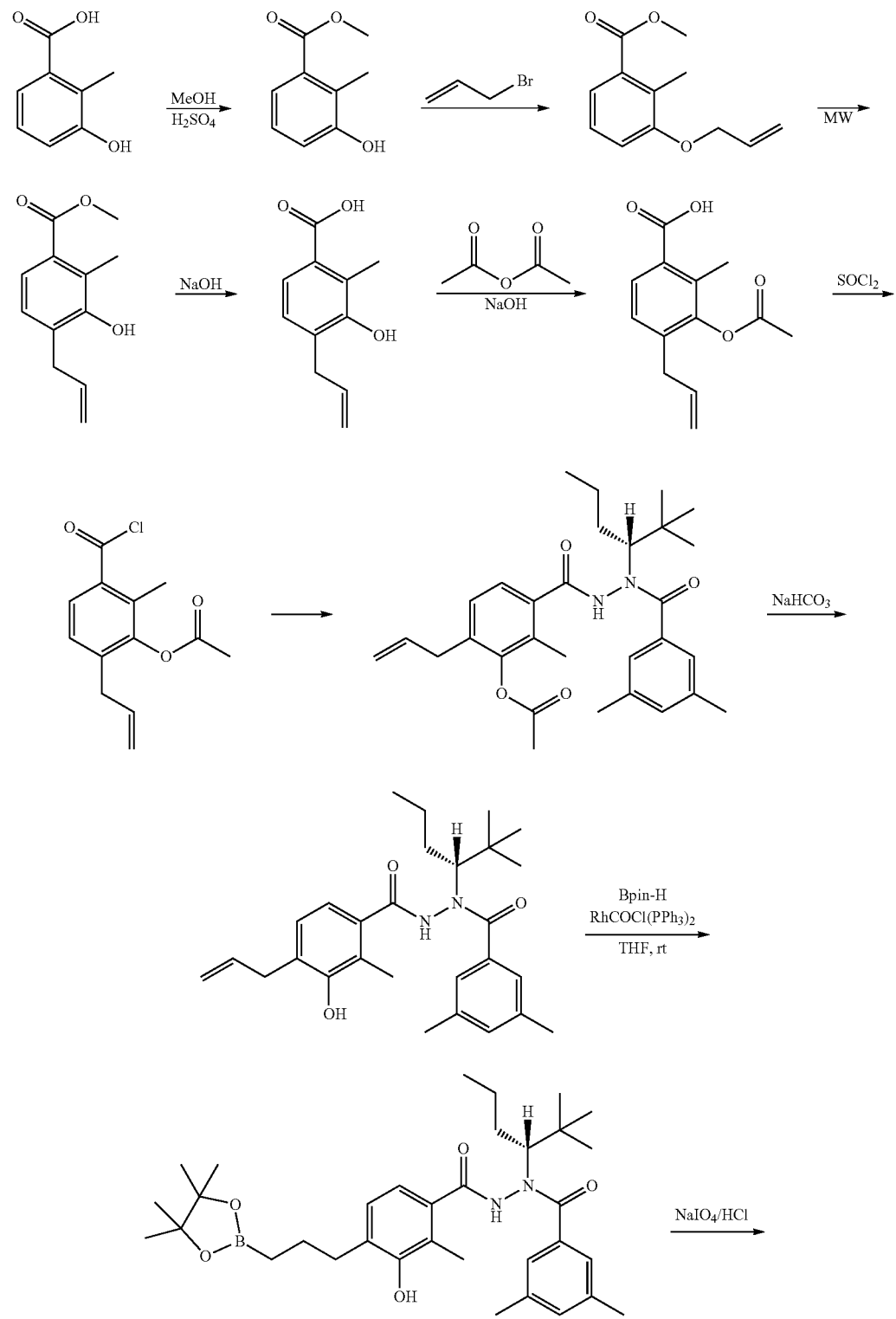

-continued

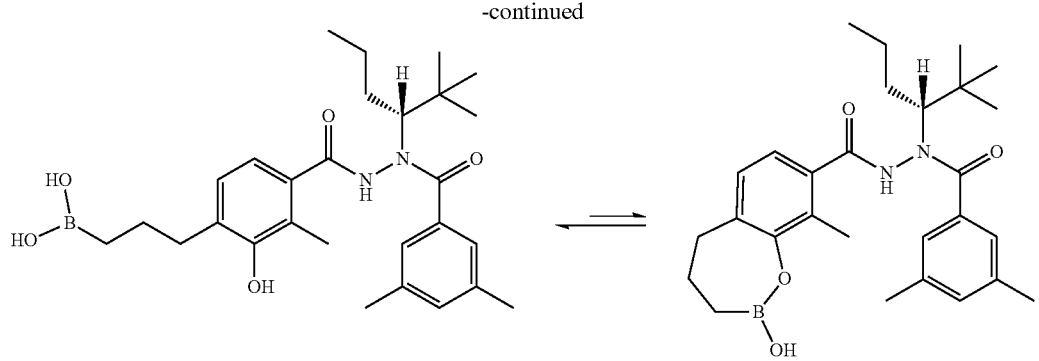

Cpd. No. 70

Step 1: Synthesis of methyl 3-hydroxy-2-methylbenzoate

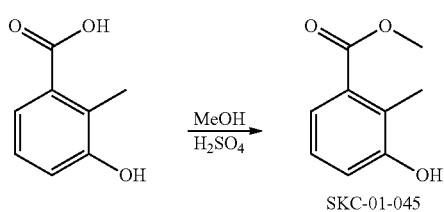

To a IL 3-necked round bottom flask equipped with a condenser and magnetic stirrer was added 3-Hydroxy 2-methyl benzoic acid (15.2 g, 100 mmol) and anhydrous MeOH (400 ml). To this, 7 ml of conc. H$_2$SO$_4$ was added and the mixture was refluxed overnight under argon. LCMS showed complete conversion to the product. The reaction mixture was collected and the solvent was removed under vacuum. The crude mixture was diluted with ethyl acetate. After aqueous work up and extraction with ethyl acetate, the mixture was purified using an ISCO system (120 g silica gel column, hexane:ethyl acetate solvent mixture) to give the methyl benzoate derivative (major peak, eluted with ~12% EtOAc in hexane) in 84% isolated yield. $^1$H NMR (400 MHz, CDCl$_3$) δ 7.57 (dd, J=7.8, 1.0 Hz, 1H), 7.26 (t, J=7.9 Hz, 1H), 7.10 (dd, J=8.0, 0.9 Hz, 1H), 5.49 (s, 1H), 4.06 (s, 3H), 2.62 (s, 3H).

Step 2: Synthesis of methyl 3-(allyloxy)-2-methylbenzoate

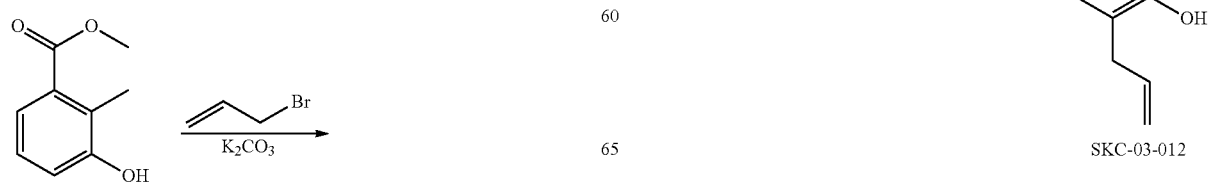

-continued

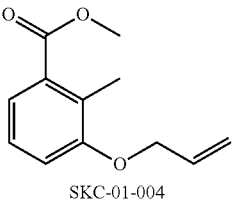

SKC-01-004

To a stirred solution of methyl 3-hydroxy-2-methyl benzoate (30 g, 180.0 mmol) in acetone in a 1 L round bottom flask at room temperature under argon was added potassium carbonate (42.4 g, 30.6 mmol). To this allyl bromide (39.3 g, 28.1 ml) was added, and the reaction mixture was stirred overnight at room temperature. After aqueous work up and extraction with ethyl acetate, the crude product was purified using an ISCO system (silica gel column, hexane:EtOAc solvent mixture) to get the product as an oil (89% yield). $^1$H NMR (400 MHz, CDCl$_3$) δ 7.41 (dd, J=7.8, 0.9 Hz, 1H), 7.22-7.08 (m, 1H), 6.97 (d, J=7.9 Hz, 1H), 6.10-6.03 (m, 1H), 5.43 (dq, J=17.3, 1.7 Hz, 1H), 5.29 (dq, J=10.6, 1.5 Hz, 1H), 4.55 (dt, J=5.0, 1.6 Hz, 2H), 3.89 (s, 3H), 2.47 (s, 3H).

Step 3: Synthesis of methyl 4-allyl-3-hydroxy-2-methylbenzoate

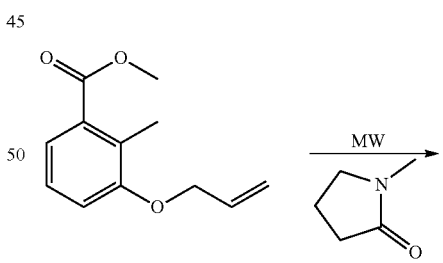

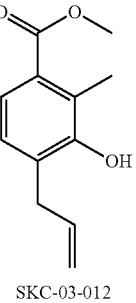

SKC-03-012

Methyl 4-allyl-3-hydroxy-2-methylbenzoate (3.5 g, 10.97 mmol) was dissolved in 1-methyl pyrrolidine-2-one (4 ml) in a microwave vial, closed with a cap and subjected to microwave irradiation (CEM discover) with stirring at 220° C., maximum pressure 300 psi, run time 5 min, hold time 50 min. After cooling the crude mixture was directly loaded on a silica gel column (220 g) and purified using ISCO system (hexane:EtOAc solvent mixture, product eluted ~12% EtOAc in hexane) to give 2.1 g (major peak, 60% yield) of the product SKC-03-012 as a light yellow solid. $^1$H NMR (400 MHz, CDCl$_3$) δ 7.40 (d. J=8.0 Hz, 1H), 7.00 (d, J=8.1 Hz, 1H), 6.04-5.95 (m, 1H), 5.21-5.16 (m, 3H), 3.88 (s, 3H), 3.44-3.43 (d, 2H), 2.47 (s, 3H).

Step 4: Synthesis of
4-allyl-3-hydroxy-2-methylbenzoic acid

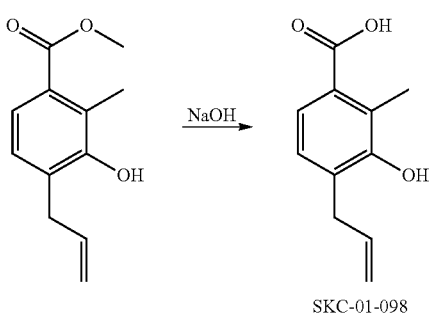

SKC-01-098

To a stirred solution of the methyl 4-allyl-3-hydroxy-2-methylbenzoate (6.5 g, 31.6 mmol) in a mixture of THF:MeOH (3:1 ratio, 80 ml) at room temperature was added 25.3 g (316 mmol) of 50 w/w % aqueous NaOH solution, and the reaction mixture was stirred at 50° C. for 4 h. LCMS showed it as a clean reaction. The reaction mixture was cooled to room temperature and the methanol was removed on a rotovapor and diluted with ethyl acetate. The crude reaction mixture was acidified with 1N HCl. Some of the product precipitated out. It was diluted with water and extracted using ethyl acetate. The organic fractions were collected, dried over anhydrous MgSO$_4$, filtered, and concentrated. The crude product was purified using an ISCO system (80 g silica column, hexane/EtOAc gradient. The product eluted ~30% EtOAc in hexane, and the product fractions were collected and concentrated. $^1$H NMR (400 MHz, CDCl$_3$) δ 7.58 (d. J=8.0 Hz, 1H), 7.03 (d, J=8.0 Hz, 1H), 6.12-5.78 (m, 1H), 5.30-5.08 (m, 2H), 3.45 (d, J=6.3 Hz, 2H), 2.54 (d, J=3.7 Hz, 3H).

Step 5: Synthesis of
3-acetoxy-4-allyl-2-methylbenzoic acid

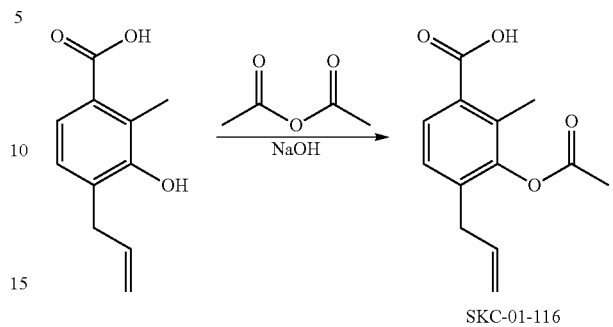

SKC-01-116

4-Allyl-3-hydroxy-2-methylbenzoic acid (2.0 g, 10.4 mmol) was slurried in 6 ml water in a 500 ml round bottom flask, cooled in an ice bath, and stirred. Aqueous NaOH solution (4.2 g of 5% NaOH in 6 ml water) was added slowly. The mixture was stirred for few minutes until the solution was clear. Acetic anhydride was added drop wise until pH 6 was obtained, by that time the reaction mixture become a thick slurry with an off white color. The mixture was stirred overnight at room temperature. The reaction mixture became a thick white slurry. The pH was adjusted to 2 with conc. HCl. A precipitate formed, and was filtered under vacuum and dried. The combined dried product was dissolved in DCM and purified on an ISCO system using 40 g silica column and hexane/EtOAc solvent gradient. The product eluted 30% EtOAc in hexane, and the fractions were collected and dried under vacuum to give (2.4 g, 98%) SKC-01-116. $^1$H NMR (400 MHz, CDCl$_3$) δ 12.0 (br s, 1H), 7.92 (d, J=8.1 Hz, 1H), 7.18 (d, J=8.1 Hz, 1H), 6.03-5.67 (m, 1H), 5.26-4.89 (m, 2H), 3.31 (d, J=6.6 Hz, 2H), 2.44 (s, 3H), 2.37 (s, 3H).

Step 6: Synthesis of (R)-6-allyl-3-(2-(3,5-dimethyl-benzoyl)-2-(2,2-dimethylhexan-3-yl)hydrazinecarbonyl)-2-methylphenyl acetate

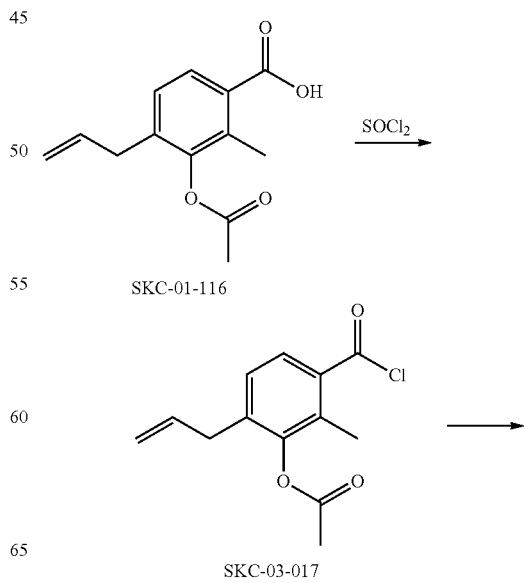

-continued

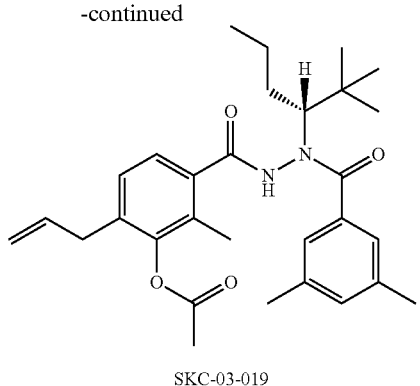

SKC-03-019

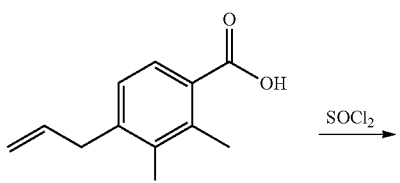

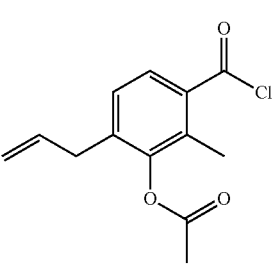

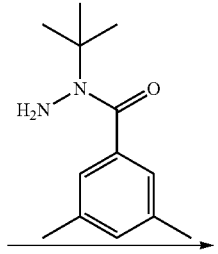

SKC-01-119

To a solution of 3-acetoxy-4-allyl-2-methylbenzoic acid (1.5 g, 6.40 mmol) in a 250 ml round bottom flask closed with a drying tube was added anhydrous DCM (10 ml), and the reaction mixture was stirred at room temperature. To this was added excess thionyl chloride (2 ml) and a drop of anhydrous DMF, and the reaction mixture was stirred overnight at room temperature. The excess thionyl chloride was removed under vacuum at 40° C. on a water bath after cooling the trap with dry ice. Anhydrous DCM was added and removed under vacuum to make the product dry. This was used as such for the next step.

The above acid chloride (1.55 g, 6.15 mmol) was dissolved in anhydrous DCM (6 ml) and was added to a stirred solution of previously synthesized (R)—N-(2,2-dimethylhexan-3-yl)-3,5-dimethylbenzohydrazide (1.7 g, 6.15 mmol, 95% ee) in 6 ml of anhydrous DCM at room temperature under argon Anhydrous triethylamine (0.86 ml, 6.15 mmol) was added and the reaction mixture was stirred overnight at room temperature LCMS showed a major peak with the expected product mass. The crude mixture was adsorbed on silica and dried under vacuum. The dry powder was loaded on a cartridge and purified using an ISCO system (40 g silica column, hexane/EtOAc gradient). The product eluted –20% EtOAc in hexane, and the product fractions were collected and concentrated to give SKC-03-019 (2.8 g, 93%). This was used as such for the next deacetylation step. $^1$H NMR (400 MHz, DMSO-$d_6$) δ 10.38 (d, J=63.8 Hz, 1H), 7.22-6.93 (m, 4H), 6.72 (dd, J=45.7, 7.8 Hz, 1H), 6.02-5.60 (m, 1H), 5.25-4.91 (m, 2H), 4.45 (dd, J=67.4, 10.2 Hz, 1H), 3.19 (d, J=6.7 Hz, 2H), 2.30 (s, 3H), 2.24 (m, 2H), 1.99 (s, 6H), 1.15-1.41 (m, 5H), 1.04 (s, 9H), 0.88-0.79 (m, 3H).

Similarly, the reaction below was conducted using the acid chloride (400 mg, 1.58 mmol), N-(tert-butyl)-3,5-dimethylbenzohydrazide (291 mg, 1.32 mmol), TEA (0.184 ml, 1.32 mmol) in anhydrous ether (25 ml). LCMS showed the main peak with the expected product mass, and the crude mixture was purified using an ISCO system (24 g silica column, hexane/EtOAc gradient). The product eluted with ~35%, EtOAc in hexane. The product fractions were collected and dried under vacuum to give SKC-01-120 (260 mg, 45%). $^1$H NMR (400 MHz, CDCl$_3$) δ 7.64 (s, 1H), 7.06 (s, 2H), 7.00 (s, 1H), 6.93 (d, J=7.7 Hz, 1H), 5.93-5.66 (m, 1H), 5.14-4.96 (m, 2H), 3.20 (d, J=6.6 Hz, 2H), 2.29 (d, J 12.3 Hz, 9H), 1.81 (br s, 3H), 1.58 (s, 9H).

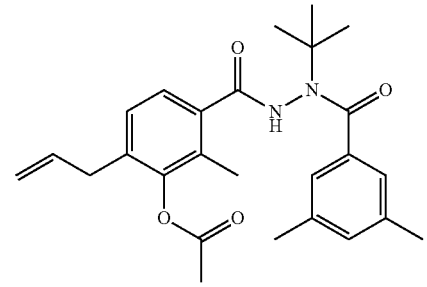

SKC-01-120

Step 7. Synthesis of (R)-4-allyl-N'-(3,5-dimethylbenzoyl)-N'(2,2-dimethylhexan-3-yl)-3-hydroxy-2-methylbenzohydrazide

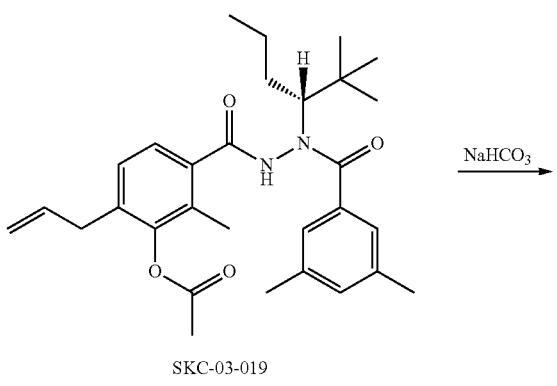

SKC-03-019

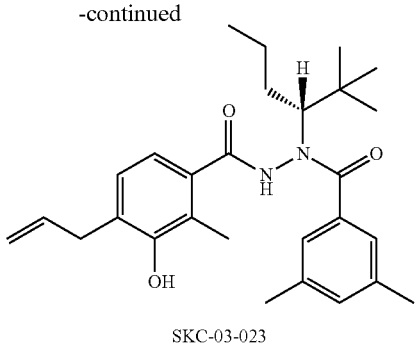

SKC-03-023

SKC-03-019 (2.7 g, 5.48 mmol) was dissolved in a mixture of MeOH:H₂O (3:1 ratio, 40 ml) in a 250 ml round bottom flask. To this, excess sodium bicarbonate (6.91 g, 82 mmol) was added, and the reaction mixture was stirred overnight at 60° C. LCMS showed a single peak with the expected product mass. The reaction mixture was cooled and the MeOH was removed on a rotavapor under vacuum. After aqueous work up and extraction with ethyl acetate, the organic fractions were dried over anhydrous MgSO₄, filtered, and concentrated. The crude mixture was dissolved in DCM, adsorbed on silica, and dried until it was free flowing. This was loaded on to a cartridge and purified using an ISCO system (40 g silica gel column, hexane/EtOAc gradient). The product eluted with 30% EtOAc in hexane, and the fractions were collected and dried under vacuum to give 2.2 g (89%) of SKC-03-023. ¹H NMR (400 MHz, DMSO-d₆) δ 10.17 (d, J=65.5 Hz, 1H), 8.37 (s, 1H), 7.10-7.03 (m, 3H), 6.87-6.84 (m, 1H), 6.24-6.23 (m, 1H), 5.90-5.83 (m, 1H), 5.20-4.87 (m, 2H), 4.52-4.42 (m, 1H), 3.64-3.60 (m, 2H), 2.24 (d, J=4.7 Hz, 6H), 1.61-1.78 (m, 4H), 1.41 (br s, 3H), 1.03 (d, J=7.2 Hz, 9H), 0.85 (t. J=6.9 Hz, 3H).

Similarly, the following reaction was conducted using SKC-01-120 (710 mg, 1.63 mmol) and sodium bicarbonate (1.37 g, 16.26 mmol) in a mixture of MeOH:H₂O (3:1 ratio, 12 ml), and stirred the mixture at 45° C. overnight. After aqueous work up and extraction with EtOAc, the crude mixture was purified using an ISCO system (24 g silica column, hexane/EtOAc gradient). The product eluted with ~38% EtOAc in hexane to give SKC-01-135 (320 mg, 50%) ¹H NMR (400 MHz, CDCl₆+ DMSO-d₆) δ 9.49 (s, 1H), 6.49 (d, J=4.7 Hz, 2H), 6.36 (d. J=3.6 Hz, 1H), 6.17 (t, J=6.8 Hz, 1H), 5.82-5.48 (m, 1H), 5.38-5.11 (m, 1H), 5.40-5.15 (m, 1H), 4.53-4.15 (m, 2H), 3.57-3.09 (m, 1H), 2.72 (d, J=5.0 Hz, 2H), 1.66 (s, 6H), 1.25 (d, J=6.2 Hz, 3H), 0.95 (dd, J=8.7, 6.9 Hz, 9H).

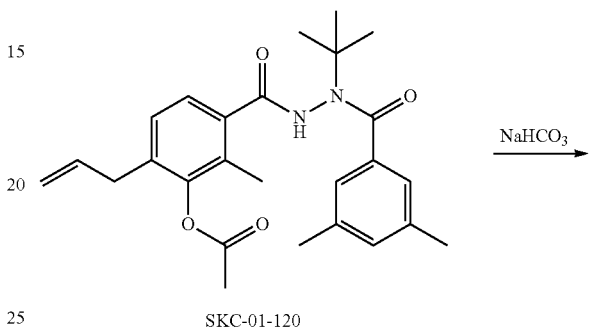

SKC-01-120

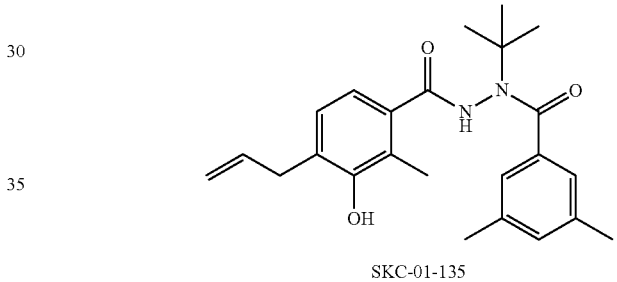

SKC-01-135

Step 8: Synthesis of (R)—N'-(3,5-dimethylbenzoyl)-N'-(2,2-dimethylhexan-3-yl)-3-hydroxy-2-methyl-4-(3-(4,4,5,5-tetramethyl-1,3,2-dioxaborolan-2-yl)propyl benzohydrazide

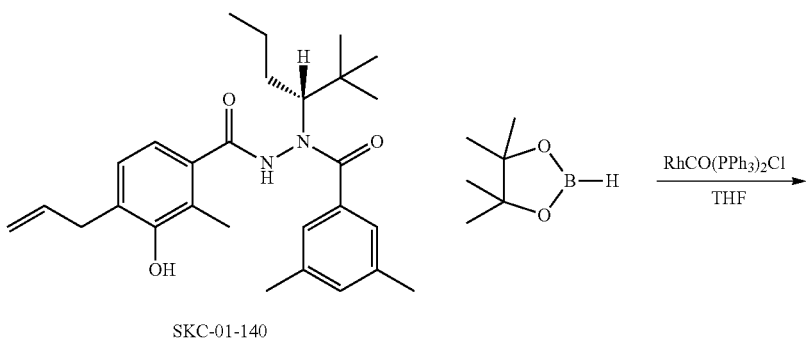

SKC-01-140

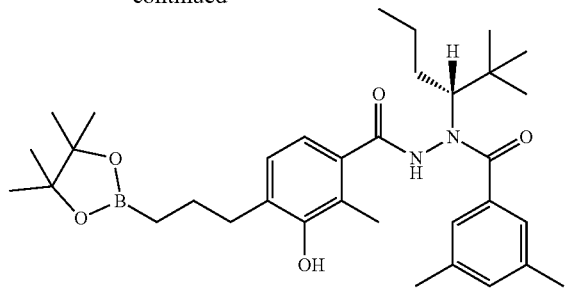

SKC-01-143

An oven dried, 100 ml two-necked round bottom flask was equipped with a teflon coated magnetic stir bar, and two rubber septum with one of the septum with a needle connected to an argon/vacuum manifold. This argon flushed round bottom flask was charged with SKC-01-140 (510 mg, 1.13 mmol), anhydrous THF (5 ml) and modified Wilkinson's catalyst (40 mg, 0.057 mmol). After three vacuum/argon purge cycles, the mixture was stirred at room temperature until all of the reagents dissolved (<2 min). To this stirred clear reaction mixture was added 4,4,5,5-tetramethyl-1,3,2-dioxaborolane (Bpin-H) (0.494 ml, 3.40 mmol) via syringe, followed by another argon/vacuum/argon purge. The reaction mixture was stirred at room temperature for overnight. The color of the reaction mixture changed from a light yellow to a dark brown solution. After overnight stirring, LCMS showed complete conversion to the product. The reaction mixture was quenched by carefully adding few drops of water (<1 ml) and MeOH (5 ml) and the solvent was under vacuum on a rotavapor. The dry crude product was dissolved in DCM and adsorbed on silica, and dried under vacuum. Once it was free flowing, it was loaded on an empty cartridge and purified using an ISCO system (12 g silica column, hexane/EtOAc gradient). The product fractions were collected (at 10% EtoAc/hexane) and dried under vacuum (630 mg, 96% yield). $^1$H NMR (400 MHz, DMSO-$d_6$) δ 10.16 (d, J=64.4 Hz, 1H), 8.21 (s, 1H), 7.92 (s, 1H), 7.11 (s, 1H), 7.03 (s, 1H), 6.83 (d, J=7.6 Hz, 1H), 6.42-6.16 (m, 1H), 4.62-4.24 (m, 1H), 2.25 (d, J=4.5 Hz, 5H), 2.00 (s, 6H), 1.60 (s, 2H), 1.55-1.38 (m, 4H), 1.17 (s, 9H), 1.08 (s, 9H), 1.05-0.99 (m, 3H), 0.88-0.78 (m, 2H).

Using the same procedure as described above, the following reaction was conducted

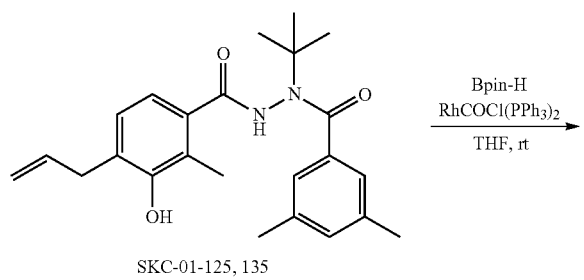

SKC-01-125, 135

$\xrightarrow{\text{Bpin-H, RhCOCl(PPh}_3)_2}{\text{THF, rt}}$

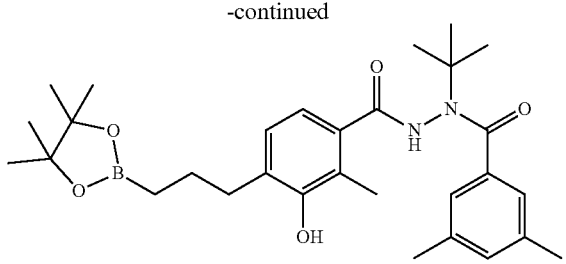

SKC-01-128, 134

An oven dried, 100 ml, two necked, round bottom flask was equipped with a teflon coated magnetic stir bar, and two rubber septum with one of the septum with a needle connected to an argon/vacuum manifold. This argon flushed round bottom flask is charged with 4-allyl-3-hydroxy-DAH (320 mg, 0.811 mmol), modified Wilkinson's catalyst (28 mg, 0.041 mmol) and anhydrous THF (5 ml). After three vacuum/argon purge cycles, the mixture was stirred at room temperature until all of the reagents dissolved (<2 min). To this stirred clear reaction mixture was added 4,4,5,5-tetramethyl-1,3,2-dioxaborolane (Bpin-H) (0.354 ml, 2.43 mmol) via syringe, followed by another argon/vacuum/argon purge. The reaction mixture was stirred at room temperature overnight. After stirring overnight, LCMS showed complete conversion to the product. The reaction mixture was quenched by carefully adding few drops of water (<1 ml) and MeOH (5 ml) and the solvent was removed under vacuum on a rotavapor. The dry crude product was dissolved in DCM and adsorbed on silica and dried under vacuum. Once it was free flowing, it was loaded on an empty cartridge and purified using an ISCO system (12 g silica column, hexane/EtOAc gradient). The product eluted with ~30% EtOAc in hexane. The product fractions were collected and dried under vacuum (310 mg, 73% yield). This experiment was repeated. (SKC-01-128, 63% yield and SKC-01-134, 73% yield). $^1$H NMR (400 MHz. DMSO-$d_6$) δ 10.34 (s, 1H), 8.24 (s, 1H), 7.13-6.96 (m, 3H), 6.80 (d, J=7.7 Hz, 1H), 6.14 (d, J=7.7 Hz, 1H), 2.26 (s, 6H), 1.74 (s, 3H), 1.51-1.47 (m, 11H), 1.17 (s, 12H), 1.12-1.00 (m, 2H), 0.65 (t, J=7.9 Hz, 2H).

Step 9: Synthesis of Cpd. No 70

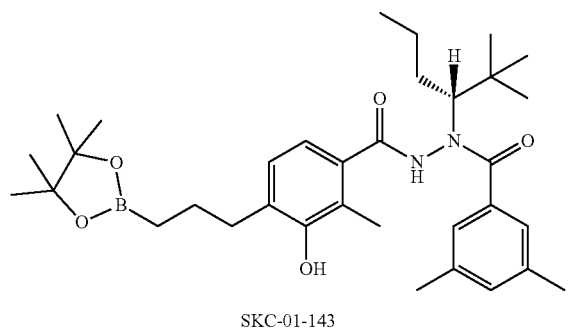

SKC-01-143

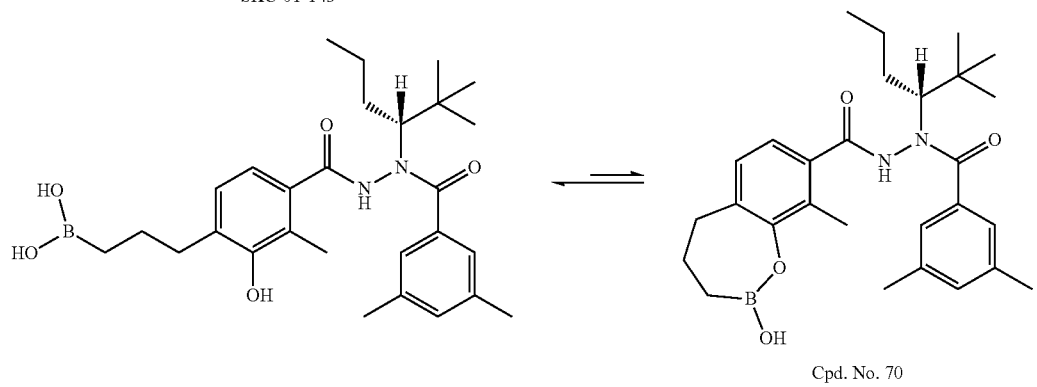

Cpd. No. 70

The above Bpin-DAH (630 mg, 1.09 mmol) was mixed with THF:water mixture (4:1, 20 ml) and sodium periodate (1.4 g, 6.53 mmol), and a 2.0 M solution of HCl in THF (1.09 ml, 2.18 mmol) was added. The reaction mixture was stirred at room temperature overnight. LCMS showed one main peak. The solvent was removed on a rotavapor, and the residue was diluted with EtOAc and extracted. The organic fractions were dried over anhydrous $MgSO_4$, filtered and concentrated. The crude product was adsorbed on neutral alumina and purified using an ISCO system (8 g neutral alumina column, DCM/MeOH solvent mixture). The product eluted with ~5% MeOH in DCM and was collected and dried. $^1$H NMR spectrum in DMSO-$d_6$ showed a mixture of at least three products. $D_2O$ was added. $^1$H NMR (400 MHz. DMSO-$d_6$+$D_2O$) δ 7.23-7.00 (m, 3H), 6.98-6.79 (m, 1H), 6.55-6.17 (m, 1H), 4.72-4.17 (m, 1H), 2.30 (s, 6H), 1.91-1.69 (m, 2H), 1.72-1.31 (m, 9H), 1.08 (s, 9H), 0.94-0.83 (m, 3H), 0.67 (t, J=7.8 Hz, 2H).

In a similar fashion, Cpd. No. 69 was prepared as follows:

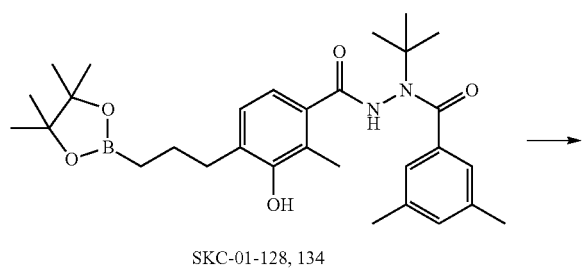

SKC-01-128, 134

-continued

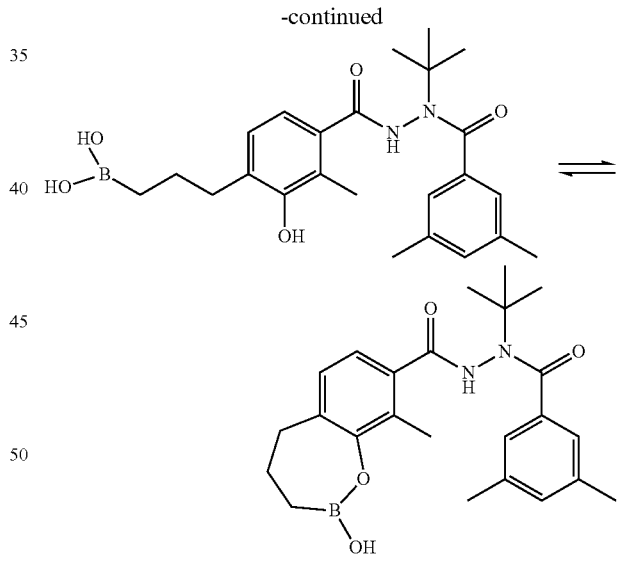

Cpd. No. 69

The above Bpin-DAH (75 mg, 0.11 mmol) was mixed with THF:$H_2O$ mixture (4:1, 10 ml) and sodium periodate (184 mg, 0.861 mmol), and a 2.0 M solution of HCl in THF (0.144 ml, 0.287 mmol) was added. The mixture was stirred at room temperature overnight. LCMS showed single peak. The solvent was removed on a rotavapor under vacuum, and the residue was diluted with EtOAc and extracted. The organic fractions were dried over anhydrous $MgSO_4$, filtered and concentrated. The crude product was adsorbed on neutral alumina and purified using an ISCO system (8 g neutral alumina column, DCM/MeOH solvent mixture). The single product eluted with ~5% MeOH in DCM was collected and dried. The product was not soluble in CDCl₃, so it was dissolved in DMSO-d₆ for ¹H NMR analysis. The ¹H NMR spectrum in DMSO-d₆ showed a mixture of at least three products. A few drops of D₂O was added to deuterate any exchangeable protons. ¹H NMR (400 MHz, DMSO-d₆+ D₂O) δ 7.01 (s, 3H), 6.87-6.72 (m, 1H), 6.13 (d, J=7.7 Hz, 1H), 2.47-2.37 (m, 2H), 2.22 (s, 6H), 1.72 (s, 3H), 1.47 (d, J=3.5 Hz, 11H), 0.58 (t, J=7.9 Hz, 2H).

Example 3

Synthesis of (R)-(3-(4-(2-(3,5-dimethylbenzoyl)-2-(2,2-dimethylhexan-3-yl)hydrazinecarbonyl)-2-methoxy-3-methylphenyl)propyl)boronic acid (Cpd. No. 27)

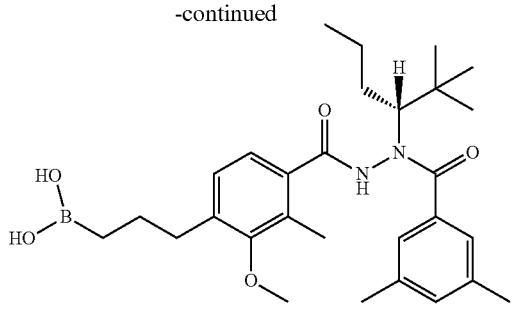

Cpd. No. 27

Step 1: Synthesis of (R)-4-allyl-N'-(3,5-dimethyl-benzoyl)-N'(2,2-dimethylhexan-3-yl)-3-methoxy-2-methylbenzohydrazide

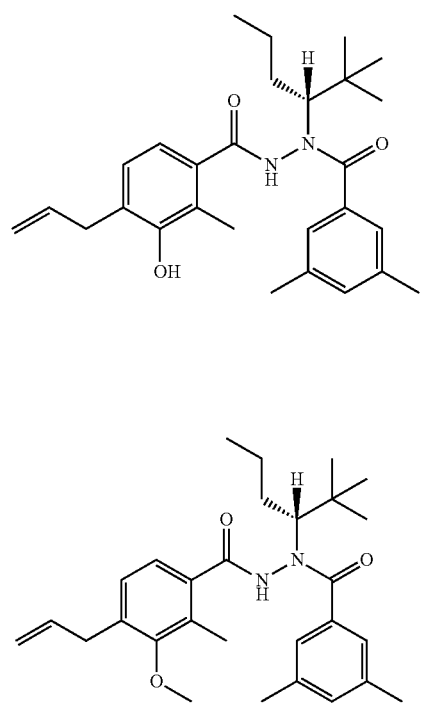

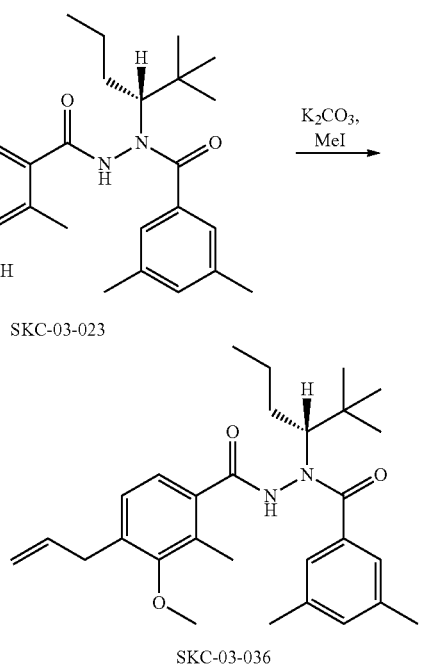

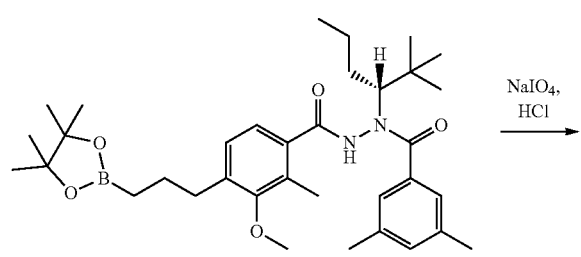

Cpd. No. 29

To a solution of SKC-03-023 (500 mg, 1.11 mmol) in anhydrous acetone (5 ml) in a 1-neck 100 ml round bottom flask fitted with a reflux condenser, at room temperature under argon was added anhydrous K₂CO₃ (169 mg, 1.22 mmol). The reaction mixture was stirred at 50° C. for 30 min. To this, MeI (0.104 ml, 1.66 mmol) was added, and the reaction mixture was stirred overnight at 50° C. LCMS showed it to be a clean reaction. The reaction mixture was diluted with EtOAc and filtered to remove K₂CO₃. The filtrate was dried under vacuum. The crude mixture was adsorbed on silica, dried to make it free flowing, loaded on a cartridge, and purified using an ISCO system (24 g silica column, hexane/EtOAc gradient). The product eluted with 15% EtOAc in hexane. The product fractions were collected and concentrated to give the methylated product SKC-03-036 (270 mg, 52%). ¹H NMR (400 MHz, CDCl₃) δ 7.16-6.83 (m, 4H), 6.48 (d, J=7.8 Hz, 1H), 5.92 (m, 1H), 5.08 (m, 2H), 4.66 (t, J=25.6 Hz, 1H), 3.663 (s, 3H), 3.38 (d, J=6.5 Hz, 2H), 2.27 (s, 6H), 1.85-1.76 (m, 4H), 1.54-1.34 (m, 3H), 1.11 (d, J=19.7 Hz, 9H), 0.94-0.86 (m, 3H).

Step 2: Synthesis of (R)—N'-(3,5-dimethylbenzoyl)-N'-(2,2-dimethylhexan-3-yl)-3-methoxy-2-methyl-4-3-(4,4,5,5-tetramethyl-1,3,2-dioxaborolan-2-yl)propyl benzohydrazide

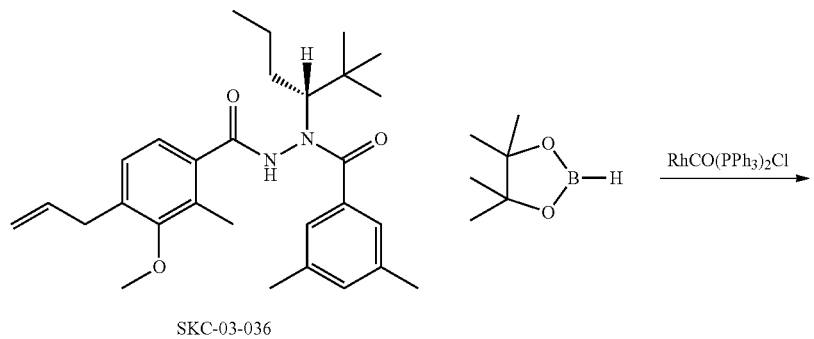

SKC-03-036

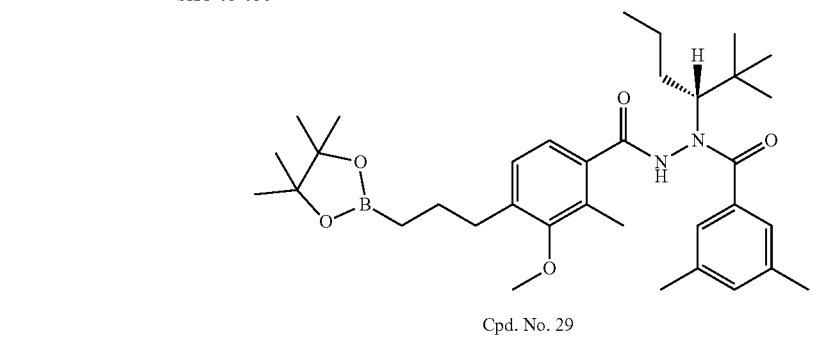

Cpd. No. 29

An oven dried, 100 ml, two necked, round bottom flask was equipped with a teflon coated magnetic stir bar, and two rubber septum with one of the septum with a needle connected to an argon/vacuum manifold. This argon flushed round bottom flask was charged with 4-allyl-3-hydroxy-DAH (SKC-03-036, 270 mg, 0.58 mmol) in anhydrous THF (2 ml) and modified Wilkinson's catalyst (20.08 mg, 0.029 mmol), and three vacuum/argon purge cycles were performed. The mixture was stirred at room temperature until all of the reagents dissolved (<2 min). To this stirred clear reaction mixture was added 4,4,5,5-tetramethyl-1,3,2-dioxaborolane (Bpin-H) (0.254 ml, 1.74 mmol) via syringe, another argon/vacuum/argon purge was performed, and the reaction mixture was stirred for 5 h. The color of the reaction mixture turned from light yellow to dark brown. LCMS showed that the reaction completed in 5 h but it was allowed to stir overnight. A few drops of water were slowly added. Once the effervescence ceased, MeOH was added and the reaction mixture was concentrated. The crude mixture was purified on an ISCO system (12 g silica column, hexane/EtOAc gradient). The product eluted with 20% EtOAc/hexane. The product fraction was collected and dried under vacuum to give 230 mg (67%) of Cpd. No. 29 $^1$H NMR (400 MHz, DMSO-$d_6$) δ 10.15 (s, 1H), 7.11 (s, 1H), 7.08-6.91 (m, 3H), 6.48 (d. J=7.8 Hz, 1H), 4.53-4.28 (m, 1H), 3.55 (d, J=4.2 Hz, 3H), 2.25 (d, J=4.5 Hz, 6H), 1.79-1.74 (m, 2H), 1.66) s, 3H), 1.7-1.39 (m, 6H), 1.17 (s, 12H), 1.03 (d, J=5.8 Hz, 9H), 0.93 (t, J=7.1 Hz, 1H), 0.85 (t, J=6.9 Hz, 3H), 0.69 (t, J=7.6 Hz, 2H).

Step 3: Synthesis of (R)-(3-(4-(2-(3,5-dimethylbenzoyl)-2-(2,2-dimethylhexan-3-yl)hydrazinecarbonyl)-2-methoxy-3-methylphenyl)propyl)boronic acid (Cpd. No. 27)

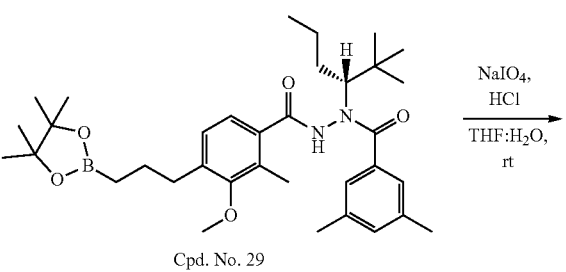

Cpd. No. 29

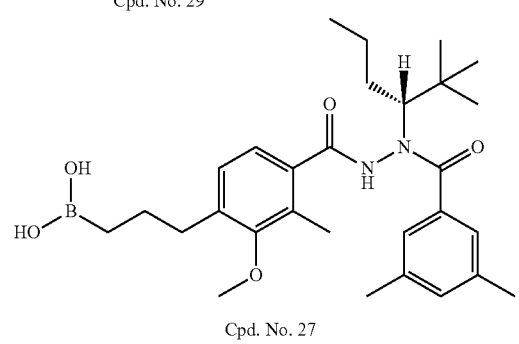

Cpd. No. 27

To a solution of Cpd. No. 29 (230 mg, 0.388 mmol) in THF/water mixture (4:1 ratio, 5 ml) was added sodium periodate (498 mg, 2.33 mmol) and then 2M HCl in ether (0.388 ml, 0.776 mmol). The reaction mixture was stirred at room temperature for few hours, the LCMS checked, and the reaction was allowed to continue to stir overnight. The reaction mixture was filtered to remove the solid, washed with DCM, and dried under vacuum. The crude reaction mixture was adsorbed on neutral alumina and dried. Once it was fee flowing it was loaded on an ISCO cartridge and purified (24 g neutral alumina column, MeOH-DCM solvent mixture). The product eluted with 2% MeOH in DCM) to give 130 mg of Cpd. No. 27 (66%) in >95% ee. $^1$H NMR (400 MHz, DMSO-$d_6$) δ 10.43-9.78 (m, 1H), 8.35-8.03 (m, 1H), 7.18-6.89 (m, 4H), 6.66-6.38 (m, 1H), 4.67-4.36 (m, 1H), 3.60-3.51 (m, 3H), 3.30 (s, 3H), 3.18 (d, J=5.3 Hz, 2H), 2.64-2.51 (m, 2H), 2.25 (d, J=4.3 Hz, 6H), 1.88-1.16 (m, 8H), 1.03 (d, J=5.9 Hz, 9H), 0.89-0.80 (m, 3H).

Example 4

Synthesis of (R)-(3-(2-difluoromethoxy)-4-(2-(3,5-di methylbenzoyl)-2-(2,2-dimethylhexan-3-yl)hydrazinecarbonyl)-3-methylphenyl)propyl)boronic acid (Cpd. No. 28)

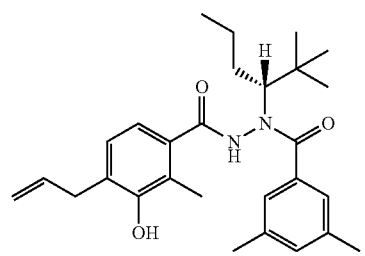 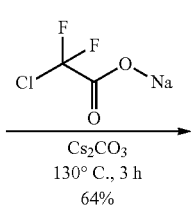

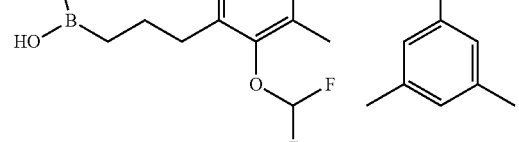

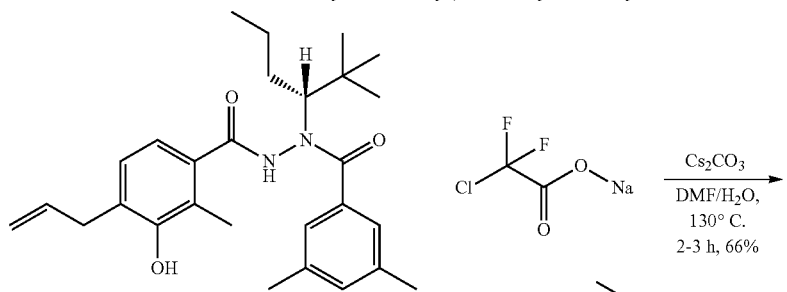

Cpd. No. 28

Step 1: Synthesis of (R)-4-allyl-3-(difluoromethoxy)-N'-(3,5-dimethylbenzoyl)-N'-(2,2-dimethylhexan-3-yl)-2-methylbenzohydrazide

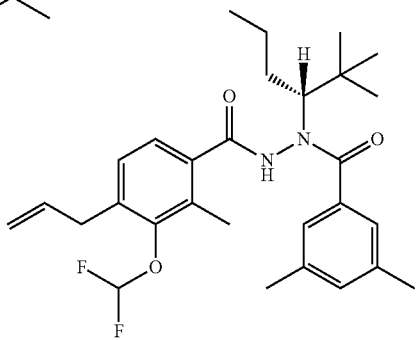

SKC-04-050

The 3-hydroxy-4-allyl DAH (2.8 g, 6.21 mmol) was dissolved in DMF/water P127C3 mixture (6:1 ratio, 11.6 ml) in a round bottom flask fitted with a reflux condenser. To this, cesium carbonate (4.05 g, 12.43 mmol) and the difluoroacetate sodium salt (1.42 g, 9.3 mmol) was added. The reaction mixture was stirred at 130° C. (condenser open to air) for 2 h 30 min. LCMS showed a conversion of 67% of product and 33% of starting material. After aqueous work up and extraction with EtOAc, the crude product was purified using an ISCO system (24 g silica column, hexane/EtOAc gradient). The product eluted with ~18% EtOAc in hexane and the starting material eluted with 25% EtOAc in hexane. The product fractions were collected and dried to give 1.13 g of pure product as a colorless solid (64% yield based on reacted SM), 1.2 g of the starting material was recovered. The product structure was assigned based on LCMS data.

Step 2: Synthesis of (R)-3-(difluoromethoxy)-N'-(3, 5-dimethylbenzoyl)-N'-(2,2-dimethylhexan-3-yl)-2-methyl-4-(3-(4,4,5,5-tetramethyl-N'-3,2-dioxaborolan-2-yl) propylbenzohydrazide To a solution of the above synthesized 4-allyl-3-(difluoromethoxy)-DAH (600 mg, 1.2 mmol) in anhydrous THF (6 ml) in a 100 ml 2-neck round bottom flask at room temperature under argon was added the catalyst (41.4 mg, 0.06 mmol). After 3-cycles of vacuum/argon purging, Bpin-H (0.523 ml, 3.60 mmol) was added via syringe and another 2 purge cycles of vacuum/argon were performed. The reaction mixture was stirred for 4 hrs while refluxing under argon. In 20 min. the color of the reaction mixture turned to light brown. LCMS after 2 h showed a ~46% conversion to product. The temperature was lowered to 76° C. and the reaction mixture was stirred overnight. LCMS showed additional two less polar peaks together with the unreacted starting material and the expected product. After the reaction, 2 ml of MeOH and few drops of water was added to the reaction mixture, the solvents were removed on a rotavapor under vacuum, and the crude mixture was dissolved in DCM and adsorbed on silica. Once it was dried and free flowing, it was loaded on a cartridge and purified using an ISCO system (12 g silica column, hexane/EtOAc gradient), 660 mg of the mixture (eluted with ~15% EtOAc in hexane, SM+ product, 36:62 ratio) was collected after ISCO column and used as such for the next step.

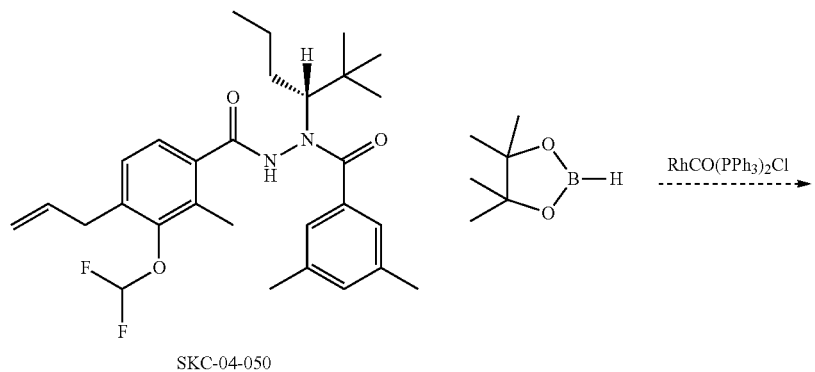

SKC-04-050

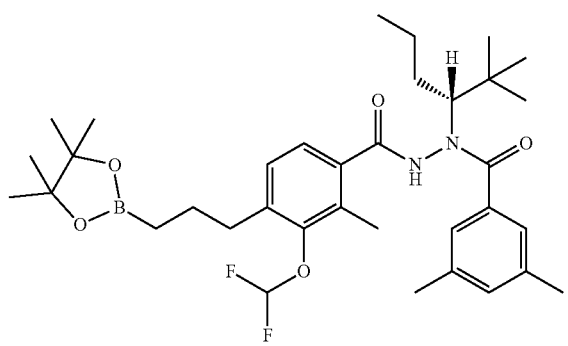

SKC-04-052

Step 3: Synthesis of (R)-(3-(2-difluoromethoxy)-4-(2-(3,5-dimethylbenzoyl)-2-(2,2-dimethylhexan-3-yl)hydrazinecarbonyl)-3-methylphenyl)propyl)boronic acid (Cpd No 28)

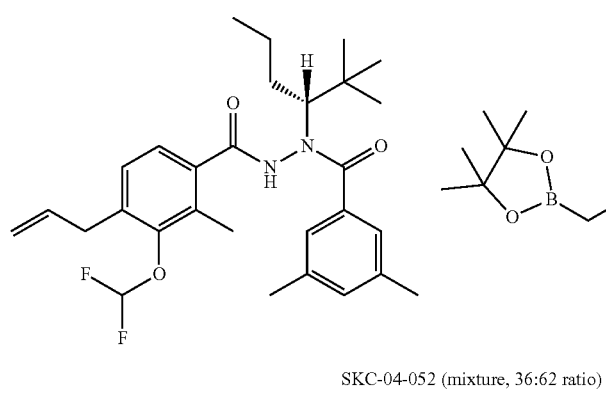

SKC-04-052 (mixture, 36:62 ratio)

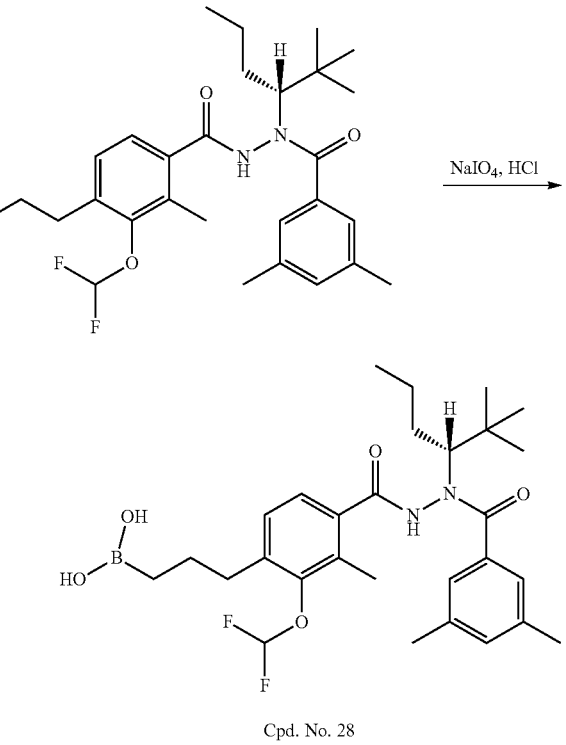

Cpd. No. 28

The above mixture (660 mg) was dissolved in a mixture of THF water (4.1, 30 ml) and sodium periodate (1.35 g, 6.30 mmol), and 2.0 M HCl in THF (1.05 ml, 2.10 mmol) was added. The reaction mixture was stirred at 40° C. for 1 h. LCMS showed a major peak for the expected product. The reaction was allowed to continue to stir at 40° C. for another 30 min and at room temperature overnight. After aqueous work up and extraction with ethyl acetate, the organic fractions collected, dried over anhydrous MgSO4, filtered, and concentrated. The crude mixture was purified using preparative HPLC to give Cpd. No. 28 based on LCMS data. (>95% ee).

Example 5

Synthesis of N'-(tert-butyl)-N'-(3,5-dimethylbenzoyl)-1-hydroxy-6-methyl-3,4-dihydro-1H-benzo[c][1,5,2]dioxaborepine-7-carbohydrazide (Cpd. No. 75)

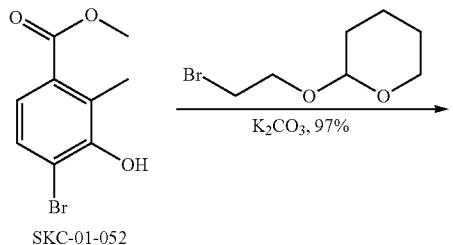

SKC-01-052

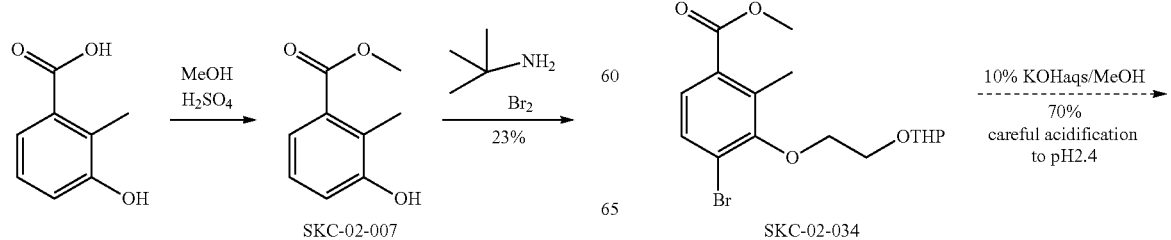

-continued

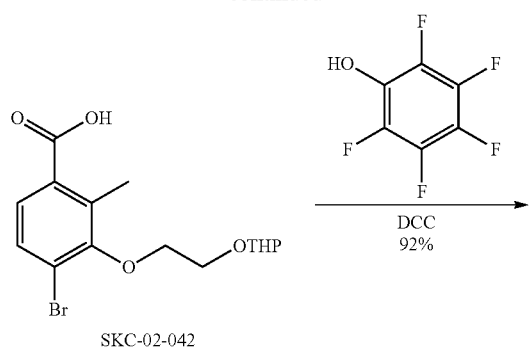

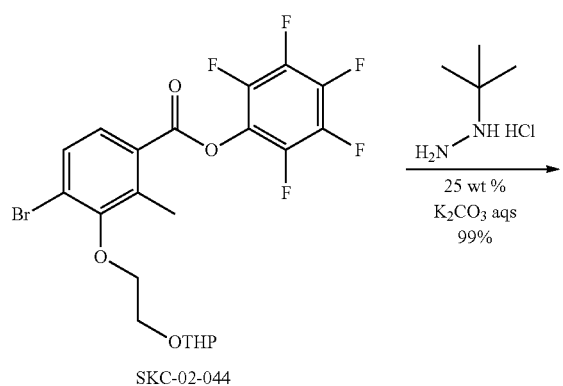

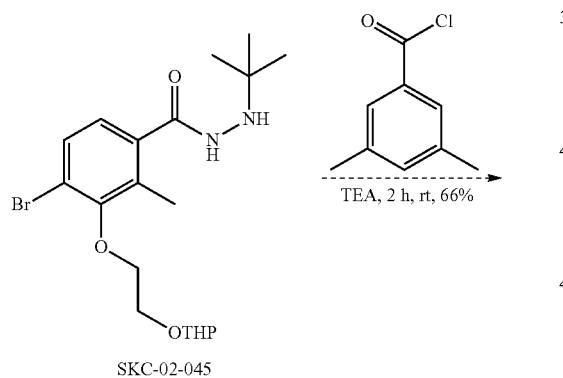

-continued

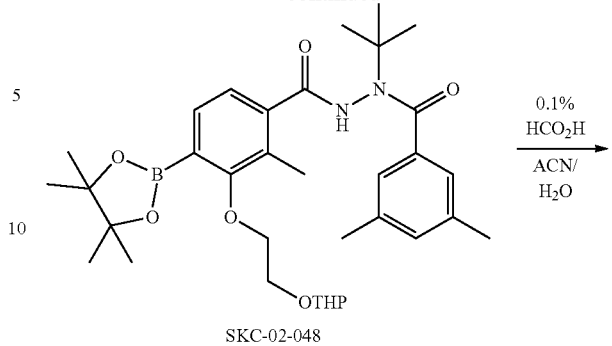

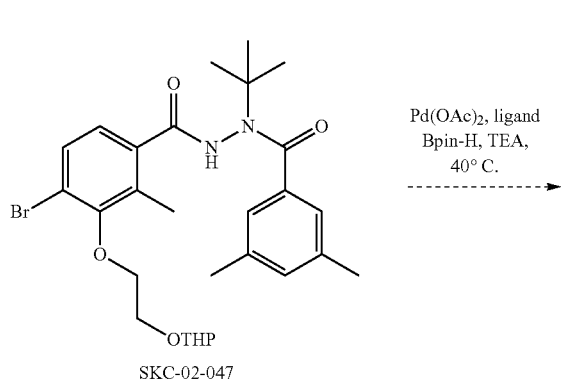

Step 1: Synthesis of methyl 3-hydroxy-2-methylbenzoate

Experimental procedure as described in EXAMPLE 1.

Step 2: Synthesis of methyl 4-bromo-3-hydroxy-2-methylbenzoate

A 500 ml 3-neck round bottom flask was fitted with two dropping funnels. To this was added a solution of the tert-butyl amine (4.4 g, 60.2 mmol) in CH2Cl2 (140 ml) and the flask was cooled to −78° C. A solution of bromine (9.6 g, 60.2 mmol) in CH$_2$Cl2 (60 ml) was added drop wise over 30 minutes from the dropping funnel. The mixture was stirred at −78° C. for another 1 h. A solution of methyl 3-hydroxy-2-methyl benzoate (10.0 g, 60.2 mmol) in CH2Cl2 (25 ml) was added from the second dropping funnel during 1 h. (US 2005110979). The reaction mixture was allowed to warm to room temperature and stir for overnight LCMS showed 3 peaks. Aqueous work up and extraction with DCM followed by flash column chromatography using an ISCO system (2×80 g silica gel column, hexane/EtOAc solvent mixture) gave the product (1st peak, fractions 4-5, 3.3 g, 22% yield). The side products isolated and characterized as dibromo and 5-bromo derivatives, 1H NMR (CDCl3): 7.29-7.21 (dd, 2H), 5.64 (s, 1H), 3.81 (s, 3H), 2.45 (s, 3H).

Step 2: Synthesis of methyl 4-bromo-2-methyl-3-2 ((tetrahydro-2H-pyran-2-yl)oxy) ethoxy)benzoate

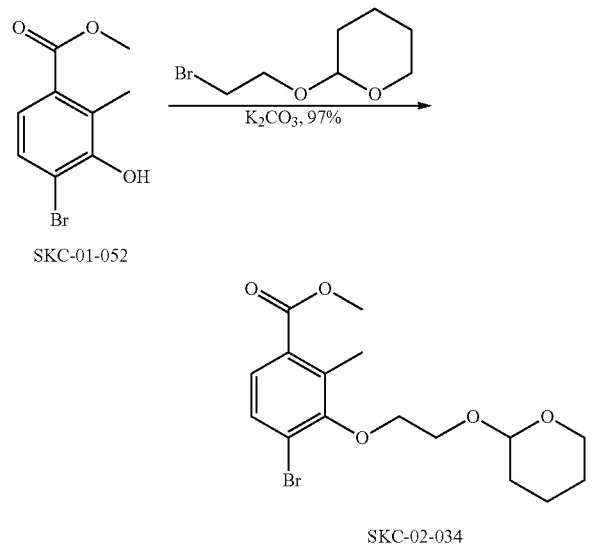

To a solution of methyl 4-bromo-3-hydroxy-2-methylbenzoate (1.0 g, 4.08 mmol) in anhydrous DMF (20 ml) under argon was added anhydrous K2CO3 (1.12 g, 8.16 mmol), and the reaction mixture was stirred at room temperature for 2 h. To this stirred mixture was added 2-(2-bromoethoxy) tetrahydro-2H-pyran (1.28 g, 6.12 mmol). The reaction mixture was heated at 60° C. for 4 h. LCMS showed a single peak with the expected product mass. The heating was stopped and stirring was continued overnight at room temperature. After aqueous work up and extraction with EtOAc, the organic fractions dried over anhydrous MgSO4, filtered, and concentrated. The crude product was purified using an ISCO system (40 g silica column, hexane/EtOAc gradient). The product eluted with ~10% EtOAc in hexane. The product fractions were collected and concentrated to give 1.48 g (97% yield) of SKC-02-034. $^1$H NMR (400 MHz, CDCl3) δ 7.53 (d, J=8.5 Hz, 1H), 7.46 (d, J=8.5 Hz, 1H), 4.78 (t, J=3.5 Hz, 1H), 4.22-4.03 (m, 3H), 4.07-3.76 (m, 5H), 3.60-3.52 (m, 1H), 2.61 (s, 3H), 1.98-1.38 (m, 6H).

Step 3: Synthesis of 4-bromo-2-methyl-3-2-((tetrahydro-2H-pyran-2-yl)oxy)ethoxy) benzoic acid

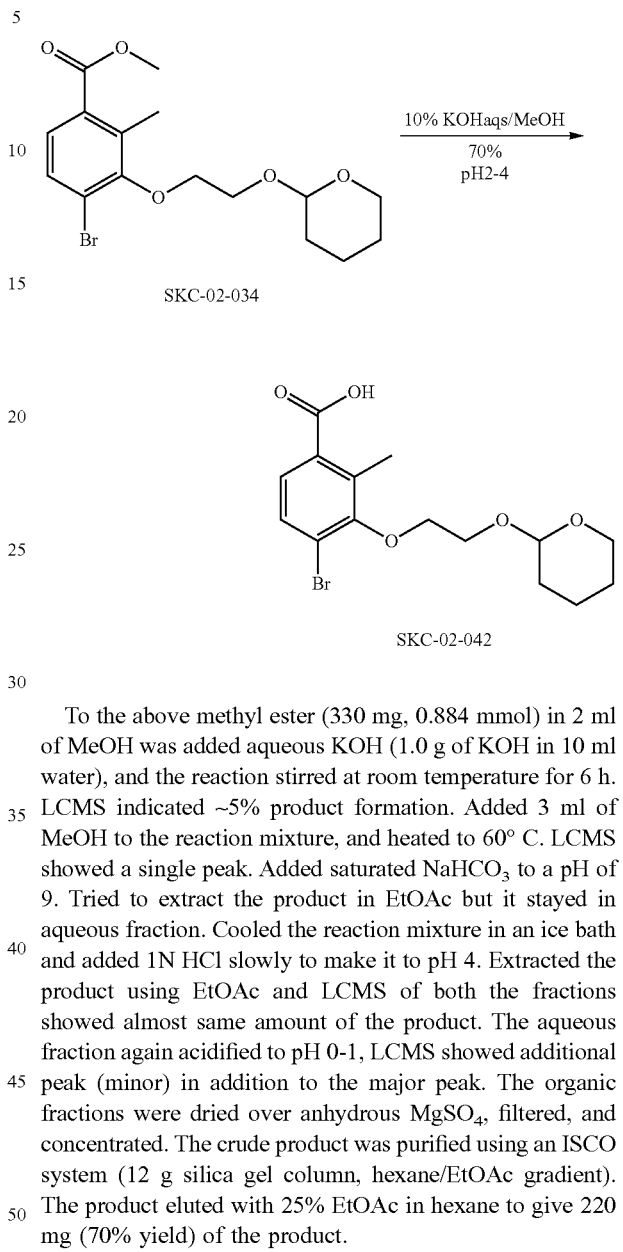

To the above methyl ester (330 mg, 0.884 mmol) in 2 ml of MeOH was added aqueous KOH (1.0 g of KOH in 10 ml water), and the reaction stirred at room temperature for 6 h. LCMS indicated ~5% product formation. Added 3 ml of MeOH to the reaction mixture, and heated to 60° C. LCMS showed a single peak. Added saturated NaHCO3 to a pH of 9. Tried to extract the product in EtOAc but it stayed in aqueous fraction. Cooled the reaction mixture in an ice bath and added 1N HCl slowly to make it to pH 4. Extracted the product using EtOAc and LCMS of both the fractions showed almost same amount of the product. The aqueous fraction again acidified to pH 0-1, LCMS showed additional peak (minor) in addition to the major peak. The organic fractions were dried over anhydrous MgSO4, filtered, and concentrated. The crude product was purified using an ISCO system (12 g silica gel column, hexane/EtOAc gradient). The product eluted with 25% EtOAc in hexane to give 220 mg (70% yield) of the product.

The experiment was repeated in 2.2 g scale in a mixture of 30 ml of MeOH and 50 ml of 10% KOH aqueous. The reaction was completed in 6 h at 55° C. Saturated NaHCO3 added and the mixture stirred at room temperature overnight. The mixture was cooled in an ice bath 1N HCl was slowly added to make it to pH 3-4. Extracted using EtOAc and then acidified the aqueous fractions again with 1N HCl to pH 1-2. Extracted a second time. The combined organic fractions were concentrated and purified using an ISCO system (40 g silica gold column, hexane/EtOAc gradient). The main peak eluted with 35% EtOAc in hexane to give SKC-02-042. $^1$H NMR (400 MHz, CDCl3) δ 7.67 (d, J=8.5 Hz, 1H), 7.48 (d, J=8.5 Hz, 1H), 4.77 (t, J=3.5 Hz, 1H), 4.26-4.02 (m, 3H), 3.91-3.80 (m, 2H), 3.69-3.40 (m, 1H), 2.65 (s, 3H), 2.01-1.39 (m, 6H).

151

Step 4: Synthesis of perfluorophenyl-4-bromo-2-methyl-3-(2-((tetrahydro-2H-pyran-2-yl)oxy)ethoxy) benzoate

152

Step 5: Synthesis of 4-bromo-N'-(tert-butyl)-2-methyl-3-(2-((tetrahydro-2H-pyran-2-yl)oxy)ethoxy) benzohydrazide

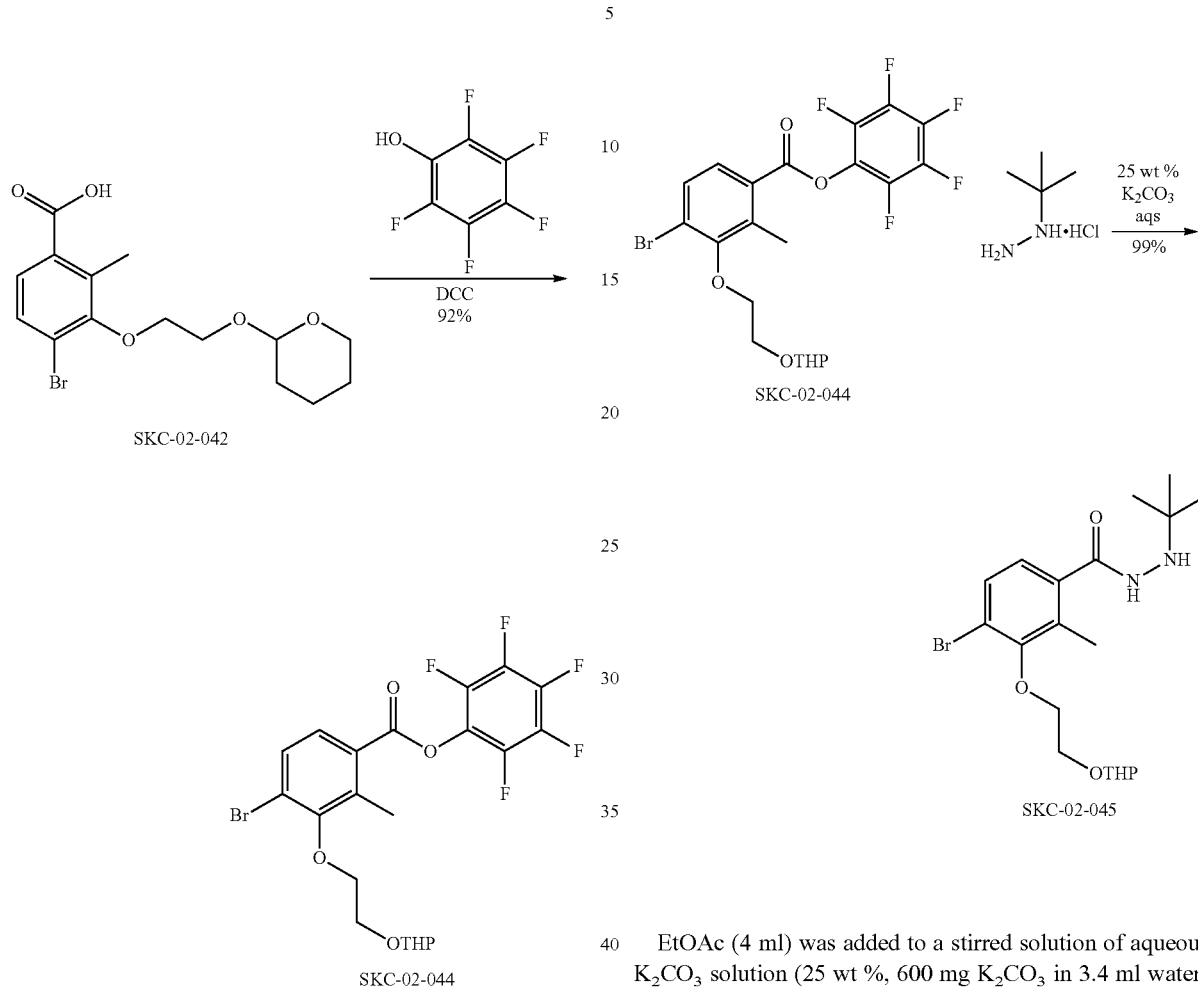

The above acid (SKC-02-042, 770 mg, 2.14 mmol) was dissolved in anhydrous ethyl acetate (9 ml) in a 200 ml round bottom flask under argon and stirred at room temperature. To this was added pentafluorophenol (434 mg, 2.36 mmol) and 1M DCC in DCM (2.36 ml, 2.36 mmol). The reaction mixture was stirred at room temperature overnight, 5 ml of water was added with stirring for another 10 min. The precipitate was filtered off. The filtrate was diluted with EtOAc and water and extracted with ethyl acetate. The organic fractions were collected, dried over anhydrous MgSO$_4$ filtered, and concentrated. The crude mixture was adsorbed on silica and purified using an ISCO system (12 g silica column, hexane/EtOAc gradient). The product eluted with ~8% EtOAc in hexane. The product fractions were collected and dried to give SKC-02-044 (1.1 g, 98% yield). $^1$H NMR (400 MHz, MeOD) δ 7.93 (d, J=8.5 Hz, 1H), 7.74 (t, J=11.3 Hz, 1H), 4.84 (t, J=3.3 Hz, 1H), 4.26-4.10 (m, 3H), 4.06-3.87 (m, 2H), 3.72-3.55 (m, 1H), 2.74 (s, 3H), 2.03-1.70 (m, 6H).

EtOAc (4 ml) was added to a stirred solution of aqueous K$_2$CO$_3$ solution (25 wt %, 600 mg K$_2$CO$_3$ in 3.4 ml water) in a 200 ml round bottom flask at room temperature. To this was added tert-butyl hydrazine hydrochloride (267 mg, 2.14 mmol) followed by the Pf ester derivative (750 mg, 1.43 mmol) dissolved in EtOAc (3 mil). The reaction mixture was stirred at room temperature overnight. For checking the LCMS, a small amount of the sample was mixed with slightly acidic buffer solution (pH 6.5 from Aldrich) in order to quench any unreacted free hydrazine. The crude mixture was diluted with buffer solution (pH 6.5) and stirred for few minutes. LCMS showed two peaks, the major one with the expected product mass. After usual aqueous work up and extraction with ethyl acetate, the organic fractions were dried over anhydrous MgSO$_4$, filtered and concentrated. The crude mixture was redissolved in DCM, adsorbed on silica, and purified using an ISCO system (12 g silica column, hexane/EtOAc gradient). The product eluted with ~45% EtOAc in hexane. The product fractions were collected to give 490 mg, 80% yield of the hydrazide product SKC-02-050. $^1$H NMR (400 MHz, CDCl$_3$) δ 7.38 (d, J=8.2 Hz, 1H), 7.26 (s, 1H), 6.96 (d, J=8.2 Hz, 1H), 4.89 (s, 1H), 4.72 (d, J=2.8 Hz, 1H), 4.15-4.03 (m, 3H), 3.97-3.73 (m, 2H), 3.51-3.49 (m, 1H), 2.41 (s, 3H), 1.91-1.44 (m, 6H), 1.13 (s, 9H).

Step 6: Synthesis of 4-bromo-N'-(tert-butyl)-N'-(3,5-dimethylbenzoyl)-2-methyl-3-(2-((tetrahydro-2H-pyran-2-yl)oxy)ethoxy)benzohydrazide

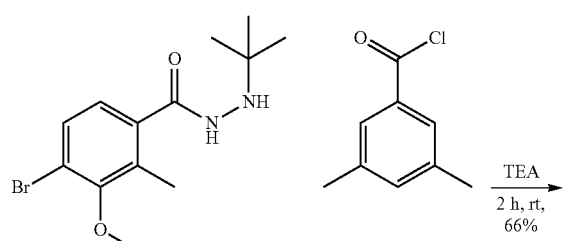

SKC-02-045

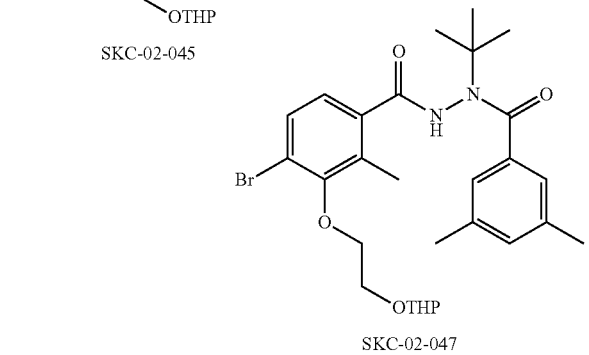

SKC-02-047

To a stirred solution of the SKC-02-045 (500 mg, 1.16 mmol) in DCM (2 ml) in a 100 ml round bottom flask was added 3,5-dimethyl benzoyl chloride (196 mg, 1.16 mmol). The solution became clear. To this, TEA (0.162 ml, 1.16 mmol) was added drop wise. The reaction mixture was stirred under argon at room temperature overnight. LCMS showed two peaks, the major one showed the expected product mass. The crude mixture was adsorbed on silica and purified using an ISCO system (12 g silica gel column, hexane/EtOAc gradient). The product eluted with ~40% EtOAc in hexane. The product fractions were collected to give 560 mg (86% yield) of the solid product SKC-02-047. ¹H NMR (400 MHz, DMSO-d₆) δ 10.55 (s, 1H), 7.45 (d, J=8.1 Hz, 1H), 7.03 (d, J=4.2 Hz, 3H), 6.42 (dd, J=8.2, 1.9 Hz, 1H), 4.65 (t, J=3.1 Hz, 1H), 4.14-3.58 (m, 5H), 3.55-3.37 (m, 1H), 2.24 (s, 6H), 1.79 (s, 3H), 1.77-1.37 (m, 1H).

Step 7: Synthesis of N'-(tert-butyl)-N'-(3,5-dimethylbenzoyl)-2-methyl-3-(2-((tetrahydro-2H-pyran-2-yl)oxy)ethoxy)-4-(4,4,5,5-tetramethyl-1,3,2-dioxaborolan-2-yl)benzohydrazide

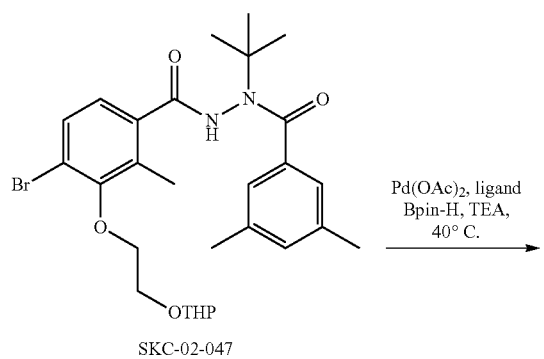

SKC-02-047

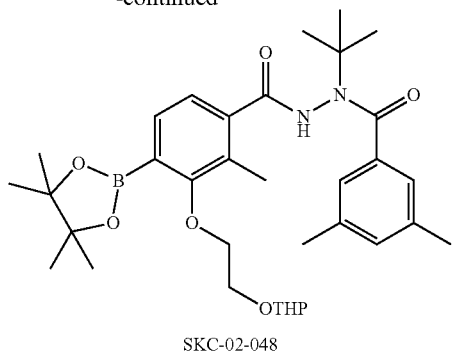

SKC-02-048

To a stirred solution of the above synthesized 4-bromo-DAH (200 mg, 0.36 mmol) in anhydrous 1,4-dioxane (2 ml) in a 100 ml 2-necked round bottom flask at room temperature under argon was added palladium (II) acetate (4.0 mg, 0.018 mmol), phosphine ligand (25.0 mg, 0.071 mmol) and triethylamine (0.15 ml, 1.069 mmol). After 3-cycles of vacuum/argon purging, Bpin-H (0.16 ml, 1.069 mmol) was added via syringe followed by another 2 purge cycles of vacuum/argon. The reaction mixture was stirred at room temperature for 10 min and then heated to 40° C. and stirred for 4 h. LCMS showed product peak. After the reaction, 2 ml of MeOH and few drops of water were added to the reaction mixture and the solvents were removed on a rotavapor. The crude mixture was redissolved in DCM and adsorbed on silica. Once it was dried and free flowing, it was loaded on a cartridge and purified using an ISCO system (12 g silica column, hexane/EtOAc gradient) to give 50 mg of SKC-02-048.

Step 8: Synthesis of N'-(tert-butyl)-N'-(3,5-dimethylbenzoyl)-1-hydroxy-6-methyl-3,4-dihydro-1H-benzo[c][1,5,2]dioxaborepine-7-carbohydrazide

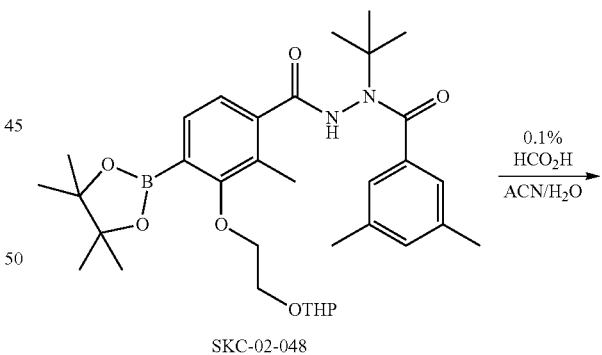

SKC-02-048

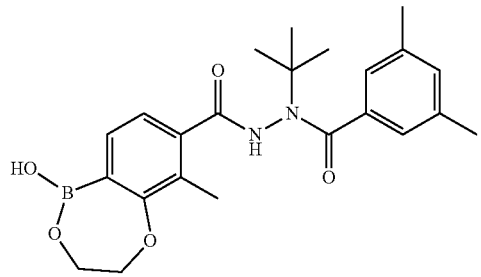

Cpd. No. 75

50 mg of SKC-02-048 was stirred in 2 ml of a 1:1 mixture of water/acetonitrile containing 0.1% formic acid at 40° C. overnight, and checked by LCMS. After the reaction was complete, the solvent was removed on a rotavapor under vacuum and the crude product was purified by preparative HPLC and lyophilized to give 17 mg of Cpd. No. 75 as a pure dry powder. $^1$H NMR (400 MHz, DMSO-d$_6$) δ 10.49 (s, 1H), 8.39 (s, 1H), 7.57 (d, J=7.8 Hz, 1H), 7.04 (s, 3H), 6.19 (d, J=7.9 Hz, 1H), 4.41-4.18 (m, 2H), 4.16-3.96 (m, 2H), 2.25 (s, 6H), 1.70 (s, 3H), 1.49 (s, 9H).

Example 6

Synthesis of (R)—N'-(3,5-dimethylbenzoyl)-N'-(2,2-dimethylpentan-3-yl)-1-hydroxy-6-methyl-3,4-dihydro-1H-benzo[c][1,5,2]dioxaborepine-7-carbohydrazide (Cpd. No. 79)

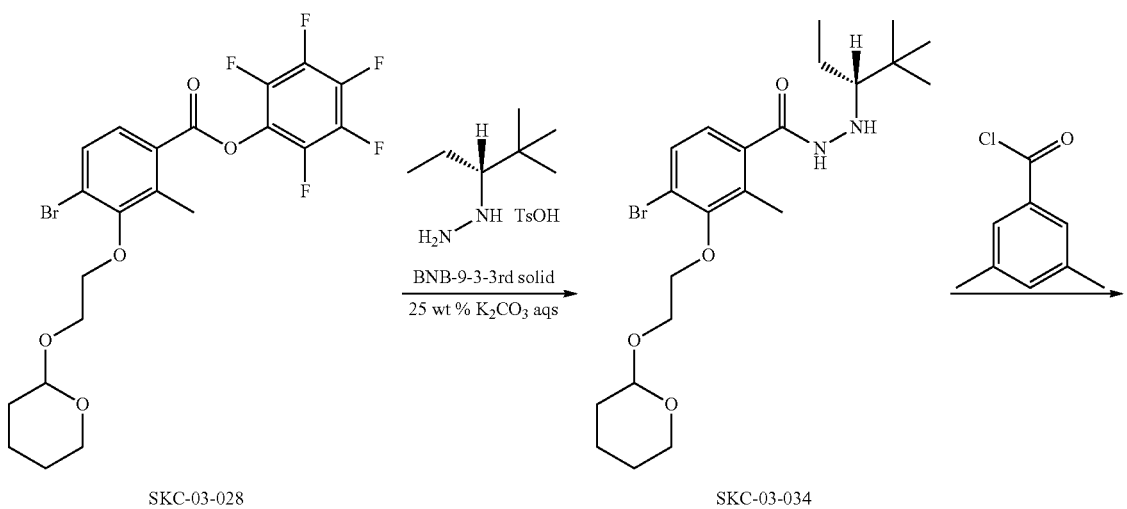

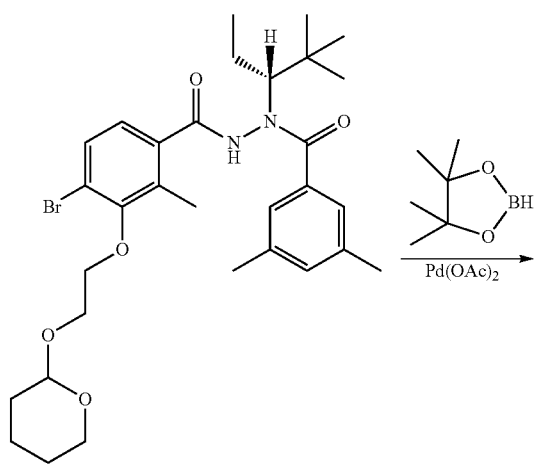

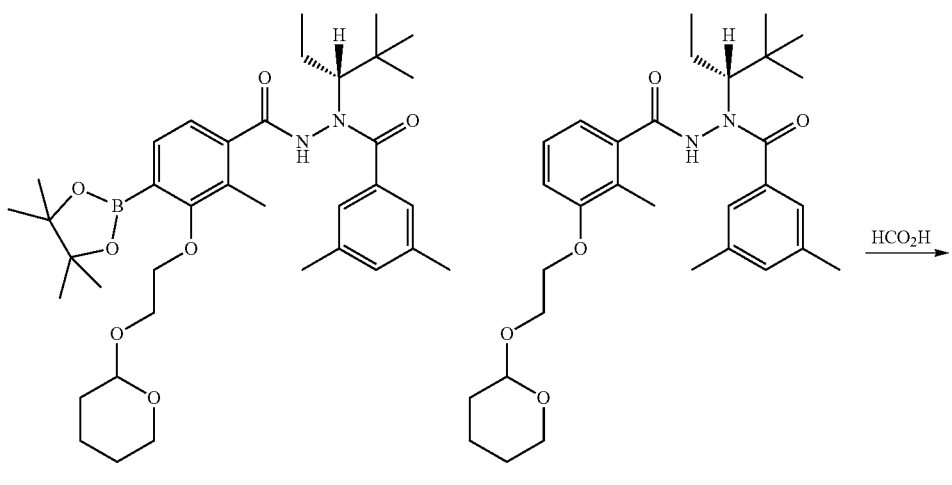

SKC-03-040

SKC-03-040-1

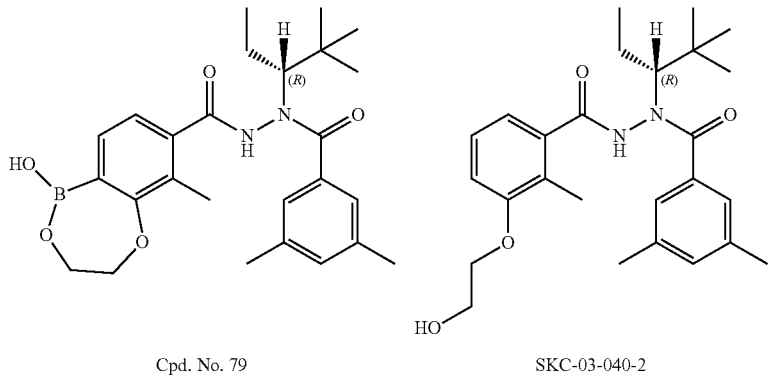

Cpd. No. 79

SKC-03-040-2

Step 1: Synthesis of 4-bromo-N'—((R)-2,2-dimethylpentan-3-yl)-2-methyl-3-(2-((tetrahydro-2H-pyran-2-yl)oxy)ethoxy)benzohydrazide

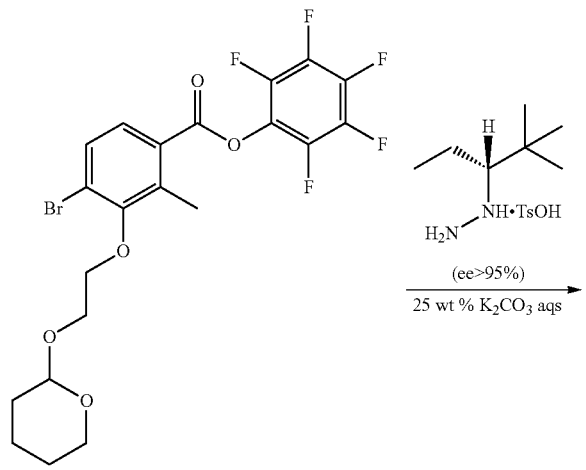

SKC-03-028

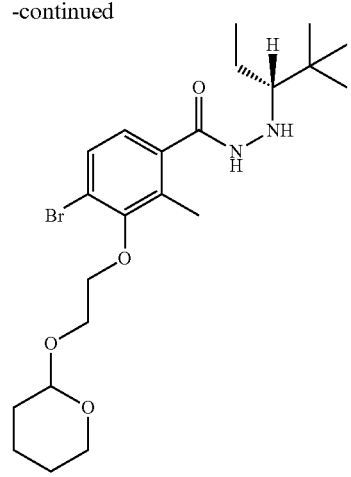

SKC-03-034

EtOAc (6 ml) was added to a stirred solution of 25 wt % aqueous $K_2CO_3$ solution (800 mg $K_2CO_3$ in 3.2 ml water) in a round bottom flask at room temperature. To this was added tert-butyl hydrazine followed by the Pf ester compound (1.0 g, 1904 mmol) dissolved in EtOAc (4 ml). The reaction mixture was stirred at room temperature overnight. LCMS showed a single peak. The crude mixture was diluted with MeOH, concentrated, dissolved in DCM, adsorbed on silica, and purified using an ISCO system (40 g silica gel column, hexane/EtOAc gradient). The product eluted with ~35% EtOAc in hexane to give 610 mg (68%) of the product. $^1$H NMR (400 MHz, DMSO-$d_6$) δ 9.66 (s, 1H), 7.52 (d, J=8.1 Hz, 1H), 697 (d, J=8.2 Hz, 1H), 4.85 (s, 1H), 4.70 (t, J=33 Hz, 1H), 4.06-4.01 (m, 2H), 3.97-3.89 (m, 1H), 3.84-3.70 (m, 2H), 3.51-3.40 (m, 1H), 2.32 (s, 3H), 1.82-1.35 (m, 8H), 1.04 (t, 1=7.5 Hz, 3H), 0.93 (s, 9H).

Step 2: Synthesis of 4-bromo-N'-(3,5-dimethylbenzoyl)-N'—((R)-2,2-dimethylpentan-3-yl)-2-methyl-3-(2-(((tetrahydro-2H-pyran-2-yl)oxy)ethoxy)benzohydrazide

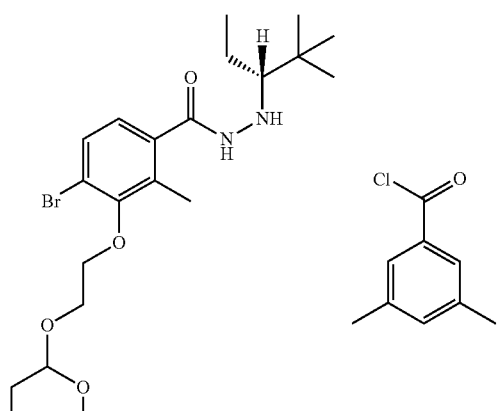

SKC-03-034

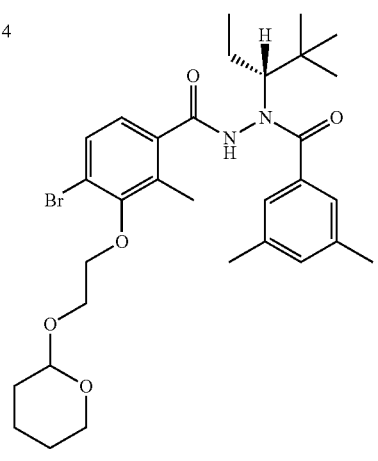

SKC-03-037

To a solution of SKC-03-034 (310 mg, 0.658 mmol) in 2 ml DCM was added the acid chloride (111 mg, 0.658 mmol). The solution became clear. TEA (66.5 mg, 0.092 ml) was added drop wise, and the reaction mixture was stirred under argon at room temperature for 2 hours. The reaction mixture became a colorless thick slurry, and it was stirred overnight. LCMS showed a single peak with the expected product mass. The reaction mixture was adsorbed on silica gel and purified using an ISCO system (12 g silica gel column, hexane/EtOAc gradient). The product eluted with ~20% EtOAc in hexane to give 380 mg (96%) of SKC-03-037. $^1$H NMR (400 MHz, DMSO-$d_6$) δ 10.33 (d. J=57.6 Hz, 1H), 7.47 (d, J=8.1 Hz, 1H), 7.10 (s, 1H), 7.06-6.97 (m, 2H), 6.62-6.41 (m, 1H), 4.70-4.60 (m, 1H), 4.33 (dd, J=82.0, 10.4 Hz, 1H), 3.99-3.82 (m, 3H), 3.82-3.71 (m, 1H), 3.71-3.58 (m, 1H), 3.52-3.34 (m, 1H), 2.24 (d, J=4.9 Hz, 6H), 1.83-1.28 (m, 11H), 1.12-0.99 (m, 12H).

Step 3: Synthesis of (R)—N'-(3,5-dimethylbenzoyl)-N'-(2,2-dimethylpentan-3-yl)-1-hydroxy-6-methyl-3,4-dihydro-1H-benzo[c][1,5,2]dioxaborepine-7-carbohydrazide (Cpd. No. 79)

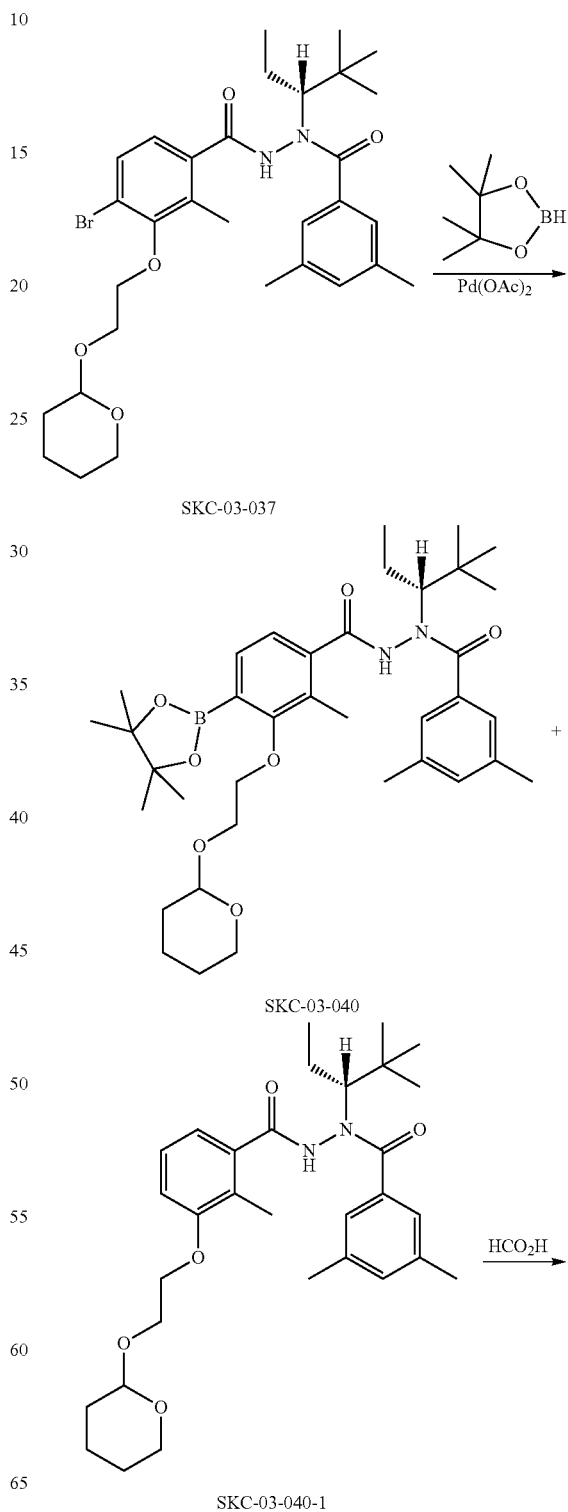

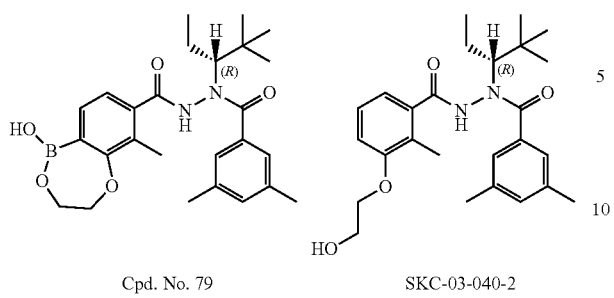

Cpd. No. 79    SKC-03-040-2

To a solution of SKC-03-037 (380 mg, 0.630 mmol) in anhydrous 1,4-dioxane (3 ml) in a 100 ml 2-necked round bottom flask at room temperature under argon was added palladium (II)acetate (7.07 mg, 0.031 mmol), phosphine ligand (44.1 mg, 0.126 mmol) and triethylamine ((0.263 ml, 1.889 mmol). After 3-cycles of vacuum/argon purging. Bpin-H (0.273 ml, 1.889 mmol) was added via syringe followed by another 2 purge cycles of vacuum/argon. The reaction mixture was stirred at room temperature for 10 min and then warmed to 40° C. and stirred for 4 h LCMS showed the product peak and a more polar peak corresponding to the protonated product (SKC-03-040-1). After the reaction, 2 ml of MeOH and few drops of water were added to the reaction mixture and it was concentrated under vacuum. The crude mixture was redissolved in DCM and adsorbed on silica. Once it was dried and free flowing, it was loaded on a cartridge and purified using an ISCO system (12 g silica column, hexane/EtOAc gradient). The main fraction (Cpd. No. 70) eluted with 20% EtOAc in hexane. The second peak (SKC-03-040-1) eluted with 25% EtOAc in hexane. The two product peaks were separated. $^1$H NMR of SKC-03-040 (400 MHz, DMSO-$d_6$) δ 10.33 (d, J=58.0 Hz, 1H), 7.48 (d, J=8.2 Hz, 1H), 7.07 (d, J=25.0 Hz, 3H), 6.70-6.23 (m, 1H), 4.78-4.60 (m, 1H), 4.43 (d, J=9.9 Hz, 1H), 3.99-3.80 (m, 3H), 3.84-3.71 (m, 1H), 3.68 (d, J=3.2 Hz, 1H), 3.50-3.39 (m, 1H), 2.24 (d, J=4.9 Hz, 6H), 1.80-1.34 (m, 8H), 1.09-0.92 (m, 24H).

The B pinlated product (SKC-03-040) obtained was stirred with 2 ml of a 1:1 mixture of water/acetonitrile containing 0.1% formic acid at 40° C. overnight. LCMS showed it as a clean reaction. The solvent was removed and the residue was purified by preparative HPLC and lyophilized to give Cpd. No. 79 (83 mg; >95% ee) as a dry powder.

The protonated product obtained from the first step was also stirred with 2 ml of 1:1 mixture of water/acetonitrile containing 0.1% formic acid at 40° C. overnight to give 41 mg of SKC-03-040-2 (>95% ee) as a dry powder.

Using the procedure described above, Cpd. No. 82 was prepared from SKC-06-005:

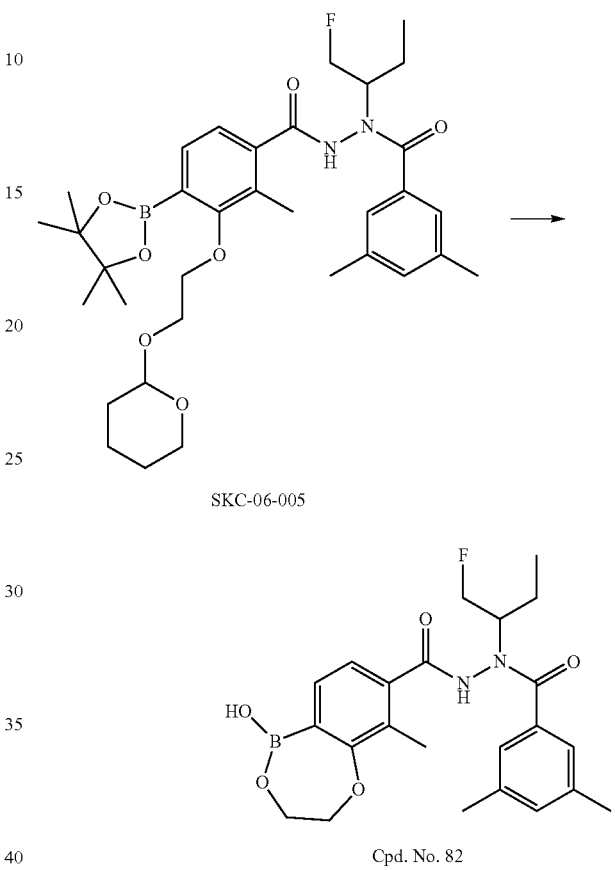

SKC-06-005

Cpd. No. 82

Cpd. No 82 LCMS [MH+]=443.

Example 7

Synthesis of (R)-(4-(2-(3,5-dimethylbenzoyl)-2-(2,2-dimethylpentan-3-yl) hydrazinecarbonyl)-2-(2-methoxyethoxy)-3-methylphenyl)boronic acid (Cpd No. 26)

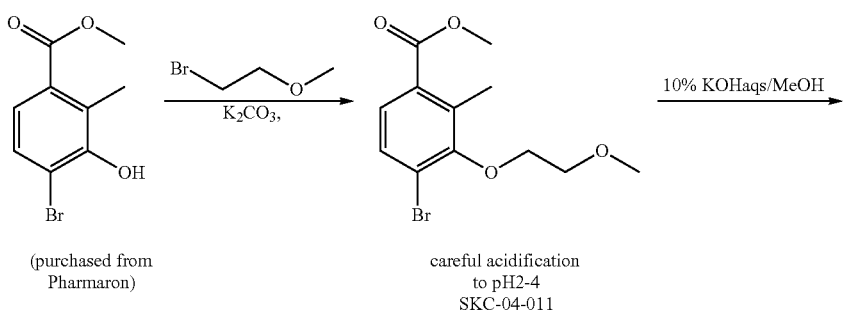

(purchased from Pharmaron)

careful acidification to pH 2-4
SKC-04-011

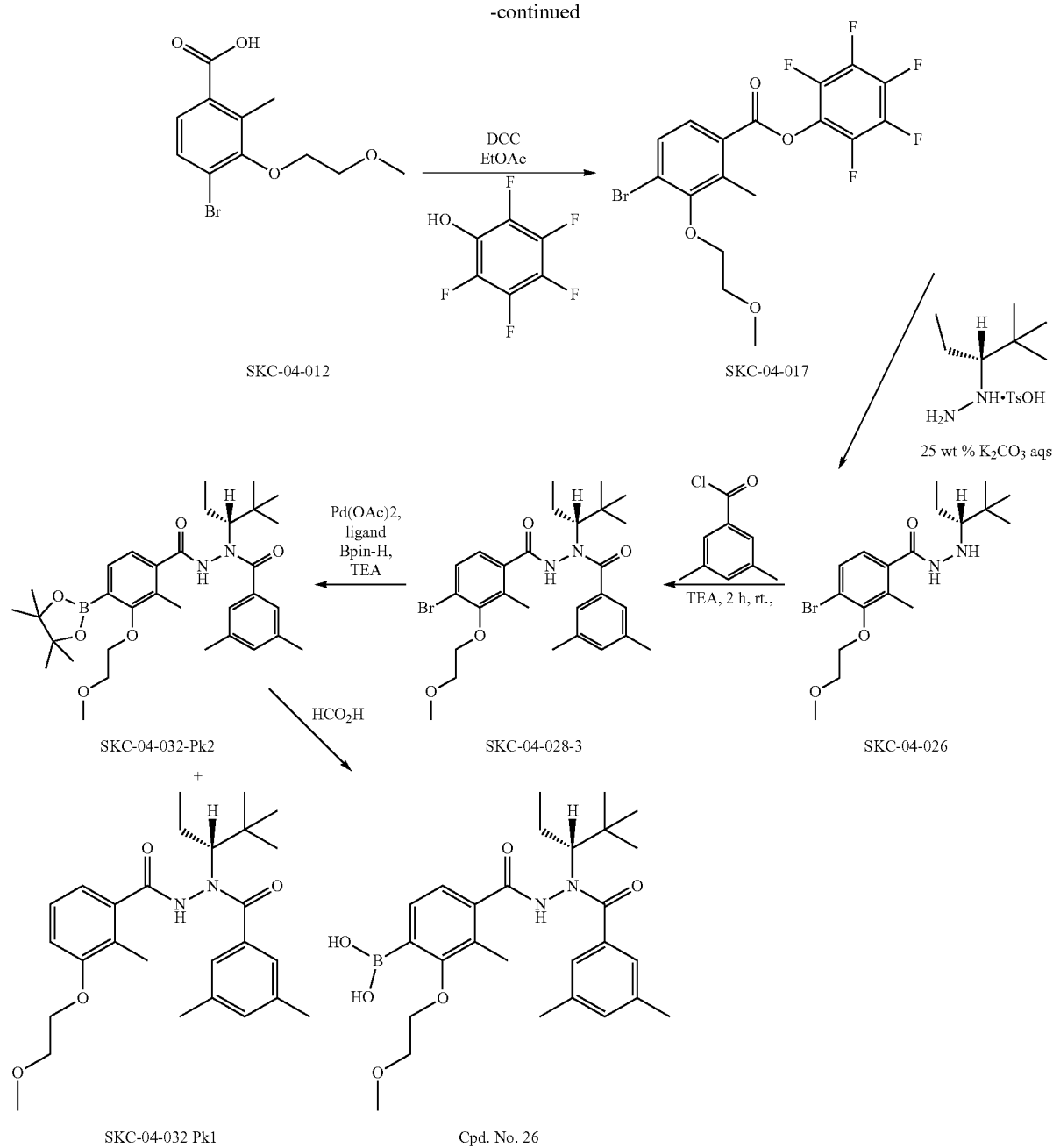
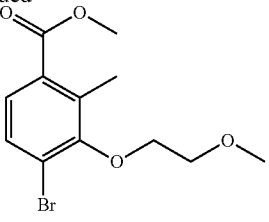
Step 1: Synthesis of methyl 4-bromo-3-(2-methoxyethoxy)-2-methylbenzoate
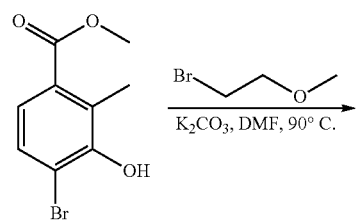
2-Methyl-3-hydroxyl-4-Bromo methyl ester (2.0 g, 8.16 mmol) was dissolved in anhydrous DMF (20 ml) in a 100 ml round bottom flask fitted with a reflux condenser, and anhydrous potassium carbonate (2.26 g, 16.32 mmol) was added to it. The reaction mixture was stirred at room temperature under argon for 15 min. To this, 1-bromo-2-methoxyethane (1.70 g, 12.24 mmol) was added and the reaction mixture was heated to 90° C. and stirred overnight under argon. LCMS showed single peak. The reaction mixture was cooled. After aqueous work up and extraction with EtOAc, the organic fractions were collected, dried over anhydrous MgSO$_4$, filtered, and concentrated. It was used in the next step without further purification.

Step 2: Synthesis of 4-bromo-3-(2-methoxyethoxy)-2-methylbenzoic acid

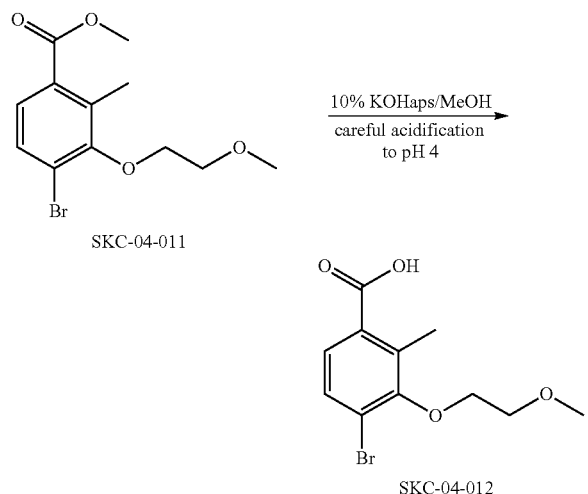

To a MeOH (25 ml) solution of the above methyl ester SKC-04-011, (crude wt of 3.1 g, but calculated for 2.0 g of pure compound) was added 50 ml of 10% KOH aqueous solution. The reaction mixture was stirred at 50° C. overnight. LCMS showed that reaction is only 75% complete. The reaction was heated for another 7 hours, and then stirred overnight at room temperature LCMS showed a single peak with expected product mass. Removed all MeOH under vacuum. The aqueous reaction mixture was cooled in an ice bath 1N HCl was slowly added to pH 4-5. A white product precipitated out. It was filtered and dried under vacuum at 40° C. overnight to give 1.34 g (70%) of the acid SKC-04-012 as colorless powder. $^1$H NMR (400 MHz, DMSO-d$_6$) δ 13.15 (br s, 3H), 7.54 (d, J=8.4 Hz, 1H), 7.46 (d, 1=8.4 Hz, 1H), 4.09-3.90 (m, 2H), 3.73-3.63 (m, 2H), 3.33 (s, 3H), 2.47 (s, 3H).

Step 3: Synthesis of perfluorophenyl 4-bromo-3-(2-methoxyethoxy)-2-methylbenzoate

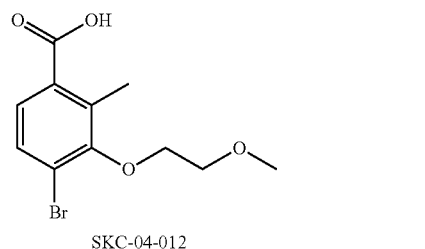

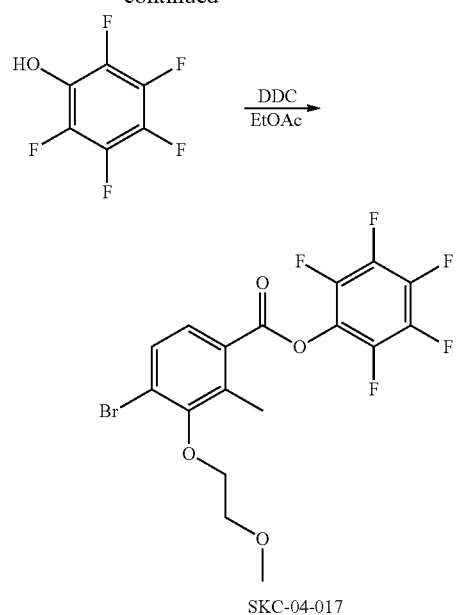

4-Bromo-3-(2-methoxyethoxy)-2-methylbenzoic acid (SKC-04-012, 1.37 g, 4.74 mmol) was dissolved in anhydrous EtOAc (20 ml) in a 250 ml round bottom flask under argon and stirred at room temperature. To this was added pentafluorophenol (0.959 g, 5.21 mmol) and 1M DCC in DCM (5.21 ml, 5.21 mmol). The reaction mixture was stirred at room temperature overnight, 2 ml of water was added with stirring for another 10 min. The precipitate was filtered off. The filtrate was diluted with EtOAc and extracted. After aqueous work up, the organic fractions collected, dried over anhydrous MgSO$_4$, filtered and concentrated. The crude mixture was adsorbed on silica and purified using an ISCO system (24 g silica column, hexane/EtOAc gradient). The product fractions eluted with 5% EtOAc in hexane to give 1.79 g (83% yield) of the Pf ester derivative SKC-04-017 as a colorless solid.

Step 4: Synthesis of (R)-4-bromo-N'-(2,2-dimethylpentan-3-yl)-3-(2-methoxyethoxy)-2-methylbenzohydrazide

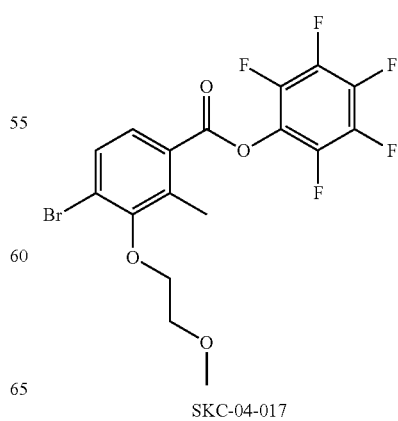

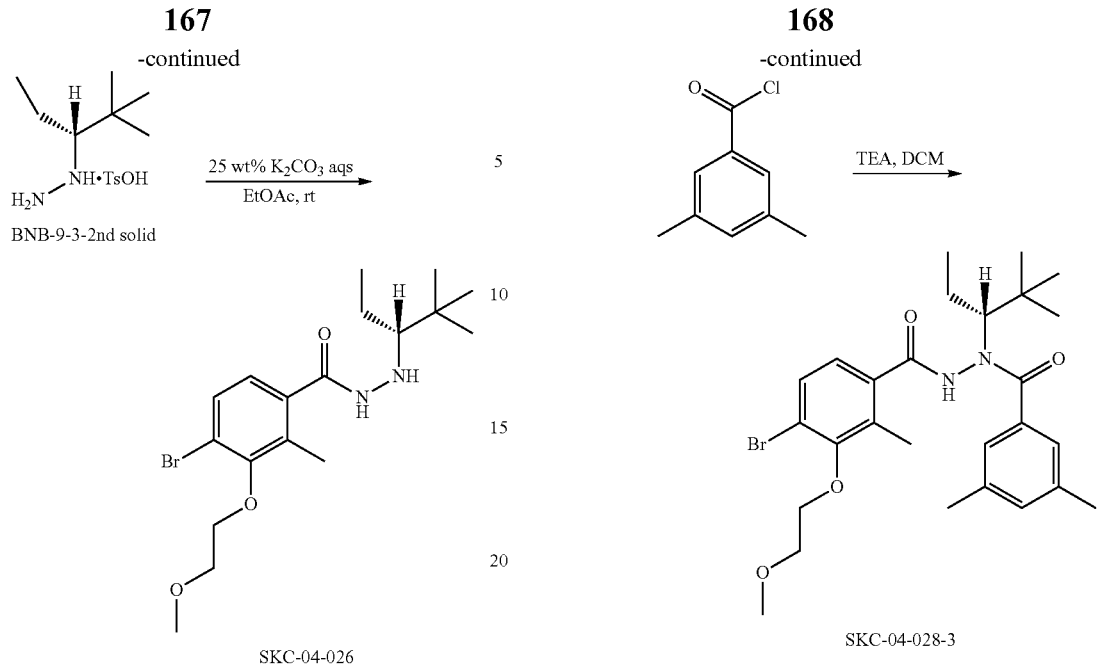

SKC-04-026

EtOAc (12 ml) was added to a stirred solution of 25 wt % aqueous $K_2CO_3$ solution (1.63 g $K_2CO_3$ in 6.5 ml water) in a round bottom flask at room temperature. To this was added tert-butyl hydrazine salt (1.784 g, 5.90 mmol) followed by the above Pf ester derivative (1.79 g, 3.93 mmol) dissolved in EtOAc (8 ml). The reaction mixture was stirred at room temperature overnight LCMS showed a main peak with the expected product mass. The crude mixture was diluted with acidic buffer solution (Aldrich. pH 6.5) and extracted with EtOAc. The organic fractions collected, dried over anhydrous $MgSO_4$, filtered and concentrated. The crude product was redissolved in DCM, adsorbed onto silica, and purified using an ISCO system (40 g silica gel column, hexane/EtOAc gradient). The product eluted ~30% EtOAc in hexane mixture to give 1.6 g (99%) of SKC-04-026. $^1$H NMR (400 MHz, DMSO-$d_6$) δ 9.66 (d, J=6.5 Hz, 1H), 7.51 (d, J=8.2 Hz, 1H), 6.96 (d, J=8.2 Hz, 1H), 4.84 (dd, J=6.5, 3.3 Hz, 1H), 4.01-3.96 (m, 2H), 3.72-3.63 (m, 2H), 3.34 (s, 3H), 2.38-2.31 (m, 1H), 2.29 (s, 3H), 1.60-1.49 (m, 1H), 1.34-1.21 (m, 1H), 1.03 (t, J=7.5 Hz, 3H), 0.93 (s, 9H).

Step 5: Synthesis of (R)-4-bromo-N'-(2,2-dimethylpentan-3-yl)-3-(2-methoxyethoxy)-2-methylbenzohydrazide To a solution of (R)-4-bromo-N-(2,2-dimethylpentan-3-yl)-3-(2-methoxyethoxy)-2-methylbenzohydrazide (SKC-04-026, 750 mg, 1.869 mmol) in anhydrous DCM (2 ml) was added 3,5-dimethylbenzoyl chloride (315 mg, 1.869 mmol) and triethylamine (0.260 ml, 1.869 mmol). The reaction mixture was stirred at room temperature under argon overnight. LCMS showed two major peaks. The crude mixture was dissolved in DCM and adsorbed on silica, and purified using an ISCO system (40 g silica gel column, hexane/EtOAc gradient). The product fraction eluted with 30% EtOAc in hexane to give SKC-04-028-3. $^1$H NMR (400 MHz, DMSO-$d_6$) δ 10.57-10.08 (m, 1H), 7.48 (d, J=8.1 Hz, 1H), 7.19-6.96 (m, 3H), 6.49 (dd, J=50.2, 8.2 Hz, 1H), 4.33 (dd, 0.1=82.0, 10.2 Hz, 1H), 3.96-3.78 (m, 2H), 3.62 (t, J=4.6 Hz, 2H), 3.31 (s, 3H), 2.25 (s, 6H), 1.78-1.29 (m, 5H), 1.12-0.92 (m, 12H).

Step 6: Synthesis of (R)-(4-(2-(3,5-dimethylbenzoyl)-2-(2,2-dimethylpentan-3-yl) hydrazinecarbonyl)-2-(2-methoxyethoxy)-3-methylphenyl)boronic acid (Cpd. No. 26)

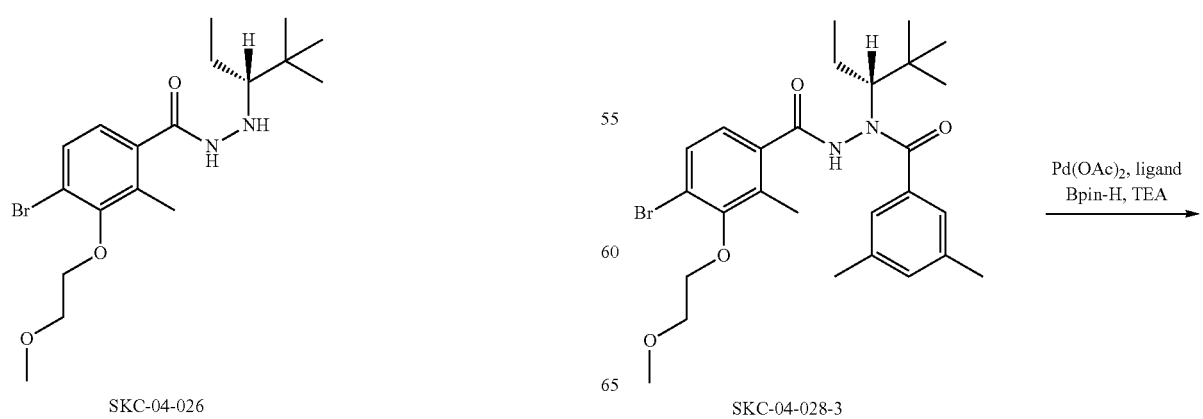

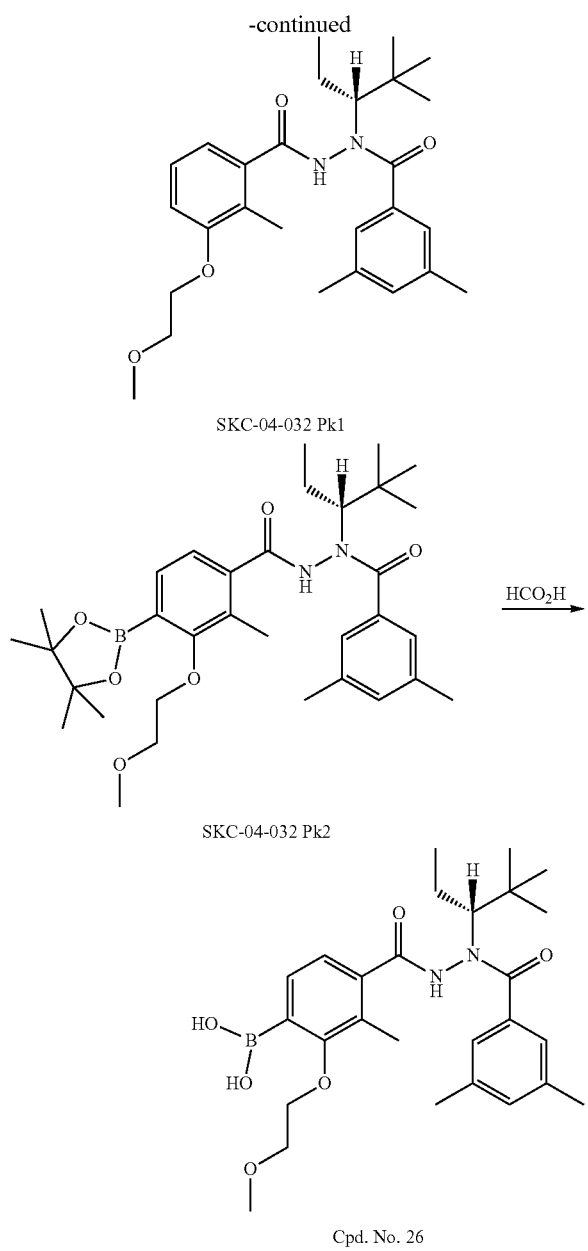

SKC-04-032 Pk1

SKC-04-032 Pk2

Cpd. No. 26

To a solution of the above synthesized 4-bromo-DAH (SKC-04-028-3, 400 mg, 0.750 mmol) in anhydrous 1,4-dioxane (4 ml) in a 100 ml 2-necked round bottom flask at room temperature under argon was added palladium (11) acetate (8.42 mg, 0.037 mmol), phosphine ligand (52.6 mg, 0.150 mmol) and triethylamine (0.314 ml, 2.249 mmol). After 3-cycles of vacuum/argon purging. Bpin-H (0.327 ml, 2.249 mmol) was added via syringe followed by another 2 purge cycles of vacuum/argon. The reaction mixture was stirred at room temperature for 10 min and then warmed to 40° C. and stirred overnight. LCMS showed Bpinlated product peak and a more polar peak with a mass corresponding to the protonated product. After the reaction, 2 ml of MeOH and few drops of water were added to the reaction mixture. The solvents were removed on a rotavapor under vacuum and the crude mixture was redissolved in DCM and adsorbed on silica. Once it was dried and free flowing, it was loaded on a cartridge and purified using an ISCO system (24 g silica column, hexane/EtOAc gradient). The two products eluted together. The fractions were combined and purified using preparative HPLC. SKC-04-032 Pk1 was isolated (31 mg.>95% ee). During HPLC purification, the Bpinlated product hydrolyzed slowly to the boronic acid derivative. After stirring overnight in the HPLC solvent mixture (0.1% HCO₂H in water/ACN mixture, 2 ml) at 40° C., the material was re-purified by prep HPLC to give Cpd. No 26 (9 mg) (>95% ee).

Example 8

Synthesis of (R)-(3-(1-(2,2-dimethylpentan-3-yl)-2-(3-methoxy-2-methylbenzoyl) hydrazinecarbonyl)-5-methylphenyl)boronic acid (Cpd No 33)

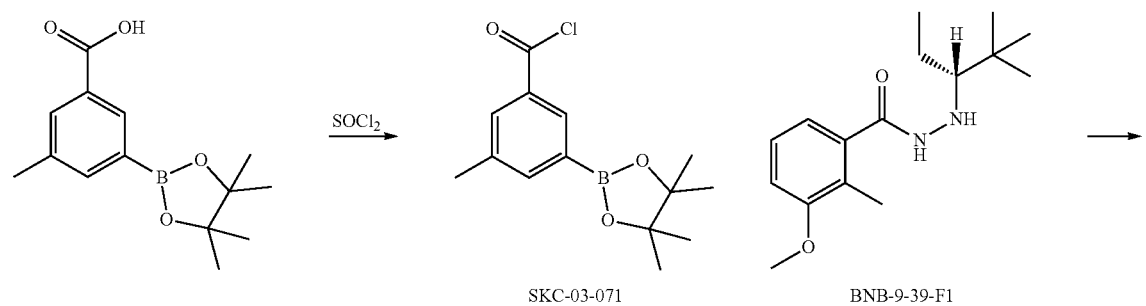

SKC-03-071

BNB-9-39-F1

-continued

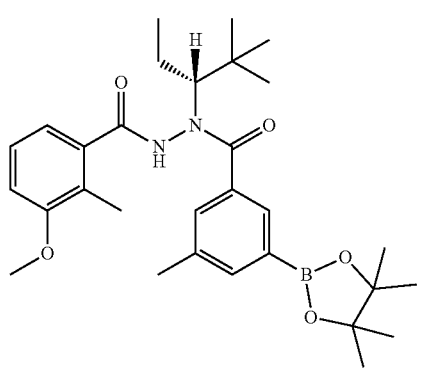 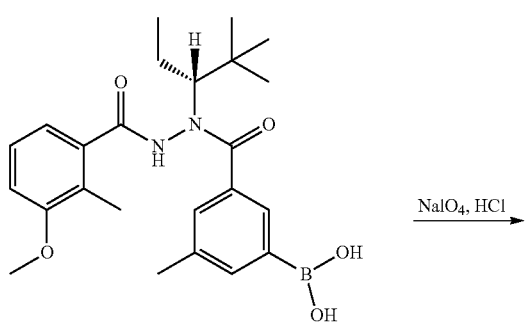

SKC-03-072

NaIO₄, HCl →

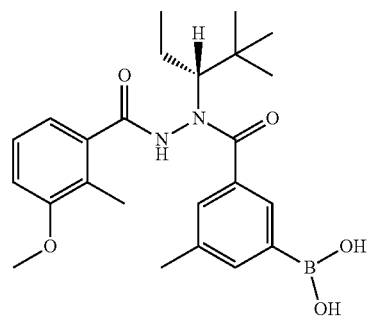

Cpd. No. 33

Step 1: Synthesis of 3-methyl-5-(4,4,5,5-tetramethyl-1,32-dioxaborolan-2-yl)benzoyl chloride

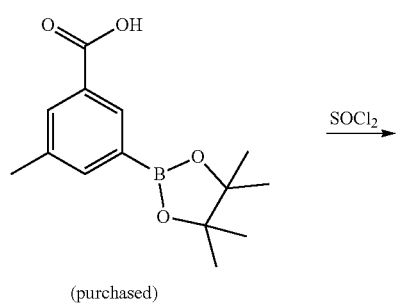

(purchased)

SOCl₂ →

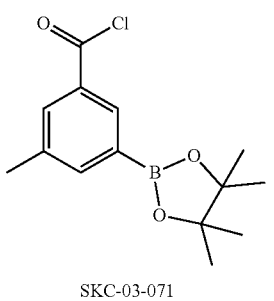

SKC-03-071

3-Methyl-5-(4,4,5,5-tetramethyl-[1,3,2]dioxaborolan-2-yl)-benzoic acid (700 mg, 2.67 mmol) was placed into 100 ml round bottom flask equipped with a stir bar, 3.0 ml of anhydrous chloroform was added to the flask followed by 2.0 ml of thionyl chloride and 1 drop of anhydrous DMF. The reaction mixture was stirred at 35° C. for 3 hours and then at room temperature overnight. LCMS of the sample after quenching a small amount with MeOH showed that no acid left. The solvent and excess thionyl chloride was removed under vacuum to give SKC-03-071. SKC-03-071 was used in the next step without further purification.

Step 2: Synthesis of (R)—N-2,2-dimethylpentan-3-yl)-3-methoxy-2-methyl-N'-(3-methyl-5-(4,4,5,5-tetramethyl-1,3,2-dioxaborolan-2-yl)benzoyl)benzohydrazide

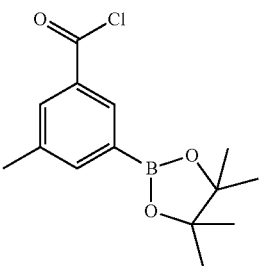

SKC-03-071

173
-continued

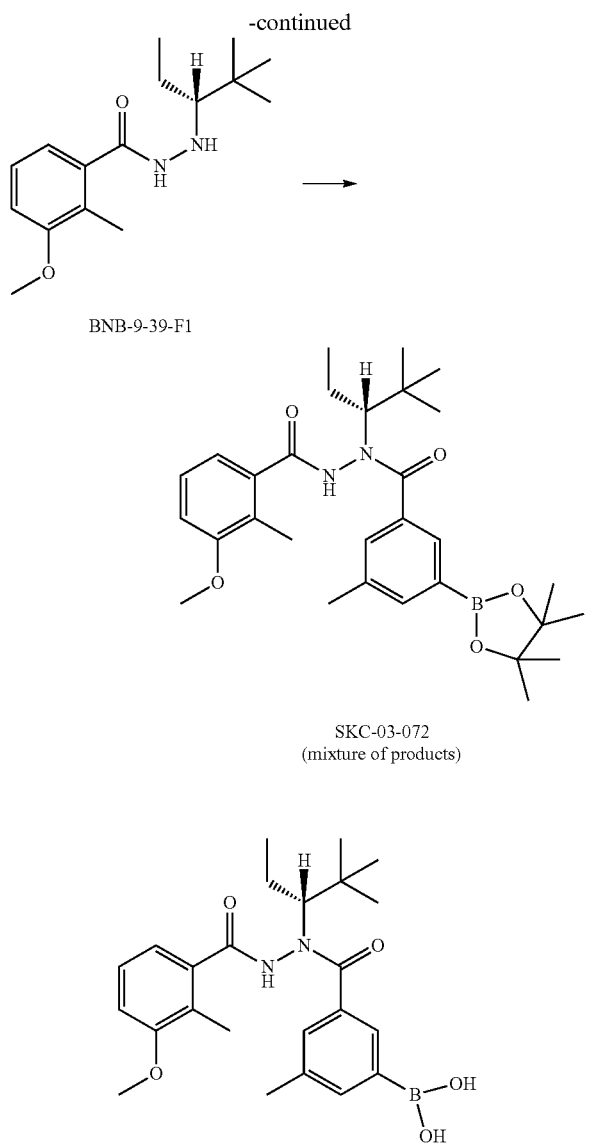

BNB-9-39-F1

SKC-03-072
(mixture of products)

The above acid chloride (SKC-03-071, 403 mg, 1.437 mmol) was dissolved in anhydrous DCM (2 ml) and was added to a stirred solution of previously synthesized (R)—N'-(2,2-dimethylpentan-3-yl)-3-methoxy-2-methylbenzohydrazide (400 mg, 1.437 mmol, >95% ee) in 3 ml of anhydrous DCM at room temperature under argon. Anhydrous triethylamine (0.200 ml, 1.437 mmol) was added and the reaction mixture was stirred at room temperature for 3 hours. LCMS showed a major peak with the expected product mass together with some other minor peaks. The crude mixture was adsorbed on neutral alumina and dried under vacuum. The dry powder was loaded on a cartridge and purified using an ISCO system (24 g neutral alumina column, hexane/EtOAc gradient). At ~15% EtOAc in hexane, the product eluted together with the hydrolysis product to give SKC-03-072 (270 mg) as a mixture. This was used as such for the next hydrolysis step.

Step 3: Synthesis of (R)-(3-(1-(2,2-dimethylpentan-3-yl)-2-(3-methoxy-2-methylbenzoyl)hydrazinecarbonyl)-5-methylphenyl)boronic acid (Cpd. No. 33)

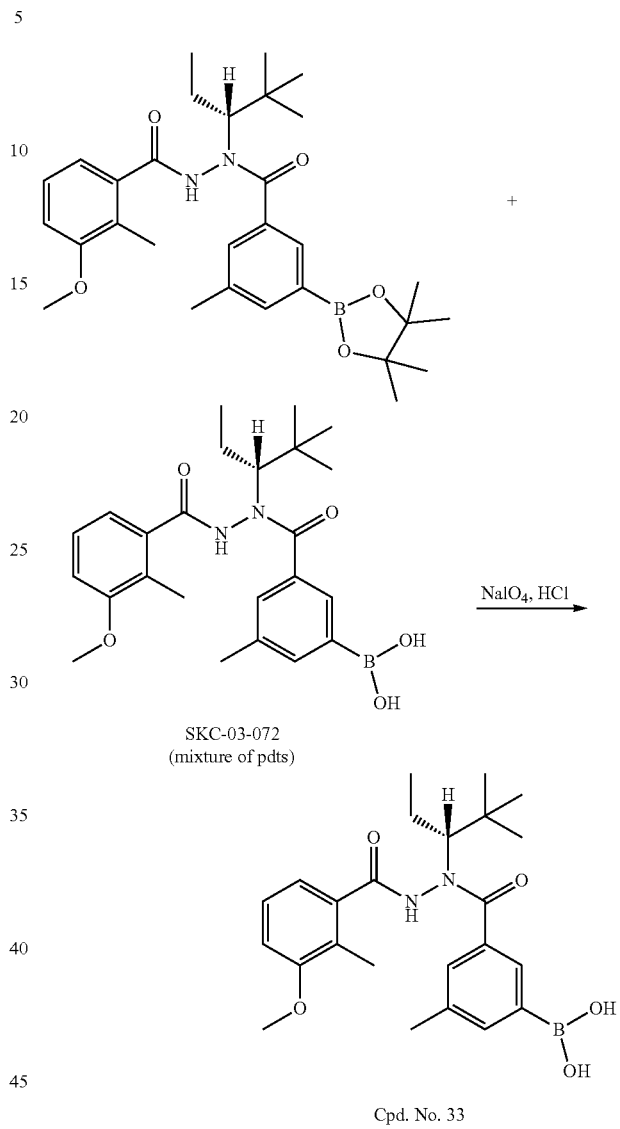

SKC-03-072
(mixture of pdts)

Cpd. No. 33

The above mixture, SKC-03-072 (270 mg, 0.517 mmol) was mixed with THF:H$_2$O mixture (4:1, 15 ml) and sodium periodate (221 mg, 1.034 mmol), and 2.0 M solution of HCl in THF (1.55 ml, 3.10 mmol) was added. The reaction mixture was stirred at room temperature for 2 hours. LCMS showed single peak with the expected mass of the boronic acid. The solvent was removed on a rotavapor under vacuum. After aqueous work up and extraction with EtOAc, the organic fractions were dried over anhydrous MgSO$_4$, filtered and concentrated. The crude product was purified using prep HPLC to give 32 mg (14%) of Cpd. No. 33. $^1$H NMR (400 MHz, DMSO-d$_6$) δ 10 51-987 (m, 1H), 799 (brs, 1H), 764 (dd, J=202, 11.7 Hz, 2H), 7.40-7.25 (m, 1H), 7.13-7.03 (m, 1H), 6.98-6.89 (m, 1H), 6.48-6.17 (m, 1H), 4.58-4.12 (m, 1H), 3.76-3.68 (m, 3H), 2.28 (d, J=6.5 Hz, 3H), 1.49 (d, J=31.9 Hz, 5H), 1.16-0.92 (m, 12H).

Using the method described above, (R)-(4-(2-(3,5-dimethylbenzoyl)-2-(2,2-dimethylhexan-3-yl)hydrazinecarbonyl)-3-fluorophenyl)boronic acid (Cpd. No. 13) was prepared from SKC-07-018:

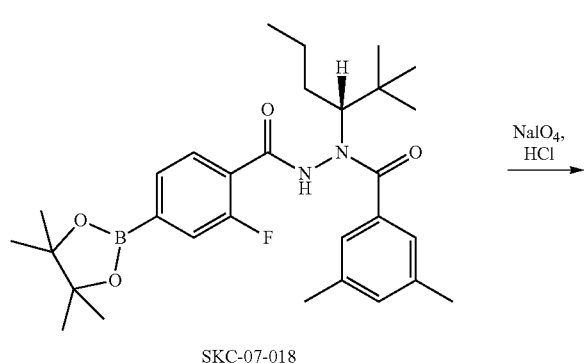

SKC-07-018

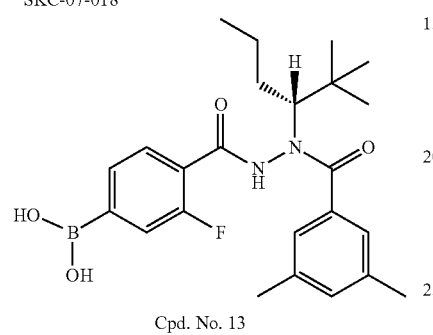

Cpd. No. 13

Cpd No. 13 LCMS [MH+]=443.

Potassium (R(4-(2-(3,5-dimethylbenzoyl-2 (2,2-dimethylhexan-3-yl)hydrazine-1-carbonyl)-3-fluorophenyl)trifluoroborate (Cpd. No. 93) was prepared from Cpd. No 13 as follows:

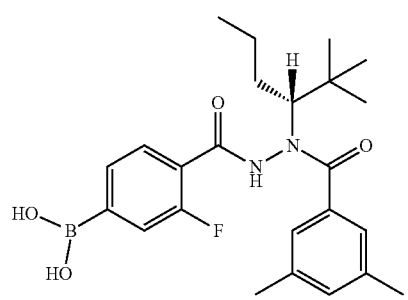

Cpd. No. 13 aqs KHF₂ →(MeOH)→

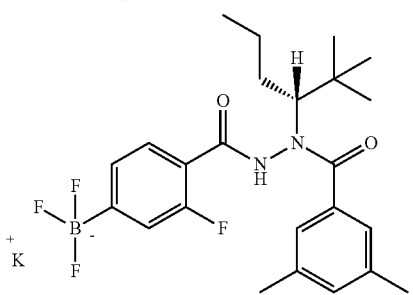

Cpd. No. 93

A solution of potassium hydrogen fluoride (1.81 ml, 5.43 mmol, 3.0 M in H₂O from Aldrich) was added to a stirring solution of Cpd. No. 13 (0.300 g, 0.68 mmol) at room temperature (*J. Org. Chem.* 77:6384-6393 (2012)). The colorless clear solution starts to precipitate slowly in 5 minutes and resulted in a thick white precipitate in 20 min. The mixture was stirred for 2.5 h at room temperature and then concentrated under reduced pressure to get a white solid. Acetone was added to the white solid and filtered through a filter funnel. The filtrate was concentrated under reduced pressure on a rotavapor until a small amount of precipitation was observed. Diethyl ether was added to the resulting white solid to encourage precipitation. The precipitate was collected by filtration, washed with ether and dried to get the white borate salt Cpd. No 93 (0.276 g, 81% yield) ¹H NMR (400 MHz, DMSO) δ 10.18 (d, J=56.9 Hz, 1H), 7.00-6.92 (m, 5H), 6.52 (dd, J=14.2, 7.1 Hz, 1H), 4.43 (dd, J=58.4, 8.6 Hz, 1H), 2.24 (s, 6H), 1.79-1.34 (m, 4H), 1.02 (d, J=3.2 Hz, 9H), 0.88 (dt, J=31.9, 6.9 Hz, 3H).

Using the method described above. (R)-(4-(2-(3,5-dimethylbenzoyl)-2-(2,2-dimethylhexan-3-yl)hydrazinecarbonyl)-2-fluorophenyl)boronic acid (Cpd. No. 22) was prepared from SKC-07-055A:

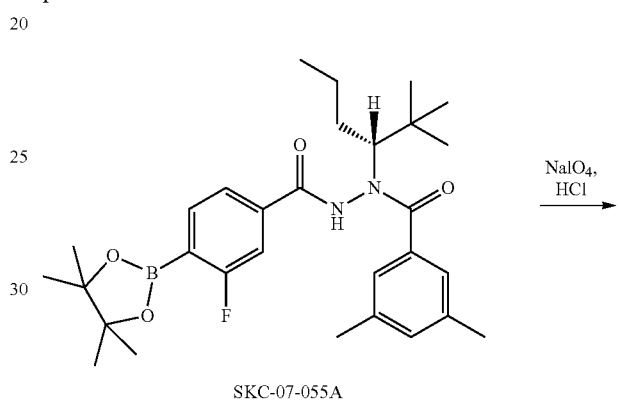

SKC-07-055A

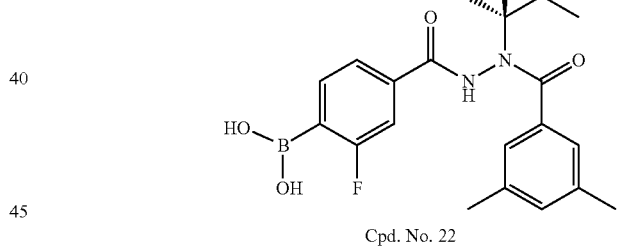

Cpd. No. 22

Cpd. No. 22 LCMS [MH+]=443.

Using the method described above, (4-(2-(tert-butyl)-2-(3,5-dimethylbenzoyl) hydrazinecarbonyl)-2-fluorophenyl)boronic acid (Cpd. No. 23) was prepared from SKC-07-055B:

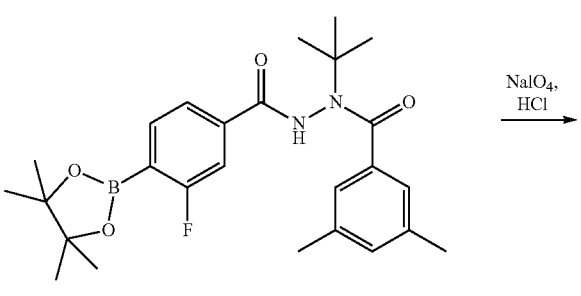

SKC-07-055B

-continued

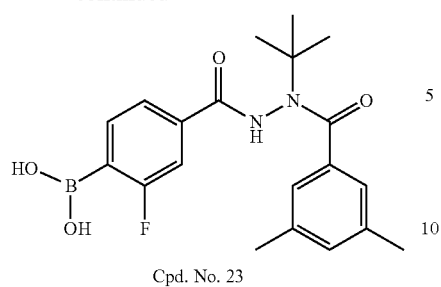

Cpd. No. 23

Using the method described above, (R)-(4-(2-(3,5-dimethylbenzoyl)-2-(2,2-dimethylhexan-3-yl)hydrazinecarbonyl)-3,5-difluorophenyl)boronic acid (Cpd. No. 24) was prepared from SKC-07-043A:

-continued

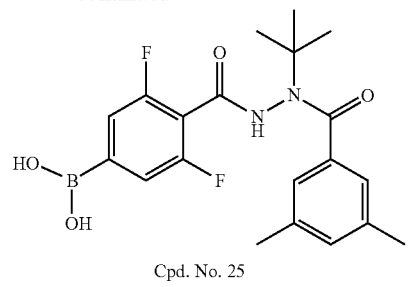

Cpd. No. 25

Example 9

Preparation of Synthetic Intermediates

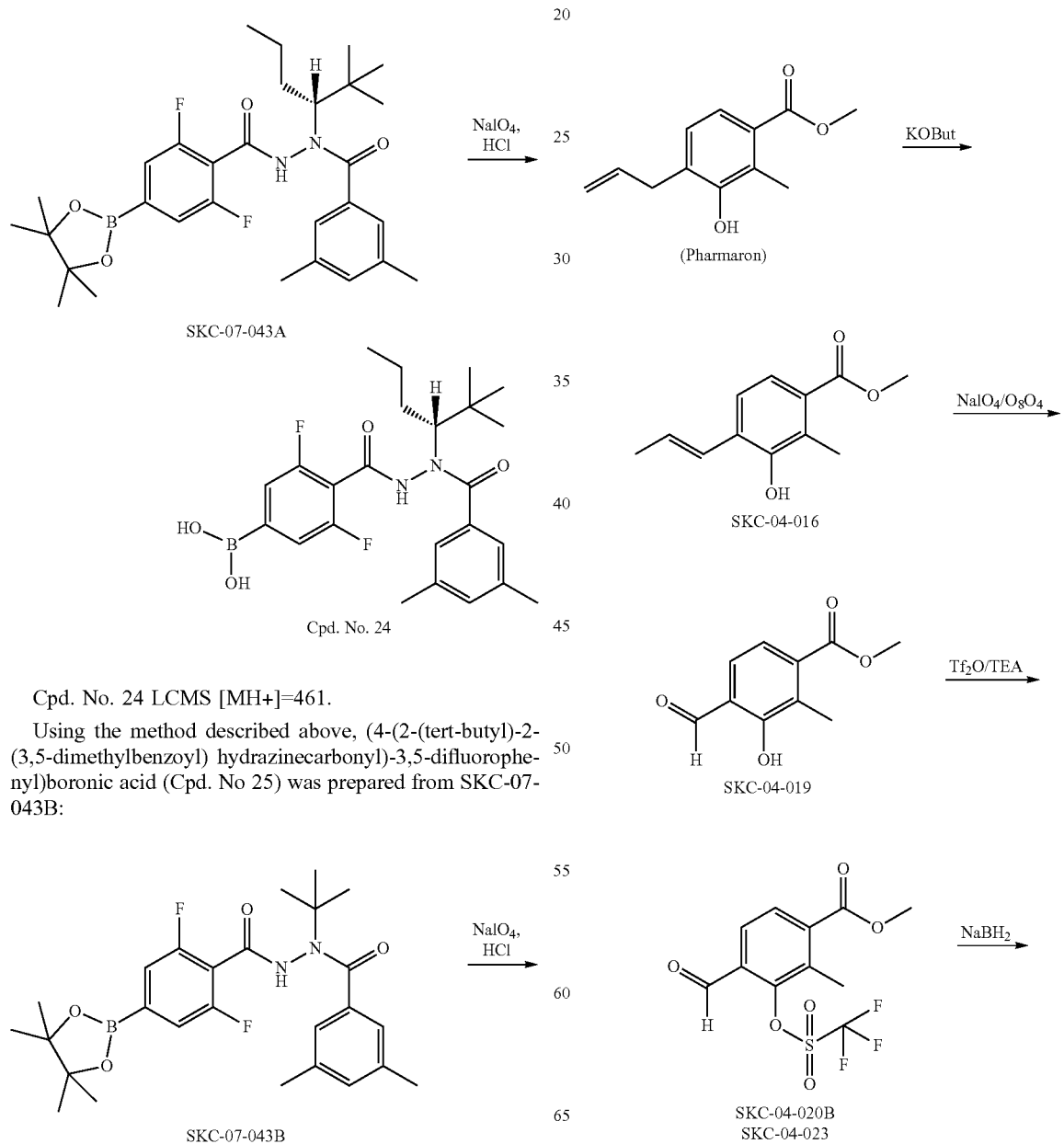

Cpd. No. 24 LCMS [MH+]=461.

Using the method described above, (4-(2-(tert-butyl)-2-(3,5-dimethylbenzoyl) hydrazinecarbonyl)-3,5-difluorophenyl)boronic acid (Cpd No 25) was prepared from SKC-07-043B:

Step 1: Synthesis of methyl 3-hydroxy-2-methyl-4-(prop-1-en-1yl)benzoate

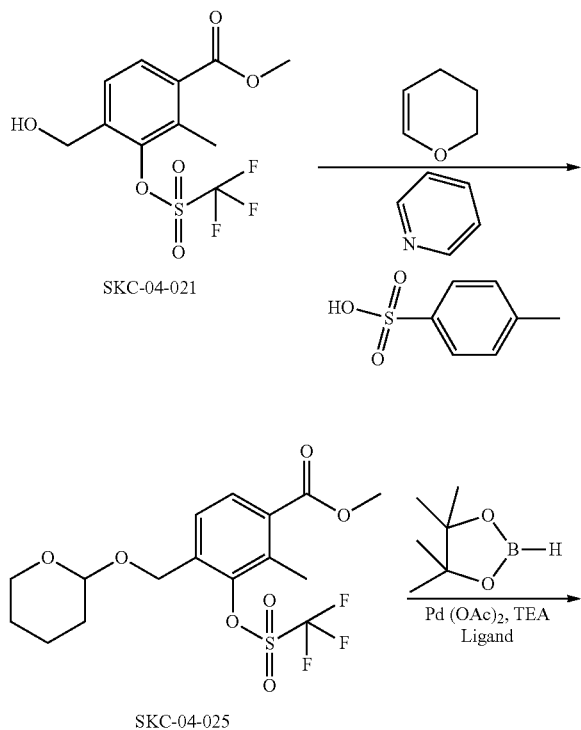

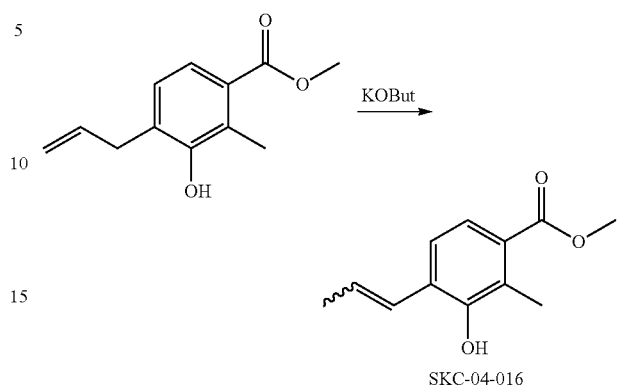

In a round bottom flask fitted with a dropping funnel was added methyl 4-allyl-3-hydroxy-2-methylbenzoate (4.12 g, 20 mmol) in anhydrous DMSO (20 ml) at room temperature under argon, t-BuOK in 1.0 M THF (5.61 g, 50 mmol) was added drop wise to the stirred solution. After the addition, the reaction mixture was heated at 55° C. overnight. The reaction was monitored using LCMS. After the reaction was complete, it is cooled, acidified with 1N HCl and stirred for 30 min. Aqueous work up and extraction with ethyl acetate gave the crude mixture which was purified using an ISCO system (40 g silica gel column, hexane/EtOAc solvent gradient) to give 4.12 g (77%) of the product. $^1$H NMR (400 MHz, CDCl$_3$) δ 7.42 (d, J=8.2 Hz, 1H), 7.18 (d, J=8.2 Hz, 1H), 6.61 (dd, J=15.9, 1.7 Hz, 1H), 6.37-6.13 (m, 1H), 3.90 (s, 3H), 2.50 (s, 3H), 1.96 (dd, J=6.6, 1.7 Hz, 3H).

Step 2: Synthesis of methyl 4-formyl-3-hydroxy-2-methylbenzoate

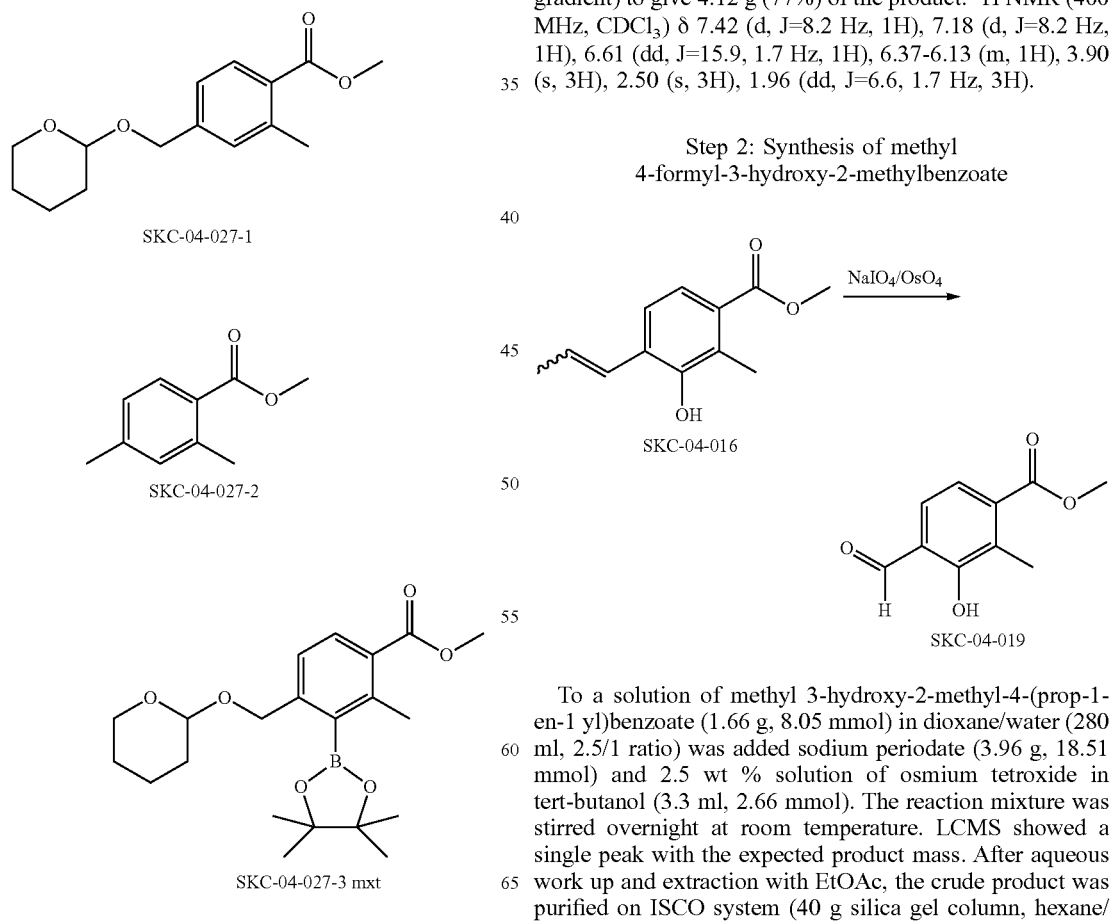

To a solution of methyl 3-hydroxy-2-methyl-4-(prop-1-en-1 yl)benzoate (1.66 g, 8.05 mmol) in dioxane/water (280 ml, 2.5/1 ratio) was added sodium periodate (3.96 g, 18.51 mmol) and 2.5 wt % solution of osmium tetroxide in tert-butanol (3.3 ml, 2.66 mmol). The reaction mixture was stirred overnight at room temperature. LCMS showed a single peak with the expected product mass. After aqueous work up and extraction with EtOAc, the crude product was purified on ISCO system (40 g silica gel column, hexane/EtOAc gradient) to get 1.2 g (77% yield) of the aldehyde. $^1$H NMR (400 MHz, CDCl₃) δ 11.39 (s, 1H), 9.93 (s, 1H), 7.45 (d, J=8.1 Hz, 1H), 7.38 (d, J=8.1 Hz, 1H), 3.93 (s, 3H), 2.44 (s, 3H).

Step 3: Synthesis of methyl 4-formyl-2-methyl-3-(((trifluoromethyl)sulfonyl) oxy)benzoate

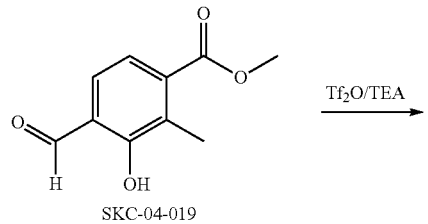
SKC-04-019

Tf₂O/TEA →

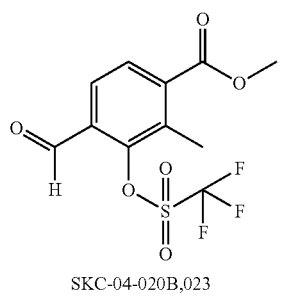
SKC-04-020B,023

To a stirred solution of methyl 4-formyl-3-hydroxy-2-methylbenzoate (1.1 g, 5.66 mmol) in anhydrous DCM (22 ml) at −78° C. under argon was added triflic anhydride (1.6 g, 5.66 mmol) drop wise followed by triethylamine (0.79 ml, 5.66 mmol). The reaction mixture was stirred overnight and allowed to warm to room temperature. The reaction mixture turned colorless to yellow during addition and then light brown overnight. LCMS overnight stirring showed single peak. After regular aqueous work up and extraction with DCM, the organic fractions were collected, dried over anhydrous MgSO₄, filtered and concentrated. The crude mixture was adsorbed on silica gel and dried. This was loaded on the cartridge and purified using an ISCO system (24 g silica gel column, hexane/EtOAc gradient). The product fractions were collected and dried under vacuum to give 1.58 g (85% of the final product). ¹H NMR (400 MHz, CDCl₃) δ 10.26 (s, 1H), 7.99 (d, J=8.1 Hz, 1H), 7.89 (d, J=8.1 Hz, 1H), 3.96 (s, 3H), 2.63 (s, 3H).

Step 4: Synthesis of methyl 4-(hydroxymethyl)-2-methyl-3-(((trifluoromethyl) sulfonyl)oxy)benzoate

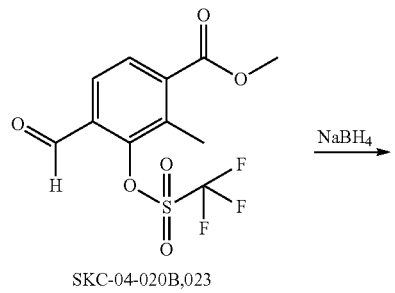
SKC-04-020B,023

NaBH₄ →

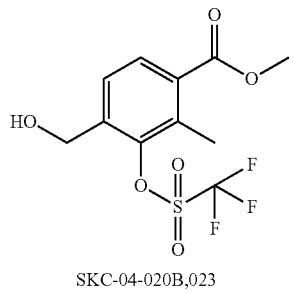
SKC-04-020B,023

To a stirred solution of the above compound (1.58 g, 4.84 mmol) in MeOH (10 ml) at ice temperature under argon was added sodiumborohydride (0.183 g, 4.84 mmol). LCMS after 2 hours showed a new main peak. The reaction was quenched by adding water (~2 ml). The MeOH was removed on a rotavapor. The reaction mixture was extracted with EtOAc, dried over anhydrous MgSO₄, filtered, concentrated, and purified using an ISCO system (24 g silica column, hexane-EtOAc gradient). The product fractions were collected to give 970 mg (61%) of the final alcohol ¹H NMR (400 MHz, CDCl₃) δ 7.93 (d, J=8.1 Hz, 1H), 7.56 (d, 1H), 4.84 (d. J=6.2 Hz, 2H), 3.92 (s, 3H), 2.59 (s, 3H), 2.14 (t, J=6.2 Hz, 1H).

Step 5: Synthesis of methyl 2-methyl-4-(((tetrahydro-2H-pyran-2-yl)oxy)methyl)-3-(((trifluoromethyl)sulfonyl)oxy)benzoate

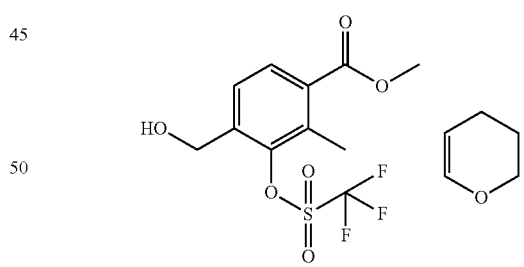
SKC-04-021, 024

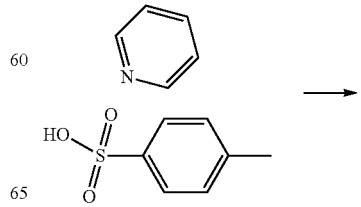
→

-continued

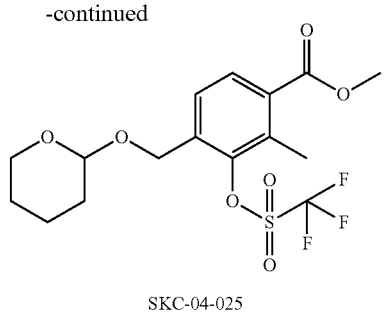

SKC-04-025

To a stirred solution of the above alcohol (970 mg, 2.95 mmol) in anhydrous DCM (35 ml) in a round bottom flask was added 3,4-dihydro-2H-pyran (2.48 g, 29.5 mmol) and pyridinium p-toluenesulfonate (371 mg, 1.47 mmol). The reaction mixture was stirred overnight at room temperature under argon. LCMS showed a single peak. After aqueous work up and extraction with DCM, the crude reaction mixture was purified using an ISCO system-silica gel column, (24 g, hexane/EtOAc gradient) to give 780 mg (64%) of the final product. $^1$H NMR (400 MHz, CDCl$_3$) δ 7.90 (d, J=8.1 Hz, 1H), 7.55 (d, J=8.2 Hz, 1H), 4.90 (d, J=13.9 Hz, 1H), 4.75-4.56 (m, 2H), 3.91 (s, 3H), 3.89-3.82 (m, 1H), 3.60-3.48 (m, 1H), 2.59 (s, 3H), 1.93-1.50 (m, 6H).

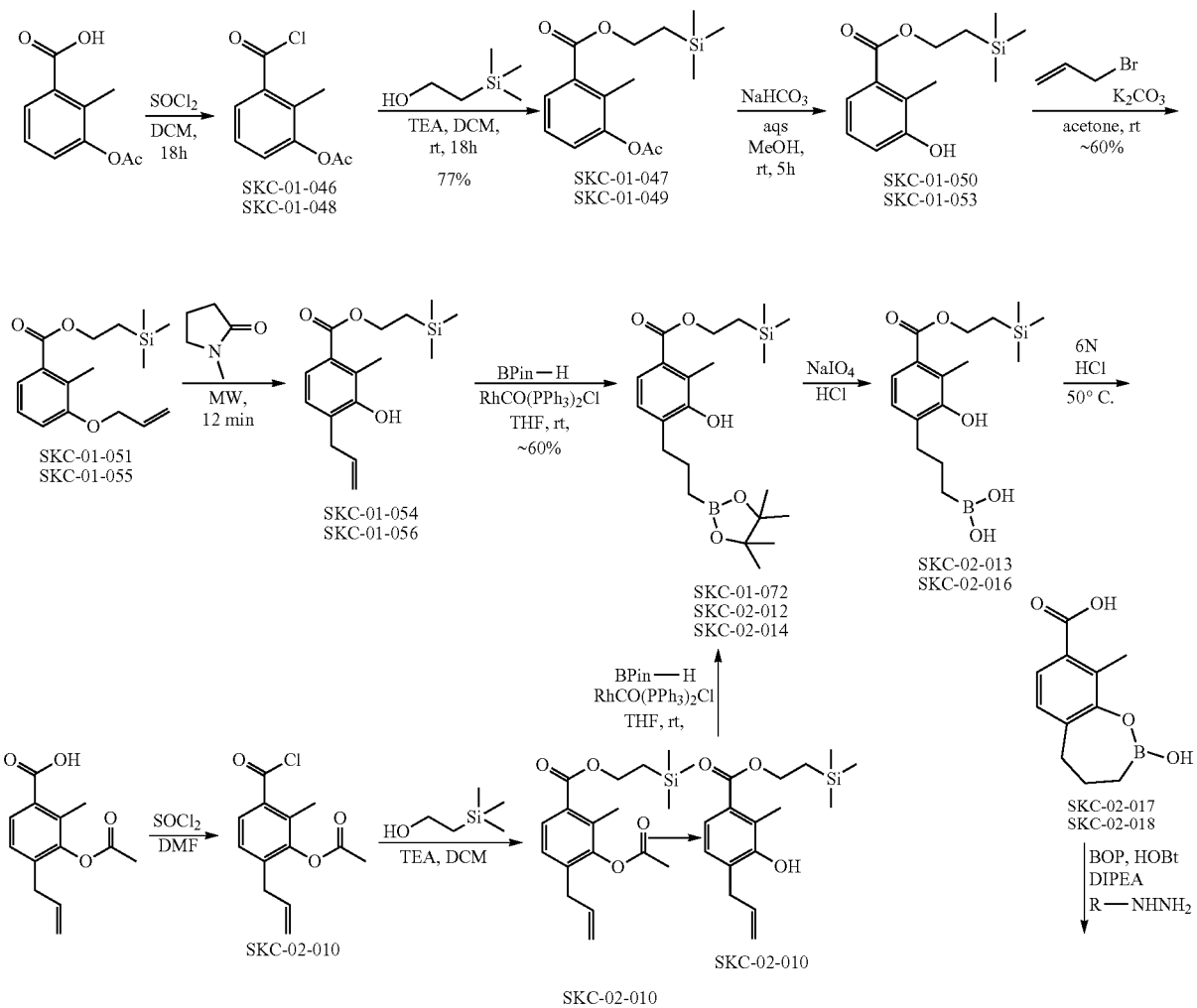

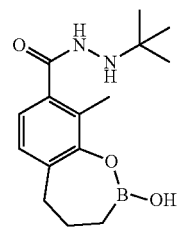

Step 1 Synthesis of 2-(trimethylsilyl)ethyl 3-acetoxy-2-methylbenzoate

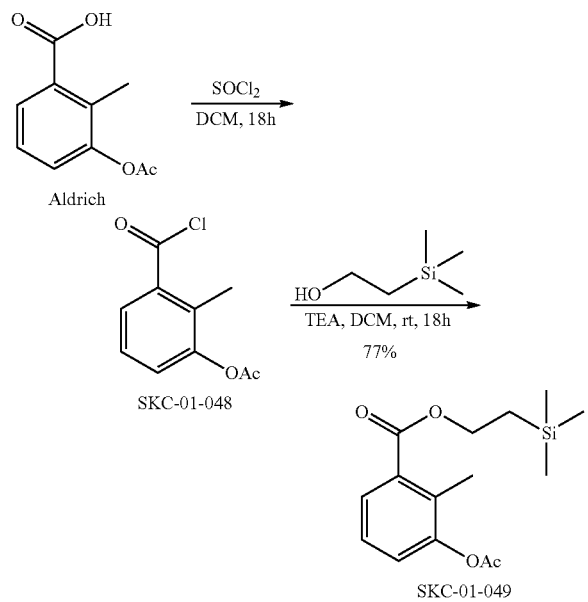

Aldrich

SKC-01-048

SKC-01-049

To a solution of the above benzoic acid (1554 g, 80.00 mmol) in anhydrous DCM (100 ml) in a 500 ml round bottom flask was added 10 ml of thionyl chloride and 1 drop of anhydrous DMF. The reaction mixture was stirred overnight at room temperature. The solvent and excess thionyl chloride were removed under vacuum to give the product SKC-01-048. SKC-01-048 was used without further purification in the next step.

To a stirred solution of the above acid chloride (13.61 g, 64.00 mmol) in anhydrous DCM (100 ml) in a 500 ml round bottom flask fitted with a drying tube was added the silyl alcohol (11.35 g, 96.00 mmol). To this mixture, triethylamine was added dropwise. The reaction mixture was stirred at room temperature for 4 hours. LCMS showed a new major peak. The reaction was allowed to stir at room temperature to 48 h. After aqueous work up and extraction with DCM, the organic fractions were dried over anhydrous MgSO$_4$, filtered, and concentrated. The crude mixture was purified using an ISCO system (120 g silica column, hexane/EtOAc gradient). The product eluted with 5% EtOAc in hexane to give 18.84 g (77%) of SKC-01-049. $^1$H NMR (400 MHz, CDCl$_3$) δ 7.71-7.57 (m, 1H), 7.25-6.98 (m, 2H), 4.37-4.23 (m, 2H), 2.31 (s, 3H), 2.26 (s, 3H), 1.09-1.00 (m, 2H), −0.00 (s, 9H).

Step 2: Synthesis of 2-(trimethylsilyl)ethyl 3-hydroxy-2-methylbenzoate

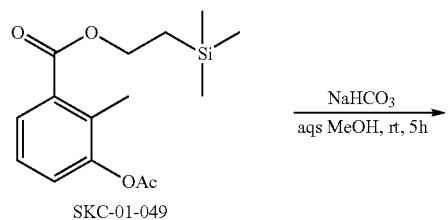

SKC-01-049

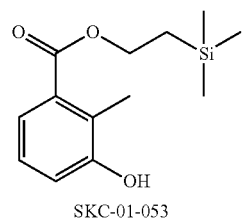

SKC-01-053

The above silyl ester (SKC-01-049, 14.43 g, 49.00 mmol) was mixed with MeOH:water (1:4, 100 ml) and sodium bicarbonate (20.57 g, 245.00 mmol) and stirred at room temperature overnight. LCMS showed a single peak. The methanol was removed and the reaction mixture was extracted with DCM. The organic fractions were collected, dried over anhydrous MgSO$_4$, filtered, and concentrated. The crude mixture was purified using an ISCO system (120 g silica column, hexane/EtOAc gradient) to give 12.0 (99%) of SKC-01-053. $^1$H NMR (400 MHz, CDCl$_3$) δ 7.56 (dd, J=7.8, 1.1 IHz, 1H), 7.26 (t, J=7.9 Iz, 1H), 7.11 (dd, J=8.0, 0.9 Hz, 1H), 5.47 (s, 1H), 4.61-4.53 (m, 2H), 2.63 (s, 3H), 1.38-1.18 (m, 2H), 0.25 (s, 9H).

Step 3: Synthesis of 2-(trimethylsilyl)ethyl 3-(allyloxy)-2-methylbenzoate

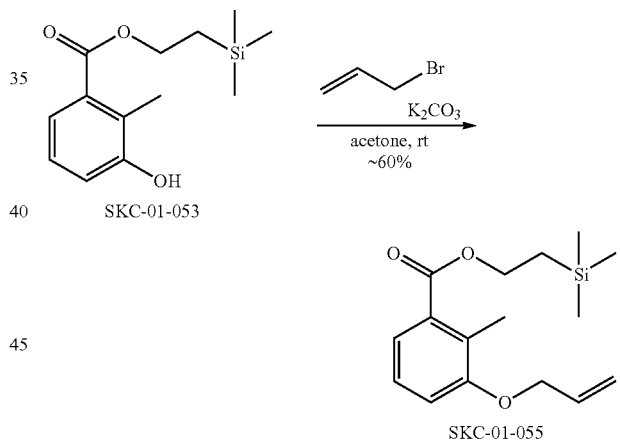

To a stirred solution of the silyl ester (SKC-01-053, 290 mg, 1.15 mmol) in anhydrous acetone (20 ml) in a 100 ml round bottom flask was added anhydrous potassium carbonate (318 mg, 2.30 mmol) followed by allyl bromide (0.15 ml, 1.73 mmol). The reaction mixture was stirred at room temperature overnight. LCMS showed a single peak with the expected product mass. The solvent was removed on a rotavapor and the reaction mixture was extracted with DCM. The crude product was purified using an ISCO system (12 g silica column, hexane/EtOAc gradient). The product eluted with −5% EtOAc in hexane to give 180 mg (54%) of the product SKC-01-055. $^1$H NMR (400 MHz, CDCl$_3$) δ 7.31 (dd, J=7.8, 0.9 Hz, 1H), 7.08 (t, J=8.0 Hz, 1H), 6.88 (d, J=8.0 Hz, 1H), 6.08-5.88 (m, 1H), 5.40-5.29 (m, 1H), 5.26-5.15 (m, 1H), 4.50-4.41 (m, 2H), 4.35-4.24 (m, 2H), 2.38 (s, 3H), 1.10-0.99 (m, 2H), −0.00 (s, 9H).

Step 4: Synthesis of 2-(trimethylsilyl)ethyl 4-allyl-3-hydroxy-2-methylbenzoate

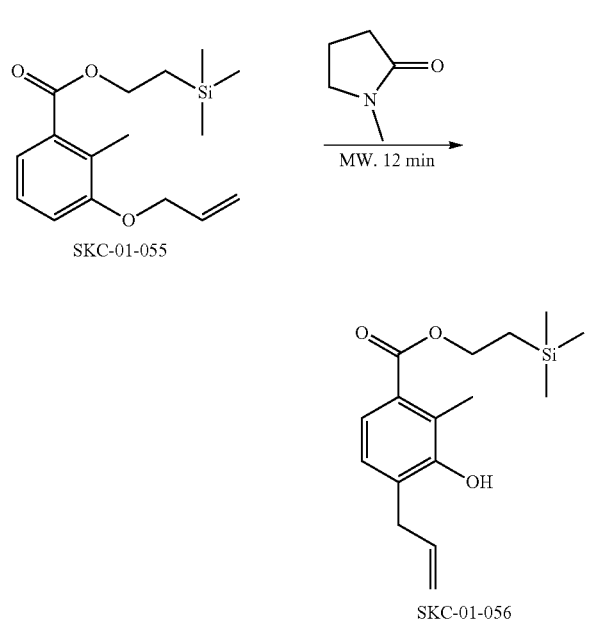

SKC-01-055

SKC-01-056

2-(Trimethylsilyl)ethyl 3-(allyloxy)-2-methylbenzoate (500 mg, 1.70 mmol) was dissolved in 1-methyl pyrrolidine-2-one (1 ml) in a microwave vial, closed with a cap and subjected to microwave irradiation (CEM discover) with stirring at 220° C. maximum pressure 300 psi, run time 5 min, hold time 15 min. LCMS showed 3 peaks including a major peak with the expected product mass. After cooling, the crude mixture was directly loaded on a silica gel column (12 g) and purified using an ISCO system (hexane:EtOAc solvent mixture, product eluted ~5% EtOAc in hexane) to give SKC-01-056. The above experiment was repeated several times in 1-2 g scale Total wt of the product isolated was 3.6 g.

Step 5: Synthesis of 2-(trimethylsilyl)ethyl-3-hydroxy-2-methyl-4-(3-(4,4,5,5-tetramethyl-1,3,2-dioxaborolan-2-yl)propyl)benzoate

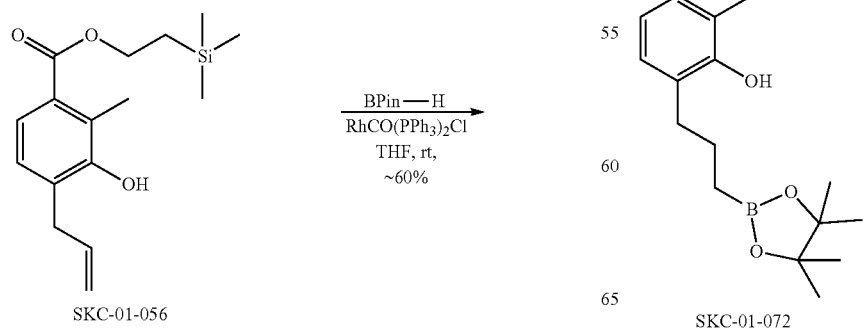

SKC-01-056

SKC-01-072

An oven dried, 100 ml, two necked, round bottom flask was equipped with a teflon coated magnetic stir bar, and two rubber septum with of the septum with a needle connected to an argon/vacuum manifold. This argon flushed round bottom flask was charged with 2-(trimethylsilyl)ethyl 4-allyl-3-hydroxy-2-methylbenzoate (1.2 g, 4.10 mmol), modified Wilkinson's catalyst (129 mg, 0.129 mmol) and anhydrous THF (13 ml). Three vacuum/argon purge cycles were performed, and the mixture was stirred at room temperature until all of the reagents dissolved (<2 min). To this stirred clear reaction mixture was added 4,4,5,5-tetramethyl-1,3,2-dioxaborolane (Bpin-H) (1.790 ml, 12.31 mmol) via syringe followed by another argon/vacuum/argon purge. After stirring overnight, LCMS showed complete conversion to the product. The reaction mixture was quenched by carefully adding few drops of water (<1 ml) and MeOH (5 ml) and the solvent was removed under vacuum on a rotavapor. The dry crude product was dissolved in DCM, adsorbed on silica and dried under vacuum. Once it was free flowing, it was loaded on an empty cartridge and purified using an ISCO system (40 g silica column, hexane/EtOAc gradient). The product eluted with ~5% EtOAc in hexane to give SKC-02-014 (1.32 g, 77% yield). $^1$H NMR (400 MHz, CDCl$_3$) δ 7.32 (d, 1H), 6.95 (d, J=7.9 Hz, 1H), 6.60 (s, 1H), 4.48-4.30 (m, 2H), 2.69-2.54 (m, 2H), 2.50 (s, 3H), 1.76-1.60 (m, 2H), 1.33 (s, 12H), 1.19-1.07 (m, 2H), 1.05-0.83 (m, 2H), 0.14-0.04 (m, 8H).

Step 6: Synthesis of (3-(2-hydroxy-3-methyl-4-((2-(trimethylsilyl)ethoxy)carbonyl) phenyl)propyl)boronic acid

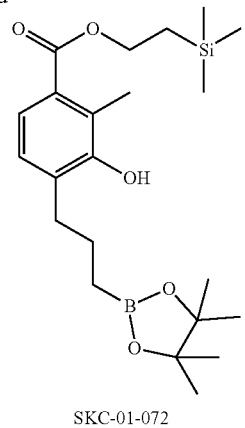

SKC-01-072

Step 7: Synthesis of 2-hydroxy-9-methyl-2,3,4,5-tetrahydrobenzo[f][1,2]oxaborepine-8-carboxylic acid

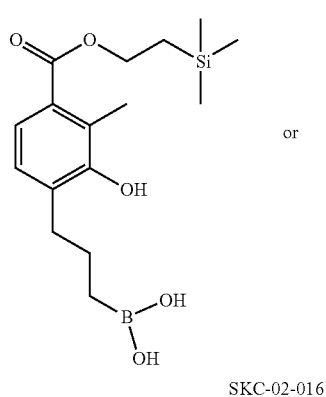

SKC-02-016

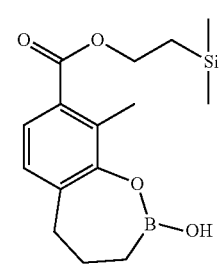

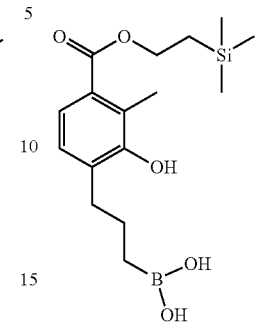

SKC-02-016

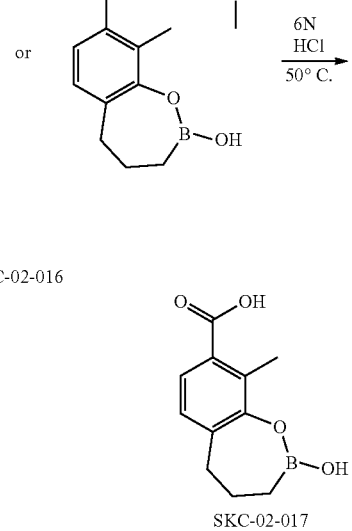

SKC-02-017

To a solution of SKC-02-014 (1.32 g, 3.14 mmol) in a THF/water mixture (4:1 ratio, 90 ml) was added sodium periodate (4.03 g, 18.84 mmol) and then 2M HCl in ether (3.14 ml, 6.28 mmol). The reaction mixture was stirred at room temperature overnight. The reaction mixture was diluted with water and extracted with EtOAc. The crude reaction mixture was adsorbed on silica gel and dried. Once it was free flowing, it was loaded on ISCO cartridge (40 g silica column, hexane/EtOAc solvent mixture). The product eluted with ~32% EtOAc in hexane to give 700 mg (66%) of SKC-02-016. The most preferred structure is the closed form based on $^1$H NMR. $^1$H NMR (400 MHz, CDCl$_3$) δ 7.50 (d, J=7.9 Hz, 1H), 7.00 (d, J=7.9 Hz, 1H), 4.44-4.31 (m, 2H), 2.74-2.59 (m, 2H), 2.46 (s, 3H), 2.01-1.82 (m, 2H), 1.21-1.05 (m, 2H), 1.00-0.75 (m, 2H), 0.08 (s, 9H).

SKC-02-16 (150 mg, 0.443 mmol) was dissolved in anhydrous toluene in a round bottom flask fitted with a dropping funnel containing some 5A molecular sieves and a condenser under argon. To this p-toluene sulfonic acid mono hydrate (56.2 mg, 0.296) was added. The reaction mixture was refluxed for 1 h and cooled. LCMS showed complete conversion. The toluene was removed under vacuum and the crude product adsorbed on silica gel and purified on an ISCO system (using 4 g silica column and hexane/EtOAc solvent gradient). The product eluted with 30% EtOAc in hexane to give the product. $^1$H NMR (400 MHz, Acetone) 6.7.57 (d, J=7.9 Hz, 1H), 7.09 (d, J=7.9 Hz, 1H), 2.69 (t, =6.8 Hz, 2H), 2.46 (s, 3H), 1.95-1.83 (m, 2H), 0.85-0.71 (m, 2H).

Example 10

Synthesis of IXS-1-54-1

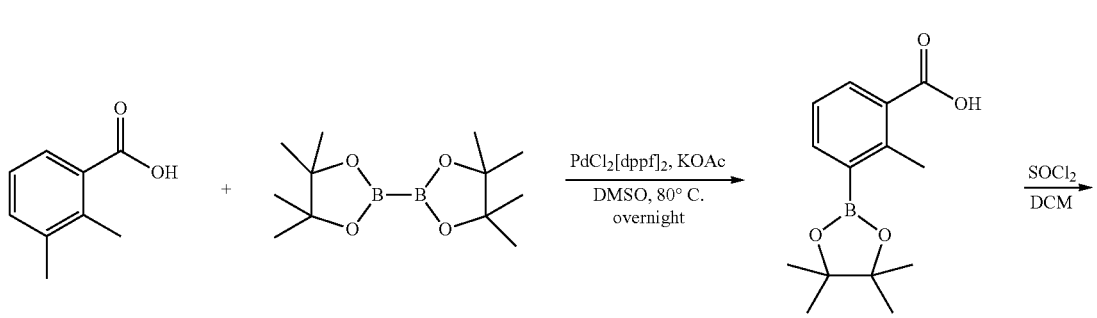

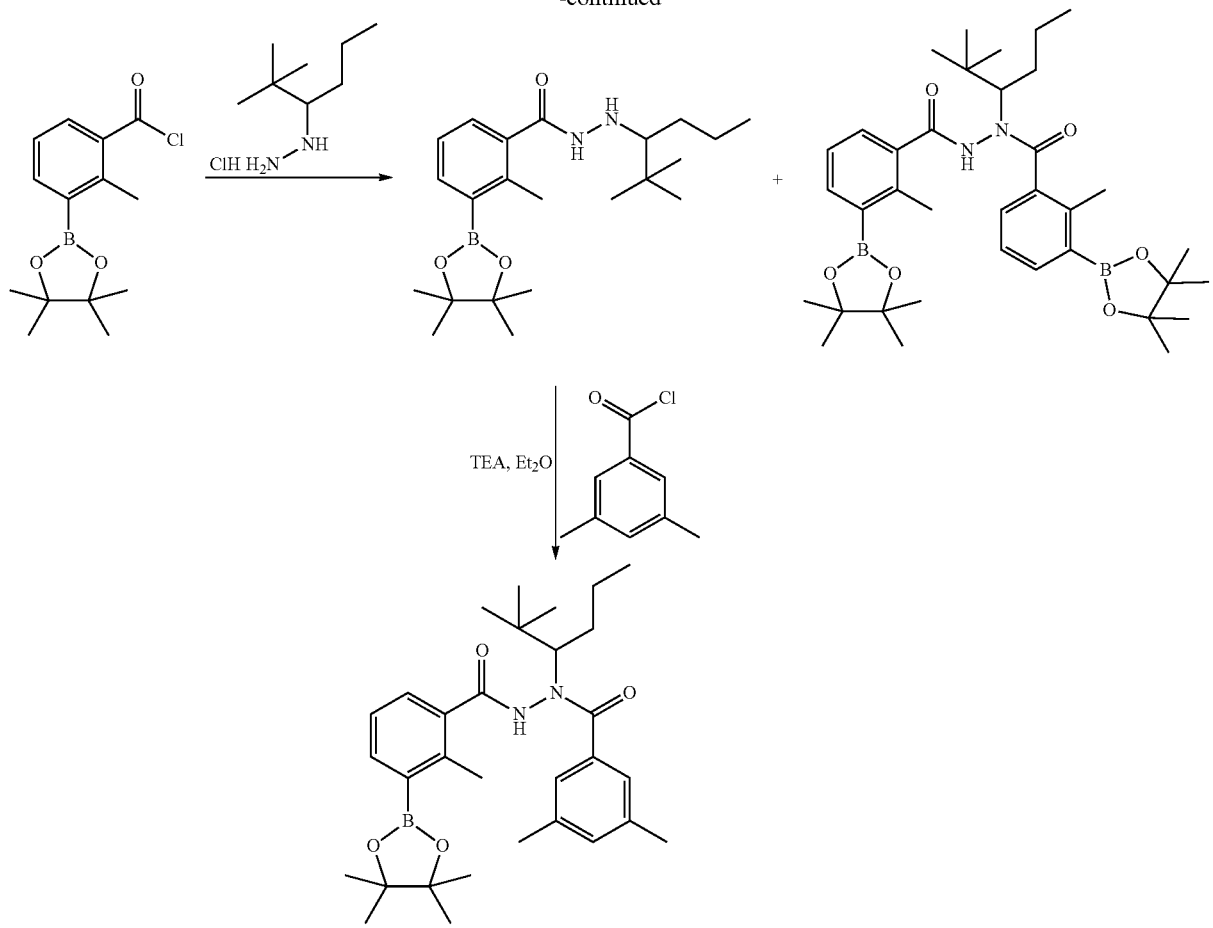

Step 1: 2-Methyl-3-(4,4,5,5-tetramethyl-[1,3,2]di-oxaborolan-2-yl)-benzoic acid

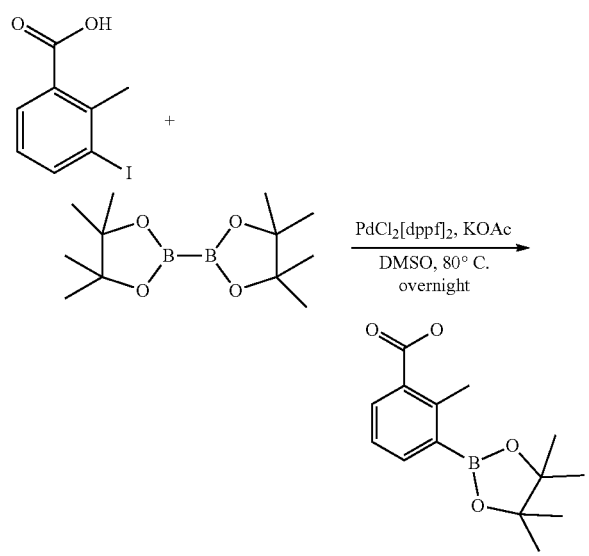

IXS-1-18-1

To a 300 ml round bottom three neck flask equipped with condenser, magnetic stirrer and an inert-gas outlet, were added 3-iodo-2-Methyl-Benzoic acid (10 g, 38.2 mmol), Bis(pinacolato)diboron (11.64 g, 46.0 mmol), potassium acetate (11.23 g, 112.0 mmol) and 100 ml of anhydrous DMSO. The flask was purged with nitrogen for 15-20 min. The catalyst dichloro[1,1'-bis(diphenylphosphino)ferrocene]palladium dichloromethane (0.85 g, 1.1 mmol) was added through an open neck under slight positive nitrogen flow. The reaction mixture was stirred at 80° C. overnight. The reaction mixture was allowed to cool then poured into 500 ml of water. After 1 hour of stirring at room temperature, a brownish precipitant was filtered onto flitted filter funnel and washed with water. The precipitant was redissolved in 200 ml of ether and filtered through a 1" thick layer of celite to remove traces of Pd. The filter cake was washed with 100 ml ether. The combined etherial solution was washed with 4×200 ml of 2N NaOH. The water phases were combined and acidified with 6N HCl until pH=5-6 (approx 100 ml). A white precipitant was filtered onto fritted filter, washed with 200 mil of water, and dried in a vacuum oven at 60° C. for 2 hours. The filtrate was placed into fridge for overnight, and a second crop of white precipitant was isolated via filtration. Overall amount of product obtained was 5.5 g (55% yield).
$^1$H NMR (CDCl$_3$, 300 MHz) δ 8.05 (d, 1H), 7.9 (d, 1H), 7.25 (t, 1H), 2.6 (s, 3H), 1.4 (s, 12H).

Step 2: 2-Methyl-3-(4,4,5,5-tetramethyl-[0.3.2]dioxaborolan-2-yl)-benzoyl chloride

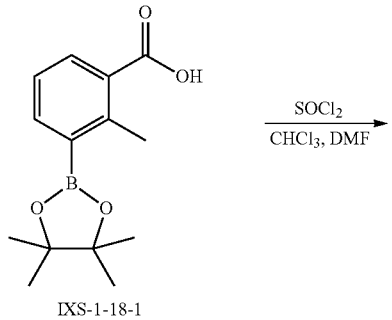

IXS-1-18-1

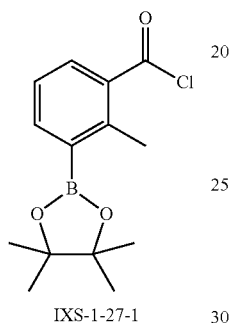

IXS-1-27-1

2-Methyl-3-(4,4,5,5-tetramethyl-[1,3,2]dioxaborolan-2-yl)-benzoic acid (1.2 g, 46.0 mmol) was placed into 40 ml scintillation vial equipped with a small stir bar, 10.0 ml of anhydrous chloroform was added following by 1.8 ml of thionyl chloride and 2 drops of anhydrous DMF. After 3 hours, the solvent and excess thionyl chloride were evaporated under vacuum. The brown residue was treated with 40 ml of hexane, filtered, and concentrated to give 985 mg (Yield=70.5%) of the product as a greenish oil. $^1$H NMR (CDCl$_3$, 400 MHz) δ 8.15 (d, 1H), 7.95 (d, 1H), 7.3 (t, 1H), 2.75 (s, 3H), 1.4 (s, 12H). The reaction was run several times and the yield was ranging from 60 to 99%.

Step 2: 3-Methoxy-2-methyl-benzoic acid N'-(1-ethyl-2,2-dimethyl-propyl)-hydrazide

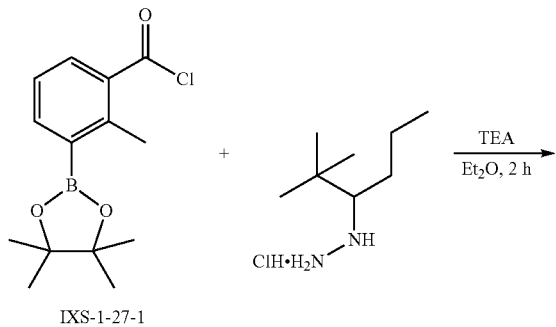

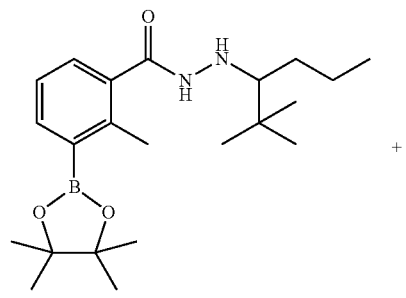

IXS-1-52-2-major compound

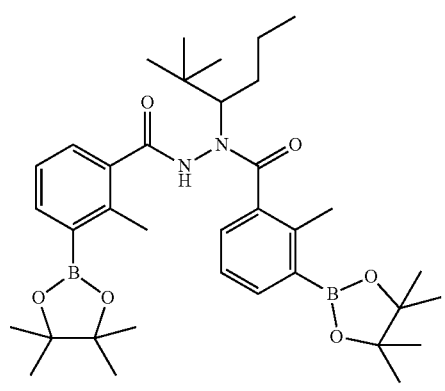

IXS-1-52-1-minor compound

The reaction was carried out in a 20 ml scintillation vial with a mini-stir bar. To a stirred suspension of 2,2-di-me-pentylhydrazine chloride (0.181 g, 1.0 mol) in anhydrous ether (10 ml) at room temperature was added 2-methyl-3-(4,4,5,5-tetramethyl-[1,3,2]dioxaborolan-2-yl)-benzoyl chloride (0.281 g, 0.1 mmol) and excess of triethylamine (0.28 ml, 20 mmol). A precipitate formed right away. The reaction mixture was stirred at room temperature for 2 hours, and the precipitate was filtered off and washed with methylene chloride (20 ml). The solvent was evaporated and the residue was redissolved in 20 ml of pentane with a few drops of ether. The flask was cooled for 2 hours to give a precipitant that was filtered and dried under vacuum for 1 hour. W$_1$=0.05 g. $^1$H NMR and MS showed to this to IXS-1-52-1. The filtrate was evaporated, redissolved in 1 ml of methylene chloride and purified on a 24 g ISCO column with a hexane/ethyl acetate gradient. The product fractions were combined, to give 0.110 g (yield=44%) of IXS-1-52-2. $^1$H NMR (CDCl$_3$, 400 MHz) δ 7.85 (d, 1H), 7.4 (d, 1H), 7.25 (t, 1H), 7.05 (s, 1H), 4.9 (m, 1H), 2.65 (s, 3H), 2.05 (d, 1H), 1.8 (m, 1H), 1.6 (m, 2H), 1.4 (s, 12H), 1.35 (s, 3H), 1.15 (m, 1H), 1.05 (s, 9H). MS: [MH+]=389 mv.

Step 3: 2-Methyl-3-(4,4,5,5-tetramethyl-[1,3,2]dioxaborolan-2-yl)-benzoic acid N'-(1-tert-butyl-butyl)-hydrazide

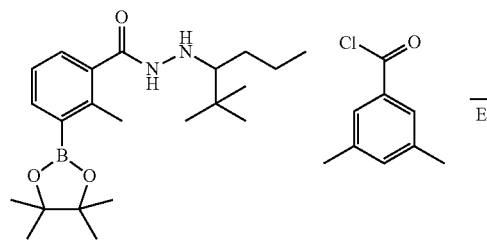

IXS-1-44-1

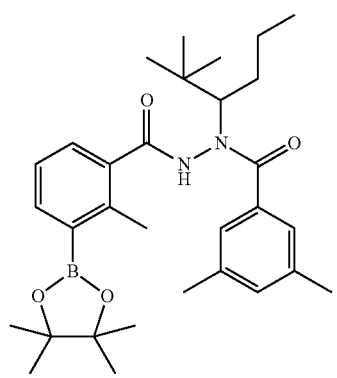

IXS-1-54-1

The reaction was carried out in a 20 ml scintillation vial with a mini-stir bar. To a stirred suspension of 2-methyl-3-(4,4,5,5-tetramethyl-[1,3,2]dioxaborolan-2-yl)-benzoic acid N'-(1-tert-butyl-butyl)-hydrazide (IXS-1-44-1, 0.194 g, 0.5 mmol) in ether (5 ml) was added 3,5-dimethyl-benzoyl chloride (0.084 g, 0.0005 mol) followed by triethylamine (0.07 ml, 0.5 mmol). A precipitate formed right away. The reaction mixture was stirred at room temperature for 2 hours then the precipitate was filtered off and washed with some ether (10-20 ml). TLC of ether solution in 50:50=hexane: ethyl acetate shows that the major spot is a mono-substituted product with Rf=0.6. The solvent was evaporated till almost dryness and redissolved in 20 ml of hexane. A precipitate formed, and it was washed with cold hexane and dried in vacuum for 2 hours to give 0.177 g of IXS-1-54-1 (Yield=68%). The structure was confirmed by $^1$H NMR (CDCl$_3$, 400 MHz) and MS: ([MH+]=521 mv).

Example 11

Synthesis of Cpd. No. 58

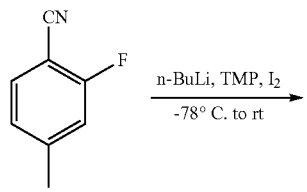

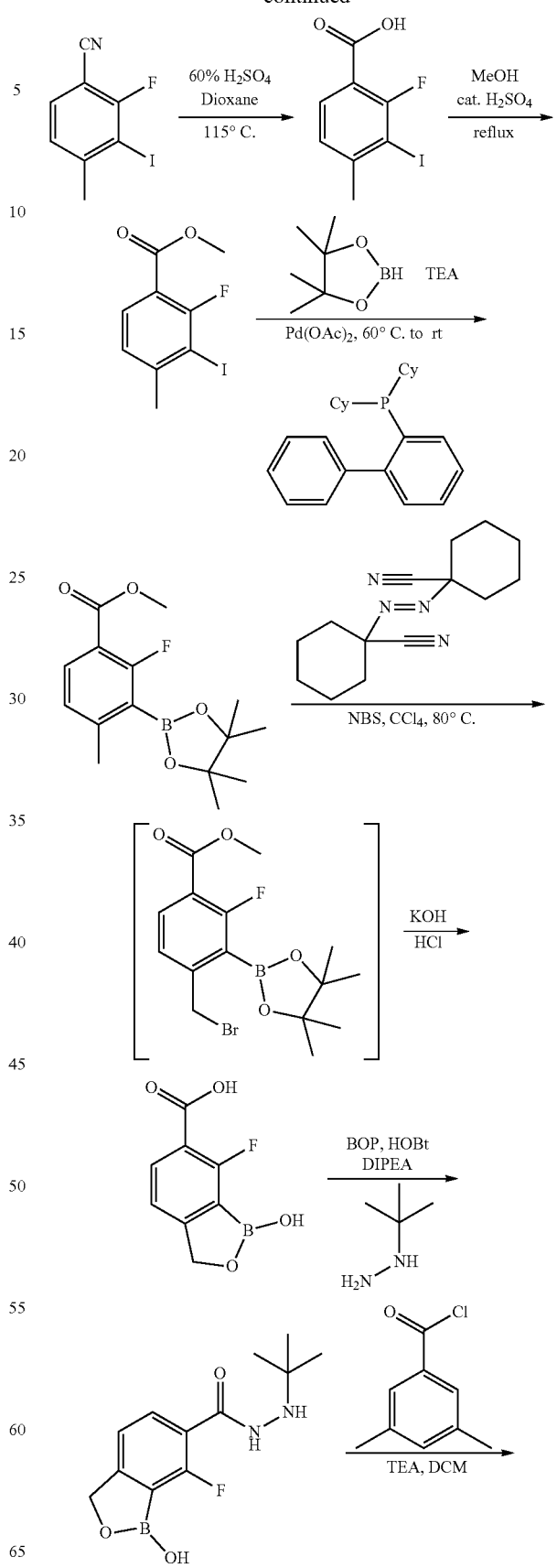

-continued

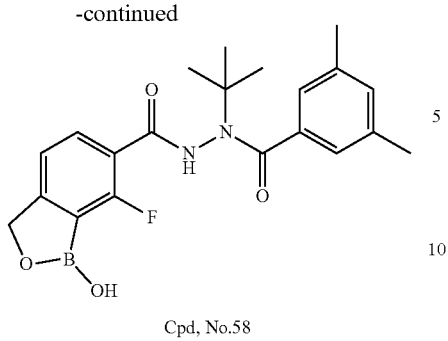

Cpd, No.58

Step 1: Synthesis of 2-Fluoro-3-iodo-4-methyl-benzonitrile

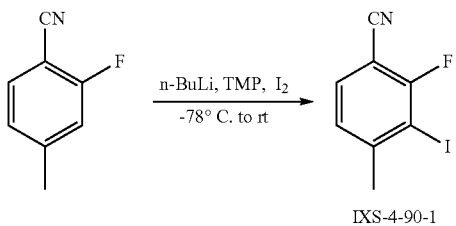

IXS-4-90-1

An oven-dried, 3-necked 500 ml round bottom flask with magnetic stirrer, thermometer, addition funnel, and nitrogen inlet was purged with $N_2$ for 20 min. 2,2,6,6-tetramethylpiperidine (41.84 ml, 241 mmol) was introduced into flask via syringe, followed by 100 ml of anhydrous THF. The reaction mixture was cooled to −78° C., and n-BuLi (2.5M solution in hexane, 102 ml, 254 mmol) was introduced via cannula. The addition was done slowly, drop-wise, making sure that temperature stayed in the −70° C. to −80° C. range. (~40 min). The addition flask was washed with 100 ml of anhydrous THF and the reaction mixture warmed to −50° C. for 30 min. during which time the clear solution became turbid. The reaction mixture was cooled to −78° C. again and 2-fluoro-4-methylbenzonitrile (30 g, 222 mmol) dissolved in 80 ml of anhydrous THF was added drop wise to the stirred solution while the internal temperature was maintained below −70° C. (approx 20 min). The addition funnel was washed once with 100 ml portion of THF and the reaction mixture was warmed up to −50° C. for 60 min. The reaction mixture was cooled again to −78° C. and a saturated solution of iodine (62 g, 244 mmol) in 100 ml of THF was introduced into the addition funnel. The quench was done stepwise, and the resulting yellow mixture was kept at an internal temperature below −60° C. (approx 20 min). The addition funnel was washed twice with 50 mil of THF and then the mixture was allowed to warm-up to room temperature. After stirring overnight, the entire mixture was added to a solution of 20 g thiosulfate in 1000 ml of water, stirred for 1 hour, and washed with ethyl acetate 3×250 ml. The combined organic layers were dried over magnesium sulfate, filtered and concentrated. The residue was purified using an ISCO system. The product fractions were combined and concentrated. The product was re-crystallized from ether/hexane to give 33 g (57%) of the product. $^1$H NMR (CDCl$_3$, 400 MHz) δ 7.50 (dd, 1H), 7.16 (d, 1H), 2.50 (s, 3H). LC-MS (M+1)=262 M/Z.

Step 2: Synthesis of 2-Fluoro-3-Iodo-4-Methyl benzoic acid

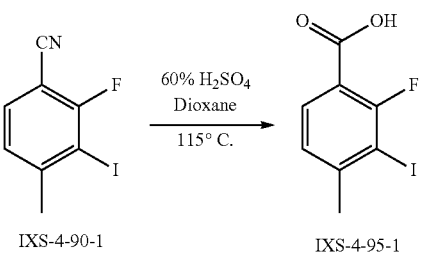

IXS-4-90-1                IXS-4-95-1

To a 500 ml round bottom, three neck flask equipped with a condenser and magnetic stirrer, was added 2-fluoro-3-iodo-4-methyl-benzonitrile (33 g, 126.4 mmol), 70 ml of methanol, and 70 ml of 60% aqueous sulfuric acid. The flask was sealed and temperature was raised to 115° C. The reaction mixture was stirred at this temperature overnight. The precipitate that formed was filtered onto fritted filter, washed with IL of water, and dried under vacuum for 2 h and then in vacuum oven at 60° C. for 3 h to give 31.5 g of IXS-4-95-1. $^1$H NMR (DMSO-d$_6$, 400 MHz) δ 13.2 (broad s, 1H), 7.74 (t, 1H), 7.26 (d, 1H), 2.47 (s, 3H), and MS [MH+]=280).

Step 3: Synthesis of 2-Fluoro-3-Iodo-4-Methyl-benzoic acid methyl ester

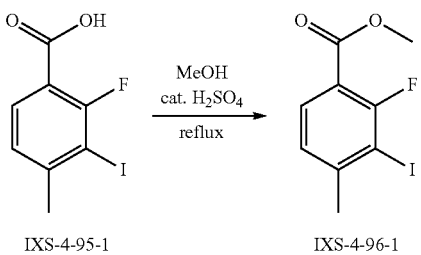

IXS-4-95-1                IXS-4-96-1

In a 500 ml one-neck flask equipped with a magnetic stir-bar and condenser was added 2-fluoro-3-Iodo-4-methyl-benzoic acid (31.5 g, 112.5 mmol), 250 ml of methanol and 10 ml of sulfuric acid. The reaction was heated at 90° C. overnight. LCMS showed that the reaction was 90% complete. The methanol was evaporated and residue was dissolved in ethyl acetate and washed and water. The organic phase was slowly basified until pH-9 with 25% NaOH solution in water. The organic phase was washed with 2×200 ml of water. The separated water washes were extracted with 100 ml of ethyl acetate twice. All of the organic phases were combined and concentrated to give an oily residue that re-crystallized from ether/hexane. The crystals were isolated in two batches, washed with pure hexane, and dried under vacuum for 2 hours to give 31 g (94%) of the product. $^1$H NMR (CDCl$_3$, 400 MHz) 5.7.78 (t, 1H), 7.08 (d, 1H), 3.90 (s, 3H), 2.50 (s, 3H) and MS: [MH+]=295).

Step 4. Synthesis of Methyl 2-fluoro-4-methyl-3-(4,4,5,5-tetramethyl-1,3,2-dioxaborolan-2-yl)benzoate

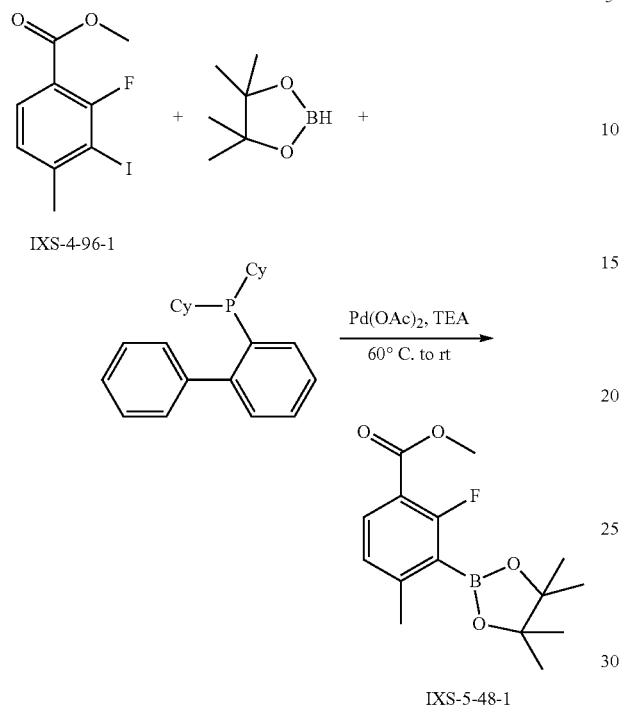

In a 100 ml 3-neck round bottom flask equipped with a condenser, magnetic stirrer and nitrogen outlet was placed methyl 2-fluoro-3-iodo-4-methylbenzoate (2.0 g, 6.80 mmol), 100 ml of anhydrous 1,4-dioxane, diacetoxypalladium (0.076 g, 0.340 mmol) and [1,1'-biphenyl]-2-yldicyclohexylphosphine (0.477 g, 1.360 mmol) under nitrogen, 4,4,5,5-tetramethyl-1,3,2-dioxaborolane (2.96 ml, 20.40 mmol) was added drop wise via syringe. The reaction mixture was heated at 60° C. for 2 hours and stirred at room temperature overnight. LCMS showed almost 100% conversion. The dioxane was removed and the residue was purified on 80 g ISCO silica column using ethyl acetate/hexane gradient and then switched to methanol/DCM gradient to give 1.25 g (62.5%) of IXS-5-48-1, 1.25 g (62.5%). $^1$H NMR (DMSO-ds, 400 MHz) δ 7.81 (t, 1H), 7.16 (d, 1H), 3.83 (s, 3H), 2.42 (s, 3H), 1.33 (s, 12H), and MS: [MH+]=295).

Step 5: Synthesis of 7-fluoro-1-hydroxy-1,3-dihydrobenzo[c][1,2]oxaborole-6-carboxylic acid

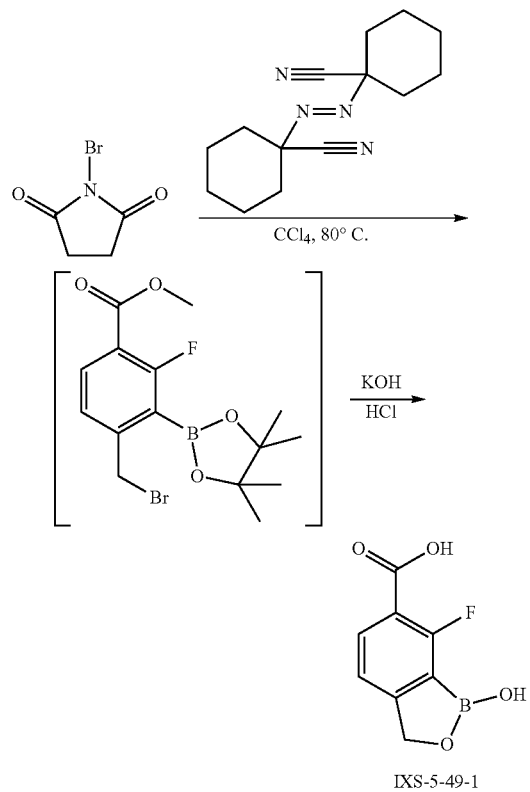

To a solution of methyl 2-fluoro-4-methyl-3-(4,4,5,5-tetramethyl-1,3,2-dioxaborolan-2-yl) benzoate (0.6 g, 2.040 mmol) in 40 ml CCl$_4$ was added N-Bromosuccinimide (0.363 g, 2.040 mmol) and (E)-1,1'-(diazene-1,2-diyl)dicyclohexanecarbonitrile (0.050 g, 0.204 mmol). The mixture was stirred at 80° C. overnight. The reaction mixture was extracted with 5% KOH in water (3×20 ml). The water phase stirred for 1 hour and then the solution was cooled to 0° C. and slowly acidified to pH<1 with 1N HCl. The precipitant that formed was filtered onto fritted filter and dried in vacuum for overnight to give 0.137 g of IXS-5-49-1, $^1$H NMR in DMSO-d$_6$ is consistent with desired product. MS [MH+]=196.

Step 6: Synthesis of N'-(tert-butyl)-7-fluoro-1-hydroxy-1,3-dihydrobenzo[c][1,2]oxaborole-6-carbohydrazide

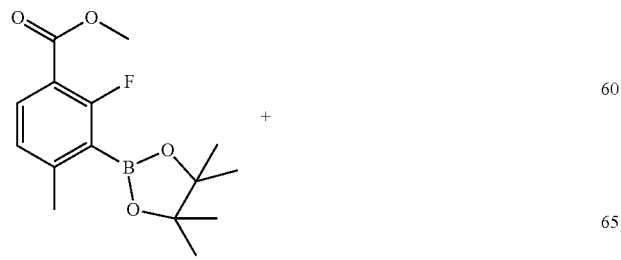

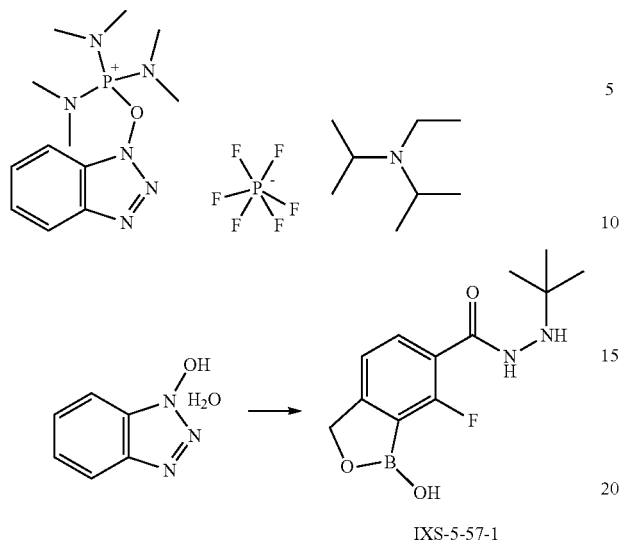

IXS-5-57-1

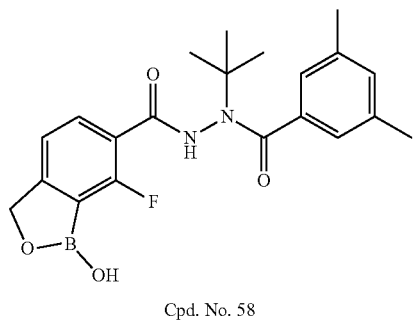

Cpd. No. 58

To a stirred solution of the boroxozole carboxylic (INX-5-49-1, 130.0 mg, 0.663 mmol) in anhydrous DMF (1.5 ml) in a 20 ml scintillation vial purged with nitrogen were added BOP (197.0 mg, 0.663 mmol), HOBt (90.0 mg, 0.663 mmol) and DIPEA (0.579 ml, 3.32 mmol) at room temperature. The reaction mixture was stirred for 5 min. To this was added tert-butyl hydrazine hydrochloride (105 mg, 0.84 mmol), and the reaction mixture was stirred at room temperature overnight. LCMS showed complete conversion of the boroxozole carboxylic acid a new peak. The DMF was removed using a Genevac. The sticky crude mixture was dissolved in 5% aqueous KOH (50 ml) and EtOAc (50 ml) and extracted. The combined aqueous fractions containing the product was neutralized with 0.1N HCl and then water was removed on a rotavapor. The residue washed with 10% MeOH in DCM and purified using an ISCO system. The product eluted in ~2% MeOH in DCM give 100 mg (57%) of the boroxazole carbohydrazide INX-5-57-1 which was used for the next step. $^1$H NMR (400 MHz, DMSO-d$_6$) δ 9.69 (d, J=6.2 Hz, 1H), 7.67 (t, J=7.1 Hz, 1H), 7.27 (d. J=22.8 Hz, 1H), 5.03 (s, 2H), 492 (d, J=79 Hz, 1H), 1.06 (s, 9H).

Step 7: Synthesis of N'-(tert-butyl)-N'-(3,5-dimethylbenzoyl)-7-fluoro-1-hydroxy-1,3-dihydrobenzo[c][1,2]oxaborole-6-carbohydrazide (Cpd No 58)

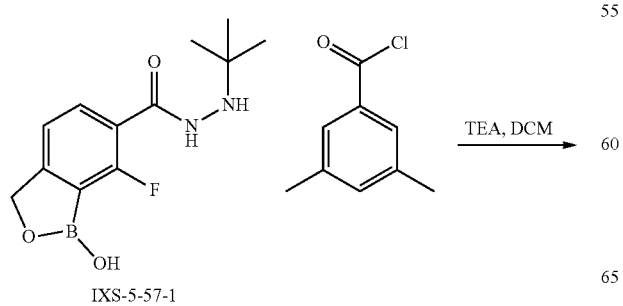

IXS-5-57-1

3,5-dimethylbenzoyl chloride (0.076 g, 0.451 mmol) in a round bottom flask was dissolved in diethyl ether (2.0 ml). To this, N'-(tert-butyl)-7-fluoro-1-hydroxy-1,3-dihydrobenzo[c][1,2]oxaborole-6-carbohydrazide (0.100 g, 0.376 mmol) was added following by TEA (0.105 ml, 0.752 mmol). After triethyl amine addition a precipitant came out of solution. After 90 min of stirring, another equivalent of TEA was added and reaction was allowed to stir for 60 min at room temperature. The solvent was evaporated and the residue was purified by using preparative HPLC to give Cpd. No. 58. $^1$H NMR (400 MHz, DMSO-d$_6$) δ 10.39 (s, 1H), 6.97 (d, J=7.7 Hz, 1H), 6.89-6.83 (m, 3H), 6.72-6.64 (m, 1H), 4.76 (s, 2H), 2.04 (d, J=4.5 Hz, 6H), 1.29 (s, 9H).

Example 12

Synthesis of 4-hydroxymethyl-2-fluoro-benzoic acid

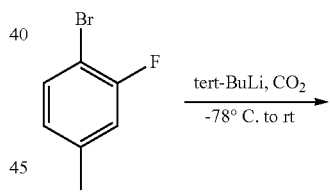

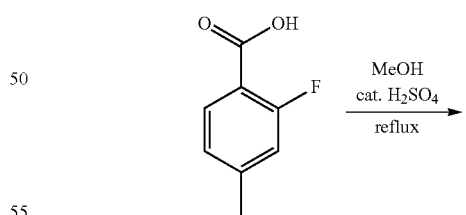

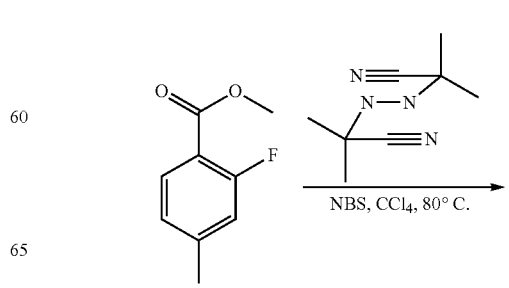

Step 2: Synthesis of 2-Methyl-3-hydroxy-benzoic acid methyl ester

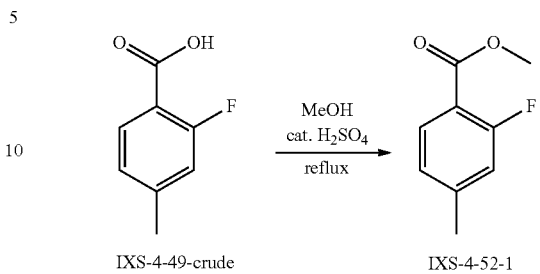

IXS-4-49-crude        IXS-4-52-1

In a 500 ml one-neck round bottom flask, equipped with a magnetic stir-bar and condenser was added 2-fluoro-4-methyl-benzoic acid (10.0 g, 64.88 mmol), 250 ml of methanol and 5 ml of sulfuric acid. The reaction was heated at 90° C. overnight. The methanol was evaporated and residue was purified on 125 g. Filter Silica ISCO column using a hexane/ethyl acetate gradient to give 10.01 g of IXS-4-52-1. Overall yield is 91.75%. $^1$H NMR (CDCl$_3$, 400 MHz) δ 7.80 (t, 1H), 6.95 (2 d, 2H), 3.89 (s, 3H), 2.37 (s, 3H).

Step 3: Synthesis of 4-Bromomethyl-2-fluoro-methyl-benzoate

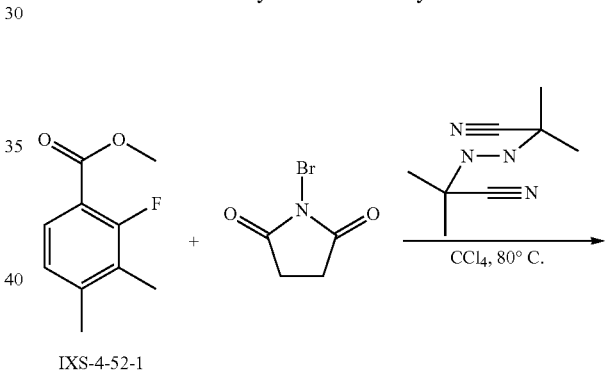

IXS-4-52-1

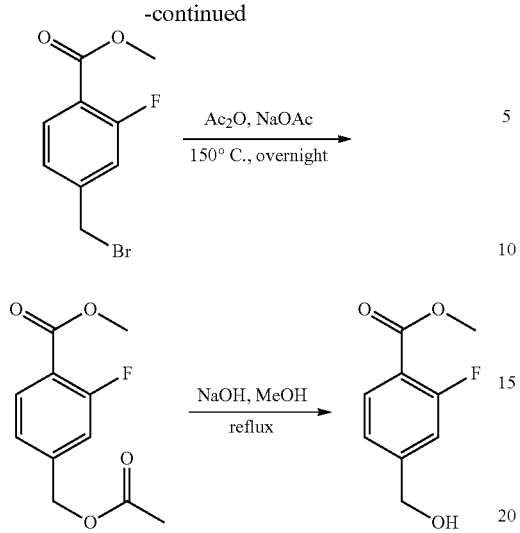

Step 1: Synthesis of 2-fluoro-4-methyl-benzoic acid

To a 1 L three-neck round bottom flask, equipped with a magnetic stir bar, addition funnel and nitrogen inlet was added 1-bromo-2-fluoro-4-methyl-benzene (43.0 g, 227.47 mmol) and 300 ml of anhydrous THF. The flask was purged with nitrogen for 30 min and then cooled to −78° C. using acetone-dry-ice bath. T-BuLi, 2.5 M solution in hexanes (100.00 ml, 250.00 mmol) was added drop-wise over 30 min. The addition funnel was washed with 100 ml of anhydrous THF into the reaction flask. The resulting slightly-yellow reaction mixture was stirred at −78° C. for 1 hour. The entire mixture poured onto 200 g of dry-ice in 150 ml of THF via cannula transfer. The mixture was allowed to warm-up to room temperature while stirring, diluted with 500 ml of water, transferred into separatory funnel, and extracted with ether (2×500 ml). The ether phase was discarded. The aqueous phase was acidified with 1N HCl until pH<<2 (then extracted with ether again (2×500 ml) and ethyl acetate (2×200 ml). The combined organic phases were dried over magnesium sulfate and concentrated at reduced pressure. The white crystalline residue thus obtained was dried in vacuum for 1 hour to yield 35.06 g IXS-4-49-crude. $^1$H NMR (DMSO-d$_6$, 400 MHz) δ 13.04 (bs, 1H), 7.76 (t, 1H), 7.15 (t, 2H), 2.36 (s, 3H). Overall yield is 89.55%.

IXS-4-53-1

To a 250 ml three-neck round bottom flask, equipped with a magnetic stir bar and condenser and glass-stopper was added 2-fluoro-4-methyl methyl benzoate (10.01 g, 59.52 mmol), 100 ml of carbon tetrachloride, N-bromosuccinimide (10.70 g, 60.12 mmol), and 2,2'-azobisisobutyronitrile (AIBN, 0.39 g, 2.38 mmol). The reaction was heated at 100° C. for 6 hours then stirred at room temperature overnight. The flask was cooled in ice for 30 min and the resulting precipitant was collected by filtration and washed with hexane. The filtrate was set aside. The precipitant was redissolved in ethyl acetate and hexane added until a solid started form. The flask was left standing for 1 hour. The precipitated solid was collected by filtration and dried. The solid was placed into Erlenmeyer flask and stirred with 100 ml of water for 3 hours. The solid was re-isolated by filtration, washed with hexane, and dried in vacuum oven at 60° C. for 2 hours to give 4.36 g of 4-bromomethyl-2-fluoro-methyl-benzoate (IXS-4-53-1) as indicated by $^1$H NMR (CDCl$_3$, 400 MHz) δ 7.89 (t, 1H), 7.18 (2 d, 2H), 4.42 (s, 2H) 3.91 (s, 3H).

Step 4: Synthesis of 4-Hydroxymethyl-2-fluoro-benzoic acid

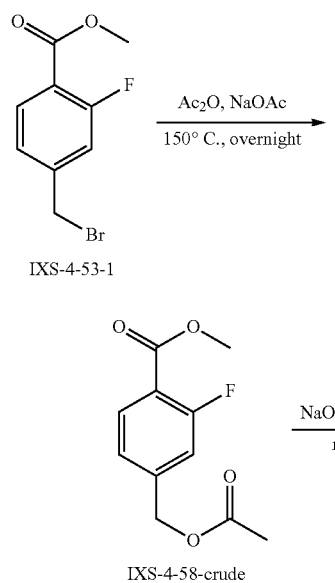

In a 250 ml one-neck round bottom flask, equipped with a magnetic stir bar and condenser was added 2-fluoro-4-bromomethyl methyl benzoate (5.94 g, 24.04 mmol), 70 ml of acetic anhydride and sodium acetate (2.56 g, 31.26 mmol). The reaction was heated at 150° C. overnight. The reaction was cooled to room temperature and checked by TLC, 200 ml of water was added carefully, and the reaction mixture was transferred to separatory funnel. The aqueous phase was extracted with ether 2×100 ml and ethyl acetate 3×100 ml. The organic fractions were combined and concentrated. The residue was dissolved in 50 ml of methanol and transferred into 250 ml one-neck flask equipped with a magnetic stir bar Potassium hydroxide (6.75 g, 120 mmol) was dissolved in 20 ml methanol and added into the reaction flask, and the reaction mixture was heated at 90° C. for overnight. The reaction was cooled to room temperature and checked by TLC, 100 ml of water was added carefully and the reaction mixture was carefully acidified with 3M HCl solution until pH<2. The aqueous phase was extracted with ethyl acetate. The organic phase was concentrated and purified on an ISCO system using an ethyl acetate/hexane gradient to give 2.32 g of IXS-4-60-2. $^1$H NMR (CDCl$_3$, 400 MHz). Overall yield is 57.0%. $^1$H NMR (CDCl$_3$, 400 MHz) δ 13.02 (bs, 1H), 7.80 (t, 1H), 7.21 (t, 2H), 5.44 (bs, 1H), 4.45 (s, 2H).

Example 13

Synthesis of N'-benzoyl-N'-(tert-butyl)-1-butyl-7-fluoro-1,3-dihydrobenzo[c][1,2]oxaborole-6-carbohydrazide (Cpd. No. 64)

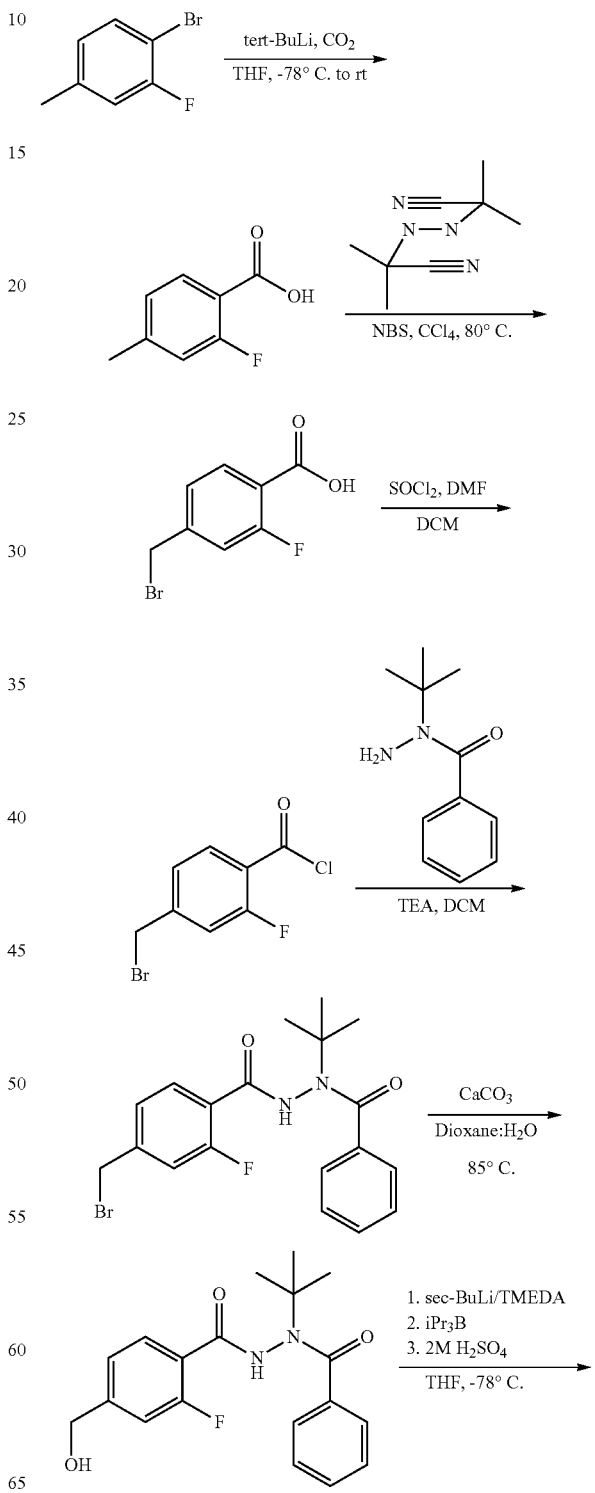

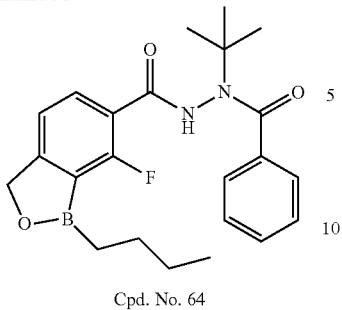

Cpd. No. 64

Step 1: Synthesis of 2-fluoro-4-methylbenzoic acid

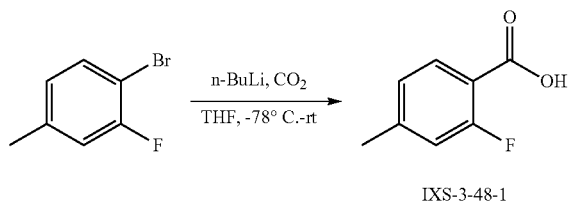

IXS-3-48-1

An oven dried IL 3-necked round bottom flask fitted with a with magnetic stirrer, addition funnel, reflux condenser, and nitrogen inlet was purged with nitrogen for 45 min. The flask was charged with 1-bromo-2-fluoro-4-methyl benzene (43.0 g, 227.47 mmol) and anhydrous THF (250 ml). The mixture was cooled to −78° C. in a dry ice-acetone bath and n-BuLi (2.5M solution in hexane, 100.09 ml, 250.22 mmol) was added drop wise to the stirred reaction while the temperature was maintained at around −78° C. The addition funnel was washed with two 10 ml portion of anhydrous THF and then the reaction stirred at −78° C. for condenser. The entire mixture was poured onto solid carbon dioxide in flask (50 m) and allowed to warm to room temperature, 300 ml of water was added and everything dissolved. The resulting mixture was transferred into a separation funnel and extracted with ether (2×500 ml). The ether phase was discarded. The combined aqueous phase was acidified with 3N HCl to pH <3 of and a white precipitate formed. The water phase was extracted with ether (2×500 ml) and ethyl acetate (3×500 ml). The combined organic phase was dried over anhydrous MgSO₄, filtered and concentrated to give 31.4 g of IXS-3-48 as a pinkish white crystalline powder. ¹H NMR (CDCl₃, 400 MHz) δ 12.99 (s, 1H), 7.77-7.73 (t, 1H), 7.14-7.09 (m, 2H), 2.30 (s, 3H).

Step 2: Synthesis of
4-(bromomethyl)-2-fluorobenzoic acid

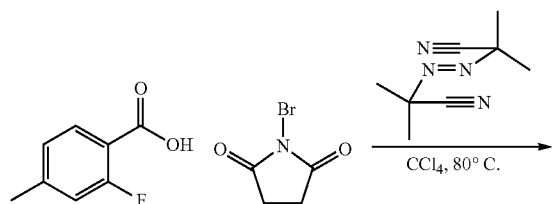

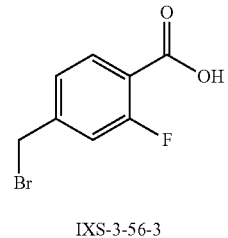

IXS-3-56-3

4-Fluoro-4-methyl benzoic acid (10.0 g, 64.88 mmol) was added to a 500 ml 3-neck round bottom flask flitted with a reflux condenser, magnetic stir bar drying tube, 100 ml of CCl₄ was added the reaction mixture was heated to 80° C. NBS was weighed into 20 ml scintillation vial and added in 8 portions using a spatula during 4 hour period. Similarly AIBN was added in 8 portions. The resulting mixture was stirred for another 3 h at 80° C. then cooled to room temperature and stirred overnight. The light yellow suspension was filtered onto a filter funnel with about 1.5 inch layer of silica gel then washed with IL of dichloromethane. Some precipitate came out of filtrate so ethyl acetate was added to make it clear. The filtrate was collected into 100 ml aliquots in small Erlenmeyer flasks that were analyzed by TLC. Aliquots containing starting material and other impurities were discarded. The product aliquots were combined and concentrated. The residue was triturated with 50 ml of ether, filtered onto fritted filter, and dried under vacuum for 1 h to give 14.98 g of crude product. ¹H NMR showed it as a 1:2 mixture of product and succinimide byproduct. The product was transferred into fritted funnel, washed with water and hexane, and dried under vacuum for 2 hours. ¹H NMR showed that it still contained 20% of the succinimide side product. The mixture was purified using an ISCO system (40 g silica column, hexane/EtOAc gradient) to give IXS-2-56-3 (800 mg). ¹H NMR (CDCl₃, 400 MHz) δ 12.25 (s, 1H), 6.87-6.83 (t, 1H), 6.42-6.36 (m, 2H), 3.73 (s, 2H).

Step 3: Synthesis of N'-benzoyl-4-(bromomethyl)-
N'-(tert-butyl)-2-fluorobenzohydrazide

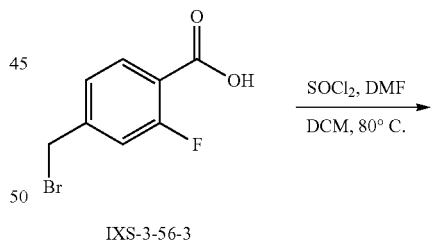

IXS-3-56-3

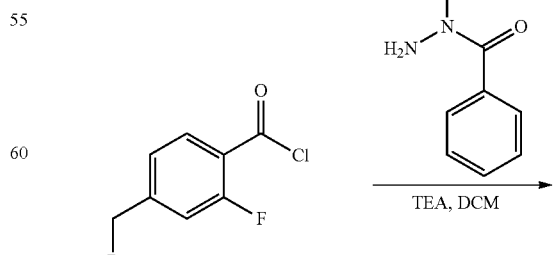

IXS-3-57

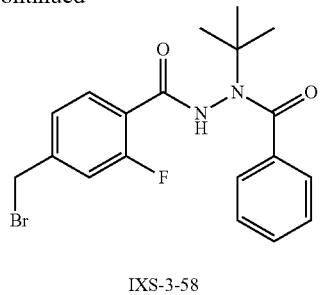

IXS-3-58

The above benzoic acid (IXS-3-56-3, 8.0 g, 0.034 mmol) was added to a 250 ml 1-neck round bottom flask fitted with a drying tube, 50 ml anhydrous chloroform was added and the reaction mixture was stirred. To this stirred mixture, thionyl chloride 12.49 ml, 0.17 mmol) was added followed by 3 drops of anhydrous DMF. After stirring overnight, the solvent and excess thionyl chloride were removed under vacuum and resultant residue was washed several times with anhydrous dichloromethane, evaporated and dried under vacuum, 40 ml hexane was added and the resulting mixture was filtered through a fritted filter funnel to give 8.0 g of a greenish colored oil that was used in the next step without further purification.

For the next step, hydrazine (4.89 g, 25.45 mmol), acid chloride (8.0 g, 31.81 mmol) and 100 ml of ether were added into a 250 ml 1-necked round bottom flask, and the reaction mixture was stirred at room temperature. To this triethylamine (4.43 ml, 31.81 mmol) was added. After stirring overnight, TLC showed complete conversion to the product. Dichloromethane was added to dissolve all the precipitate and the product was purified using and ISCO system (2×80 g silica column, hexane/EtOAc gradient) to give 8.75 g of IXS-3-58. $^1$H NMR (DMSO-d$_6$, 400 MHz) δ 10.72 (s, 1H), 7.53-7.28 (m, 6H), 7.23-7.21 (d, 1H), 6.84-6.75 (t, 1H), 4.60 (s, 2H), 1.50 (s, 9H).

Step 4: Synthesis of N'-benzoyl-N'-(tert-butyl)-2-fluoro-4-(hydroxymethyl) benzohydrazide

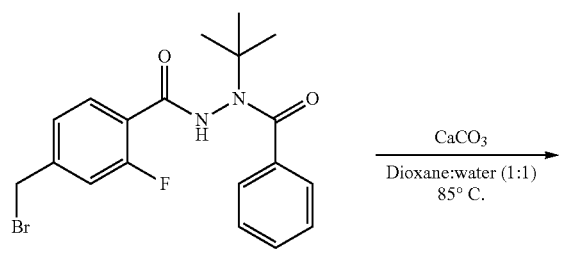

To a 250 ml 1-neck round bottom flask the above 4-bromomethyl DAH derivative (8.75 g, 21.48 mmol), CaCO$_3$ (1.08 g, 10.74 mmol) and a 1:1 mixture of dioxane and water (140 ml) were added, and the mixture was stirred overnight at 85° C. Most of the dioxane was removed on a rotavapor. After aqueous work up and extraction with EtOAc, the organic phases were combined, dried over anhydrous MgSO$_4$, filtered, and concentrated. The residue was purified using an ISCO system (80 g silica column, hexane/EtOAc gradient to give IXS-3-59-2 (6.35 g, 86%) $^1$H NMR (DMSO-d$_6$, 400 MHz) δ 10.56 (s, 1H), 7.41-7.26 (m, 5H), 7.18-7.04 (m, 2H), 6.73-6.69 (m, 1H), 5.37-5.32 (t, 1 h) 4.47-4.46 (d, 2H), 1.54 (s, 9H).

Step 5: Synthesis of N'-benzoyl-N'-(tert-butyl)-1-butyl-7-fluoro-1,3-dihydrobenzo[c][1,2]oxaborole-6-carbohydrazide (Cpd. No. 64)

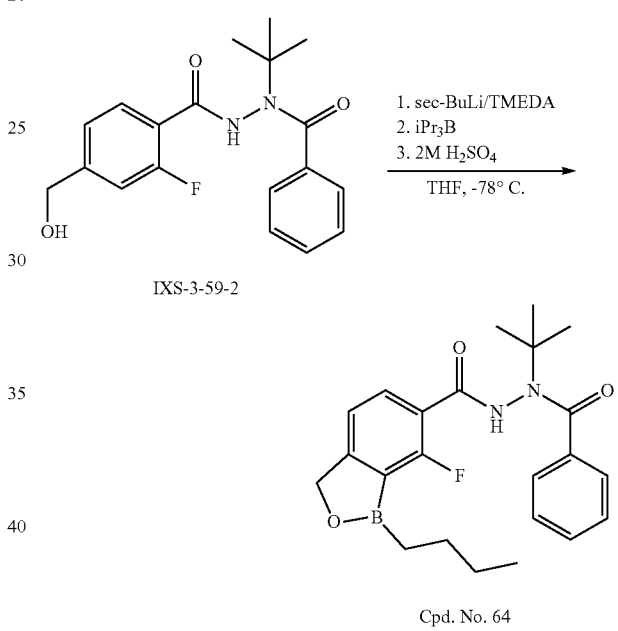

An oven dried 3-neck 250 ml round bottom flask with magnetic stirrer, thermometer, graduated pressure-equalized addition funnel and nitrogen inlet was purged with nitrogen for 20 min. The flask was charged with 2,2,6,6-tetramethylpiperidine (3.65 ml, 21.48 mmol) and anhydrous THF (40 ml) and cooled to −30° C. in a dry ice-acetone bath, n-BuLi (13.07 ml, 20.91 mmol) was added drop wise to the stirred reaction while the temperature was maintained between −30° C. and −35° C. (~10 min). The addition funnel was washed twice with 10 ml portions of anhydrous THF and the reaction mixture cooled to −76° C. Triisopropyl borate (5.34 ml, 23.23 mmol) was added drop wise to the stirred creamy-yellow solution while the internal temperature was maintained below −73° C. (~10 min). IXS-3-59-2 (2.0 g, 5.81 mmol) was dissolved in anhydrous THF (10 ml) was added drop wise to the reaction mixture over 10 min. The addition funnel was washed twice with 10 ml portions of anhydrous THF, the reaction mixture cooled to −76° C. for 3.5 hours, and slowly allowed to warm to room temperature. After 1 h at room temperature, the reaction mixture was quenched with 20 ml of 2M H$_2$SO$_4$ in water. The resulting mixture stirred for 1 h at room temperature then diluted with water and ether. The organic phase was separated and the aqueous phase was washed with ether (2×100 ml) and EtOAc (2×100 ml). The organic fractions were combined, concentrated, and purified using an ISCO system (80 g silica column, hexane/EtOAc gradient) to give 71 mg of Cpd No. 69. $^1$H NMR (DMSO-d$_6$ 400 MHz) δ 10.55 (s, 1H), 7.42-7.39 (m, 2H), 7.34-7.30 (m, 3H), 7.14-7.12 (m, 1H), 6.76-6.66 (m, 1H), 5.10 (s, 2H), 1.55 (s, 9H), 1.40-1.29 (m, 4H), 1.25-1.09 (m, 2H), 0.88-0.83 (m, 3H).

Example 14

Synthesis of N'-(tert-butyl)-N'-(3,5-dimethylbenzoyl)-1-hydroxy-6-methyl-1,2,3,4-tetrahydrobenzo[f][1,4,5]oxazaborepine-7-carbohydrazide (Cpd. No. 91)

and (R)—N'-(3,5-dimethylbenzoyl)-N' (2,2-dimethylpentan-3-yl)-1-hydroxy-6-methyl-1,2,3,4-tetrahydrobenzo[f][1,4,5]oxazaborepine-7-carbohydrazide (Cpd. No. 92)

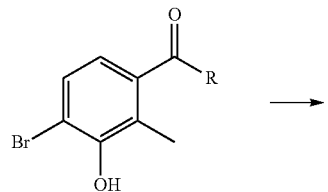

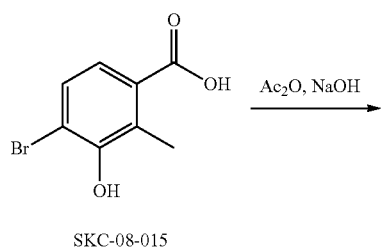

SKC-08-015

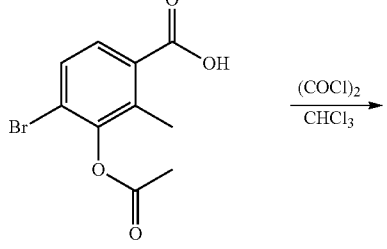

SKC-08-016

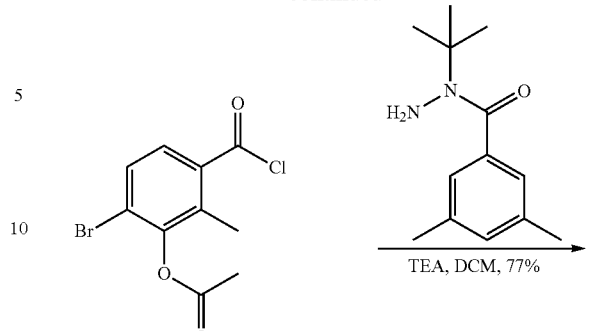

SKC-09-014

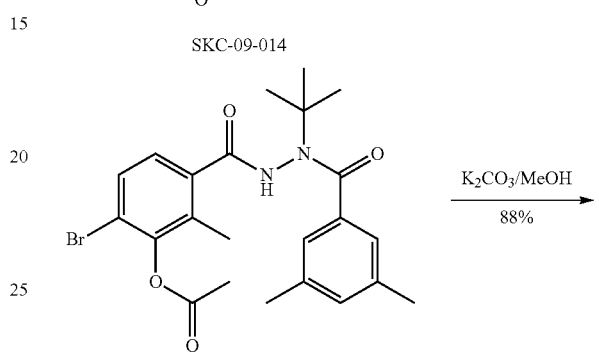

SKC-09-015

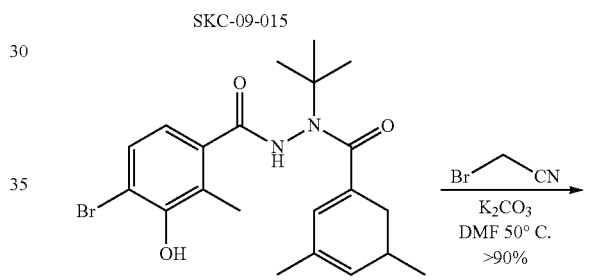

SKC-09-021

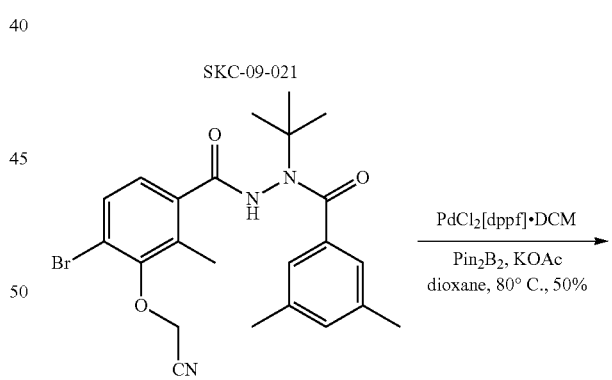

SKC-09-023

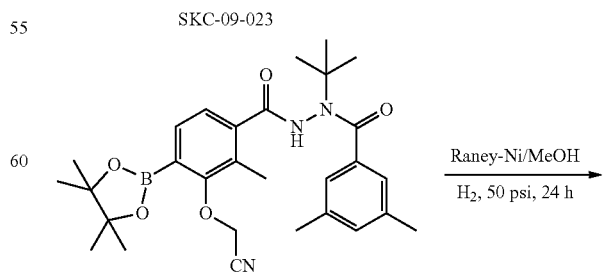

SKC-09-028

213
-continued

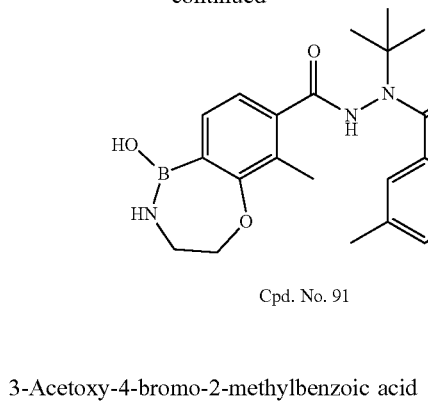

Cpd. No. 91

3-Acetoxy-4-bromo-2-methylbenzoic acid

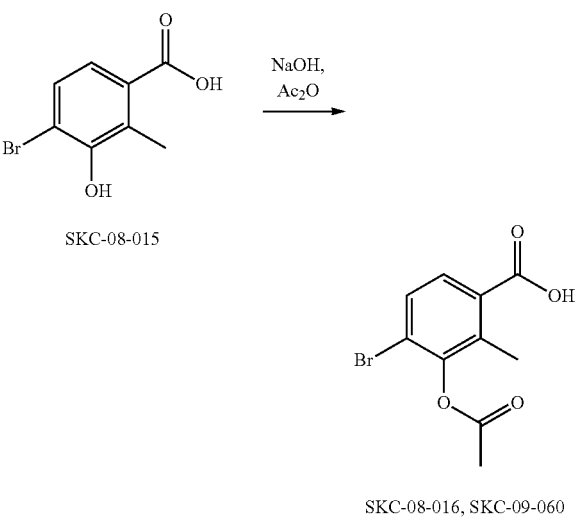

Water (12 mL) was added to 4-bromo-3-hydroxy-2-methylbenzoic acid (5 g, 21.6 mmol) in an. Erlenmeyer flask and cooled in an ice bath, 50% Aqueous NaOH solution (8.06 g mixed with 12 mL water, 108 mmol) was added and the mixture stirred for few minutes until the solution was clear. Acetic anhydride (2.04 mL, 21.6 mmol) was added drop wise until pH 5 was reached; by that time the reaction mixture became a thick slurry having an off white color. The mixture was stirred overnight at room temperature LCMS showed a major peak with the expected product mass and a minor polar peak of the starting material. The pH was adjusted to 2 and the precipitate was filtered. LCMS of the precipitate showed it as a 3:1 mixture of the expected acetate and the starting phenol. The filtrate also contained some product, so combined everything, dried and adsorbed on silica and subjected to silica gel column chromatography using ISCO. The main peak was collected, the solvent was removed and the product dried under vacuum. $^1$H NMR (400 MHz, DMSO) δ 13.27 (s, 1H), 7.81-7.33 (m, 2H), 2.37 (s, 6H), 2.34 (s, 3H).

To a solution of the above acid SKC-09-060 (3.3 g, 12.1 mmol) in anhydrous chloroform (12 mL) was added oxalyl chloride (2.12 mL, 24.2 mmol) and 1 drop of DMF The reaction mixture was stirred at 40° C. for 1 h LCMS showed complete conversion to the acid chloride. Removed the solvent under vacuum on a rotavapor and dried to get 6-bromo-3-(chlorocarbonyl)-2-methylphenyl acetate (SKC-09-062) as a solid.

214
(R)-6-bromo-3-(2-(3,5-dimethylbenzoyl)-2-(2,2-dimethylpentan-3-yl)hydrazine-1-carbonyl)-2-methylphenyl acetate

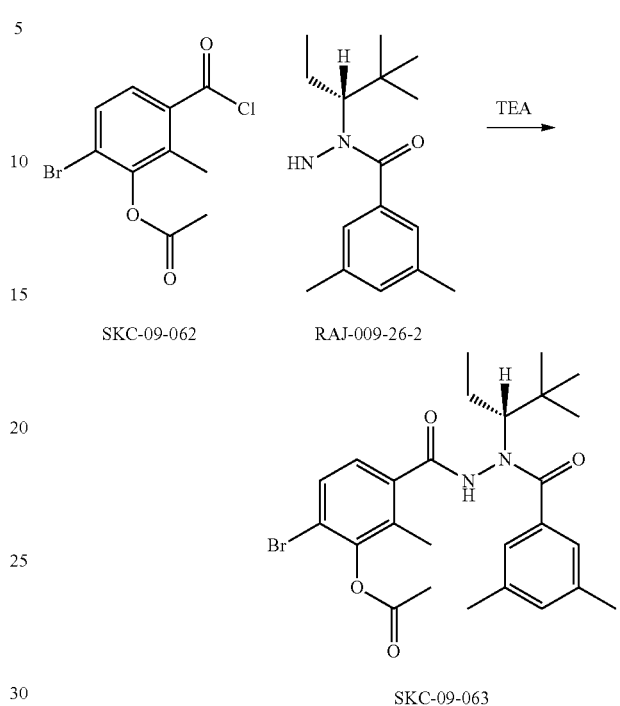

To a stirred solution of (R)—N-(2,2-dimethylpentan-3-yl)-3,5-dimethylbenzohydrazide (2.86 g, 10.9 mmol, >95% ee) in anhydrous DCM (10 mL) was added TEA (2.288 mL, 16.4 mmol) at room temperature under argon. To this, a DCM solution (5 mL) of the acid chloride (3.5 g, 12.0 mmol) was added and stirred at room temperature. LCMS after 30 min showed that the reaction is complete. The crude mixture was adsorbed on silica and purified by silica gel column chromatography using ISCO (hexane/EtOAc gradient). The main fractions were collected and dried to get a colorless solid product SKC-09-063 (2.2 g, 39%). $^1$H NMR (400 MHz, DMSO) δ 10.47 (d, J=61.1 Hz, 1H), 7.60 (d, J=8.2 Hz, 1H), 7.06 (t, J=15.3 Hz, 3H), 6.70 (dd, J=45.3, 8.0 Hz, 1H), 4.33 (dd, J=80.7, 9.5 Hz, 1H), 2.34 (s, 3H), 2.24 (d, J=5.5 Hz, 6H), 1.48 (d, J=24.5 Hz, 4H), 1.11-1.02 (m, 12H), 0.91 (dt, J=42.5, 7.2 Hz, 5H).

6-bromo-3-(2-(tert-butyl)-2-(3,5-dimethylbenzoyl) hydrazine-1-carbonyl)-2-methylphenyl acetate

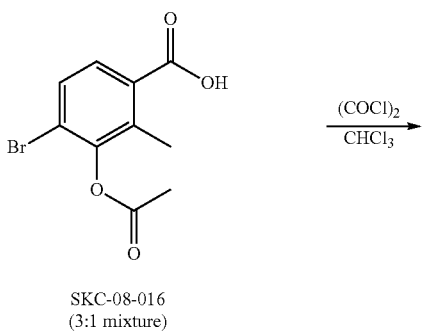

SKC-08-016
(3:1 mixture)

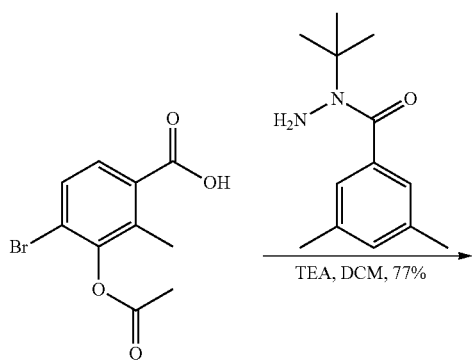

SKC-09-014

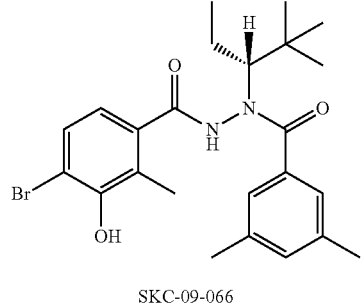

SKC-09-066

K₂CO₃ (1.76 g, 12.8 mmol) was added to a colorless suspension of SKC-09-063 (2.2 g, 4.3 mmol) in 20 ml of MeOH at room temperature. In few minutes, the color of the reaction mixture turned light yellow and the acetate start to dissolve. The reaction was completed in 30 min based on LCMS. Filtered to remove the solid, rinsed with EtOAc and removed the solvent under vacuum and the crude mixture was purified by silica gel column chromatography on ISCO (hexane/EtOAc gradient) to get a white powder of SKC-09-066 (1.8 g, 89%/). LCMS: 477.19 (M+1).

4-Bromo-N'-(tert-butyl)-N'-(3,5-dimethylbenzoyl)-3-hydroxy-2-methylbenzohydrazide

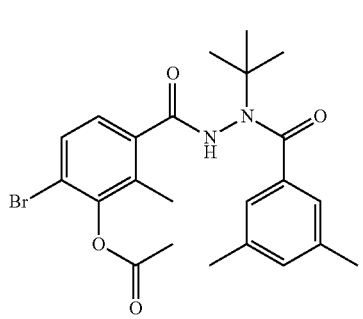

SKC-09-015

Following the same procedure, the title compound was made in 77% yield (2.29 g) starting with N-(tert-butyl)-3,5-dimethylbenzohydrazide (1.37 g, 6.2 mmol), TEA (1.3 mL, 9.4 mmol) and the acid chloride (2.0 g, 6.9 mmol) in DCM (10 mL). ¹H NMR (400 MHz, DMSO) δ 10.68 (s, 1H), 7.56 (d, J=8.2 Hz, 1H), 7.04 (s, 3H), 6.56 (d, J=8.2 Hz, 1H), 2.34 (s, 3H), 2.24 (s, 6H), 165 (s, 3H), 1.49 (s, 9H).

(R)-4-bromo-N'-(3,5-dimethylbenzoyl)-N'-(2,2-dimethylpentan-3-yl)-3-hydroxy-2-methylbenzohydrazide

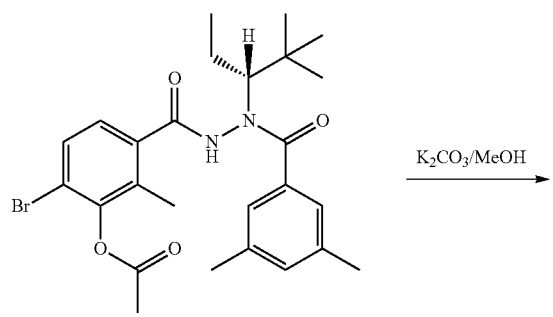

SKC-09-063

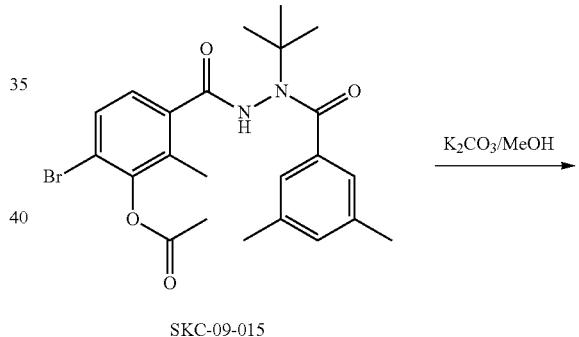

SKC-09-015

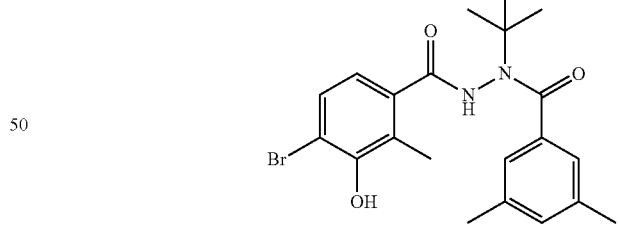

SKC-09-021

Following the above procedure with SKC-09-015 (2.29 g, 4.8 mml) and K₂CO₃ (1.99 g, 14.5 mmol), in 20 mL MeOH for 30 min, SKC-09-021 was isolated after triturating in pentane/ether solvent mixture (1.83 g, 880 yield). ¹H NMR (400 MHz, DMSO) δ 10.47 (s, 1H), 9.32 (s, 1H), 7.30 (d, J=8.2 Hz, 1H), 7.03 (s, 3H), 6.09 (d, J=8.2 Hz, 1H), 2.24 (s, 6H), 1.73 (s, 3H), 1.48 (s, 91-). ¹H NMR (400 MHz, DMSO+2 drops of D₂O) 6.7.27 (d, J=8.2 Hz, 11H), 7.01 (d. J=7.1 Hz, 3H), 6.09 (d, J=8.2 Hz, 1H), 2.22 (s, 6H), 1.70 (s, 3H), 1.46 (s, 9H).

(R)-4-bromo-3-(cyanomethoxy)-N'3,5-dimethylbenzoyl)-N'-(2,2-dimethylpentan-3-yl)-2-methylbenzohydrazide

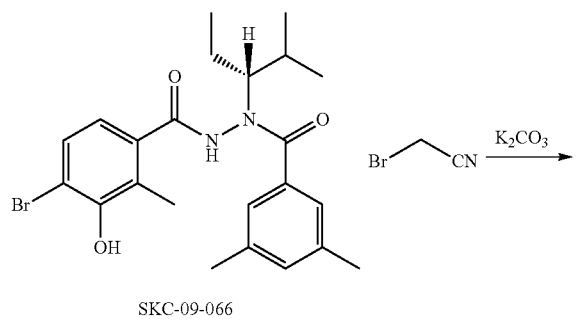

SKC-09-066

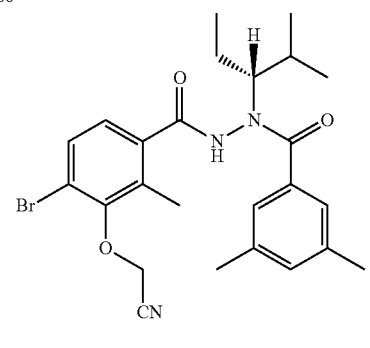

SKC-09-068

Mixed together SKC-09-066 (1.35 g, 2.8 mmol), K$_2$CO$_3$ (0.510 g, 3.7 mmol) and 2-bromoacetonitrile (0.24 mL, 3.4 mmol) in anhydrous DMF (10 mL) in around bottom flask under argon and heated at 50° C. The reaction completed in 10' (based on LCMS), the colorless RM turned yellow in color. Diluted with water, extracted in EtOAc and dried over anhy. MgSO$_4$, filtered and removed the solvent. The crude mixture was adsorbed on silica and purified using ISCO (12 g silica column, hexane/EtOAc gradient). A white solid product SKC-09-068 (1.53 g) was isolated in quantitative yield. $^1$H NMR (400 MHz, DMSO) δ 10.40 (d, J=59.5 Hz, 1H), 7.95 (s, 1H), 7.56 (d, J=8.2 Hz, 1H), 7.16-6.95 (m, 3H), 6.58 (dd, J 46.5, 8.2 Hz, 1H), 5.01-4.91 (m, 2H), 4.50-4.17 (m, 1H), 2.89 (s, 1H), 2.73 (s, 1H), 2.25 (d, J=5.1 Hz, 6H), 1.99 (s, 1H), 1.76-1.62 (m, 4H), 1.62-1.33 (m, 2H), 1.12-0.82 (m, 14H).

4-Bromo-N'-(tert-butyl)-3-(cyanomethoxy)-N'-(3,5-dimethylbenzoyl)-2-methylbenzohydrazide

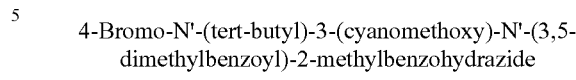

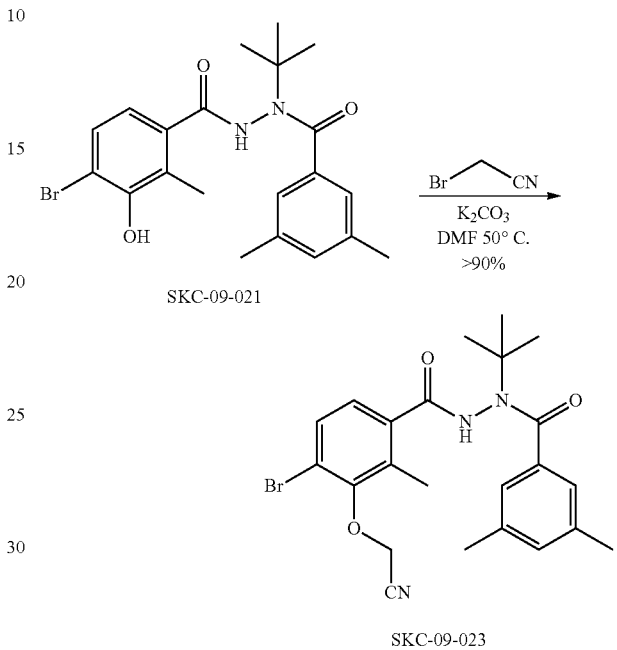

Followed the above procedure using SKC-09-021 (1.8 g, 4.2 mmol), K$_2$CO$_3$ (0.750 g, 5.4 mmol) and 2-bromoacetonitrile (0.35 mL, 4.9 mmol) in anhydrous DMF (7 mL) at 50° C. Reaction completed in 2 hr. After chromatography, 1.67 g of the product SKC-09-023 was isolated in 85% yield (LCMS: 473, M+1).

(R)-3-(cyanomethoxy)-N'-(3,5-dimethylbenzoyl)-N'-(2,2-dimethylpentan-3-yl)-2-methyl-4-(4,4,5,5-tetramethyl-1,3,2-dioxaborolan-2-yl)benzohydrazide

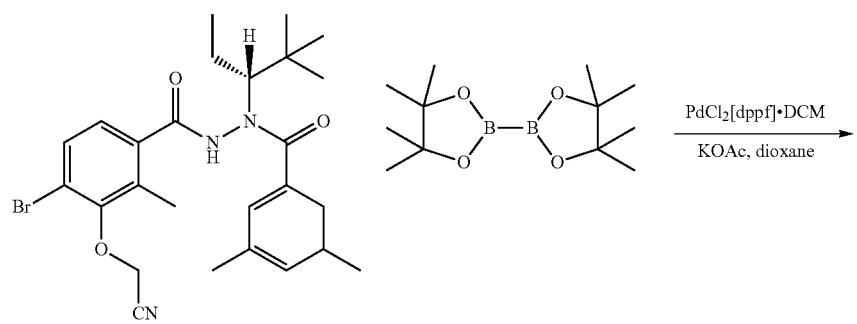

SKC-09-068

-continued

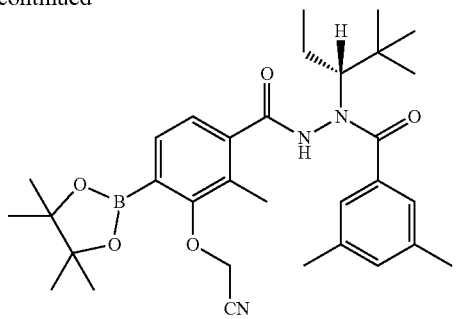

SKC-09-071

To a solution of SKC-09-068 (1.53 g, 2.9 mmol) in 1,4-dioxane (10 mL) were added KOAc (0.876 g, 8.9 mmol), $Pin_2B_2$ (1.13 g, 4.5 mmol). The mixture was evacuated and backfilled with argon, this process repeated three times. $PdCl_2$[dppf].DCM (0.097 g, 0.119 mmol) was added. The RM was quickly evaluated and backfilled with argon three times total and the reaction was stirred under argon at 80° C. overnight, cooled, filtered and evaporated. Water was added to the crude mixture and extracted with ethyl acetate. The residue was purified by column chromatography over silica gel using ISCO, hexane/EtOAc solvent gradient and isolated SKC-09-071 (0.600 g, 36% yield). $^1$H NMR (400 MHz, DMSO) δ 10.39 (dd, J=62.5, 11.4 Hz, 1H), 7.64-7.38 (m, 1H), 7.15-6.97 (m, 3H), 6.57 (dd, 1H), 4.95-4.68 (m, 2H), 4.33 (dd, J=82.4, 10.3 Hz, 1H), 2.25 (d, J=5.9 Hz, 6H), 1.71-1.62 (m, 3H), 1.29 (s, 12H), 1.14-0.91 (m, 15H).

N'-(tert-butyl)-3-(cyanomethoxy)-N'-(3,5-dimethylbenzoyl)-2-methyl-4-(4,4,5,5-tetramethyl-1,3,2-dioxaborolan-2-yl)benzohydrazide To a solution of SKC-09-023 (1.20 g, 2.5 mmol) in 1,4-dioxane (8 mL) were added KOAc (0.748 g, 7.6 mmol), $Pin_2B_2$ (0.968 g, 3.8 mmol). The mixture was evacuated and backfilled with argon, this process repeated three times. $PdCl_2$[dppf].DCM (0.062 g, 0.076 mmol) was added. The RM was quickly evaluated and backfilled with argon three times total and the reaction was stirred under argon at 80° C. overnight, cooled, filtered and evaporated. Water was added to the crude mixture and extracted with ethyl acetate. The residue was purified by column chromatography over silica gel using ISCO, hexane/EtOAc solvent gradient and isolated SKC-09-071 (0.650 g, 49% yield, LCMS: 520.41, M+1).

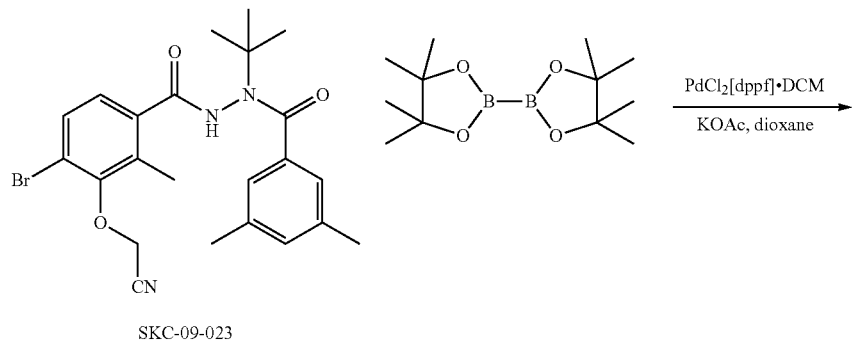

SKC-09-023

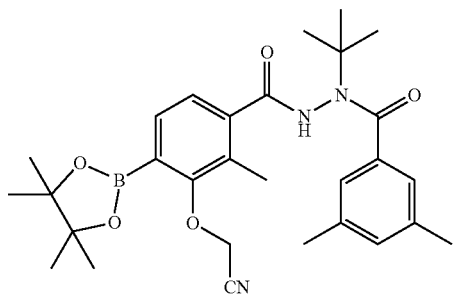

SKC-09-028

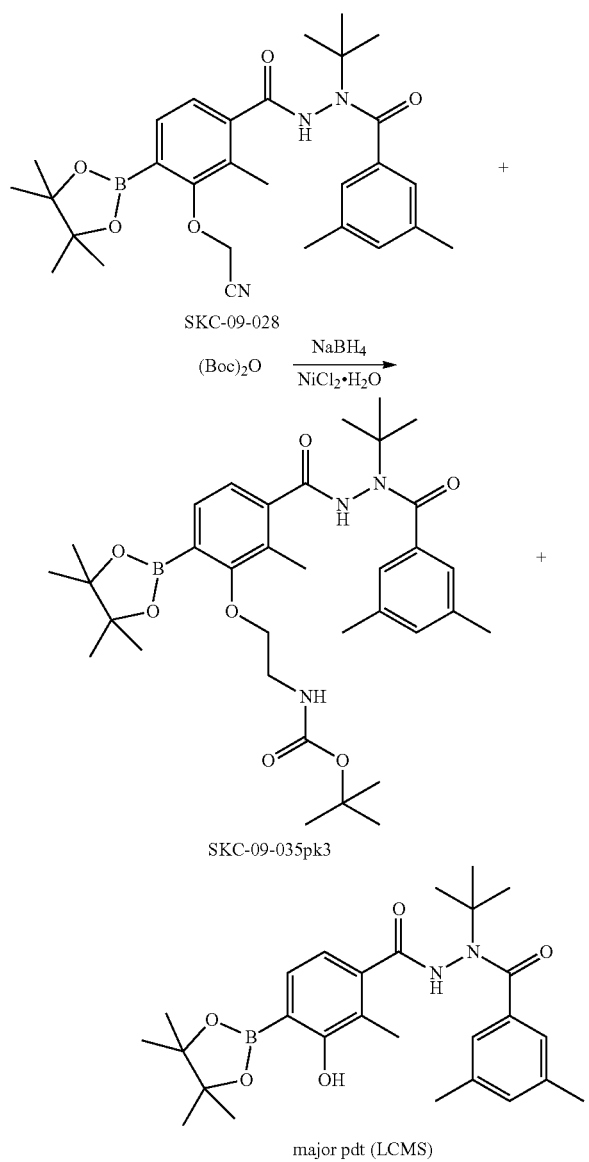

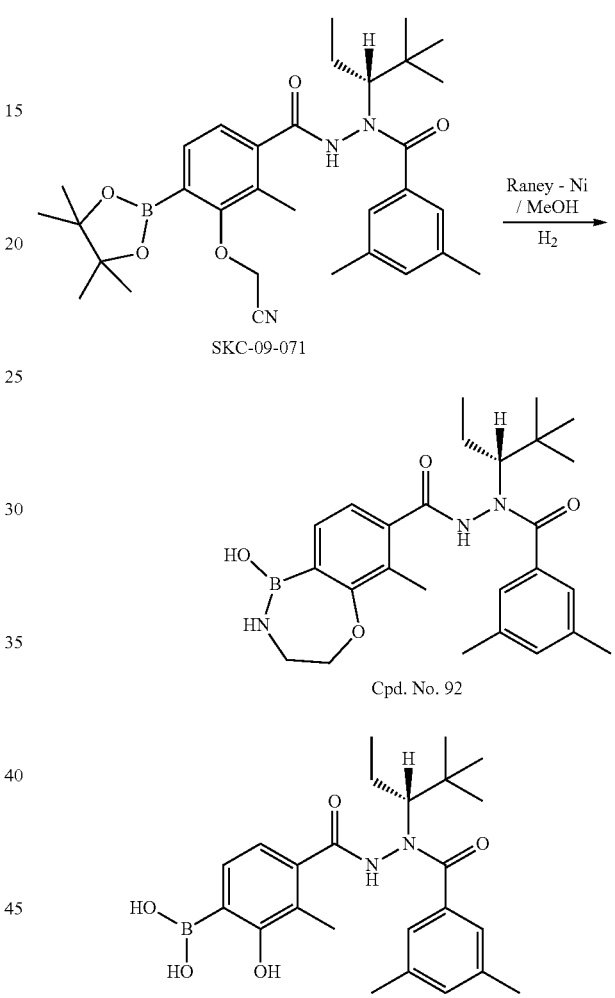

J=20.0 Hz, 3H), 6.46-6.31 (m, 1H), 3.82-3.58 (m, 2H), 3.24 (dt, J=14.4, 5.6 Hz, 2H), 2.25 (s, 5H), 1.72 (d, J=7.5 Hz, 3H), 1.48 (d, J=6.4 Hz, 9H), 1.38 (s, 9H), 1.33-1.25 (m, 12H).

(R)—N'-(3,5-dimethylbenzoyl)-N' (2,2-dimethyl-pentan-3-yl)-1-hydroxy-6-methyl-1,2,3,4-tetrahydrobenzo[f][1,4,5]oxazaborepine-7-carbohydrazide (Cpd. No 92)

To an ice cold MeOH (8 mL) solution of the methoxy nitrile (SKC-09-028, 0.200 g, 0.39 mmol) in a 100 ml 2-necked round bottom flask under argon was added Boc-anhydride and NiCl$_2$.hexahydrate. The RM was quickly evaluated and backfilled with argon three times total and stirred 0° C. for 5 min. To this sodium borohydride was added in 3 portions. The clear colorless solution turned black in color in few minutes, lots of bubbles formation also noticed. Continued to stir the reaction mixture overnight allowing it to warm to RT. LCMS showed 3 peaks, the less polar peak with the expected product mass. Quenched the reaction by adding few drops of water. Removed MeOH under vacuum. After aqueous work up and extraction with EtOAc, the organic fractions collected, dried over anhy MgSO$_4$, filtered and removed the solvent on a rotavapor. The crude mixture was finally purified using C18 RediSep column (100 g) using a acetonitrile/water solvent gradient. Three peaks isolated and the less polar peak is characterized as the expected N-Boc protected amine (SKC-09-035; 0.040 g) based on $^1$H NMR and LCMS. $^1$H NMR (400 MHz, DMSO) δ 10.60-10.35 (m, 1H), 7.47-7.26 (m, 1H), 7.01 (d, To a solution of SKC-09-071 (0.500 g, 0.89 mmol) in MeOH (20 ml) in a hydrogenation bottle was added a spec of Raney-Ni (after rinsing commercially available sample of Raney-Ni in water with MeOH few times). The mixture was hydrogenated in a Parr shaker for 24 hrs (H$_2$, 50 psi). LCMS checked, it showed two major peaks, one with the expected product mass and the second one was the phenol compound as shown in the scheme. The crude mixture (pH 8.0) was filtered through a short pad of celite and removed the solvent under vacuum. Diluted with water and extracted the reaction mixture with ethyl acetate. The product went into the aqueous fractions while the side product (phenol derivative) remained in the organic fraction. The aqueous fraction was acidified to pH–3 on an ice bath, immediately extracted with ethyl acetate. The product came in the EtOAc fractions, dried over anhydrous MgSO₄, filtered and removed the solvent under vacuum. Finally the crude mixture was purified using reverse phase column by ISCO (C18 column, CH₃CN/water solvent gradient) to give Cpd. No. 92 (0.233 g, 56% yield). LCMS: 466.3 (M+1).

The ¹H NMR spectrum suggested that the compound is a mixture; it could be different tautomers and/or the equilibrium with the open and closed form. After adding 2 drops of D₂O to the same sample another ¹H NMR was taken. ¹H NMR (400 MHz, DMSO) δ 10.49-9.90 (m, 1H), 8.35-7.51 (m, 1H), 7.37-6.87 (m, 4H), 6.66-5.99 (m, 2H), 4.52-3.83 (m, 4H), 3.29-2.76 (m, 2H), 2.26 (dd, J=19.3, 14.3 Hz, 6H), 1.76-1.33 (m, 5H), 1.15-0.90 (m, 12H). ¹H NMR (400 MHz, DMSO+2 drops of D₂O) δ 8.37-7.15 (m, 2H), 7.15-6.94 (m, 3H), 6.59-6.22 (m, 1H), 4.29 (dd, J=79.9, 10.3 Hz, 1H), 4.07 (s, 1H), 3.89 (d. J=4.8 Hz, 1H), 3.19-2.88 (m, 2H), 2.44-2.11 (m, 6H), 1.79-1.27 (m, 5H), 1.14-0.72 (m, 12H).

N'-(tert-butyl)-N'-(3,5-dimethylbenzoyl)-1-hydroxy-6-methyl-1,2,3,4-tetrahydrobenzo[f][1,4,5]oxazaborepine-7-carbohydrazide (Cpd. No. 91)

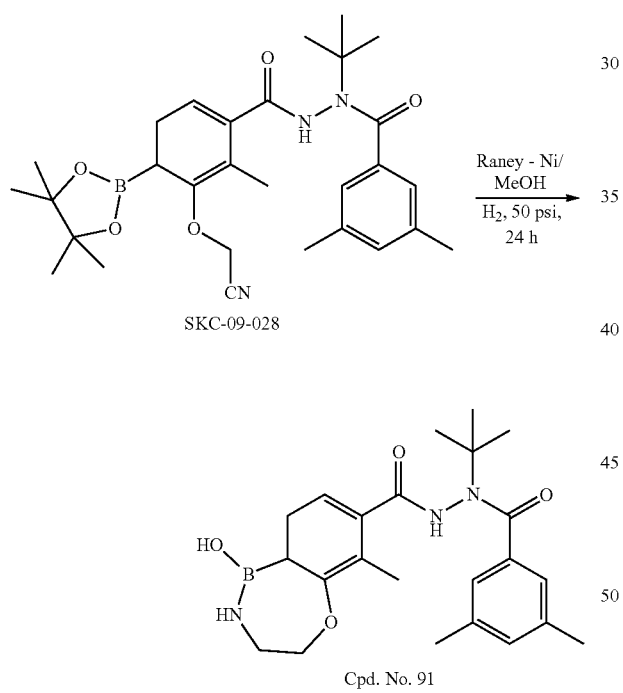

Following the above procedure, the Cpd. No. 91 (0.040 g) was prepared starting with SKC-09-028 (240 mg), Raney-Ni under hydrogen (50 psi) in a Parr shaker. LCMS: 424 (M+1). The ¹H NMR spectrum suggested that the compound is a mixture; it could be different tautomers and/or the equilibrium with the open and closed form.

¹H NMR (400 MHz, DMSO) δ 10.54-10.09 (m, 1H), 7.81 (dt, J=26.6, 11.2 Hz, 1H), 7.29-6.94 (m, 4H), 6.52-6.03 (m, 1H), 4.11 (s, 2H), 2.95 (d, J=26.1 Hz, 3H), 2.28-2.14 (m, 6H), 1.78-1.68 (m, 3H), 1.48 (d, J=4.2 Hz, 9H).

Example 15

Synthesis of N'-(tert-butyl)-N'-(3,5-di methylbenzoyl)-2-fluoro-4-(methoxymethyl)-3-(4,4,5,5-tetramethyl-1,3,2-dioxaborolan-2-yl)benzohydrazide (Cpd. No. 94); (3-(2-tert-butyl)-2-(3,5-dimethylbenzoyl) hydrazine-1-carbonyl)-2-fluoro-6-(methoxymethyl) phenyl)boronic acid (Cpd. No. 88); (R)—N'-(3,5-dimethylbenzoyl)-N'-(2,2-dimethylpentan-3-yl)-2-fluoro-4-(methoxymethyl)-3-(4,4,5,5-tetramethyl-1,3,2-dioxaborolan-2-yl)benzohydrazide (Cpd. No 87)

and (R)-(3-(2-(3,5-dimethylbenzoyl)-2-(2,2-dimethylpentan-3-yl)hydrazine-1-carbonyl)-2-fluoro-6-(methoxymethyl)phenyl)boronic acid (Cpd. No. 86)

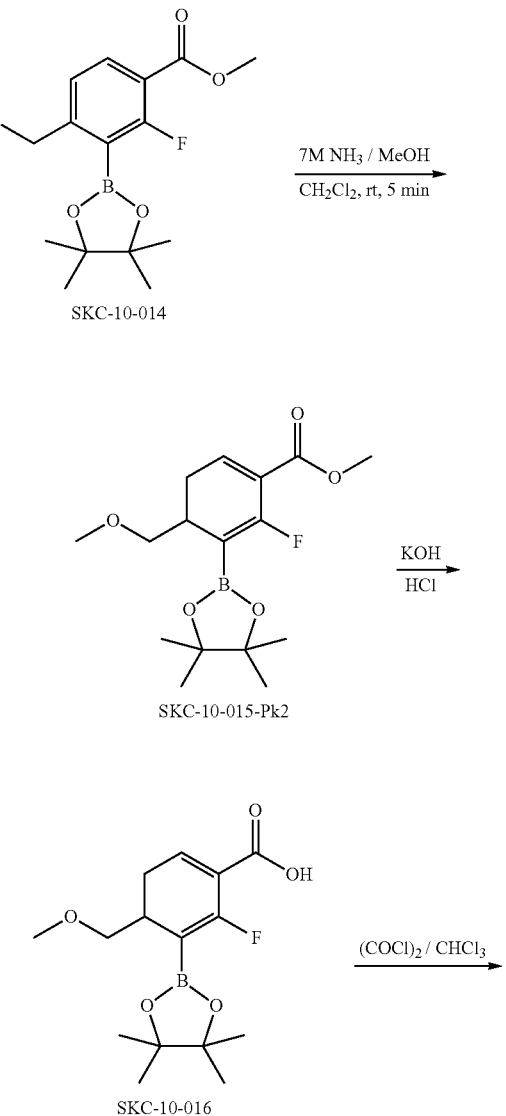

225
-continued

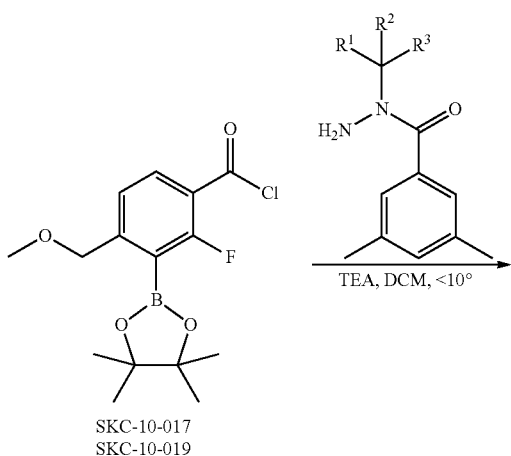

SKC-10-017
SKC-10-019

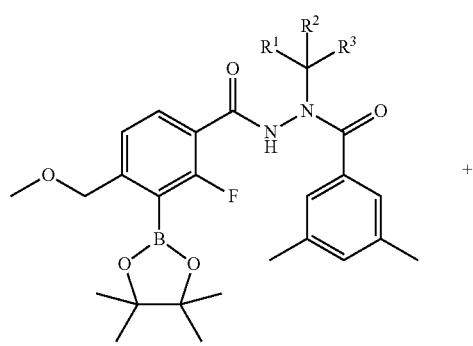

+

Methyl 2-fluoro-4-(methoxymethyl)-3-(4,4,5,5-tetramethyl-1,3,2-dioxaborolan-2-yl)benzoate

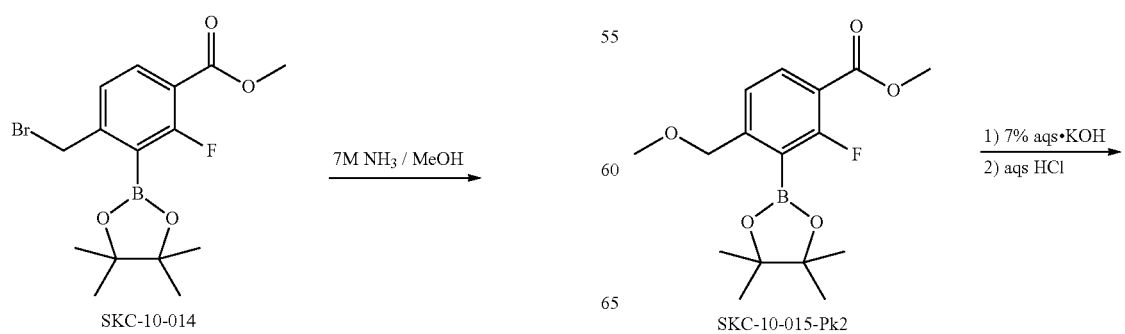

SKC-10-014

226
-continued

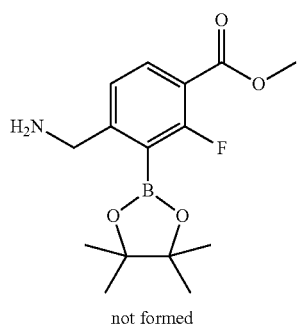

not formed

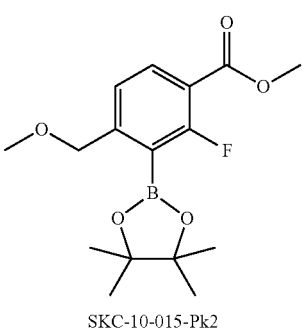

SKC-10-015-Pk2

To a stirred solution of SKC-10-014 (2 g, 5.4 mmol) in DCM (40 mL) was added 100 mL of a cold solution of $NH_3$ in MeOH (from Aldrich) at rt. LCMS showed that the reaction is completed in 15 min. Removed the solvent under vacuum on a rotavapor, diluted with water and EtOAc, cooled the reaction mixture on an ice bath and acidified with 6N HCl slowly. Immediately extracted the cold mixture with EtOAc, dried over anhydrous $MgSO_4$, filtered and removed the solvent. Purified the crude mixture using a RediSep C18 column (acetonitrile/water gradient). The $^1H$ NMR of the major product isolated confirmed it as the methoxymethyl derivative (SKC-10-015-Pk2, 1.34 g, 74% yield) and not the benzyl amine compound as expected. $^1H$ NMR (400 MHz, $CDCl_6$) δ 7.89 (t, J=7.8 Hz, 1H), 7.11 (d, J=8.0 Hz, 1H), 4.55 (s, 2H), 3.89 (s, 3H), 3.33 (s, 3H), 1.37 (s, 12H) $^{13}C$ NMR (101 MHz, $CDCl_3$) δ 166.34, 164.98, 150.36, 150.27, 133.42, 122.36, 122.33, 84.28, 77.36, 77.05, 76.73, 73.51, 58.17, 52.21, 24.85.

2-fluoro-4-(methoxymethyl)-3-(4,4,5,5-tetramethyl-1,3,2-dioxaborolan-2-yl)benzoic acid

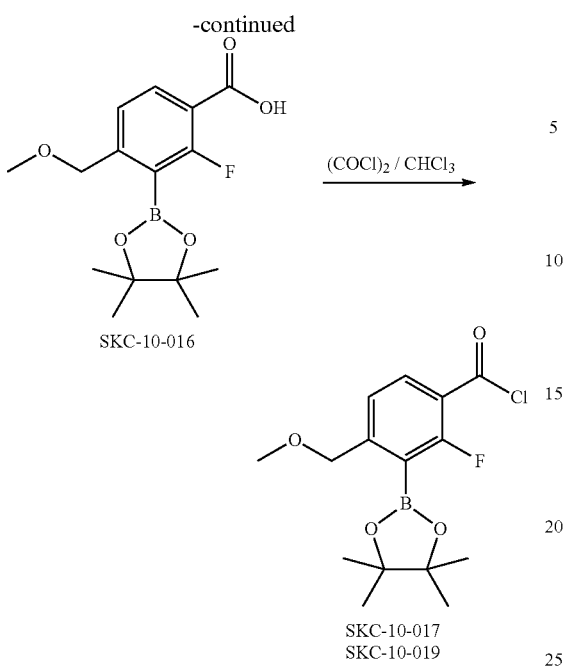

SKC-10-016

(COCl)₂ / CHCl₃ →

SKC-10-017
SKC-10-019

To a stirred suspension of the above ester SKC-10-015-Pk2 (620 mg, 1.9 mmol) in water (2 ml) in an ice bath, was added 10 mL of 7% aqueous KOH. LCMS after 5 min showed that all the starting material reacted and a new polar peak with the expected product mass observed, 6N HCl was added slowly to the stirred reaction mixture at 0° C., adjusted the pH ~2, a white precipitate formed. Immediately filtered it through a filter funnel and collected the precipitate, rinsed with water and then pentane, dried under vacuum to get SKC-10-016 (460 mg, 78% yield) as white powder.

The corresponding acid chloride (SKC-10-017) was made by the reaction of SKC-10-016 (350 mg, 1.1 mmol), oxalyl chloride (0.19 mL, 2.3 mmol) in 2 mL of chloroform and 1 drop of DMF at 0° C. The reaction is completed in <30 min. Removed the solvent under vacuum on a rotavapor, dried under high vacuum and used as such for the next step. ¹H NMR (400 MHz, DMSO) δ 13.15 (s, 1H), 7.84 (t, J=7.9 Hz, 1H), 7.20 (d, J=7.9 Hz, 1H), 4.49 (s, 2H), 3.26 (s, 3H), 1.31 (s, 12H). ¹H NMR (400 MHz, DMSO+2 drops of D₂O) δ 7.82 (s, 1H), 7.19 (d. J=7.9 Hz, 1H), 4.46 (s, 2H), 3.24 (s, 3H), 1.29 (s, 12H).

N'-(tert-butyl)-N'-(3,5-dimethylbenzoyl)-2-fluoro-4-(methoxymethyl)-3-(4,4,5,5-tetramethyl-1,3,2-dioxaborolan-2-yl)benzohydrazide (Cpd. No. 94) and (3-(2-tert-butyl)-2-(3,5-dimethylbenzoyl)hydrazine-1-carbonyl)-2-fluoro-6-(methoxymethyl)phenyl) boronic acid (Cpd. No 88)

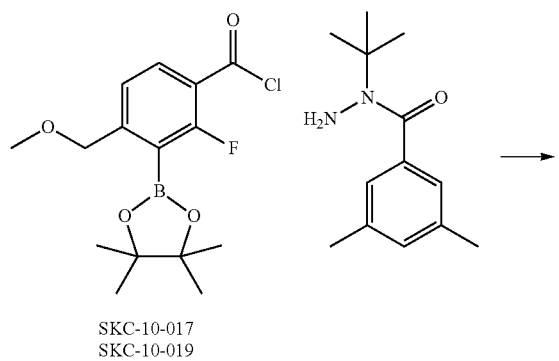

SKC-10-017
SKC-10-019

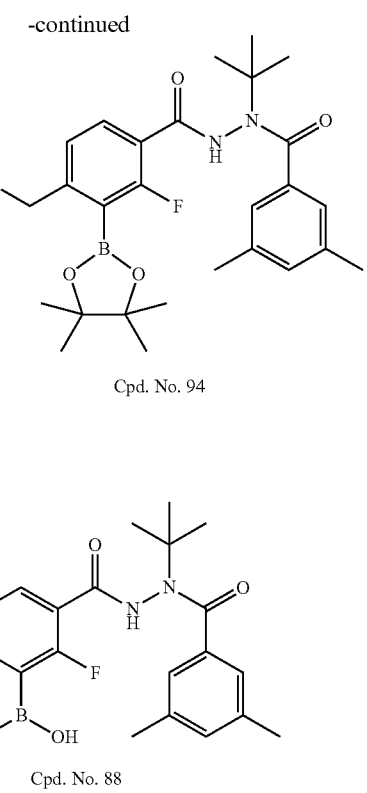

Cpd. No. 94

Cpd. No. 88

To a stirred solution of N-(tert-butyl)-3,5-dimethylbenzohydrazide (0.300 g, 0.83 mmol) in anhydrous DCM (2 mL) was added TEA (0.17 mL, 1.25 mmol) under argon. The reaction mixture is cooled on an ice water bath. To this the above prepared acid chloride (SKC-10-019) was added and stirred the mixture for few minutes LCMS after 5 minutes showed a major peak at 4.02 min. with the expected product mass of 513 (M+1), a minor peak at 2.98 with a mass corresponds to the corresponding boronic acid mass of 431 (M+1) and all the starting materials consumed. Removed the solvent under vacuum, adsorbed on silica and purified by column chromatography (RediSep Column, silica 24 g), the Bpin product Cpd. No. 94 eluted first in hexane/EtOAc gradient and later changed the solvent to DCM/MeOH containing 2% NH₄OH to isolate the 2$^{nd}$ product (Cpd. No. 88). The fractions were collected, removed the solvent under vacuum on a rotavapor and finally lyophilized to get Cpd. No. 94 (0.220 g, 52% yield) and Cpd. No. 88 (0.120 g, 34% yield) as a powder. Cpd. No. 94: ¹H NMR (400 MHz, DMSO) δ 10.58 (s, 1H), 7.05 (dd, J=26.3, 13.0 Hz, 4H), 6.86 (t, J=7.5 Hz, 1H), 4.41 (s, 2H), 3.21 (s, 3H), 2.24 (s, 6H), 1.47 (s, 9H), 1.29 (s, 12H) ¹H NMR (400 MHz, DMSO+2 drops of 120) δ 7.03 (dd, J=24.9, 10.3 Hz, 4H), 6.84 (t, J=7.5 Hz, 1H), 4.39 (s, 2H), 3.19 (s, 3H), 2.22 (s, 6H), 1.46 (s, 9H), 1.27 (s, 12H). Cpd. No. 88: ¹H NMR (400 MHz, DMSO) δ 10.49 (s, 1H), 8.22 (s, 2H), 7.14-6.89 (m, 4H), 6.72 (t, J=7.5 Hz, 1H), 4.38 (s, 2H), 3.23 (s, 3H), 2.24 (s, 6H), 1.48 (s, 9H).

(R)—N'-(3,5-dimethylbenzoyl)-N'-(2,2-dimethyl-pentan-3-yl)-2-fluoro-4-(methoxymethyl)-3-(4,4,5,5-tetramethyl-1,3,2-dioxaborolan-2-yl)benzohydrazide (Cpd. No. 87) and (R)-(3-(2-(3,5-dimethylbenzoyl)-2-(2,2-dimethylpentan-3-yl) hydrazine-1-carbonyl)-2-fluoro-6-(methoxymethyl)phenyl)boronic acid (Cpd. No 86)

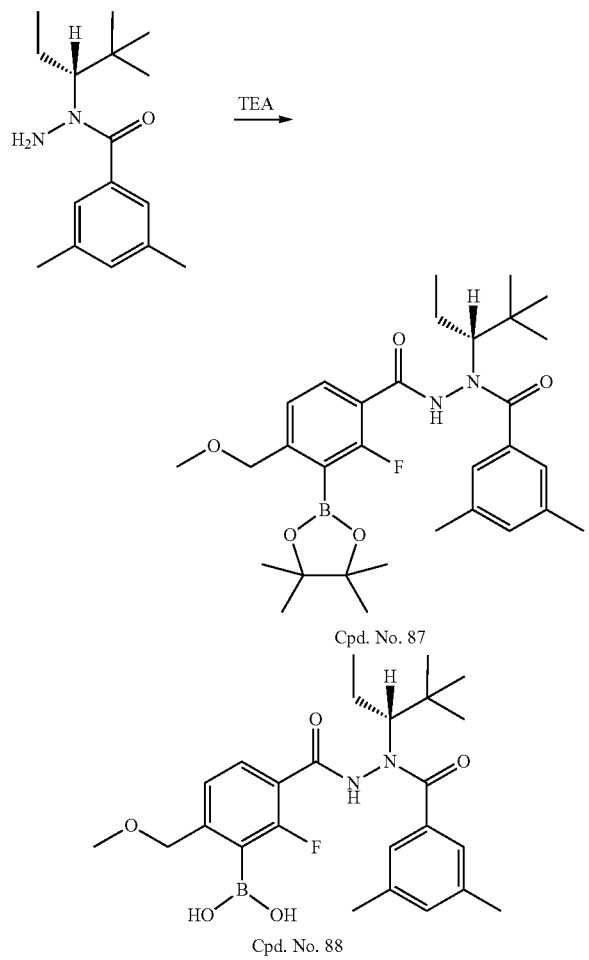

Following the above procedure, mixed together (R)—N-(2,2-dimethylpentan-3-yl)-3,5-dimethylbenzohydrazide (0.254 g, 0.97 mmol, >96% ee), TEA (0.202 mL, 1.45 mmol) in DCM (2 mL) followed by the acid chloride, SKC-10-017 (0.350 g, 1.07 mmol) and stirred for 10 minutes, finally purified using column chromatography to get Cpd. No. 87 (0.070 g) and Cpd No. 86 (0.100 g) after a 2$^{nd}$ purification on RedeisepC18 column (water/acetonitrile, with 0.1% Formic acid) as solvent mixture Cpd. No. 87: $^1$H NMR (400 MHz, DMSO) δ 10.36 (d, J=60.2 Hz, 1H), 7.20-6.92 (m, 4H), 6.64 (t, J=7.4 Hz, 1H), 4.48-4.20 (m, 3H), 3.21 (s, 3H), 2.24 (s, 6H), 1.75-1.50 (m, 2H), 129 (s, 12H), 1.04-0.84 (m, 12H). $^1$H NMR (400 MHz, DMSO+D$_2$O) δ 7.13-6.94 (m, 4H), 6.63 (t, J=7.3 Hz, 1H), 4.44-4.00 (m, 3H), 3.18 (s, 3H), 2.22 (s, 6H), 1.68-1.51 (m, 2H), 1.28 (d, J=12.5 Hz, 12H), 1.03-0.81 (m, 12H). Cpd. No. 86: $^1$H NMR (400 MHz, DMSO) δ 10.29 (d, J=54.2 Hz, 1H), 8.21 (d, J=23.6 Hz, 2H), 7.22-6.92 (m, 4H), 6.54 (dd, J=13.1, 5.7 Hz, 1H), 4.43-4.34 (m, 3H), 3.22 (s, 3H), 2.25 (s, 6H), 1.76-1.38 (m, 2H), 1.09-0.95 (m, 12H). $^1$H NMR (400 MHz, DMSO+2 drops of D$_2$O) δ 7.14-6.86 (m, 4H), 6.55 (t, J=7.5 Hz, 1H), 4.44-4.15 (m, 3H), 3.20 (s, 3H), 2.23 (s, 6H), 1.68-1.48 (m, 2H), 1.06-0.91 (m, 12H).

Example 16

Synthesis of (R)-(4-(2-(3,5-dimethylbenzoyl)-2-(2,2-dimethylpentan-3-yl)hydrazine-1-carbonyl)-3-fluorophenyl)boronic acid (Cpd. No. 85)

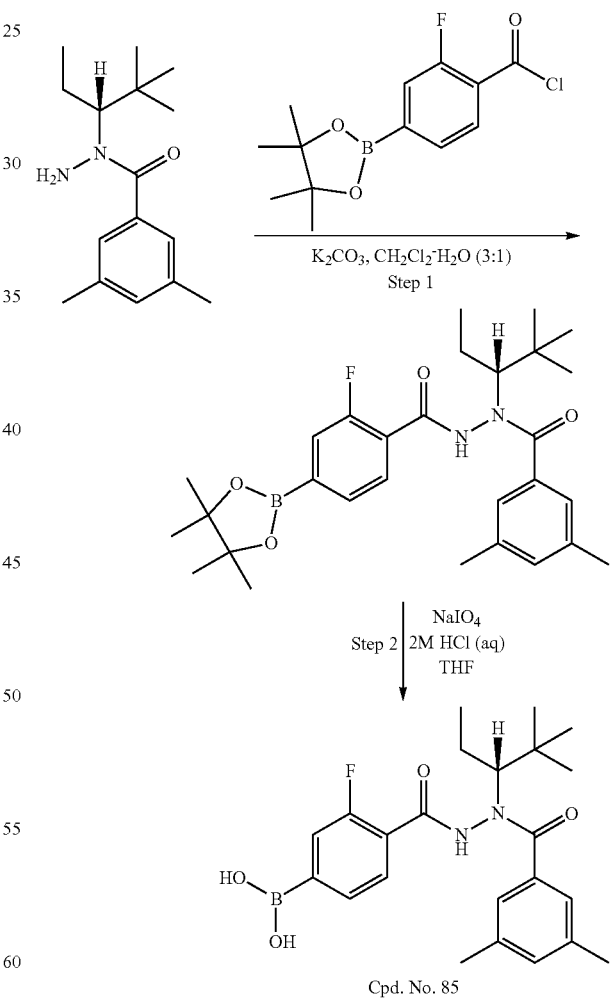

Step 1

In a 25 mL round bottom flask equipped with a magnetic stir bar were added (R)—N-(2,2-dimethylpentan-3-yl)-3,5- dimethylbenzohydrazide (1.317 g, 5.02 mmol) in 7 mL CH$_2$Cl$_2$ and a solution of potassium carbonate (I 388 g, 10.04 mmol) in distilled water (4 mL) were cooled in an ice bath at 0-4° C. and stirred for 10 min. The 2-fluoro-4-(4,4,5,5-tetramethyl-1,3,2-dioxaborolan-2-yl)benzoyl chloride (1.714 g, 6.02 mmol) was added as a solution in 3.5 mL dichloromethane. The reaction was stirred at 0-4° C. for 30 min., the ice bath was removed and the mixture was stirred for 16 h at room temperature. The reaction was analyzed by LCMS and shows the reaction was complete. The organic layer was separated using a Biotage phase separator column and was transferred to a 40 g Redisep SiO$_2$ column on the ISCO HPLC system. The compound was eluted with 0-100% EtOAc—hexanes and then with 10% MeOH—CH$_2$Cl$_2$. The desired fractions were combined and concentrated on a rotary evaporator to give the desired compound as an off-white foam (1.518 g, 59% yield). MS (ESI) calcd for C$_{29}$H$_{40}$BFN$_2$O$_4$ ([M+H]$^+$) 511, found 511.

Step 2

A solution of ((R)—N'-(3,5-dimethylbenzoyl)-N'-(2,2-dimethylpentan-3-yl)-2-fluoro-4-(4,4,5,5-tetramethyl-1,3,2-dioxaborolan-2-yl)benzohydrazide (1.518 g, 2.97 mmol) in THF (24 mL) and water (6 mL) was treated with sodium periodate (2.148 g, 10.04 mmol) and HCl (2.0 M) (3.77 ml, 7.53 mmol) and the resulting yellow mixture was stirred at room temperature for 16 h. The mixture was filtered and the solids were washed with EtOAc. The filtrate was diluted with 10 ml H$_2$O and extracted with EtOAc (2×20 mL). The combined organic layers were dried over MgSO$_4$ filtered and concentrated on a rotary evaporator. The resulting residue was eluted with 0-100% EtOAc—hexanes and then with 10% MeOH—CH$_2$Cl$_2$ on an ISCO HPLC system. The desired fractions were combined and concentrated under reduced pressure on a rotary evaporator to afford Cpd. No. 85 as a white powder (1.25 g, 58% yield). $^1$H NMR (400 MHz, DMSO) δ 10.47-10.30 (d, 1H), 8.33 (s, 2H), 7.57-7.49 (m, 2H), 7.17-7.00 (m, 3H), 6.63-6.60 (t, 1H), 4.44-4.24 (d, 1H), 2.26 (s, 6H), 1.66-1.46 (br m, 2H), 1.11-0.96 (m, 12H); MS (ESI) calcd for C$_{23}$H$_{30}$BFN$_2$O$_4$ ([M+H]$^+$) 429, found 429.

Example 17

Synthesis of N'-(2,2-dimethyl-1-phenylpropyl)-N'-(3,5-dimethylbenzoyl)-1-hydroxy-6-methyl-3,4-dihydro-1H-benzo[c][1,5,2]dioxaborepine-7-carbohydrazide (Cpd. No. 83)

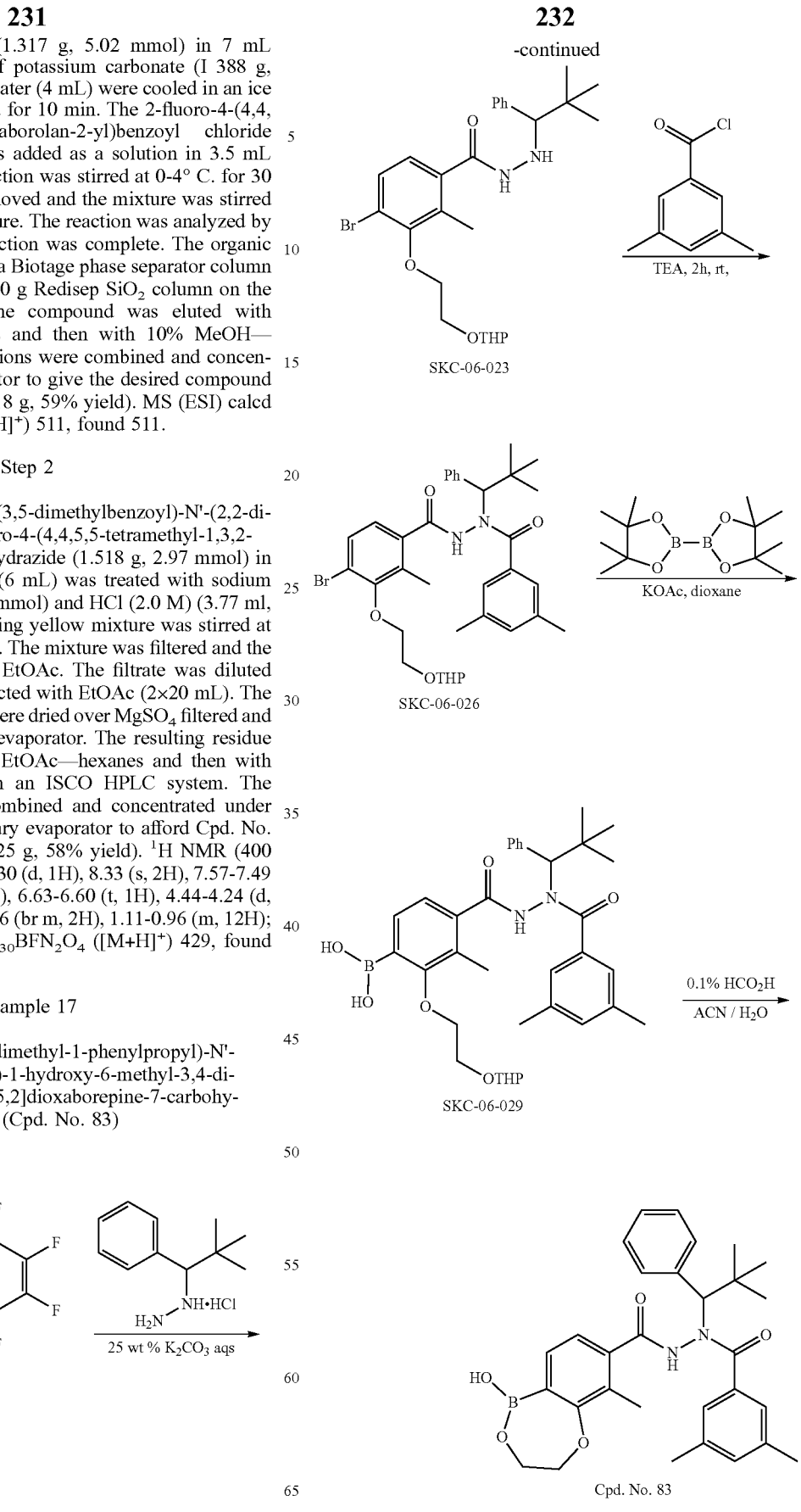

233

4-Bromo-N'-(2,2-dimethyl-1-phenylpropyl)-2-methyl-3-(2 ((tetrahydro-2H-pyran-2-yl)oxy)ethoxy)benzohydrazide

234

4-Bromo-N'-(2,2-dimethyl-1-phenylpropyl)-N'-(3,5-dimethylbenzoyl)-2-methyl-3-(2-((tetrahydro-2H-pyran-2-yl)oxy)ethoxy)benzohydrazide

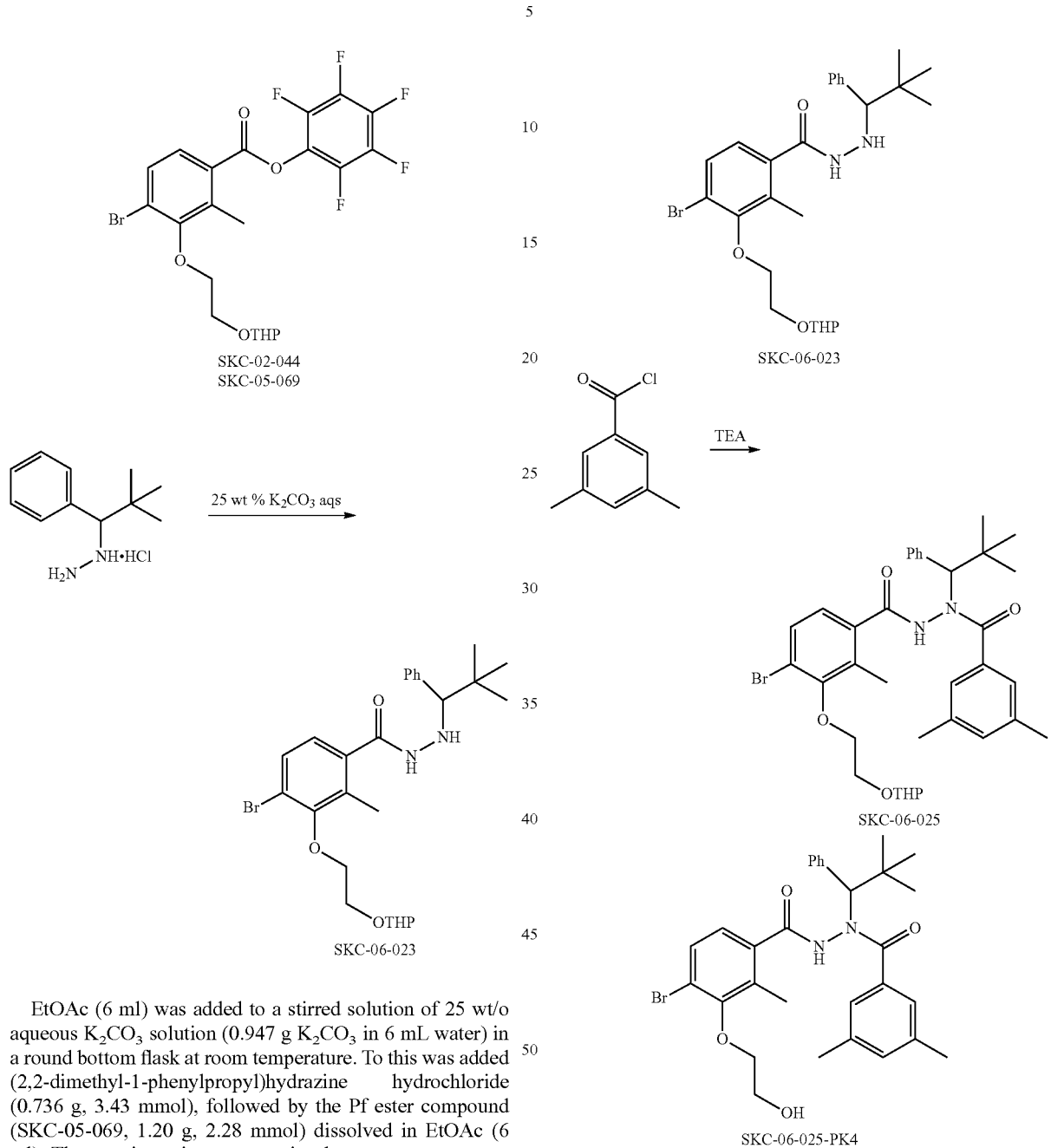

EtOAc (6 ml) was added to a stirred solution of 25 wt/o aqueous $K_2CO_3$ solution (0.947 g $K_2CO_3$ in 6 mL water) in a round bottom flask at room temperature. To this was added (2,2-dimethyl-1-phenylpropyl)hydrazine hydrochloride (0.736 g, 3.43 mmol), followed by the Pf ester compound (SKC-05-069, 1.20 g, 2.28 mmol) dissolved in EtOAc (6 ml). The reaction mixture was stirred at room temperature overnight. LCMS showed a major peak at 4.77 with a mass of 521.14. After aqs work up and extraction with EtOAc, the organic fractions dried over anhydrous $MgSO_4$, filtered and remove dteh solvent on a rotavapor under vacuum. Finally purified by column chromatography using RediSep Column (silica 40 g. hexane/EtOAc solvent gradient) and isolated the expected product in 1.15 g SKC-06-023 (1.15 g, 97% yield) $^1$H NMR (400 MHz, DMSO) δ 9.43 (d, J=58 Hz, 1H), 7.54-7.13 (m, 6H), 6.67 (d, J=8.2 Hz, 1H), 5.39 (dd, J=5.5, 4.3 Hz, 1H), 4.78-4.46 (m, 1H), 3.97-3.59 (m, 6H), 3.44 (dd, J=10.6, 5.4 Hz, 1H), 1.96 (s, 3H), 1.78-1.38 (m, 7H), 1.24 (s, 1H), 0.93 (s, 9H).

To a solution of SKC-06-023 (0.600 g, 1.16 mmol) in 3 mL DCM was added the acid chloride (0.195 g, 1.16 mmol). The solution became clear. TEA (0.161 mL, 1.16 mmol) was added drop wise, and the reaction mixture was stirred under argon at room temperature overnight. LCMS showed a peak with the expected product mass of 651.09 (M+1) and another one with a mass of 569.01 The reaction mixture was adsorbed on silica gel and purified using an ISCO system (RediSep Column, silica 24 g, hexane/EtOAc gradient). The product eluted with ~30% EtOAc in hexane to give 0.230 g (30% yield) of the expected product SKC-06-025. Compound SKC-06-025-peak4 eluted with ~40% EtOAc in hexane and was characterized as the 2-hydroxyethoxy derivative (0.450 g, 69% yield). The reaction was repeated and the purification was done on RediSep Column (Al$_2$O$_3$ pH=7, 24 g) and isolated the expected product (46% yield). Deprotection of the THP group is not observed in this case. $^1$H NMR of SKC-06-025; (400 MHz, DMSO) δ 10.67 (s, 1H), 7.48 (dd, J=7.4, 3.7 Hz, 3H), 7.36-7.19 (m, 4H), 7.14 (s, 2H), 7.01 (s, 1H), 6.66 (dd, J=8.3, 3.9 Hz, 1H), 6.14 (d, J=5.4 Hz, 1H), 5.77 (s, 1H), 4.73-4.53 (m, 2H), 3.97-3.59 (m, 6H), 3.52-3.38 (m, 2H), 2.24 (s, 6H), 1.78-1.42 (m, 9H), 1.35 (s, 3H), 1.08 (s, 9H). $^1$H NMR of SKC-06-025 PK4; (400 MHz, DMSO) δ 10.67 (s, 1H), 7.57-7.43 (m, 3H), 7.37-7.25 (m, 3H), 7.15 (s, 2H), 7.04 (s, 1H), 6.64 (d, J=8.3 Hz, 1H), 5.77 (br s, 1H), 4.85 (s, 1H), 3.68 (dd, J=24.1, 4.7 Hz, 4H), 2.24 (s, 6H), 1.37 (s, 4H), 1.08 (s, 10H).

(4-2-(2,2-dimethyl-1-phenylpropyl)-2-(3,5-dimethyl-benzoyl)hydrazine-1-carbonyl-3 methyl-2-(2-((tetra-hydro-2H-pyran-2-yl)oxy)ethoxy)phenyl)boronic acid red to dark brown. The reaction stopped in 10 min. LCMS showed a major peak at 5.35 with the expected product mass of the Bpinlated compound (697.32, M+1) and a minor peak at 4.80 with a mass of 571.34 corresponds to the side product without Boron attached. Cooled the reaction mixture, filtered and removed the solvent under vacuum. The crude mixture was adsorbed on neutral alumina and purified using RediSep column (Al$_2$O$_3$ pH=7, 24 g). The side product eluted with ~15% EtOAc in hexane and the major product eluted with 90% EtOAc in hexane and obtained 0.041 g of the title compound SKC-09-029. It seems the Bpin got hydrolyzed to boronic acid (based on LCMS: 615.24 M+1). Run the same column again in MeOH/DCM gradient and isolated another 0.196 g of the boronic acid derivative (SKC-06-029, 0.237 g total, 61% yield). LCMS: 615.24 (M+1). Used as such for the next step.

N'-2,2-dimethyl-1-phenylpropyl)-N'-(3,5-dimethyl-benzoyl)-1-hydroxy-6-methyl-3,4-dihydro-1H-benzo[c][1,5,2]dioxaborepine-7-carbohydrazide

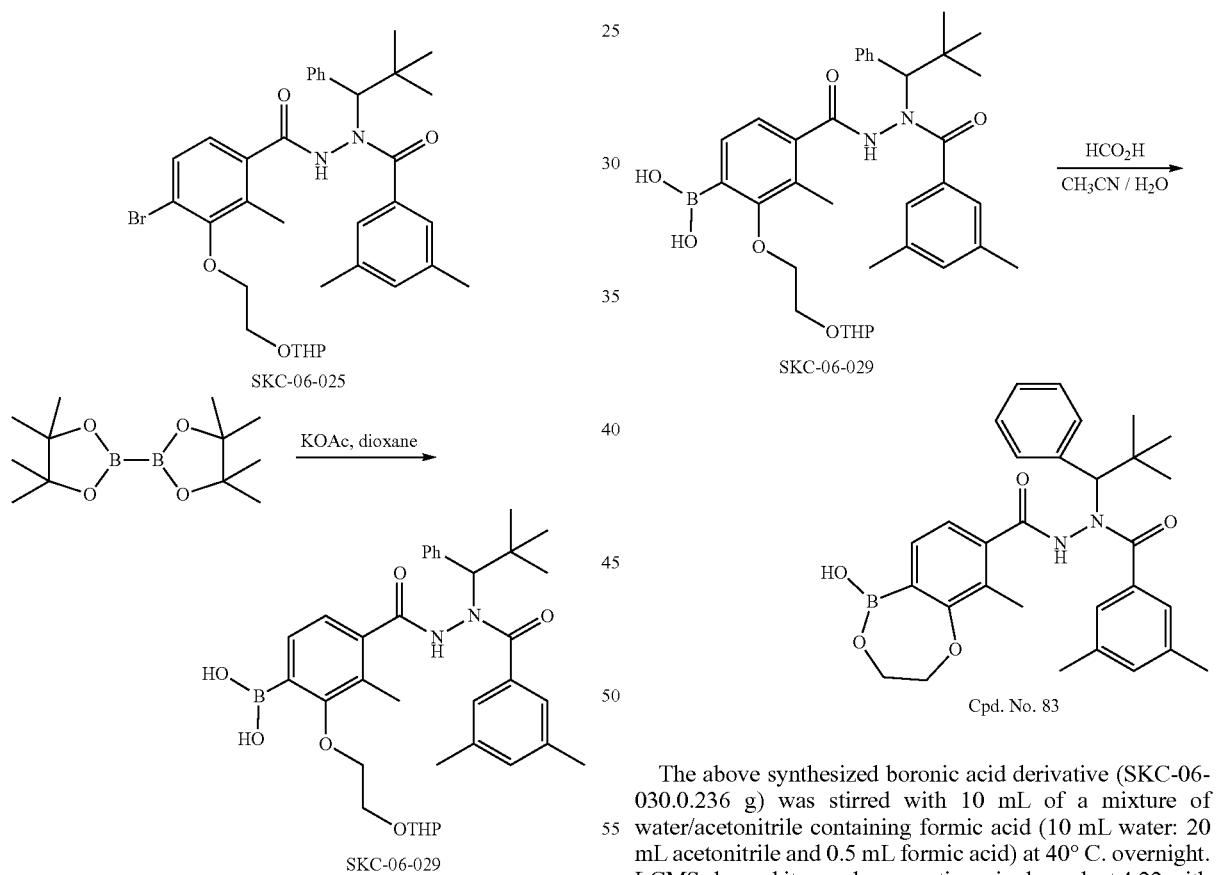

To a solution of SKC-06-025 (0.410 g, 0.63 mmol) in 1,4-dioxane (2 mL) were added KOAc (0.185 g, 1.88 mmol), Pin$_2$B$_2$ (0.240 g, 0.94 mmol). The mixture was evacuated and backfilled with argon, this process repeated three times. PdCl$_2$[dppf].DCM adduct (0.015 g, 0.02 mmol) was added. The RM was quickly evaluated and backfilled with argon three times total and the reaction was stirred and set to heat to 80° C. Accidentally, the temperature became 190° C. and the reaction mixture turned the color from light The above synthesized boronic acid derivative (SKC-06-030.0.236 g) was stirred with 10 mL of a mixture of water/acetonitrile containing formic acid (10 mL water: 20 mL acetonitrile and 0.5 mL formic acid) at 40° C. overnight. LCMS showed it as a clean reaction, single peak at 4.22 with the expected product mass of 515.28 (M+1). The solvent was removed and the residue was purified using RediSep column (Al$_2$O$_3$ pH=7, 24 g, dichloromethane/MeOH solvent gradient). The product eluted with ~7% MeOH in DCM mixture. After drying the fractions, Cpd. No 83 (0.140 g, 71% yield) was isolated as a solid. $^1$H NMR (400 MHz, DMSO) δ 10.63 (s, 1H), 8.37 (s, 1H), 7.60 (d, J=7.9 Hz, 1H), 7.55-6.78 (m, 8H), 6.44 (d, J=7.9 Hz, 1H), 5.76 (s, 1H), 4.24 (d. J=4.4 Hz, 3H), 4.08 (d. J=4.4 Hz, 2H), 2.25 (s, 6H), 1.26 (s, 3H), 1.08 (d, J=12.0 Hz, 9H).

Example 18

In Vitro Activity

Representative Compounds of the Disclosure were tested for biological activity in an in vitro gene switch assay (Tables 1 and 1A). Gene switch assays are disclosed, e.g., in U.S. Pat. Nos. 8,076,517; 7,456,315; 7,304,161, and 6,258,603.

Stable Cell-Line Production

CHO-K1 cells were stably transfected with a plasmid (RS-1, FIG. 1) coding for firefly Luciferase (fLUC) under the control of the RheoSwitch® resulting in the stable cell line CHO-K1_RS-1 A master cell bank was created containing approximately 100 vials at $5 \times 10^6$ cells per vial. One vial of CHO-K1_RS-1 was thawed and cultured for two weeks prior to each in vitro potency screening. The nucleic acid sequence of RS-1 showing the location of the components is presented in FIGS. 2A-2E Potency Screen Twenty-four (24) hours prior to treatment with the control and test compounds the CHO-K1_RS-1 cells were seeded into white-opaque 384-well cell culture plates at 3,600 cells per well in 30 µl of culture medium. The cells were incubated in a humidified $CO_2$ incubator at 37° C. until compound treatment.

Compounds were prepared at 25 mM in 100% dry DMSO and stored at room temperature in sealed 1 ml tubes prior to subsequent dilution and assay. On the day of cell treatment the tubes containing the control and test compounds were sorted and the ligands transferred to a 96-well polypropylene plate for subsequent dilution. The compounds were diluted in 100% dry DMSO in an 8-point, 10-fold dilution series ranging from 25 mM to 2.5 nM using the Biomek FX automated liquid handler.

The diluted compounds were then transferred to each well of 384-well polypropylene plate in quadruplicate resulting in a single 384-well plate with four replicates of each compound dilution in a different quadrant of the plate. Each well on the 384-well plate received 20 µl of diluted compound. The 384-well plates containing diluted compound and the plates containing cells in culture were loaded onto the Biomek FX and 30 nl of compound was delivered to each well containing cells using a 384-pin V&P Scientific Pin Tool. The resulting 1000-fold dilution (30 nl to 30 µl) generated a final dosing range of 25 µM to 2.5 µM in 0.1% DMSO. Two replicate plates were produced to supply a dedicated plate for the Luciferase expression assay and the APH cell viability assay.

The cells were incubated with the compound for 24 hours in a humidified $CO_2$ incubator at 37° C. Following incubation, the cells were assayed for Luciferase expression (fLUC assay) using the Steady Glo assay from Promega. Cells were equilibrated to room temperature for 15 minutes prior to reagent addition. Thirty micro liters (30 µl) of assay reagent was added to each well of the 384-well plate using the Biomek FX. The reagent was incubated with the cells for 10-120 minutes prior to reading on a Molecular Devices Spectramax L luminometer. The assay reagents were prepared as per the manufacturer's instructions.

Data Analysis

The Luciferase expression data was normalized to the baseline signal from cells treated with DMSO alone. The ratio of signal from treated cells to vehicle-treated cells was plotted and non-linear regress was performed using Graph Pad Prism software. $EC_{50}$, $(\log)EC_{50}$ and Hill slope data was generated. Reporter gene expression, e.g., luciferase expression, serves as a proxy for the expression of a gene of interest See, e.g., US 2009/0123441 and WO 2011/119773

TABLE 1

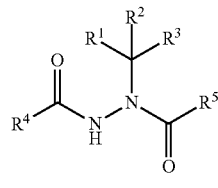

I

| Cpd. No. | $R^1/R^2/R^3$ config. | $R^4$ | $R^5$ | $R^1$ | $R^2$ | $R^3$ | fLUC assay $EC_{50}$ (µM) |
|---|---|---|---|---|---|---|---|
| 1 | achiral | 2-$CH_3$, 3-$B(OH)_2$—Ph | 3,5-di-$CH_3$—Ph | Me | Me | Me | 0.872 (2) |
| 2 | R | 2-$CH_3$, 3-$B(OH)_2$—Ph | 3,5-di-$CH_3$—Ph | nPr | H | tBu | 0.78 (4) |
| 3 | achiral | 2-Cl, 3-$B(OH)_2$—Ph | 3,5-di-$CH_3$—Ph | Me | Me | Me | 1.66 (2) |
| 4 | R | 2-Cl, 3-$B(OH)_2$—Ph | 3,5-di-$CH_3$—Ph | nPr | H | tBu | 0.066 (2) |
| 5 | achiral | 2-F, 3-$B(OH)_2$—Ph | 3,5-di-$CH_3$—Ph | Me | Me | Me | 0.3 |
| 6 | R | 2-F, 3-$B(OH)_2$—Ph | 3,5-di-$CH_3$—Ph | nPr | H | tBu | 0.09267 |
| 7 | achiral | 4-$B(OH)_2$—Ph | 3,5-di-$CH_3$—Ph | Me | Me | Me | 1.01 (2) |
| 8 | R | 4-$B(OH)_2$—Ph | 3,5-di-$CH_3$—Ph | nPr | H | tBu | 0.103 (2) |
| 9 | achiral | 2-$CH_3$, 4-$B(OH)_2$—Ph | 3,5-di-$CH_3$—Ph | Me | Me | Me | 1.421 |
| 10 | R | 2-iPr-4-$B(OH)_2$—Ph | 3,5-di-$CH_3$—Ph | nPr | H | tBu | 1.243 |
| 11 | achiral | 2-iPr-4-$B(OH)_2$—Ph | 3,5-di-$CH_3$—Ph | Me | Me | Me | 14.1 |
| 12 | achiral | 2-F, 4-$B(OH)_2$—Ph | 3,5-di-$CH_3$—Ph | Me | Me | Me | 0.2714 |
| 13 | R | 2-F, 4-$B(OH)_2$—Ph | 3,5-di-$CH_3$—Ph | nPr | H | tBu | 0.064 (3) |
| 14 | R | 2-F-4-$B(OH)_2$—Ph | 3,5-di-$CH_3$—Ph | tBu | H | $CH_2CH_2CH_2F$ | 0.203 |
| 15 | R | 2-F-4-$B(OH)_2$—Ph | 3,5-di-$CD_3$—Ph | Et | H | tBu | 0.05227 |
| 16 | R | 2-F-4-$B(OH)_2$—Ph | 4-N-3,5-di-CH3—Ph | Et | H | tBu | 7864 |
| 17 | R | 2-F-4-$B(OH)_2$—Ph | 2,6-N-3,5-di-CH3—Ph | Et | H | tBu | 9.302 |
| 18 | racemic | 2-F-4-$B(OH)_2$—Ph | 3,5-di-$CH_3$—Ph | Et | H | Ph | 0.2033 |
| 19 | racemic | 2-F-4-$B(OH)_2$—Ph | 3,5-di-$CD_3$—Ph | Et | H | Ph | 0.2581 |
| 20 | R | 2-Cl-4-$B(OH)_2$—Ph | 3,5-di-$CH_3$—Ph | Et | H | tBu | 0.1832 |
| 21 | achiral | 2-Cl-4-$B(OH)_2$—Ph | 3,5-di-$CH_3$—Ph | Me | Me | Me | 1.627 |

TABLE 1-continued

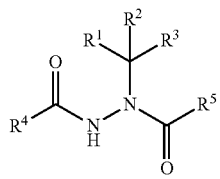

I

| Cpd. No. | R¹/R²/R³ config. | R⁴ | R⁵ | R¹ | R² | R³ | fLUC assay EC₅₀ (μM) |
|---|---|---|---|---|---|---|---|
| 22 | R | 3-F-4-B(OH)₂—Ph | 3,5-di-CH₃—Ph | nPr | H | tBu | 0.1051 |
| 23 | achiral | 3-F-4-B(OH)₂—Ph | 3,5-di-CH₃—Ph | Me | Me | Me | 1.797 |
| 24 | R | 2,6,-di-F-4-B(OH)₂—Ph | 3,5-di-CH₃—Ph | nPr | H | tBu | 0.08573 |
| 25 | achiral | 2,6,-di-F-4-B(OH)₂—Ph | 3,5-di-CH₃—Ph | Me | Me | Me | 0.7956 |
| 26 | R | 2-CH₃, 3-OCH₂CH₂OCH₃, 4-B(OH)₂—Ph | 3,5-di-CH₃—Ph | Et | H | tBu | 1.67 (3) |
| 27 | R | 2-CH₃, 3-OCH₃, 4-CH₂CH₂CH₂B(OH)₂—Ph | 3,5-CH₃—Ph | nPr | H | tBu | 0.27 (5) |
| 28 | R | 2-CH₃, 3-OCHF₂, 4-CH₂CH₂CH₂B(OH)₂—Ph | 3,5-di-CH₃—Ph | nPr | H | tBu | 0.0577 (7) |
| 29 | R | 2-CH₃-3-OCH₃-4-CH₂CH₂CH₂Bpin-Ph | 3,5-di-CH₃—Ph | nPr | H | tBu | 0.24/13 |
| 30 | R | 2-CH₃-3-OCHF₂-4-CH₂CH₂CH₂Bpin-Ph | 3,5-di-CH₃—Ph | nPr | H | tBu | 0.0508 (3) |
| 31 | racemic | 2-CH₃, 3-OCH₃—Ph | 2-B(OH)₂—Ph | Et | H | tBu | 25 |
| 32 | racemic | 2-CH₃, 3-OCH₃—Ph | 3-B(OH)₂—Ph | Et | H | tBu | 2.884 |
| 33 | R | 2-CH₃, 3-OCH₃—Ph | 3-CH₃, 5-B(OH)₂—Ph | Et | H | tBu | 0.191 (3) |
| 34 | racemic | 2-CH₃, 3-OCH₃—Ph | 2-F, 5-B(OH)₂—Ph | Et | H | tBu | 25 |
| 35 | racemic | 2-CH₃, 3-OCH₃—Ph | 3-F, 5-B(OH)₂—Ph | Et | H | tBu | 2.595 |
| 36 | racemic | 2-CH₃, 3-OCH₃—Ph | 3-NO₂, 5-B(OH)₂—Ph | Et | H | tBu | >25 |
| 37 | racemic | 2-CH₃, 3-OCH₃—Ph | 3-OCH₃, 5-B(OH)₂—Ph | Et | H | tBu | 2.112 |
| 39 | R | 2-CH₃, 3-OCH₃—Ph | 3-CH₃-5-Bpin-Ph | Et | H | tBu | 0.1684 |
| 40 | achiral | 2-Et, 3-OCH₃—Ph | 4-B(OH)₂—Ph | Me | Me | Me | 5.245 |
| 41 | racemic | 2-CH₃-3-Bpin-Ph | 2-CH₃-3-Bpin-Ph | nPr | H | tBu | ~14 (2) |
| 42 | R | 3-CH₃, 5-B(OH)₂—Ph | 3-CH₃, 5-B(OH)₂—Ph | Et | H | tBu | 25 |
| 43 | achiral | 2-CH₃-3-Bpin-Ph | 3,5-di-CH₃—Ph | Me | Me | Me | 1.42 (2) |
| 44 | racemic | 2-CH₃-3-Bpin-Ph | 3,5-di-CH₃—Ph | nPr | H | tBu | 0.25 (2) |
| 45 | R | 2-CH₃-3-Bpin-Ph | 3,5-di-CH₃—Ph | nPr | H | tBu | 0.122 (2) |
| 46 | racemic | 2-CH₃-3-Bpin-Ph | 3-CH₃-5-Cl—Ph | nPr | H | tBu | 0.24/25 |
| 47 | racemic | 2-CH₃-3-Bpin-Ph | 3,5-di-OCH₃-4-CH₃—Ph | Et | H | tBu | 1.64 (2) |
| 48 | racemic | 2-CH₃-3-Bpin-Ph | 2,5-di-OCH₃—Ph | nPr | H | tBu | 22.2 (2) |
| 49 | racemic | 2-CH₃-3-Bpin-Ph | 2-OH-3-N | nPr | H | tBu | >25 (2) |
| 50 | achiral | 3-B(OH)—OCH₂-4-Ph | 3,5-di-CH₃—Ph | Me | Me | Me | 1.2 (2), 7.5, 25 |
| 51 | racemic | 3-B(OH)—OCH₂-4-Ph | 3,5-di-CH₃—Ph | Et | H | tBu | 0.432 (2) |
| 52 | R | 3-B(OH)—OCH₂-4-Ph | 3,5-di-CH₃—Ph | Et | H | tBu | 0.287 (2) |
| 53 | S | 3-B(OH)—OCH₂-4-Ph | 3,5-di-CH₃—Ph | Et | H | tBu | 1.0 (2) |
| 54 | S | 3-B(OH)—OCH₂-4-Ph | 3,5-di-CD₃—Ph | Et | H | tBu | 9.1 (2) |
| 55 | achiral | 3-B(OH)—OCH₂-4-Ph | 2,6-N-3,5-di-CH₃ | Me | Me | Me | >25 |
| 56 | R | 3-B(OH)—OCH₂-4-Ph | 2,6-N-3,5-di-CH₃ | Et | H | tBu | >25 |
| 57 | achiral | 3-B(OH)—OCH₂-4-Ph | 4-N-3,5-di-CH₃ | Me | Me | Me | >25 |
| 58 | achiral | 2-F, 3-B(OH)—OCH₂-4-Ph | 3,5-di-CH₃—Ph | Me | Me | Me | 0.64 (4) |
| 59 | R | 2-F, 3-B(OH)—OCH₂-4-Ph | 3,5-di-CH₃—Ph | Et | H | tBu | 0.108 (3) |
| 60 | R | 2-F, 3-B(OH)—OCH₂-4-Ph | 3,5-di-CD₃—Ph | Et | H | tBu | 0.1227 |
| 61 | S | 2-F, 3-B(OH)—OCH₂-4-Ph | 3,5-di-CH₃—Ph | Et | H | tBu | 5.8 (2) |
| 62 | S | 2-F, 3-B(OH)—OCH₂-4-Ph | 3,5-di-CD₃—Ph | Et | H | tBu | 0.803 (2) |
| 64 | achiral | 2-F, 3-B(Bu)OCH₂-4-Ph | Ph | Me | Me | Me | 25/>25 |
| 65 | achiral | 2-F, 3-CH₂OB(OH)-4-Ph | 3,5-di-CH₃—Ph | Me | Me | Me | 3.184 |
| 66 | achiral | 2-F, 3-CH₂OB(OH)-4-Ph | 3,5-di-CD₃—Ph | Me | Me | Me | 3.268 |
| 67 | R | 2-F, 3-CH₂OB(OH)-4-Ph | 3,5-di-CH₃—Ph | Et | H | tBu | 0.309 |
| 69 | achiral | 2-CH₃, 3-OB(OH)CH₂CH₂CH₂-4-Ph | 3,5-di-CH₃—Ph | Me | Me | Me | 0.203 (2) |
| 70 | R | 2-CH₃, 3-OB(OH)CH₂CH₂CH₂-4-Ph | 3,5-di-CH₃—Ph | nPr | H | tBu | 0.0406 (4) |
| 71 | achiral | 2-CH₃, -3-OCH₂CH₂OB(OH)-4-Ph | 3,5-di-CH₃—Ph | H | H | tBu | 0.430 (2) |
| 72 | achiral | 2-CH₃, -3-OCH₂CH₂OB(OH)-4-Ph | 3-CH₃-5-Cl—Ph | H | H | tBu | 0.443 (3) |
| 73 | achiral | 2-CH, -3-OCH₂CH₂OB(OH)-4-Ph | 3,5-di-CH₃—Ph | Me | H | Me | 7.4, >25 |
| 74 | achiral | 2-CH₃, -3-OCH₂CH₂OB(OH)-4-Ph, | 3,5-di-CH₃—Ph | —CH₂CH₂CH₂CH₂— | H | | |
| 75 | achiral | 2-CH₃, -3-OCH₂CH₂OB(OH)-4-Ph | 3,5-di-CH₃—Ph | Me | Me | Me | 0.259 (7) |
| 76 | achiral | 2-CH₃, -3-OCH₂CH₂OB(OH)-4-Ph | 3,5-di-CH₃—Ph | CH₃ | CH₃ | Et | 0.358 (2) |

TABLE 1-continued

| Cpd. No. | R¹/R²/R³ config. | R⁴ | R⁵ | R¹ | R² | R³ | fLUC assay EC$_{50}$ (μM) |
|---|---|---|---|---|---|---|---|
| 77 | achiral | 2-CH₃, -3-OCH₂CH₂OB(OH)-4-Ph | 3,5-di-CD₃—Ph | CH₃ | CH₃ | Et | 0.181 |
| 78 | achiral | 2-CH₃, -3-OCH₂CH₂OB(OH)-4-Ph | 3,5-di-CH₃—Ph | CH₃ | CH₃ | iPr | 0.222 (2) |
| 79 | R | 2-CH₃, -3-OCH₂CH₂OB(OH)-4-Ph | 3,5-di-CH₃—Ph | Et | H | tBu | 0.407 (7) |
| 80 | S | 2-CH₃, -3-OCH₂CH₂OB(OH)-4-Ph | 3,5-di-CH₃—Ph | Et | H | tBu | 0.867 (2) |
| 81 | S | 2-CH₃, -3-OCH₂CH₂OB(OH)-4-Ph | 3,5-di-CD₃—Ph | Et | H | tBu | 0.564 (2) |
| 82 | racemic | 2-CH₃, -3-OCH₂CH₂OB(OH)-4-Ph | 3,5-di-CH₃—Ph | Et | H | CH₂F | 2.61 (2) |
| 83 | racemic | 2-CH₃, -3-OCH₂CH₂OB(OH)-4-Ph | 3,5-di-CH₃—Ph | tBu | H | Ph | 0.0659 (2) |
| 84 | tbd | 2-CH₃, -3-OCH₂CH₂OB(OH)-4-Ph | 3,5-di-CH₃—Ph | tBu | H | Ph | 0.2192 |

The abbreviations used in Table 1 are provided in Table 2.

TABLE 2

| | |
|---|---|
| Me | methyl |
| Et | ethyl |
| nPr | n-propyl |
| tBu | tert-butyl |
| Ph | phenyl |
| Bpin | (pinacol boronate ester group) |
| 4-N-3,5-di-CH3—Ph | (2,6-dimethylpyridin-4-yl group) |
| 2,6-N-3,5-di-CH3—Ph | (4,6-dimethylpyrimidin-2-yl group) |
| 2-OH-3-N | (2-oxo-1,2-dihydropyridin-3-yl group) |
| tbd | compound is a single enantiomer but the configuration has not been determined |

TABLE 1A

| Cpd. No. | Name | fLUC assay EC$_{50}$ (nM) Run 1 | fLUC assay EC$_{50}$ (nM) Run 2 |
|---|---|---|---|
| 85 | (R)-(4-(2-(3,5-dimethylbenzoyl)-2-(2,2-dimethylpentan-3-yl)hydrazine-1-carbonyl)-3-fluorophenyl)boronic acid | 69.35 | 66.56 |
| 86 | (R)-(3-(2-(3,5-dimethylbenzoyl)-2-(2,2-dimethylpentan-3-yl)hydrazine-1-carbonyl)-2-fluoro-6-(methoxymethyl)phenyl)boronic acid | 48.85 | 74.48 |
| 87 | (R)-N'-(3,5-dimethylbenzoyl)-N'-(2,2-dimethylpentan-3-yl)-2-fluoro-4-(methoxymethyl)-3-(4,4,5,5-tetramethyl-1,3,2-dioxaborolan-2-yl)benzohydrazide | 47.60 | 96.41 |
| 88 | (3-(2-(tert-butyl)-2-(3,5-dimethylbenzoyl)hydrazine-1-carbonyl)-2-fluoro-6-(methoxymethyl)phenyl)boronic acid | 667.00 | 839.8 |
| 89 | N'-(2,2-dimethyl-1-phenylpropyl)-N'-(3,5-dimethylbenzoyl)-4-fluoro-1-hydroxy-1,3-dihydrobenzo[c][1,2]oxaborole-5-carbohydrazide | –362.4 | –302.5 |
| 90 | (R)-(3-(2-(3,5-dimethylbenzoyl)-2-(2,2-dimethylpentan-3-yl)hydrazine-1-carbonyl)-6-(ethoxymethyl)-2-fluorophenyl)boronic acid | 388.70 | –266.3 |
| 91 | N'-(tert-butyl)-N'-(3,5-dimethylbenzoyl)-1-hydroxy-6-methyl-1,2,3,4-tetrahydrobenzo[f][1,4,5]oxazaborepine-7-carbohydrazide | 132.40 | 86.92 |
| 92 | (R)-N'-(3,5-dimethylbenzoyl)-N'-(2,2-dimethylpentan-3-yl)-]-hydroxy-6-methyl-1,2,3,4-tetrahydrobenzo[f][1,4,5]oxazaborepine-7-carbohydrazide | 186.90 | 116.5 |
| 93 | potassium (R)-(4-(2-(3,5-dimethylbenzoyl)-2-(2,2-dimethylhexan-3-yl)hydrazine-1-carbonyl)-3-fluorobenyl)trifluoroborate | 66.75 | 122.1 |

TABLE 1A-continued

| Cpd. No. | Name | fLUC assay EC$_{50}$ (nM) | |
|---|---|---|---|
| | | Run 1 | Run 2 |
| 94 | N'-(tert-butyl)-N'-(3,5-dimethylbenzoyl)-2-fluoro-4-(methoxymethyl)-3-(4,4,5,5-tetramethyl-1,3,2-dioxaborolan-2-yl)benzohydrazide | 778.20 | 1651 |

Example 19

Pharmacokinetic (PK) Study

The pharmacokinetics of representative Compounds of the Disclosure (Chart 1) and representative DAHs that do not contain a boron atom (Chart 2) were determined according to the following protocol:

Animal Dosing

Female Sprague Dawley rats were fasted for at least 8 hours (overnight) prior to oral dosing of the compound via gavage (10 mg/kg; vehicle=2 mg/mL of Capryol 90/Triacetin (1:1, v/v); 3 animals/compound) and weighed prior to dosing. The correct volume of the appropriate formulation was administered based on that day's (animal) body weight. Body weight, dose volume, and dosing time was recorded for each animal. Animals were not fed for at least 4 hours following activator ligand administration.

Plasma Collection

Approximately 200 µL/blood sample was collected from the catheter sample points in EDTA tubes at each time point from each animal. The exact time of blood collection was recorded for each animal. Blood samples were held at 4° C. (wet ice) starting immediately after collection and were centrifuged within 15 minutes from the collection for 12 minutes at 2500 rpm. After centrifugation, plasma samples were stored at −80° C. until assay. Sample times were as follows: Day 0: 0, 0.5, 1, 2, 3, 4, 6 and 8 hours; Day 1: 24 hours.

Determination of the Compound in the Plasma

LC-MS/MS Method Liquid chromatography tandem mass spectrometry with protein precipitation method was used to quantify the compound in rat plasma samples collected from all animals dosed with the ligand. Linearity range was from 1 ng/mL to 1000 ng/mL, with correlation coefficient for calibration curves above 0.99 and analyte quantified within ±15% of target at all calibrator concentrations.

Pharmacokinetic (PK) parameters determination.

The following PK parameters of the compound in plasma were calculated using non-compartmental method of Win-Nonlin software, Version 5.3 or higher maximum concentration ($C_{max}$), time of maximum concentration ($T_{max}$), half-life ($t_{1/2}$), area under the curve from time zero to the last sample ($AUC_{0-t}$), and oral clearance.

Statistical Analyses

Descriptive statistics (mean, standard deviation [SD], coefficient of variation [CV %], median, minimum, and maximum) were used to summarize the PK parameters for the compound in all groups (data not shown).

Results and Discussion

The plasma ligand concentration was calculated by extrapolating the area under the curve values for the samples from the standard curve generated by the Analyst® software program. The ng/mL values for the plasma samples representing all the animals were used to generate the pharmacokinetic (PK) parameters. As shown in Table 3, Compounds of the Disclosure have unexpectedly higher $C_{max}$, and $T_{max}$, values, and unexpectedly lower clearance values than the DAHs that do not contain a boron atom.

Chart 1

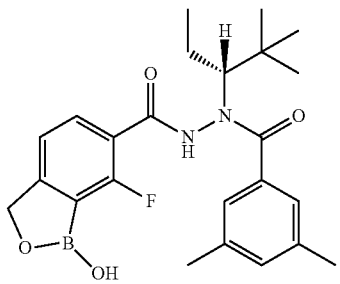

Cpd No. 59

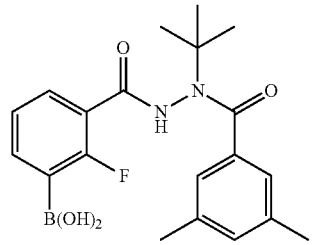

Cpd No. 5

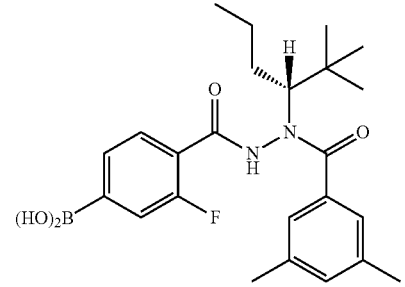

Cpd No. 13

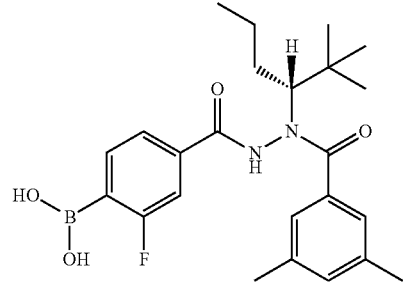

Cpd No. 22

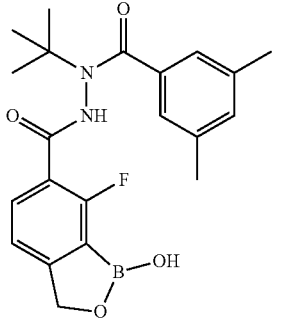

Cpd No. 58

Cpd No. 67
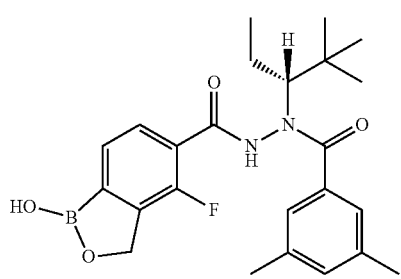

Cpd No. 75
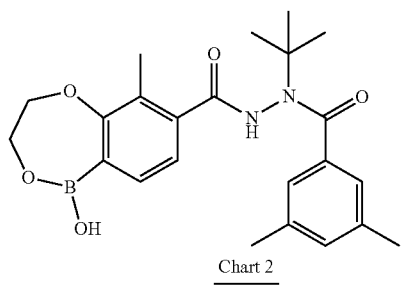

Chart 2

Cpd A
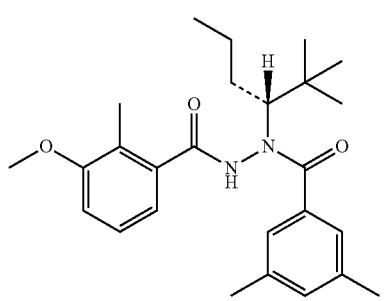

Cpd B
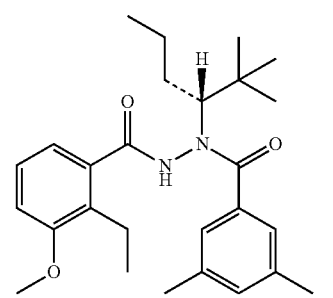

Cpd C
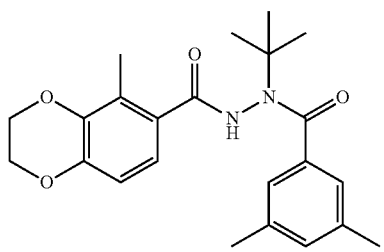

TABLE 3

| Compound | $C_{max}$ (ng/mL) | $T_{max}$ (hr) | $AUC_{0-t}$ (ng · hr/mL) | half-life (hr) | Clearance (mL/hr/kg) |
|---|---|---|---|---|---|
| Cpd. A | 255 | 4 | 773 | 2.1 | 12786 |
| Cpd. B | 116 | 3.7 | 888 | 5.4 | 11030 |
| Cpd. C | 112 | 2.5 | 510 | Not Available | Not Available |

TABLE 3-continued

| Compound | $C_{max}$ (ng/mL) | $T_{max}$ (hr) | $AUC_{0-t}$ (ng · hr/mL) | half-life (hr) | Clearance (mL/hr/kg) |
|---|---|---|---|---|---|
| Cpd. No. 5 | 1893 | 4 | 18782 | 4 | 533 |
| Cpd. No. 13 (Lot #1) | 1415 | 2.7 | 10579 | 3.2 | 938 |
| Cpd. No. 13 (Lot #2) | 7060 | 3.3 | 60407 | 4.3 | 169 |
| Cpd. No. 22 | 2733 | 3.0 | 25001 | 5.6 | 407 |
| Cpd. No. 58 | 2650 | 3.0 | 30837 | 15.4 | 214 |
| Cpd. No. 59 (Lot #1) | 11158 | 5 | 127700 | 5.2 | 84 |
| Cpd. No. 59 (Lot #2) | 18833 | 1.8 | 300721 | 10.0 | 32.3 |
| Cpd. No. 67 | 3320 | 3.0 | 24546 | 5.5 | 398 |
| Cpd. No. 75 | 1280 | 2.3 | 13241 | 11 | 611 |

Example 20

In Vivo Ad-RTS-fLUC Expression in Mice

The fLUC expression following intramuscular (IM) injection of Ad-RTS-fLUC and representative Compounds of the Disclosure by oral gavage in female CD1 mice was determined according to the following protocol:

Compound Formulation

Compounds were formulated at a concentration of 20 mg/mL in Capryol90/Triacetin (1:1, v/v) and orally administered by oral gavage at 100 mg/kg dose.

DNA

Ad-RTS-fLUC (starting concentration of $1.1 \times 10^{12}$ vp/mL) was stored in A195 storage buffer (10 mM Tris, pH 7.4, 0.1 mM EDTA, 1 mM $MgCl_2$, 10 mM Histidine, 75 mM NaCl, 5% sucrose, 0.02% Ps-80, and 0.5% EtOH) (Evans et al., 1997). The routes of administration for Ad-RTS-fLUC in this study were via IM on the right and left gastroc (gastrocnemius) muscle.

Dose Administration

Female CD1 mice were dosed according to the Tables below.

| GOI Construct | | | | | |
|---|---|---|---|---|---|
| | | | Viral Vector | | |
| Group | Animals | N | DNA Construct | Dose & Dosing Volume (uL) | Route of delivery | Day of Dosing |
| 1 | Mice/CD1 | 5 | Ad-RTS-fLUC | 1e10vp (Bilateral injection of 50 ul each) | IM | D −1 |
| 2 | Mice/CD1 | 5 | Ad-RTS-fLUC | 1e10vp (Bilateral injection of 50 ul each) | IM | D −1 |
| 3 | Mice/CD1 | 5 | Ad-RTS-fLUC | 1e10vp (Bilateral injection of 50 ul each) | IM | D −1 |
| 4 | Mice/CD1 | 5 | Ad-RTS-fLUC | 1e10vp (Bilateral injection of 50 ul each) | IM | D −1 |
| 5 | Mice/CD1 | 5 | Ad-RTS-fLUC | 1e10vp (Bilateral injection of 50 ul each) | IM | D −1 |

Compounds of the Disclosure (Oral Gavage)

| Group | Compound | Dose Volume (mL/kg) | Dose (mg/kg) | Ligand Concentration (mg/mL) | Ligand Dosing Day | IVIS Imaging Day |
|---|---|---|---|---|---|---|
| 1 | Cpd. No. 13 | 5 | 100 | 20 | Day 0 | Day 0 (6 hrs) Day 1 (24 hrs) Day 2 (48 hrs) |
| 2 | Cpd. No. 67 | 5 | 100 | 20 | Day 0 | Day 0 (6 hrs) Day 1 (24 hrs) Day 2 (48 hrs) |
| 3 | Cpd. No. 85 | 5 | 100 | 20 | Day 0 | Day 0 (6 hrs) Day 1 (24 hrs) Day 2 (48 hrs) |
| 4 | Cpd. No. 59 | 5 | 100 | 20 | Day 0 | Day 0 (6 hrs) Day 1 (24 hrs) Day 2 (48 hrs) |
| 5 | Cpd. No. 86 | 5 | 100 | 20 | Day 0 | Day 0 (6 hrs) Day 1 (24 hrs) Day 2 (48 hrs) |

In Vivo Study Overview

On Study Day −1, mice received a dose of $1\times10^{10}$ vp (100.1 μl total) of Ad-RTS-fLUC IM on the right and left gastroc muscles with 50 l each.

A single administration of the test compound was administered by oral gavage based upon body weight to the designated groups starting 24 hrs after the last set of Ad-RTS-fLUC injection on Day 0.

IVIS

IVIS was performed 6, 24, and 48 hours after the last gavage/dosing on Day 0. Once the animal was properly anesthetized, 150 mg/kg of luciferin (diluted in PBS) was administered by IP mute. The animals were placed in a nosecone on the IVIS surface. The imaging parameters and calibration curve were determined empirically (Caliper Life Sciences Living Image Software). Images were acquired within approximately 15 minutes post-injection. After imaging, animals were returned to their cage and monitored until completely recovered from anesthesia.

Data analysis and image reconstruction were performed using the Living Image Software Version 4.0. Luminescent levels were quantified by measuring individual region of interest (ROI) markers manually drawn around the area of interest. These markers isolate the ROI, filtering out any unwanted level of expression. Using the software correction tools, background noise and pixilated bleed over was removed to reduce variability. Surface radiance levels (light intensity emitted from the tissue surface) were measured by the amount of photon particles per second (p/sec) emitted by the ROT. These values are expressed as Max Radiance or Total Flux.

Statistical Analyses

The IVIS data was summarized and compared among the treatment groups to evaluate fLUC inducibility. The results are presented in FIG. 3. The data show that representative Compounds of the Disclosure activate the Rheoswitch in vivo. The placebo data depicted in FIG. 3 were taken from a similar study.

It is to be understood that the foregoing described embodiments and exemplifications are not intended to be limiting in any respect to the scope of the disclosure, and that the claims presented herein are intended to encompass all embodiments and exemplifications whether or not explicitly presented herein.

All patents and publications cited herein are fully incorporated by reference in their entirety.

What is claimed is:

1. A method regulating gene expression of a gene of interest in a host cell, the method comprising contacting the host cell with a compound having Formula I-A:

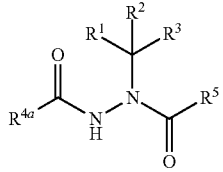

I-A wherein:
R$^1$ and R$^2$ are each independently selected from the group consisting of hydrogen, optionally substituted alkyl, and haloalkyl; or
R$^1$ and R$^2$ taken together with the carbon atom to which they are attached form a 4- to 8-membered cycloalkyl;
R$^3$ is selected from the group consisting of hydrogen, optionally substituted alkyl, haloalkyl, optionally substituted cycloalkyl, optionally substituted alkenyl, optionally substituted aryl, and optionally substituted heteroaryl;
R$^{4a}$ is selected from the group consisting of:

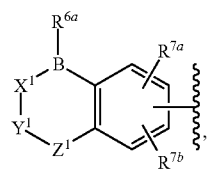

R$^4$-1

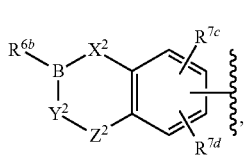

R$^4$-2

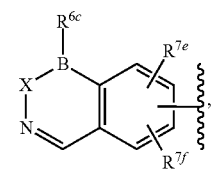

R$^4$-3

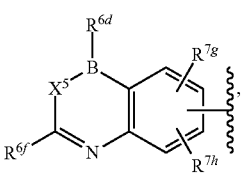

R$^4$-4

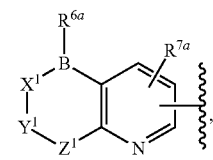

R$^4$-8

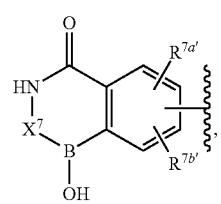

R$^4$-9

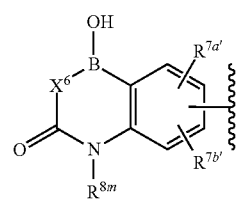

R$^4$-10

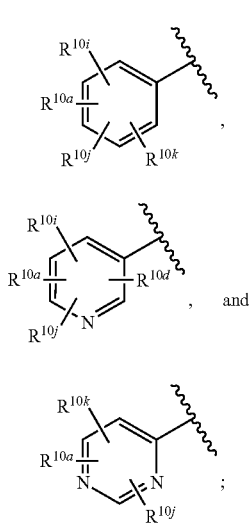

$X^1$ is selected from the group consisting of —O— and —N($R^{8a}$)—;
$Y^1$ is —(C$R^{9a}R^{9b}$)$_m$—;
$Z^1$ is selected from the group consisting of —O— and —N($R^{8b}$)—, or $Z^1$ is absent;
$R^{6a}$ is selected from the group consisting of hydroxy, alkyl, and alkoxy; or
$R^{6a}$ forms a hydroxy acid adduct or an amino acid adduct;
$R^{7a}$ and $R^{7b}$ are each independently selected from the group consisting of hydrogen, halo, nitro, cyano, hydroxy, amino, optionally substituted alkyl, haloalkyl, hydroxyalkyl, alkoxy, and alkylthio;
$R^{7a'}$ and $R^{7b'}$ are each independently selected from the group consisting of hydrogen, halo, nitro, cyano, hydroxy, amino, optionally substituted alkyl, haloalkyl, hydroxyalkyl, alkoxy, and alkylthio;
$R^{8a}$ and $R^{8b}$ are each independently selected from the group consisting of hydrogen and alkyl;
$R^{9a}$ and $R^{9b}$ are each independently selected from the group consisting of hydrogen and alkyl;
m is 1, 2, 3, or 4;
$X^2$ is selected from the group consisting of —O— and —N($R^{8c}$)—;
$Y^2$ is —(C$R^{9c}R^{9d}$)$_n$—;
$Z^2$ is selected from the group consisting of —O— and —N($R^{8d}$)—, or $Z^2$ is absent;
$R^{6b}$ is selected from the group consisting of hydroxy, alkyl, and alkoxy; or
$R^{6b}$ forms a hydroxy acid adduct or an amino acid adduct;
$R^{7c}$ and $R^{7d}$ are each independently selected from the group consisting of hydrogen, halo, nitro, cyano, hydroxy, amino, optionally substituted alkyl, haloalkyl, hydroxyalkyl, alkoxy, and alkylthio;
$R^{8c}$ and $R^{8d}$ are each independently selected from the group consisting of hydrogen and alkyl;
$R^{9c}$ and $R^{9d}$ are each independently selected from the group consisting of hydrogen and alkyl;
n is 1, 2, 3, or 4;
X is selected from the group consisting of —O— and —N($R^{8e}$)—;
$R^{6c}$ is selected from the group consisting of hydroxy, alkyl, and alkoxy; or
$R^{6c}$ forms a hydroxy acid adduct or an amino acid adduct;

$R^{7e}$ and $R^{7f}$ are each independently selected from the group consisting of hydrogen, halo, nitro, cyano, hydroxy, amino, optionally substituted alkyl, haloalkyl, hydroxyalkyl, alkoxy, and alkylthio;
$R^{8e}$ is selected from the group consisting of hydrogen and alkyl;
$R^{6d}$ is selected from the group consisting of hydroxy, alkyl, and alkoxy; or
$R^{6d}$ forms a hydroxy acid adduct or an amino acid adduct;
$R^{6f}$ is selected from the group consisting of hydrogen, alkyl, amino, and hydroxy;
$X^5$ is selected from the group consisting of —O— and —N($R^{8k}$)—;
$R^{7g}$ and $R^{7h}$ are each independently selected from the group consisting of hydrogen, halo, nitro, cyano, hydroxy, amino, optionally substituted alkyl, haloalkyl, hydroxyalkyl, alkoxy, and alkylthio;
$R^{8k}$ is selected from the group consisting of hydrogen and alkyl;
$X^6$ is selected from the group consisting of —O— and —N($R^{8l}$)—;
$X^7$ is selected from the group consisting of —O— and —N($R^{8m}$)—;
$R^{8l}$ is selected from the group consisting of hydrogen and alkyl;
$R^{8m}$ is selected from the group consisting of hydrogen and alkyl;
$R^{8n}$ is selected from the group consisting of hydrogen and alkyl;
$R^{10i}$, $R^{10j}$ and $R^{10k}$ are each independently selected from the group consisting of hydrogen, halo, nitro, cyano, hydroxy, amino, —N(H)CHO, —N(H)CN, optionally substituted alkyl, haloalkyl, alkoxyalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —CO$R^{16}$, —SO$_2R^{17}$, —N($R^{18}$)CO$R^{19}$, —N($R^{18}$)SO$_2R^{20}$ or N($R^{18}$)C=N($R^{21}$)-amino; or
$R^{10i}$ is selected from the group consisting of hydrogen, halo, nitro, cyano, hydroxy, —N(H)CHO, —N(H)CN, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —CO$R^{16}$, —SO$_2R^{17}$, —N($R^{18}$)CO$R^{19}$, —N($R^{18}$)SO$_2R^{20}$ or N($R^{18}$)C=N($R^{21}$)-amino; and/or
$R^{10j}$ and $R^{10k}$ taken together with two adjacent carbon atoms form a fused optionally substituted cycloalkyl, optionally substituted heterocyclo, or optionally substituted heteroaryl group;
$R^{11a}$ and $R^{11b}$ are each independently selected from the group consisting of hydrogen and alkyl;
$R^{12a}$ and $R^{12b}$ are selected from the group consisting of hydroxy and alkoxy; or
$R^{12a}$ and $R^{12b}$ taken together form a linkage —O(C$R^{13a}R^{13b}$)$_p$O—; or
B($R^{12a}$)($R^{12b}$) forms a fluoride adduct;
$R^{13a}$ and $R^{13b}$ are each independently selected from the group consisting of hydrogen and $C_{1-4}$ alkyl;

o is 0, 1, 2, 3, 4, or 5;
p is 2, 3, or 4;
$R^5$ is $R^4$-3, $R^4$-4, $R^4$-8, $R^4$-9, or $R^4$-10; or
$R^5$ is selected from the group consisting of:

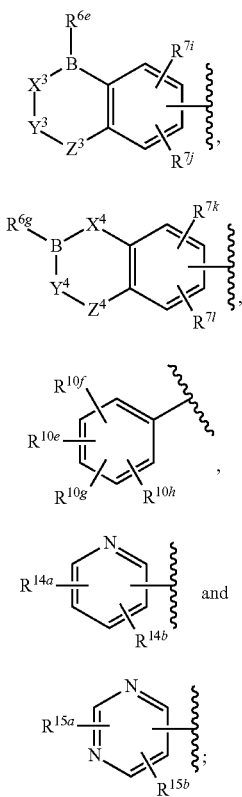

$X^3$ is selected from the group consisting of —O— and —N($R^{8f}$)—;
$Y^3$ is —(C$R^{9e}R^{9f}$)$_q$—;
$Z^3$ is selected from the group consisting of —O— and —N($R^{8g}$)—, or $Z^3$ is absent;
$R^{6c}$ is selected from the group consisting of hydroxy and alkyl; or
$R^{6e}$ forms a hydroxy acid adduct or an amino acid adduct;
$R^{7i}$ and $R^{7j}$ are each independently selected from the group consisting of hydrogen, halo, nitro, cyano, hydroxy, amino, optionally substituted alkyl, haloalkyl, hydroxyalkyl, alkoxy, and alkylthio;
$R^{8f}$ and $R^{8g}$ are each independently selected from the group consisting of hydrogen and alkyl;
$R^{9e}$ and $R^{9f}$ are each independently selected from the group consisting of hydrogen and alkyl;
q is 1, 2, 3, or 4;
$X^4$ is selected from the group consisting of —O— and —N($R^{8h}$)—;
$Y^4$ is —(C$R^{9g}R^{9h}$)$_r$—;
$Z^4$ is selected from the group consisting of —O— and —N($R^{8i}$)—, or $Z^4$ is absent;
$R^{6g}$ is selected from the group consisting of hydroxy and alkyl; or
$R^{6g}$ forms a hydroxy acid adduct or an amino acid adduct;
$R^{7k}$ and $R^{7l}$ are each independently selected from the group consisting of hydrogen, halo, nitro, cyano, hydroxy, amino, optionally substituted alkyl, haloalkyl, hydroxyalkyl, alkoxy, and alkylthio;

$R^{8h}$ and $R^{8i}$ are each independently selected from the group consisting of hydrogen and alkyl;
$R^{9g}$ and $R^{9h}$ are each independently selected from the group consisting of hydrogen and alkyl;
r is 1, 2, 3, or 4;
$R^{10e}$ is selected from the group consisting of hydrogen and —(C$R^{11c}R^{11d}$)$_s$—B($R^{12c}$)($R^{12d}$); and
$R^{10f}$, $R^{10g}$, and $R^{10h}$ are independently selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —CO$R^{16}$, —SO$_2R^{17}$, —N($R^{18}$)CO$R^{19}$, —N($R^{18}$)SO$_2R^{20}$ or N($R^{18}$)C=N($R^{21}$)-amino; or
$R^{10f}$ is selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —CO$R^{16}$, —SO$_2R^{17}$, —N($R^{18}$)CO$R^{19}$, —N($R^{18}$)SO$_2R^{20}$ or N($R^{18}$)C=N($R^{21}$)-amino; and
$R^{10g}$ and $R^{10h}$ taken together with two adjacent carbon atoms form a fused optionally substituted cycloalkyl, optionally substituted heterocyclo, or optionally substituted heteroaryl group; or
$R^{11c}$ and $R^{11d}$ are each independently selected from the group consisting of hydrogen and alkyl;
$R^{12c}$ and $R^{12d}$ are selected from the group consisting of hydroxy and alkoxy; or
$R^{12c}$ and $R^{12d}$ taken together form a linkage —O(C$R^{13c}R^{13d}$)$_t$O—; or
—B($R^{12c}$)($R^{12d}$) forms a fluoride adduct;
$R^{13e}$ and $R^{13d}$ are each independently selected from the group consisting of hydrogen and $C_{1-4}$ alkyl;
s is 0, 1, 2, 3, 4, or 5;
t is 2, 3, or 4;
$R^{14a}$ and $R^{14b}$ are each independently selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —CO$R^{16}$, —SO$_2R^{17}$, —N($R^{18}$)CO$R^{19}$, —N($R^{18}$)SO$_2R^{20}$ or N($R^{18}$)C=N($R^{21}$)-amino;
$R^{15a}$ and $R^{15b}$ are each independently selected from the group consisting of hydrogen, halo, nitro, cyano, hydroxy, amino, —N(H)CHO, —N(H)CN, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —CO$R^{16}$, —SO$_2R^{17}$, —N($R^{18}$)CO$R^{19}$, —N($R^{18}$)SO$_2R^{20}$ or N($R^{18}$)C=N($R^{21}$)-amino;
$R^{16}$ is selected from the group consisting of hydrogen, hydroxy, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, and arylalkyloxy;

$R^{17}$ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

$R^{18}$ is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

$R^{19}$ is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, arylalkyloxy, and amino;

$R^{20}$ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, and amino;

$R^{21}$ is selected from the group consisting of hydrogen, alkyl, aryl, cyano, and nitro;

with the provisos:
a) when $R^4$ is $R^4$-5, $R^4$-6, or $R^4$-7 and $R^5$ is $R^5$-3, then one of $R^{10a}$ or $R^{10c}$ is not hydrogen; and
b) when $R^4$ is $R^4$-5, $R^4$-6, or $R^4$-7 and $R^5$ is $R^5$-4 or $R^5$-5, then $R^{10a}$ is not hydrogen, or a pharmaceutically acceptable salt or solvate thereof, wherein the host cell is genetically modified to comprise:
(1) a polynucleotide encoding a gene switch comprising an ecdysone receptor ligand binding domain; and
(2) a polynucleotide encoding the gene of interest.

2. The method of claim 1, wherein the host cell is in a subject.

3. The method of claim 2, wherein the subject is human.

4. The method of claim 1, wherein the host cell is genetically modified ex vivo and then administered to the subject.

5. The method of claim 1, wherein the host cell is genetically modified in vivo.

6. The method of claim 1, comprising administering to said subject a compound having Formula II-A:

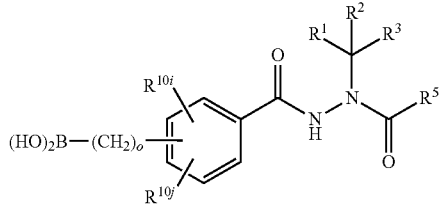

wherein $R^5$ is selected from the group consisting of $R^5$-3, $R^5$-4 and $R^5$-5, or a pharmaceutically acceptable salt or solvate thereof.

7. The method of claim 1, comprising administering to said subject a compound having Formula V:

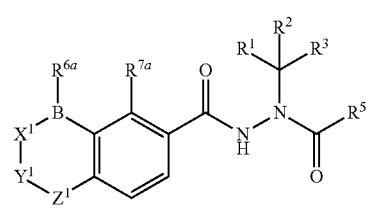

or a pharmaceutically acceptable salt or solvate thereof.

8. The method of claim 7, wherein $R^{7a}$ is selected from the group consisting of hydrogen, halogen, and alkyl, $Z^1$ is absent; $X^1$ is —O—; $R^{9a}$ and $R^{9b}$ are selected from the group consisting of hydrogen and methyl, and m is 1, 2, or 3, or a pharmaceutically acceptable salt or solvate thereof.

9. The method of claim 1, comprising administering to said subject a compound having Formula VI:

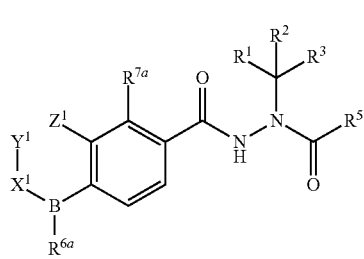

or a pharmaceutically acceptable salt or solvate thereof.

10. The method of claim 9, wherein $R^{7a}$ is selected from the group consisting of hydrogen, halogen, and alkyl, $Z^1$ is absent; and $X^1$ is —O—; $R^{9a}$ and $R^{9b}$ are selected from the group consisting of hydrogen and methyl, and m is 1, 2, or 3, or a pharmaceutically acceptable salt or solvate thereof.

11. The method of claim 1, comprising administering to said subject a compound having Formula VIII:

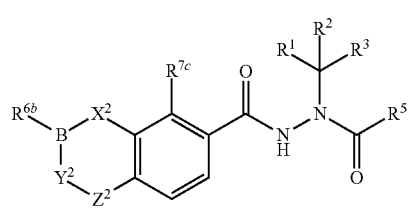

or a pharmaceutically acceptable salt or solvate thereof.

12. The method of claim 11, wherein $R^{7c}$ is selected from the group consisting of hydrogen, halogen, and alkyl; $Z^2$ is absent; $X^2$ is —O—; $R^{9c}$ and $R^{9d}$ are selected from the group consisting of hydrogen and methyl; and n is 1, 2, or 3, or a pharmaceutically acceptable salt or solvate thereof.

13. The method of claim 1, wherein:

R$^{4a}$ is selected from the group consisting of

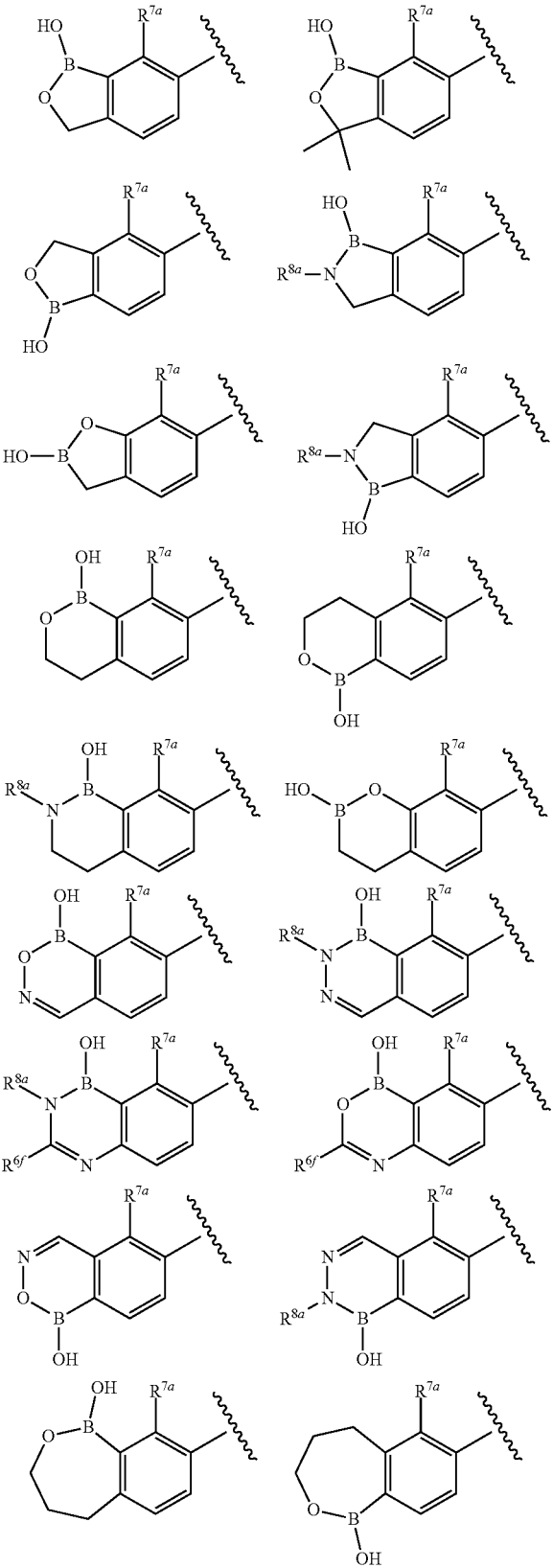

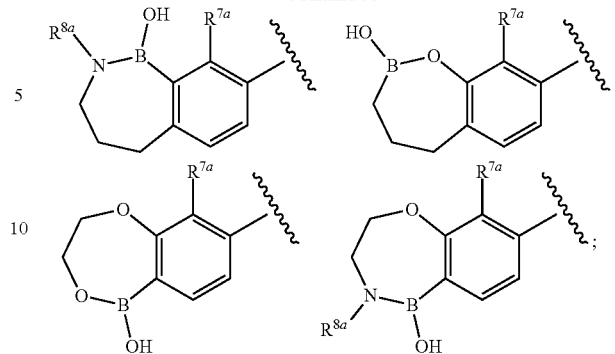

R$^5$ is selected from the group consisting of R$^5$-3, R$^5$-4, and R$^5$-5;

R$^{7a}$ is selected from the group consisting of hydrogen, halogen, hydroxy, C$_{1-4}$ alkyl, C$_{14}$ haloalkyl, C$_{1-4}$ alkoxy, and C$_{1-4}$ haloalkoxy;

R$^{8a}$ is selected from the group consisting of hydrogen and C$_{1-4}$ alkyl;

R$^{6f}$ is selected from the group consisting of hydrogen, C$_{1-4}$ alkyl, hydroxy, and —NH$_2$; and R$^{10e}$ is hydrogen, or a pharmaceutically acceptable salt or solvate thereof.

14. The method of claim 1, wherein:

R$^1$ is selected from the group consisting of methyl, ethyl, n-propyl, and n-butyl;

R$^2$ is selected from the group consisting of hydrogen and methyl; and

R$^3$ is selected from the group consisting of methyl and tert-butyl, or a pharmaceutically acceptable salt or solvate thereof.

15. The method of claim 1, wherein:

R$^1$ is optionally substituted C$_{1-6}$ alkyl;

R$^2$ is hydrogen; and

R$^3$ is selected from the group consisting of optionally substituted phenyl, optionally substituted pyridyl, and optionally substituted pyrimidinyl, or a pharmaceutically acceptable salt or solvate thereof.

16. The method of claim 14, wherein R$^1$, R$^2$, and R$^3$ are each methyl, or a pharmaceutically acceptable salt or solvate thereof.

17. The method of claim 1, comprising administering to said subject a compound having Formula XI-A:

XI-A

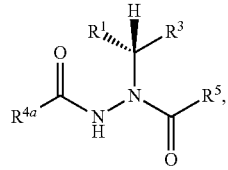

having an enantiomeric excess of at least about 60%, wherein R$^1$ does not equal R$^3$, or a pharmaceutically acceptable salt or solvate thereof.

18. The method of claim 17, wherein:
R$^{4a}$ is selected from the group consisting of:
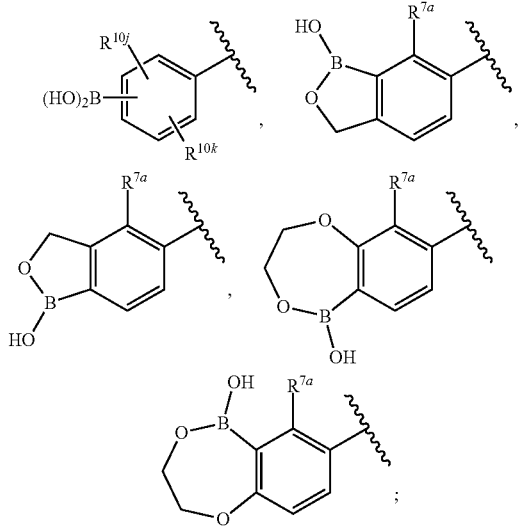
R$^5$ is selected from the group consisting of R$^5$-3, R$^5$-4, and R$^5$-5; and
R$^{10c}$ is hydrogen,
or a pharmaceutically acceptable salt or solvate thereof.
19. The method of claim 1, comprising administering to said subject a compound selected from the group consisting of:
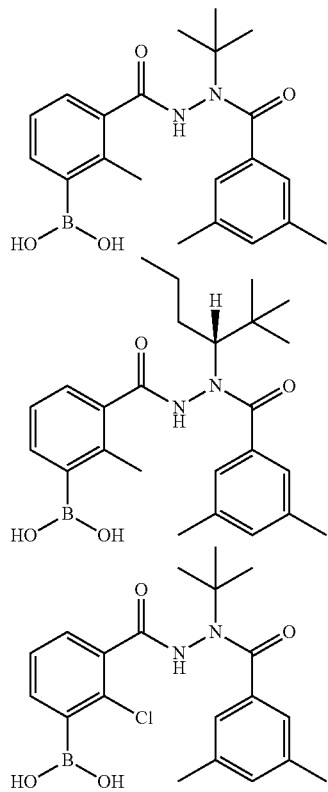
-continued
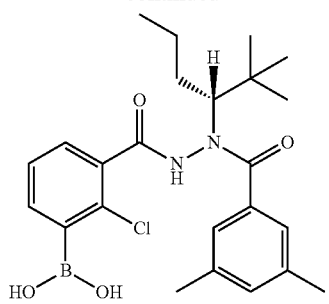
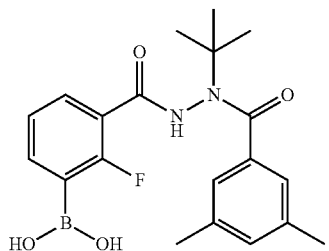
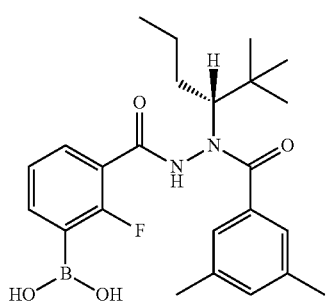
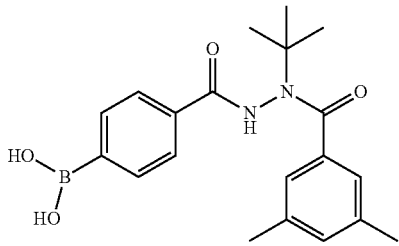
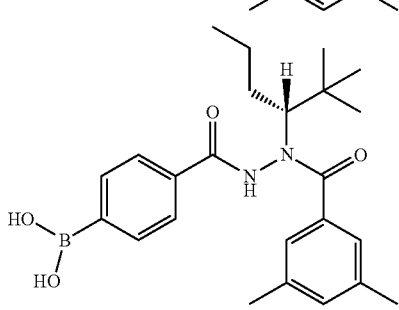
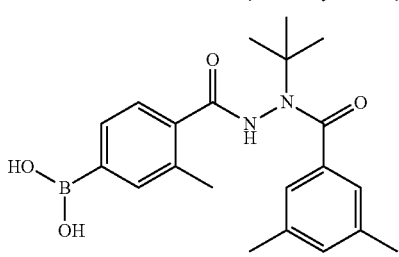

269
-continued
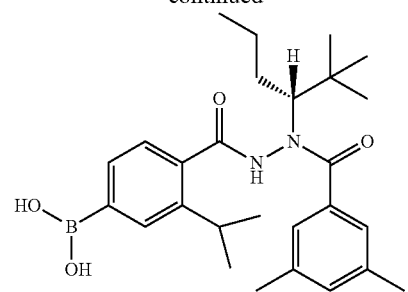
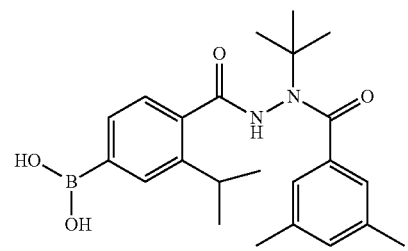
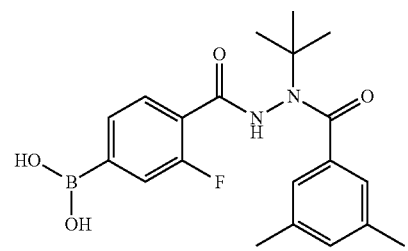
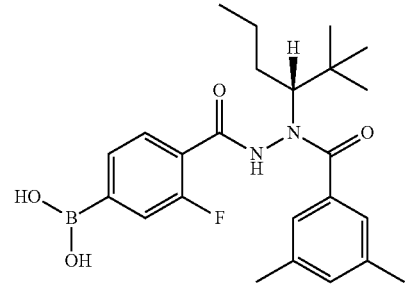
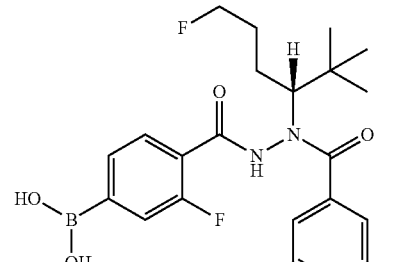
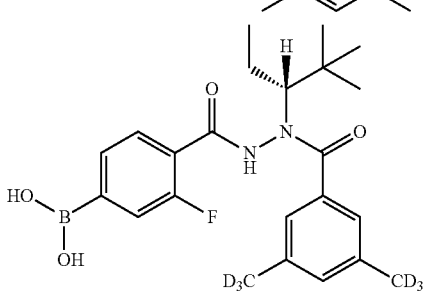
270
-continued
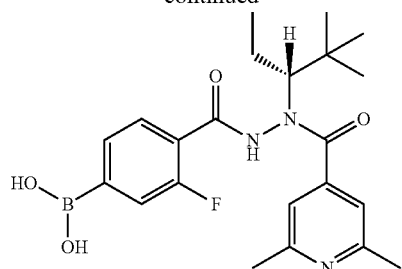
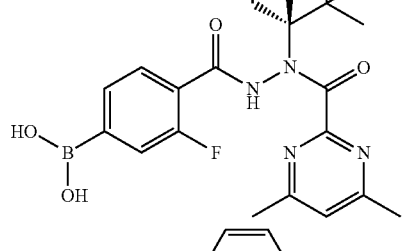
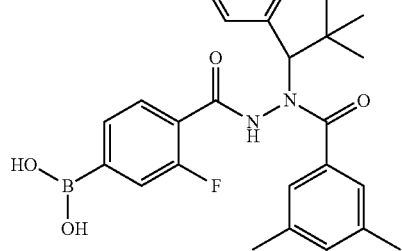
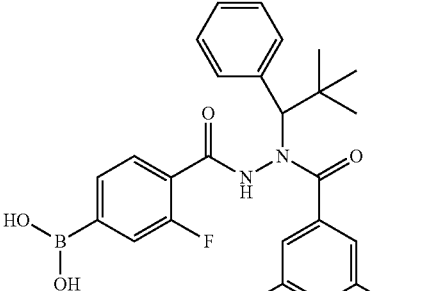
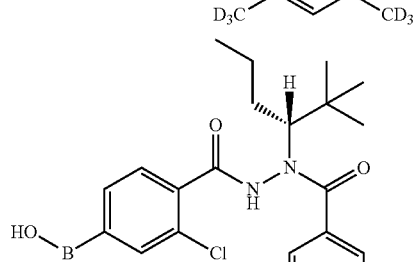
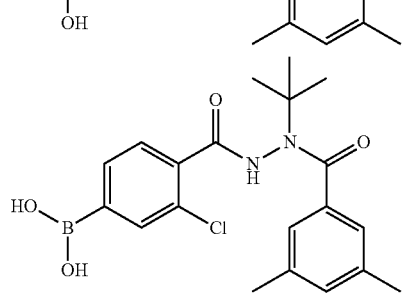

271
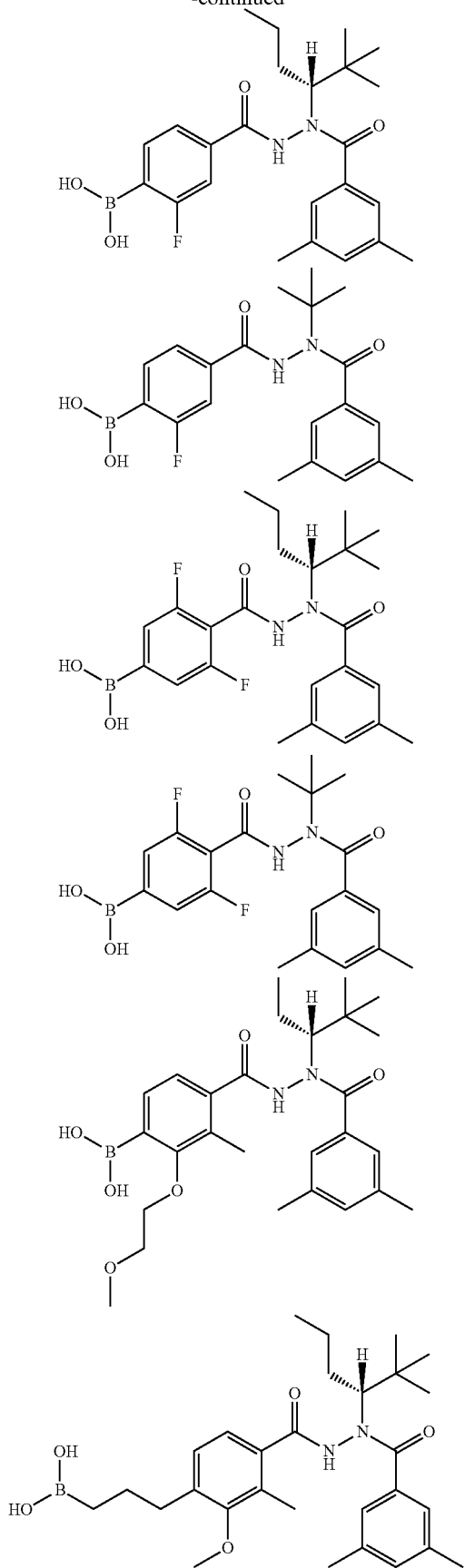
272
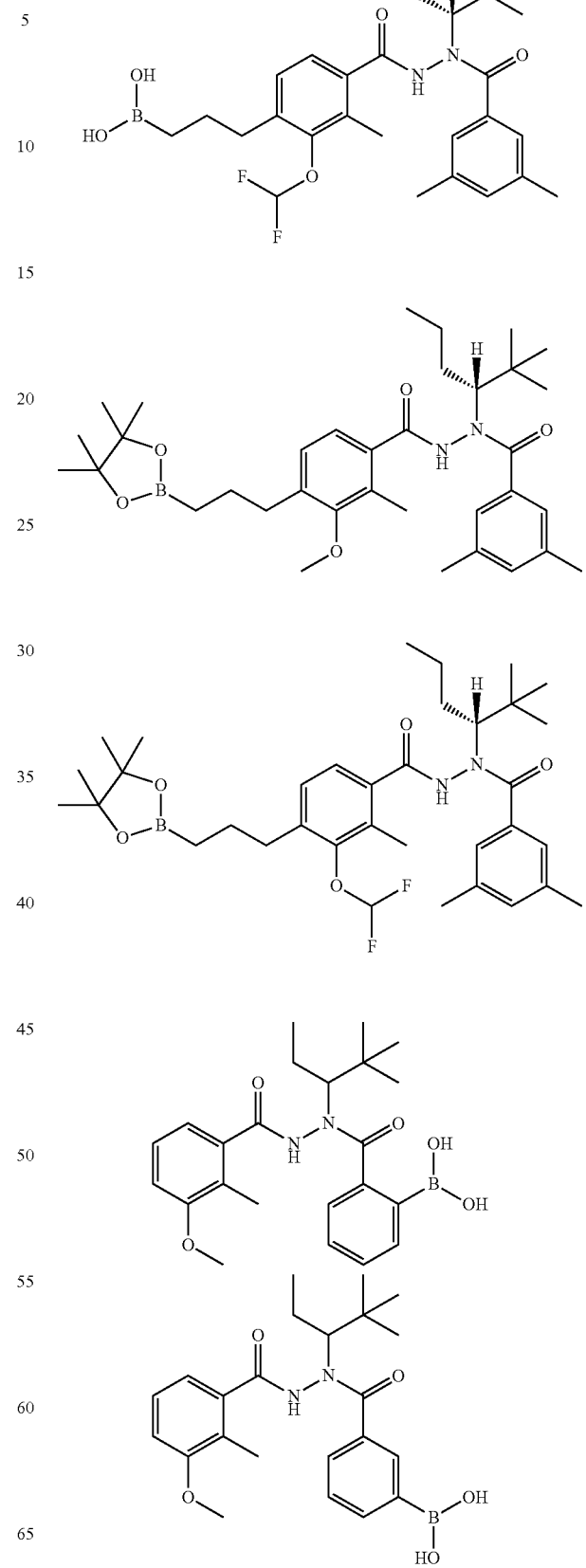

273
-continued
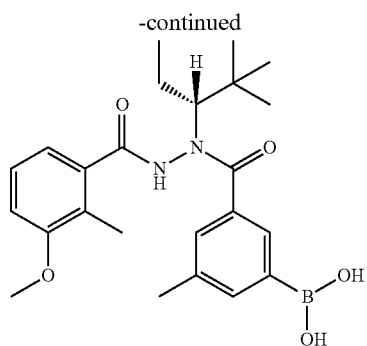
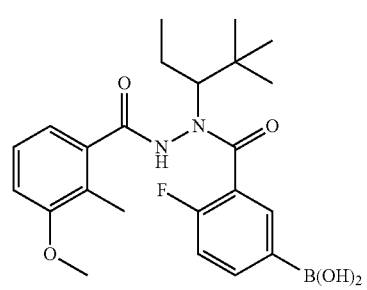
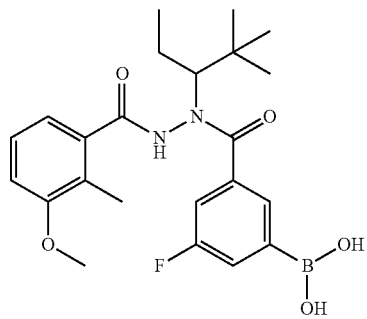
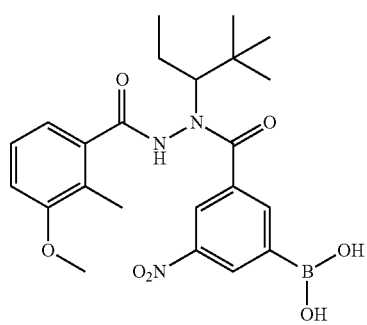
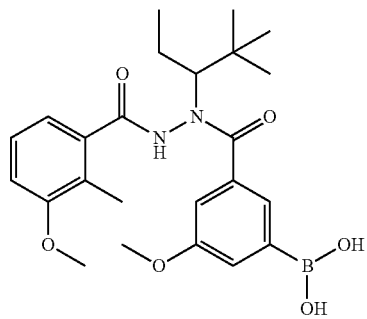
274
-continued
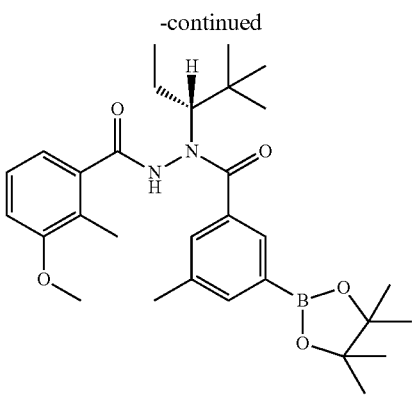
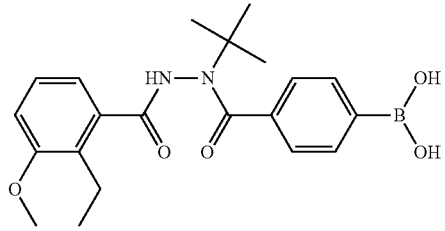
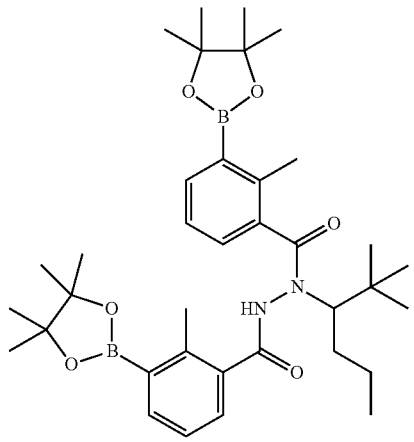
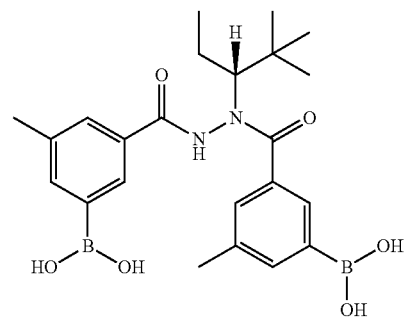
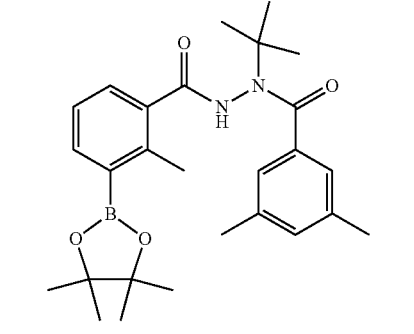

275
-continued
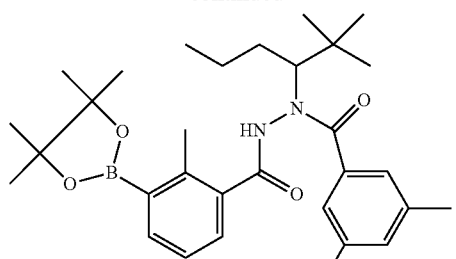
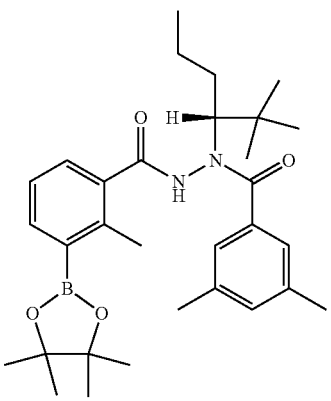
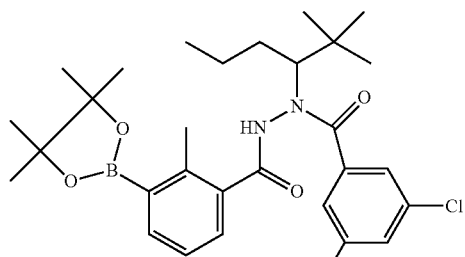
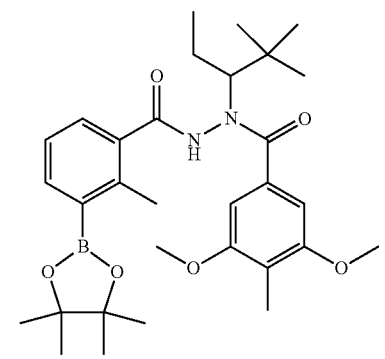
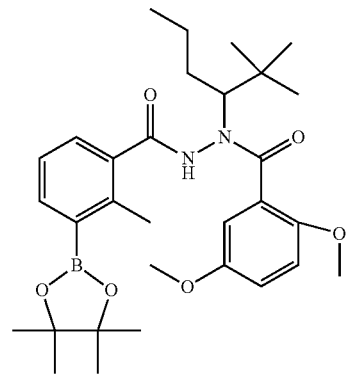
276
-continued
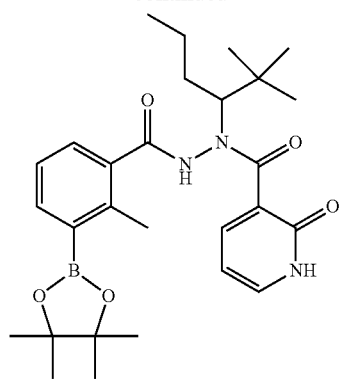
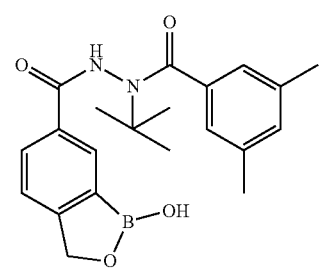
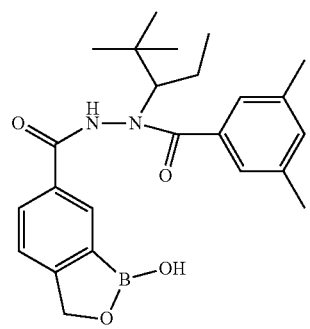
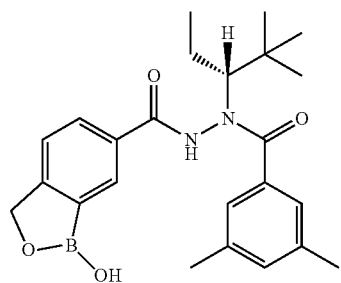
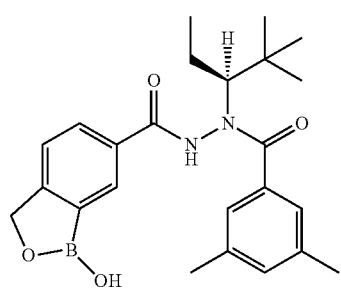

277
-continued
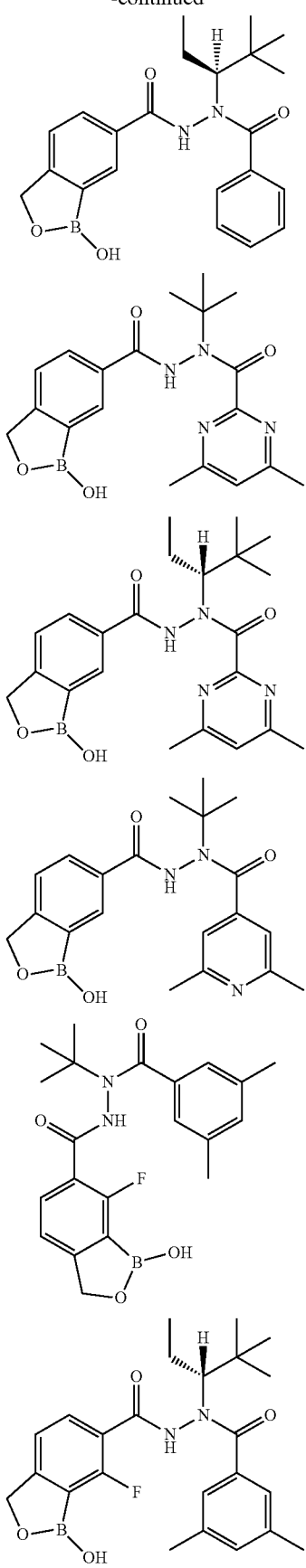
278
-continued
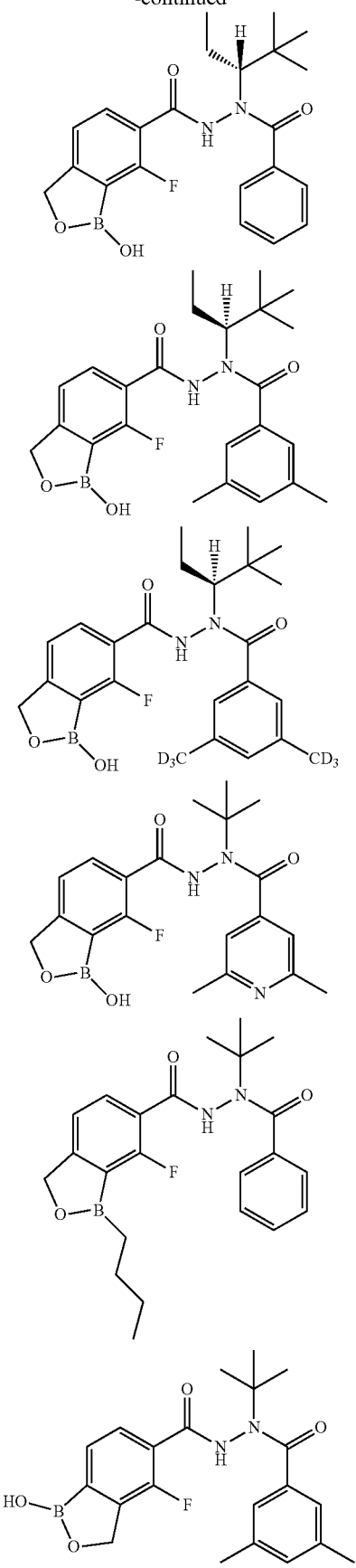

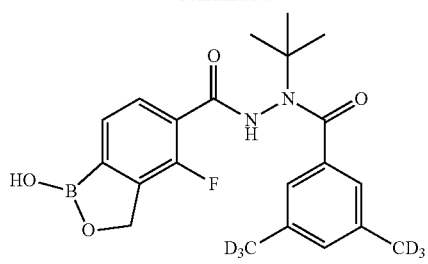
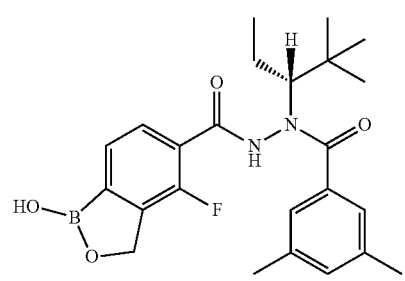
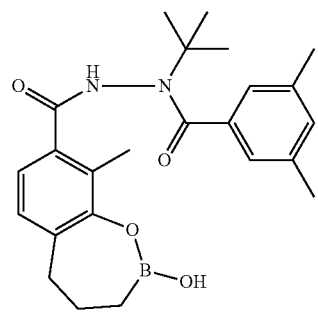
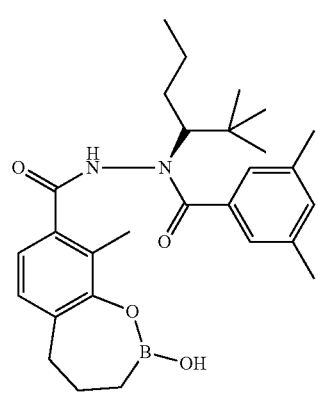
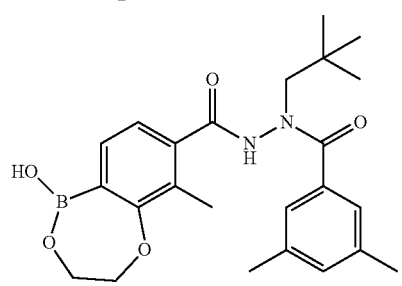
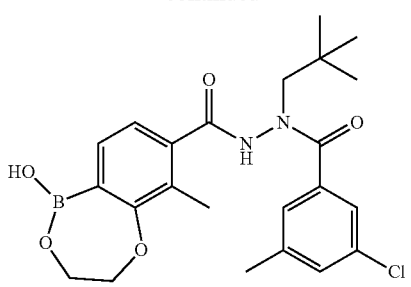
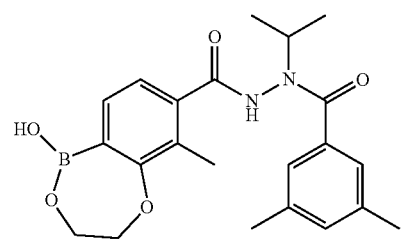
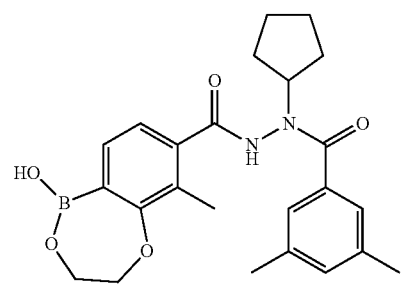
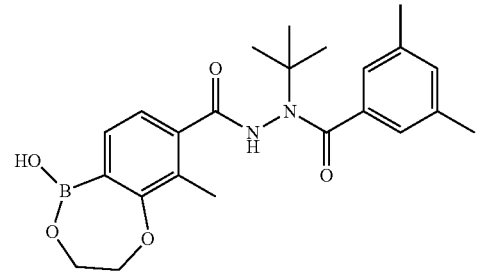
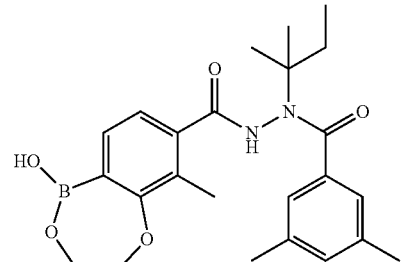
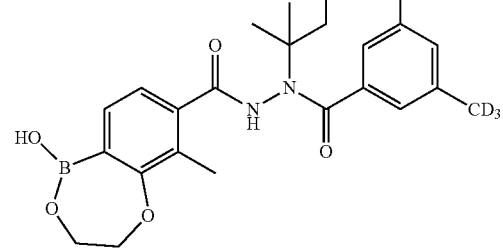

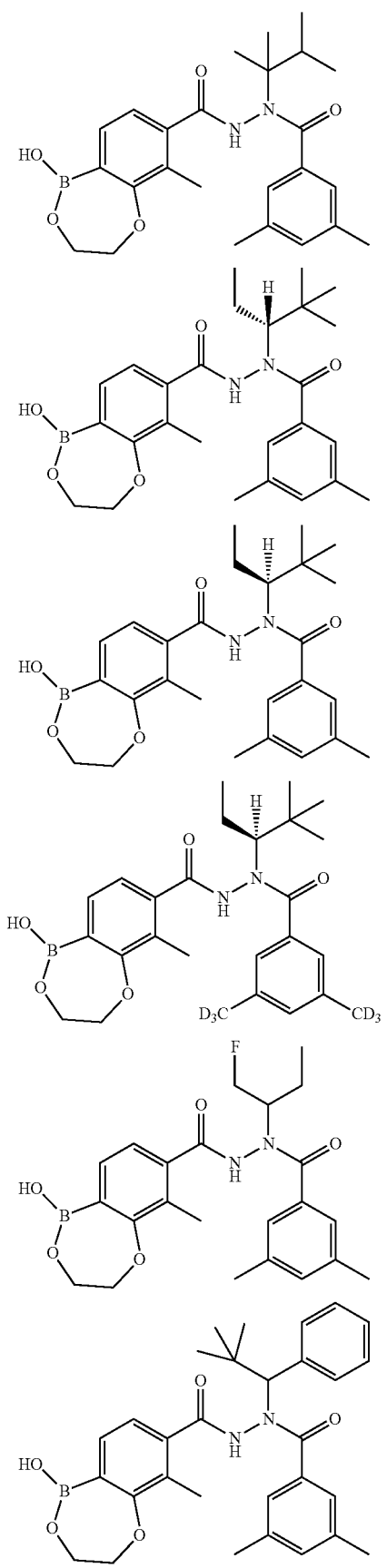
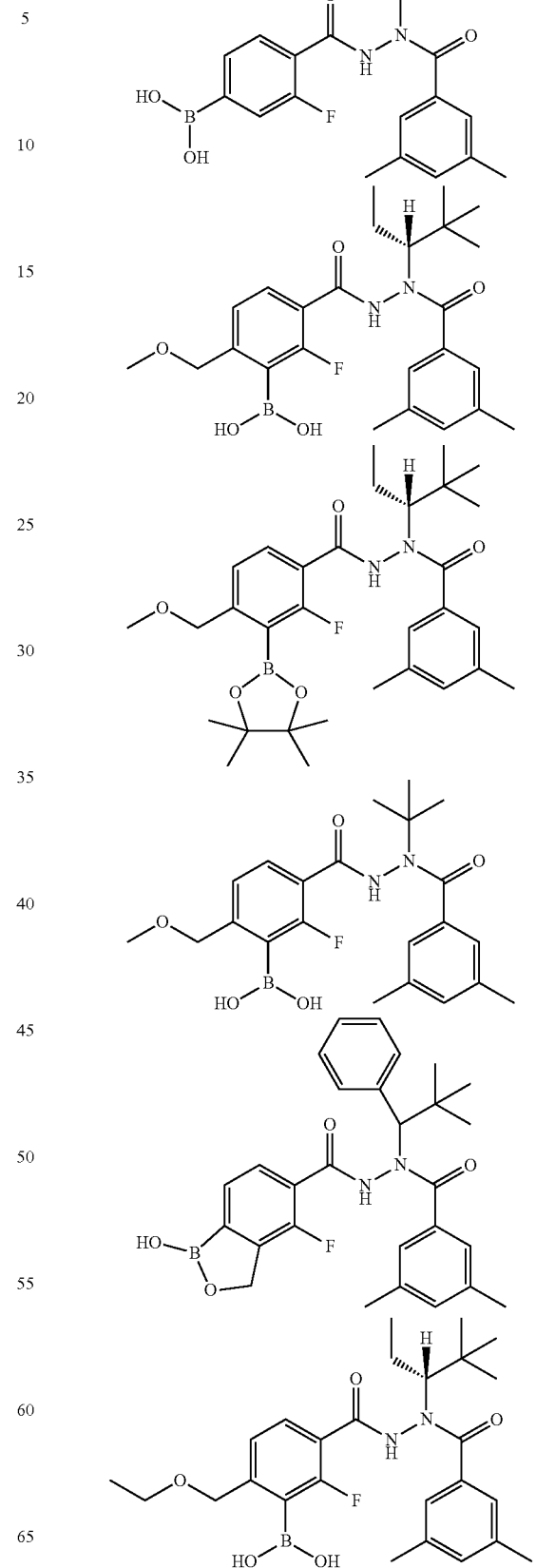

-continued
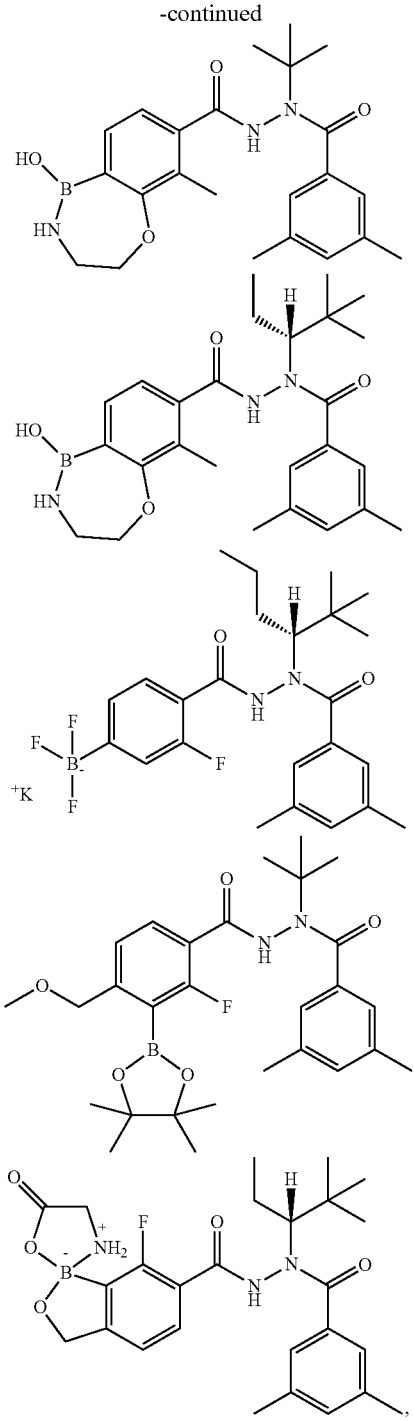
or a pharmaceutically acceptable salt or solvate thereof.
20. The method of claim 19, comprising administering to said subject a compound selected from the group consisting of
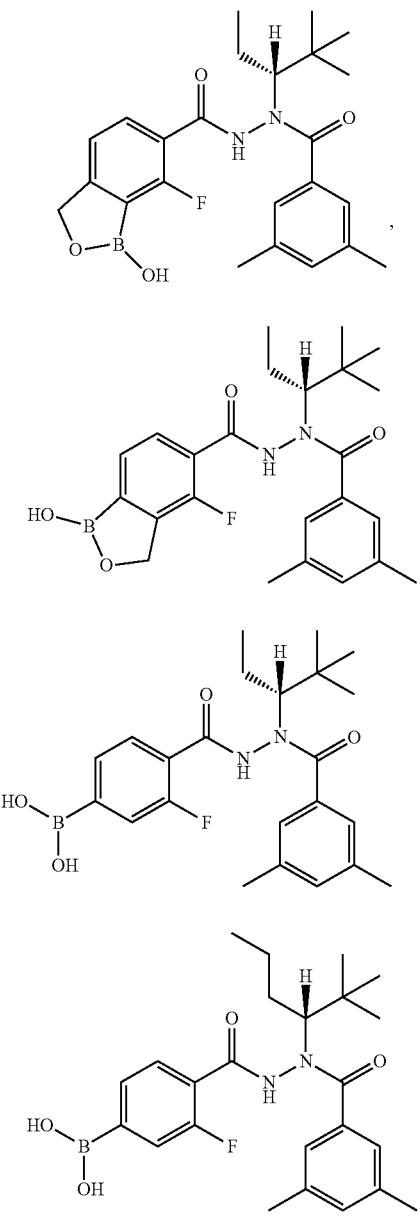
and
or a pharmaceutically acceptable salt or solvate thereof.
* * * * *

SEQUENCE LISTING

```
<160> NUMBER OF SEQ ID NOS: 1

<210> SEQ ID NO 1
<211> LENGTH: 10975
<212> TYPE: DNA
<213> ORGANISM: Artificial sequence
<220> FEATURE:
<223> OTHER INFORMATION: RheoSwitch(R) Vector

<400> SEQUENCE: 1
gctgagctat gcctaatcaa gtcacggtaa ctatgactct cttaaggtag ccaaatggcg      60
ccacgaaagg aggtcgtgaa atggataaaa aaatacagcg tttttcatgt acaactatac     120
tagttgtagt gcctaaataa tgcttttaaa acttaaaaat atcagataac agcttggtgg     180
cacccattgt gttcacagga gatacagctt tatctgtact gatattaatg acatgctgca     240
ctcggtgtga aagggcatct agtaggctat ggcagggcct gccgccccga cgttggctgc     300
gagccctggg ccttcacccg aacttggggg gtggggtggg gaaaaggaag aaacgcgggc     360
gtattggccc caatggggtc tcggtggggt atcgacagag tgccagccct gggaccgaac     420
cccgcgttta tgaacaaacg acccaacacc gtgcgtttta ttctgtcttt ttattgccgt     480
catagcgcgg gttccttccg gtattgtctc cttccgtgtt tcatcagaaa aactcgtcca     540
gcaggcggta gaaagcgatg cgctgagaat ctggtgcagc gatgccgtac agaaccagga     600
agcggtcagc ccattcgccg cccagttctt cagcgatgtc gcgggtagcc agagcgatgt     660
cctggtagcg gtcagcaacg cccagacgac cacagtcgat gaagccagag aagcggccgt     720
tttcaaccat gatgttcggc aggcaagcgt cgccgtgggt aacaaccagg tcttcgccgt     780
```

```
ctggcatacg agctttcagg cgagcgaaca gttcagccgg agccaggccc tggtgttctt    840
cgtccaggtc gtcctggtca accaggccag cttccatgcg ggtgcgagcg cgttcgatgc    900
ggtgtttagc ctggtggtcg aacggacaag tagccgggtc cagggtgtgc aggcggcgca    960
tagcgtcagc catgatagaa acttttcag ccggagccag gtgagaagac agcagatcct   1020
ggcccggaac ttcgcccagc agcagccagt cgcggccagc ttcggtaaca acgtccagaa   1080
cagcagcgca cggaacgccg gtggtagcca gccaagacag gcgagcagct tcgtcttgca   1140
gttcgttcag agcgccagac aggtcggttt taacgaacag aaccgggcgg ccctgagcag   1200
acaggcggaa aacagcagcg tcagagcagc cgatggtttg ttgtgcccag tcgtaaccaa   1260
acagacgttc aacccaagca gccggagagc cagcgtgcag gccgtcctgt tcgatcatgg   1320 tggcccccc cccccccgga atagctctga ggccgaggca gcttcggcct ctgcataaat   1380
aaaaaaaatt agtcagccat ggggcggaga atgggcggaa ctgggcggag ttaggggcgg   1440
gatgggcgga gttaggggcg ggactatggt tgctgactaa ttgagatgct tgctttgcat   1500
acttctgcct gctggggagc ctggggactt tccacacctg gttgctgact aattgagatg   1560
cttgctttgc atacttctgc ctgctgggga gcctggggac tttccacacc ctaaccatgc   1620
attcaactat cccaacgagg gattcgaagg acgatacccta cgttagactt aactataacg   1680
gtcctaaggt agcgaccact tagacgtgtt gaaaccctag gccgcacag gcccgccgac   1740 gatccgagcg tggccatcgt ggcccaccta agtggtccag gaacggcgtg ggctcgttta   1800
aaccgtacca ttagggaaag tacccactta tgtgggcgat cgcttaatta aggccggccg   1860
ccgcaataaa atatctttat tttcattaca tctgtgtgtt ggttttttgt gtgaatccat   1920
agtactaaca tacgctctcc atcaaaacaa aacgaaacaa aacaaactag caaaataggc   1980
tgtccccagt gcaagtccag gtgccagaac atttctctat ccataatgca ggggtaccgg   2040
gtgatgacgg tgaaaacctc caattgcgga gtactgtcct ccgagcgag tactgtcctc   2100 cgagcggagt actgtcctcc gagcggagta ctgtcctccg agcggagtac tgtcctccga   2160
gcggagtact gtcctccgag cggagagtcc ccggggacct agagggtata taatgggtgc   2220
cttagctggt gtgtgacctc atcttcctgt acgcccctgc aggggcgcgc cacgcgtccg   2280
cgggctagcg ccaccatgga agatgccaaa aacattaaga agggcccagc gccattctac   2340
ccactcgaag acgggaccgc tggcgagcag ctgcacaaag ccatgaagcg ctacgccctg   2400
gtgcccggca ccatcgcctt taccgacgca catatcgagg tggacattac ctacgccgag   2460
tacttcgaga tgagcgttcg gctggcagaa gctatgaagc gctatgggct gaatacaaac   2520
catcggatcg tggtgtgcag cgagaatagc ttgcagttct tcatgccgt gttgggtgcc   2580 ctgttcatcg gtgtggctgt ggccccagct aacgacatct acaacgagcg cgagctgctg   2640
aacagcatgg gcatcagcca gcccaccgtc gtattcgtga gcaagaaagg gctgcaaaag   2700
atcctcaacg tgcaaaagaa gctaccgatc atacaaaaga tcatcatcat ggatagcaag   2760
accgactacc agggcttcca aagcatgtac accttcgtga cttcccattt gccacccggc   2820
ttcaacgagt acgacttcgt gcccgagagc ttcgaccggg acaaaaccat cgccctgatc   2880
atgaacagta gtgcagtac cggattgccc aaggcgtag ccctaccgca ccgcaccgct   2940
tgtgtccgat tcagtcatgc ccgcgacccc atcttcggca accagatcat ccccgacacc   3000
gctattctca gcgtggtgcc atttcaccac ggcttcggca tgttcaccac gctgggctac   3060
ttgatctgcg gctttcgggt cgtgctcatg taccgcttcg aggaggagct attcttgcgc   3120
```

```
agcttgcaag actataagat tcaatctgcc ctgctggtgc ccacactatt tagcttcttc   3180
gctaagagca ctctcatcga caagtacgac ctaagcaact tgcacgagat cgccagcggc   3240
ggagcgcctc tcagcaagga ggtaggtgag gccgtggcca aacgcttcca cctaccaggc   3300
atccgccagg gctacggcct gacagaaaca accagcgcca ttctgatcac ccccgaaggg   3360
gacgacaagc ctggcgcagt aggcaaggtg gtgcccttct tcgaggctaa ggtggtggac   3420
ttggacacag gtaagaccct gggtgtgaac cagcgcggcg agctgtgcgt ccgtggcccc   3480
atgatcatga gcggctacgt gaacaacccc gaggctacaa acgctctcat cgacaaggac   3540
ggctggctgc acagcggcga catcgcctac tgggacgagg acgagcactt cttcatcgtg   3600
gaccggctca agagcctgat caaatacaag ggctaccagg tagccccagc cgaactggag   3660
agcatcctgc tgcaacaccc caacatcttc gacgccgggg tcgctggcct gcccgacgac   3720
gatgctggcg agctgcccgc cgcagtcgtc gtgctggaac acggtaaaac catgaccgag   3780
aaggagatcg tggactatgt ggccagccag gttacaaccg ccaagaagct gcgcggtggt   3840
gttgtgttcg tggacgaggt gcctaaagga ctgaccggca agttggacgc ccgcaagatc   3900
cgcgagattc tcattaaggc caagaagggc ggcaagatcg ccgtgtaaat cgattgcgca   3960
aagctttcgc gataggcgag accaatgggt gtgtacgtag cggccgcgtc gactgatggg   4020
tggcatccct gtgaccctc cccagtgcct ctcctggccc tggaagttgc cactccagtg   4080
cccaccagcc ttgtcctaat aaaattaagt tgcatcattt tgtctgacta ggtgtccttc   4140
tataatatta tggggtggag gggggtggta tggagcaagg ggcaagttgg gaagacaacc   4200
tgtagggcct gcggggtcta ttgggaacca agctggagtg cagtggcaca atcttggctc   4260
actgcaatct ccgcctcctg ggttcaagcg attctcctgc ctcagcctcc cgagttgttg   4320
ggattccagg catgcatgac caggctcagc taattttgt ttttttggta gagacggggt   4380
ttcaccatat tggccaggct ggtctccaac tcctaatctc aggtgatcta cccaccttgg   4440
cctcccaaat tgctgggatt acaggcgtga accactgctc ccttccctgt ccttctgatt   4500
ttaaaataac tataccagca ggaggacgtc cagacacagc ataggctacc tggccatgcc   4560
caaccggtgg gacatttgag ttgcttgctt ggcactgtcc tctcatgcgt tgggtccact   4620
cagtagatgc ctgttgaatt atttaaatcg gtccgcgtac ggctcttctc cccctcgagg   4680
gcctccgcgc cgggttttgg cgcctcccgc gggcgccccc ctcctcacgg cgagcgctgc   4740
cacgtcagac gaagggcgca gcgagcgtcc tgatccttcc gcccggacgc tcaggacagc   4800
ggcccgctgc tcataagact cggccttaga accccagtat cagcagaagg acattttagg   4860
acgggacttg ggtgactcta gggcactggt tttctttcca gagagcggaa caggcgagga   4920
aaagtagtcc cttctcggcg attctgcgga gggatctccg tggggcggtg aacgccgatg   4980
attatataag gacgcgccgg gtgtggcaca gctagttccg tcgcagccgg gatttgggtc   5040
gcggttcttg tttgtggatc gctgtgatcg tcacttggtg agtagcgggc tgctgggctg   5100
ggtacgtgcg ctcggggttg gcgagtgtgt tttgtgaagt ttttaggca ccttttgaaa   5160 tgtaatcatt tgggtcaata tgtaattttc agtgttagac tagtaaattg tccgctaaat   5220 tctgccgtt tttggctttt ttgttagacg ccgcggggg gggggggggg ctagcgccac   5280
catgggcccc aagaagaaaa ggaaggtggc ccccccacc gacgtgagcc tgggcgacga   5340
gctgcacctg gacggcgagg acgtggccat ggcccacgcc gacgccctgg acgacttcga   5400
cctggacatg ctgggcgacg gcgacagccc cggcccggg ttcacccccc acgacagcgc   5460
cccctacggc gccctggaca tggccgactt cgagttcgag cagatgttca ccgacgccct   5520
```

```
gggcatcgac gagtacggcg gcgaattcga gatgcccgtg gacaggattc tggaggccga    5580
actcgccgtg gagcagaaaa gcgaccaggg cgtggagggc cccggcggaa ccggcggcag    5640
cggcagcagc cccaacgacc ccgtgaccaa catctgccag gccgccgaca agcagctgtt    5700
caccctggtg gagtgggcca agaggattcc ccacttcagc agcctgcccc tggacgacca    5760
ggtgatcctg ctgagggccg gatggaacga gctgctgatc gccagcttca gccacaggag    5820
catcgacgtg agggacggca tcctgctggc caccggcctg cacgtccata ggaacagcgc    5880
ccacagcgcc ggagtgggcg ccatcttcga caggtgctg accgagctgg tgagcaagat    5940
gagggacatg aggatggaca agaccgagct gggctgcctg agggccatca tcctgttcaa    6000
ccccgaggtg aggggcctga aaagcgccca ggaggtggag ctgctgaggg agaaggtgta    6060
cgccgccctg gaggagtaca ccaggaccac ccaccccgac gagcccggca gattcgccaa    6120
gctgctgctg aggctgccca gcctgaggag catcggcctg aagtgcctgg agcacctgtt    6180
cttcttcagg ctgatcggcg acgtgcccat cgacaccttc ctgatggaga tgctggagag    6240
ccccagcgac agctgagcat gccccccctct ccctccccc cccctaacgt tactggccga    6300
agccgcttgg aataaggccg gtgtgcgttt gtctatatgt tattttccac catattgccg    6360
tcttttggca atgtgagggc ccggaaacct ggccctgtct tcttgacgag cattcctagg    6420
ggtctttccc ctctcgccaa aggaatgcaa ggtctgttga atgtcgtgaa ggaagcagtt    6480
cctctggaag cttcttgaag acaaacaacg tctgtagcga ccctttgcag gcagcggaac    6540
cccccacctg gcgacaggtg cctctgcggc caaaagccac gtgtataaga tacacctgca    6600
aaggcggcac aaccccagtg ccacgttgtg agttggatag ttgtggaaag agtcaaatgg    6660
ctctcctcaa gcgtattcaa caggggctg aaggatgccc agaaggtacc ccattgtatg    6720
ggatctgatc tggggcctcg gtgcacatgc tttacatgtg tttagtcgag gttaaaaaac    6780
gtctaggccc cccgaaccac ggggacgtgg ttttcctttg aaaaacacga tccatatggc    6840
caccatgaag ctgctgagca gcatcgagca ggcttgcgac atctgcaggc tgaagaagct    6900
gaagtgcagc aaggagaagc ccaagtgcgc caagtgcctg aagaacaact gggagtgcag    6960
atacagcccc aagaccaaga ggagccccct gaccagggcc cacctgaccg aggtggagag    7020
caggctggag aggctggagc agctgttcct gctgatcttc cccagggagg acctggacat    7080
gatcctgaag atgacagcc tgcaagacat caaggccctg ctgaccggcc tgttcgtgca    7140
ggacaacgtg aacaaggacg ccgtgaccga caggctggcc agcgtggaga ccgacatgcc    7200
cctgaccctg aggcagcaca ggatcagcgc caccagcagc agcgaggaga gcagcaacaa    7260
gggccagagg cagctgaccg tgagccccga gtttcccggg atcaggcccg agtgcgtggt    7320
gcccgagacc cagtgcgcca tgaaaaggaa ggagaagaag gccagaaggg agaaggacaa    7380
gctgcccgtg agcaccacca ccgtcgatga ccacatgccc ccatcatgc agtgcgagcc    7440 ccccccccc gaggccgcca ggattcacga ggtcgtgccc aggttcctga cgacaagct    7500 gctggtgacc aacaggcaga gaacatcccc ccagctgacc gccaaccagc agttcctgat    7560
cgccaggctg atctggtatc aggacggcta cgagcagccc agcgacgagg acctgaaaaa g    7620 gatcacccag acctggcagc aggccgacga cgagaacgag gagagcgaca ccccccttcag    7680 gcagatcacc gagatgacca tcctgaccgt gcagctgatc gtggagttcg ccaagggcct    7740
gcccggattc gccaagatca gccagcccga ccagatcacc ctgctgaagg cttgcagcag    7800
cgaggtgatg atgctgaggg tggccaggag gtacgacgcc gccagcgaca gcatcctgtt    7860
```

| | |
|---|---|
| cgccaacaac caggcttaca ccagggacaa ctacaggaag gctggcatgg ccgaggtgat | 7920 |
| cgaggacctc ctgcacttct gcagatgtat gtacagcatg gccctggaca acatccacta | 7980 |
| cgccctgctg accgccgtgg tgatcttcag cgacaggccc ggcctggagc agccccagct | 8040 |
| ggtggaggag atccagaggt actacctgaa caccctgagg atctacatcc tgaaccagct | 8100 |
| gagcggcagc gccaggagca gcgtgatcta cggcaagatc ctgagcatcc tgagcgagct | 8160 |
| gaggaccctg ggaatgcaga acagcaatat gtgtatcagc ctgaagctga agaacaggaa | 8220 |
| gctgcccccc ttcctggagg agatttggga cgtggccgac atgagccaca cccagccccc | 8280 |
| ccccatcctg gagagcccca ccaacctgtg aatcgattag acatgataag atacattgat | 8340 |
| gagtttggac aaaccacaac tagaatgcag tgaaaaaaat gcttaatttg tgaaatttgt | 8400 |
| gatgctattg cttaatttgt aaccattata agctgcaata aacaagttaa taaaacattt | 8460 |
| gcattcattt tatgtttcag gttcaggggg agatgtggga ggttttttaa agcaagtaaa | 8520 |
| acctctacaa atgtggtatc tagagctctt ccaaaattaa tacgcattcg cgtgcgaaat | 8580 |
| cattaccctg ttatccctac gcctagcctt agggttcaca tctatgtcgg gtgcggagaa | 8640 |
| agaggtaatg aaatggcaat aacaggctag aaccagctaa cgttaggagc atagattggg | 8700 |
| gcattccgga actataaatt gcgttgcgct cactgcccgc tttccagtcg ggaaacctgt | 8760 |
| cgtgccagct gcataaatga atcggccaac gcgcggggag aggcggtttg cgtattgggc | 8820 |
| gcgcttccgc ttcctcgctc actgactcgc tgcgctcggt cgttcggctg cggcgagcgg | 8880 |
| tatcagctca ctcaaaggcg gtaatacggt tatccacaga atcagggat aacgcaggaa | 8940 |
| agaacatgtg agcaaaaggc cagcaaaagg ccaggaaccg taaaaaggcc gcgttgctgg | 9000 |
| cgtttttcca taggctccgc ccccctgacg agcatcacaa aaatcgacgc tcaagtcaga | 9060 |
| ggtggcgaaa cccgacagga ctataaagat accaggcgtt tccccctgga agctccctcg | 9120 |
| tgcgctctcc tgttccgacc ctgccgctta ccggatacct gtccgccttt ctcccttcgg | 9180 |
| gaagcgtggc gctttctcat agctcacgct gtaggtatct cagttcggtg taggtcgttc | 9240 |
| gctccaagct gggctgtgtg cacgaacccc ccgttcagcc cgaccgctgc gccttatccg | 9300 |
| gtaactatcg tcttgagtcc aacccggtaa gacacgactt atcgccactg gcagcagcca | 9360 |
| ctggtaacag gattagcaga gcgaggtatg taggcggtgc tacagagttc ttgaagtggt | 9420 |
| ggcctaacta cggctacact agaagaacag tatttggtat ctgcgctctg ctgaagccag | 9480 |
| ttaccttcgg aaaaagagtt ggtagctctt gatccggcaa acaaaccacc gctggtagcg | 9540 |
| gtggtttttt tgtttgcaag cagcagatta cgcgcagaaa aaaaggatct caagaagatc | 9600 |
| ctttgatctt ttctacgggg tctgacgctc agtggaacga aaactcacgt taagggattt | 9660 |
| tggtcatgag attatcaaaa aggatcttca cctagatcct tttaaattaa aaatgaagtt | 9720 |
| ttaaatcaat ctaaagtata tatgagtaaa cttggtctga catgcgcagt taccaatgct | 9780 |
| taatcagtga ggcacctatc tcagcgatct gtctatttcg ttcatccata gttgcctgac | 9840 |
| tccccgtcgt gtagataact acgatacggg agggcttacc atctggcccc agtgctgcaa | 9900 |
| tgataccgcg agacccacgc tcaccggctc cagatttatc agcaataaac cagccagccg | 9960 |
| gaagcgccga gcgcagaagt ggtcctgcaa ctttatccgc ctccatccag tctattaact | 10020 |
| gttgccggga agctagagta agtagttcgc cagttaatag tttgcggagc gttgttgcca | 10080 |
| ttgctacagg catcgtggtg tcacgctcgt cgtttggtat ggcttcattc agctccggtt | 10140 |
| cccaacgatc aaggcgagtt acatgatccc ccatgttgtg caaaaaagcg gttagctcct | 10200 |
| tcggtcctcc gatggttgtc agaagtaagt tggccgcagt gttatcactc atggttatgg | 10260 |

```
cagcactgca taattctctt actgtcatgc catccgtaag atgcttttct gtgactggtg    10320
agtattcaac caagtcattc tgagaatagt gtatgcggcg accgagttgc tcttgcccgg    10380
cgtcaatacg ggataatacc gcgccacata gcagaacttt aaaagtgctc atcattggga    10440
agcgttcttc ggggcgaaaa ctctcaagga tcttaccgct gttgagatcc agttcgatgt    10500
aacccacacg agcacccaac tgatcttcag catcttttac tttcaccagc gtttctgggt    10560
gagcaaaaac aggaaggcaa aatgccgcaa aaaggggaat aagggcgaca cggaaatgtt    10620
gaatactcat actcttcctt tttcaatatt attgaagcat ttatcagggt tattgtctca    10680
tgagcggata catatttgaa tgtatttaga aaaataaaca aataggggtt ccgcgcacat    10740
ttccccgaaa agtgccacct gaggtctaag aaaccattat tatcatgaca ttaacctata    10800
aaaataggcg tatcacgagg ccctttcttc tcgcgcgttt cggtgatgac ggtgaaaacc    10860
tctgacacat gcagctcccg gatacggtca cagcttgtct gtaagcggat gccgggagca    10920
gacaagcccg tcagggcgcg tcagcgggtg ttggcgggtg tcggggctgg cttaa         10975
```